(12) United States Patent
De Souza et al.

(10) Patent No.: US 7,393,957 B2
(45) Date of Patent: Jul. 1, 2008

(54) GENERATION TRIPLE-TARGETING, CHIRAL, BROAD-SPECTRUM ANTIMICROBIAL 7-SUBSTITUTED PIPERIDINO-QUINOLONE CARBOXYLIC ACID DERIVATIVES, THEIR PREPARATION, COMPOSITIONS AND USE AS MEDICAMENTS

(75) Inventors: Noel John De Souza, Mumbai (IN); Mahesh Vithalbhai Patel, Aurangabad (IN); Prasad Keshav Deshpande, Aurangabad (IN); Shiv Kumar Agarwal, Cidco Aurangabad (IN); Kandepu Sreenivas, Aurangabad (IN); Sheela Chandrasekharan Nair, Cidco Aurangabad (IN); Yati Chugh, Cidco Aurangabad (IN); Milind Chintaman Shukla, Aurangabad (IN)

(73) Assignee: Wockhardt Limited, Aurangabad (IN)

( * ) Notice: Subject to any disclaimer, the term of this patent is extended or adjusted under 35 U.S.C. 154(b) by 622 days.

(21) Appl. No.: 10/945,504

(22) Filed: Sep. 20, 2004

(65) Prior Publication Data

US 2005/0065164 A1   Mar. 24, 2005

Related U.S. Application Data

(60) Division of application No. 10/318,367, filed on Dec. 12, 2002, now Pat. No. 6,878,713, which is a continuation-in-part of application No. 10/128,996, filed on Apr. 23, 2002, now Pat. No. 6,964,966.

(60) Provisional application No. 60/341,165, filed on Dec. 13, 2001, provisional application No. 60/286,291, filed on Apr. 25, 2001.

(30) Foreign Application Priority Data

Apr. 24, 2002   (WO) ................... PCT/IN02/00111

(51) Int. Cl.
*C07D 215/38*   (2006.01)
*A61K 31/47*   (2006.01)

(52) U.S. Cl. ........................ 546/156; 514/312
(58) Field of Classification Search ............... 546/156; 514/312
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 3,924,042 A | 12/1975 | Gerster et al. | |
| 3,984,403 A | 10/1976 | Fujisawa et al. | |
| 3,985,882 A | 10/1976 | Gerster et al. | |
| 4,008,719 A | 2/1977 | Theeuwes et al. | |
| 4,051,247 A | 9/1977 | Schuppan et al. | |
| 4,382,892 A | 5/1983 | Hayakawa et al. | |
| 4,399,134 A | 8/1983 | Ishikawa et al. | |
| 4,404,207 A | 9/1983 | Stern | |
| 4,416,884 A | 11/1983 | Ishikawa et al. | |
| 4,443,447 A | 4/1984 | Gerster et al. | |
| 4,472,406 A | 9/1984 | Gerster et al. | |
| 4,472,407 A | 9/1984 | Stern et al. | |
| 4,535,161 A | 8/1985 | Hayakawa et al. | |
| 4,552,879 A | 11/1985 | Ishikawa et al. | |
| 4,563,459 A | 1/1986 | Groher et al. | |
| 4,594,347 A | 6/1986 | Ishikawa et al. | |
| 4,599,418 A | 7/1986 | Irikura et al. | |
| 4,638,067 A | 1/1987 | Culbertson et al. | |
| 4,642,355 A | 2/1987 | Nakamura et al. | |
| 4,665,079 A | 5/1987 | Culbertson et al. | |
| 4,777,175 A | 10/1988 | Culbertson et al. | |
| 4,822,801 A | 4/1989 | Domagala et al. | |
| 4,874,764 A | 10/1989 | Ueda et al. | |
| 4,880,806 A | 11/1989 | Ueda et al. | |
| 4,894,458 A | 1/1990 | Masuzawa et al. | |
| 4,935,420 A | 6/1990 | Ueda et al. | |
| 4,997,943 A | 3/1991 | Iwata et al. | |
| 5,051,509 A | 9/1991 | Nagano et al. | |
| 5,097,032 A | 3/1992 | Domagala et al. | |
| 5,185,337 A | 2/1993 | Fujii et al. | |
| 5,290,934 A | 3/1994 | Ueda et al. | |
| 5,348,961 A | 9/1994 | Iwata et al. | |
| 5,420,140 A | 5/1995 | Perrin | |
| 5,436,367 A | 7/1995 | Iwata et al. | |
| 5,607,942 A | 3/1997 | Petersen et al. | |
| 5,639,886 A | 6/1997 | Zerbes et al. | |
| 5,677,316 A | 10/1997 | Ao et al. | |
| 5,859,026 A | 1/1999 | Ito et al. | |
| 5,869,661 A | 2/1999 | Ochi et al. | |
| 5,889,009 A | 3/1999 | Miyake et al. | |
| 6,034,100 A | 3/2000 | Adachi et al. | |
| 6,121,285 A | 9/2000 | Takemura et al. | |

(Continued)

FOREIGN PATENT DOCUMENTS

EP   0230295   7/1987

(Continued)

OTHER PUBLICATIONS

European Patent Specification 0394553 B1, dated Jun. 21, 1995.

(Continued)

*Primary Examiner*—D. Margaret Seaman
(74) *Attorney, Agent, or Firm*—Ladas & Parry LLP

(57) ABSTRACT

This invention relates to new generation triple-targeting, chiral, broad-spectrum antimicrobial 7-substituted piperidino-quinolone carboxylic acid derivatives, to their optical isomers, diastereomers or enantiomers, as well as pharmaceutically acceptable salts, hydrates, prodrugs, polymorphs and pseudopolymorphs thereof, to their preparation, to their compositions and to their use.

1 Claim, No Drawings

U.S. PATENT DOCUMENTS

| | | | |
|---|---|---|---|
| 6,136,806 | A | 10/2000 | Hittel |
| 6,184,388 | B1 | 2/2001 | Takemura et al. |
| 6,329,391 | B1 | 12/2001 | Ledoussal et al. |
| 6,514,986 | B2 | 2/2003 | de Souza et al. |
| 6,608,078 | B2 * | 8/2003 | De Souza et al. ............ 514/294 |
| 7,098,219 | B2 * | 8/2006 | de Souza et al. ............ 514/292 |

FOREIGN PATENT DOCUMENTS

| | | |
|---|---|---|
| EP | 0241206 | 10/1987 |
| EP | 0287951 | 10/1988 |
| EP | 0300735 | 1/1989 |
| EP | 0304087 | 2/1989 |
| EP | 0342675 | 11/1989 |
| EP | 0541086 | 5/1993 |
| EP | 0572259 | 12/1993 |
| EP | 0394553 | 6/1995 |
| EP | 0908181 | 4/1999 |
| EP | 0919553 | 6/1999 |
| JP | 57081486 | 5/1982 |
| JP | 57176987 | 10/1982 |
| JP | 58090511 | 5/1983 |
| JP | 63192753 | 8/1988 |
| JP | 02131483 | 5/1990 |
| JP | 02188570 | 7/1990 |
| JP | 02188589 | 7/1990 |
| JP | 05339238 | 12/1993 |
| JP | 6-145167 | 5/1994 |
| WO | 9414794 | 7/1994 |
| WO | 9415938 | 7/1994 |
| WO | 9420105 | 9/1994 |
| WO | 9724128 | 7/1997 |
| WO | 9731000 | 8/1997 |
| WO | 9744034 | 11/1997 |
| WO | 9858923 | 12/1998 |
| WO | 9914214 | 3/1999 |
| WO | 9926940 | 6/1999 |
| WO | 0018404 | 4/2000 |
| WO | 0068229 | 11/2000 |
| WO | 0185095 | 11/2001 |
| WO | 0185728 | 11/2001 |
| WO | 0209758 | 2/2002 |

OTHER PUBLICATIONS

Alsina J. et al. "Active Carbonate Resins for Solid-Phase Synthesis Through the Anchoring of a Hydroxyl Function. Synthesis of Cyclic and Alcohol Peptides", *Tetrahedron Letters*, (1997), 38(5): 883-886.
Edwards W.B. et al. "Generally Applicable, Convenient Solid-Phase Synthesis and Receptor Affinities of Octreotide Analogs", *J. Med. Chem.*, (1994), 37(22): 3749-3757.
Dhople, A.M. and M.A. Tbanez. "In vivo susceptibility of *Mycobacterium leprae* to ofloxacin either singly or in combination with Rifampicin and Rifabutin", *Arzneimittel-Forschung.*, (1994), 44(4): 563-565.
Haustein U.F. et al. "Topical quinolone nadifloxacin (OPC-7251) in bacterial skin disease: clinical evaluation in a multicenter open trial and in vitro antimicrobiological susceptibility testing", *J. Dermatological Treatment*, (1997), 8: 87-92.
Hashimoto, Koji et al. "A Practical Synthesis of (S)-(-)-Nadifloxacin: Novel Acid-Catalyzed Racemization of Tetrahydroquinaldine Derivative", *Chem. Pharm. Bull.*, (1996), 44(4): 642-645.
Irish, D. et al. "Control of an outbreak of an epidemic methicillin-resistant *Staphylococcus aureus* also resistant to mupirocin", *J. Hospital Infection*, (1998), 39: 19-26.
Kido, M. et al. "Crystal Structures of Nadifloxacin Anhydride and its Hemihydrate", *Chem. Pharm. Bull.*, (1994), 42(4):872-876.
Takahashi et al. "Reduction of in vitro Clastogenicity Induced by the Mixture of Optical Isomers of Nadifloxacin during Storage", *Arzneim.-Forsch./Drug Res.*, (1995), 45(1): 195-197.

Sloan et al. "Definition and attainment of high purity of organic compounds", Chapter 2, 179-182, *Physical and Chemistry of the Organic Solid State*, eds. D. Fox, Labes and Weissberer. Interscience Publishers, London. 1963.
Morita, S. et al. "An efficient synthesis of a key determinate towards (S)-(-)-Nadifloxacin", *Tetrahedron: Asymmetry*, (1995), 6(1): 245-254.
Morita, S. et al. "Synthesis and Antibacterial Activity of the Metabolites of 9-Fluoro-6,7-dihydro-8-(4-hydroxy-1-piperidyl)-5-methyl-1-oxo-1$H$,5$H$-benzo[,$j$]quinolizine-2-carboxylic acid (OPC-7251)", *Chem. Pharm.Bull.*, (1990), 38(7): 2027-2029.
Ishikawa, H. et al. "Studies on Antibacterial agents. I. Synthesis of Substituted 6,7-Dihydro-1-oxo-1$H$,5$H$-benzo[i,j]-quinolizine-2-carboxylic acids", *Chem. Pharm. Bull.*, (1989), 37(8): 2103-2108.
English translation of Yamada, Hirao et al. "Evaluation of the in vitro drug efficacy of Nadifloxacin Cream", *Iyakuhin Kenkyu*, (2000), 31(8): 519-524.
English abstract of Japanese patent 02131483, dated May 21, 1990.
English abstract of Japanese patent 02188589, dated Jul. 24, 1990.
English translation of Yamada, Hiroaki, et al. "Bioequivalency of 1 % Nadifloxacin lotion and 1 % of Nadifloxacin cream", *Iyakuhin Kenkyu*, (2000), 31(8): 525-528.
Berge, Stephen M. et al. "Pharmaceutical Salts", *J. Pharmaceutical Sciences*, (1977), 66(1): 1-19.
Abstract of Koike, M. et al. *Iyakuhin Kenkyu*, (1990), 21(5): 998-1021.
Abstract of Koike, M. et al. *Iyakuhin Kenkyu*, (1990), 21(5): 1022-1033.
Abstract of Fujita, S. et al. *Iyakuhin Kenkyu*, (1990), 21(6): 1158-1176.
Abstract of Koike, M. et al. *Yakubutsu Dotai*, (1990), 5(2): 199-208.
Abstract of Yasuo, A. et al. *Yakuri to Chiryo*, (1990), 18(4): 1717-1730.
Abstract of Hayakawa, R. et al. *Hifu*, (1990), 32(2): 217-230.
Abstract of Asada, Y. et al. *Yakuri to Chiryo*, (1990), 18(4): 1717-1730.
Abstract of Awogi, T. et al. *Iyakuhin Kenkyu*, (1990), 21(4): 626-635.
Abstract of Matsuzawa, A. et al. *Iyakuhin Kenkyu*. (1990), 21(4): 636-646.
Abstract of Nagao, T. et al. *Iyakuhin Kenkyu*, (1990), 21(4): 647-662.
English abstract of WO 97/44034, dated Nov. 27, 1997.
English abstract of JP 5339238, dated Dec. 21, 1993.
English abstract of JP 58090511, dated May 30, 1983.
Abstract of Matsuzawa, A. et al. *Iyakuhin Kenkyu*, (1990), 21(4): 663-670.
Abstract of Hashimoto, K. et al. *Iyakuhin Kenkyu*, (1990), 21(4): 671-677.
Abstract of Furukawa, M. et al. *Iyakuhin Kenkyu*, (1990), 21(5): 989-997.
Abstract of Yoshimura, S. et al. *Iyakuhin Kenkyu*, (1990), 21(5): 1034-1052.
English abstract of JP 63192753, dated Aug. 10, 1988.
English abstract of JP 57081486, dated May 21, 1982.
English abstract of JP 57176987, dated Oct. 30, 1982.
Abstract of Nakagiri, N. et al. *Iyakuhin Kenkyu*, (1990), 21(6): 1144-1155.
Abstract of Aoki, M. et al. *Iyakuhin Kenkyu*, (1990), 21(6): 1177-1202.
Abstract of Matsuzawa, A. et al. *Iyakuhin Kenkyu*, (1991), 22(1): 61-76.
Abstract of Kurokawa, I. et al. *J. Am. Acad. Dermatol.*, (1991), 25(4): 674-681.
English abstract of JP 02188570, dated Jul. 24, 1990.
Abstract of Bojar, R.A. et al. *Journal of Investigative Dermatology*, (1994), 103(3): 405.
Abstract of Smith, C.M. *Journal of Investigative Dermatology*, (1997), 108(3): 123.
Abstract of Hayakawa, R. et al. *Hifu*, (1998), 40(2): 165-171.
Abstract of Fujio, N. et al. *Yakuri to Chiryo*, (1998), 26(7): 1119-1132.
Kido, M. et al. "The Absolute Configuration of (R)-(+)-Nadifloxacin", *Chem. Pharm. Bull.*, (1996), 44(2): 421-423.

Miller, M.A. et al. "Development of Mupirocin Resistance Among Methicillin-Resistant *Staphylococcus aureus* After Widespread Use of Nasal Mupirocin Ointment", *Infection Control and Hospital Epidemiology*, (1996), 17(12): 811-813.

English abstract of WO99/26940, dated Jun. 3, 1999.

Mateu-de-Antonio, E.M. and M. Martin. "In vitro efficacy of several antimicrobial combinations against *Brucella canis* and *Brucella mlitensis* strains isolated from dogs", *Veterinary Microbiology*, (1995), 45: 1-10.

Nishijima, S. et al. "Sensitivity of *Staphylococcus aureus*, Isolated from Skin Infections in 1994, to 19 Antimicrobial Agents", *J. International Medical Research*, (1995), 23: 328-334.

Nishijima, S. et al. "Activity of Eight Fluoroquinolones against Both Methicillin-Susceptible and Resistant *Staphylococcus aureus* Isolated from Skin Infections", *J. Dermatology*, (1995), 22: 153-155.

Nishijima, S. et al. "Activity of Nadifloxacin Against Methicillin-Resistant *Staphylococcus aureus* Isolated from Skin Infections: Comparative Study with Seven Other Fluoroquinolones", *J. International Medical Research*, (1996), 24: 12-16.

Nishijima, S. et al. "Sensitivity of *Staphylococcus aureus* and *Streptococcus pyogenes* Isolated from Skin Infections in 1992 to Antimicrobial Agents", *J. Dermatology*, (1994), 21: 233-238.

Abstract of Kurokawa, I. et al. *European Journal of Dermatology*, (1999), 9(1): 25-28.

Abstract of Komagata, Y. et al. *Japanese Journal of Anitbiotics*, (1998), 51(2): 130-136.

Abstract of Gollnick, H. et al. *Dermatology*, (1998), 196(1): 119-125.

Abstract of Nishijima, S. et al. *J. International Medical Research*, (1997), 25(4): 210-213.

Abstract of Akamatsu, H. et al. *J. International Medical Research*, (1995), 23(1): 19-26.

Abstract of Takahashi, N. et al. *Arzneimittel-Forschung*, (1995), 45(2): 195-197.

Abstract of Takahashi, N. et al. *Arzneimittel-Forschung*, (1994), 44(11): 1265-1268.

Abstract of Patel,M.V. et al. 39th ICAAC at San Diego, (Sep. 26-29, 1999), Poster No. F0558.

Chemical Abstract: Vogt, K. et al. *Drugs* (1995), 49 (Supp.2): 266-268.

Chemical Abstract: Nishijima, S. et al. *Drugs* (1995), 49 (Suppl.2): 230-232.

Chemical Abstract: Bojar, R.A. et al. *Drugs* (1995), 49 (Supp.2): 164-167.

Chemical Abstract: Morita, S. et al. *Tetrahedron: Asymmetry* (1995), 6(1): 245-254.

Chemical Abstract: Vogt, K. et al. *Eur. J. Clin. Microbiol. Infect. Dis.* (1992), 11(10): 943-945.

Chemical Abstract: Morita, S. et al. *Chem. Pharm. Bull.* (1990), 38(7): 2027-2029.

Chemical Abstract: Muto, N. et al. *J. Immunoassay* (1990), 11(1): 1-16.

English abstract of WO 94/14794, dated Jul. 7, 1994.

Japanese patent 6-145167, dated May 24, 1994.

Chemical Abstract: Koike, M. et al. *J. Chromatogr.* (1990), 526(1): 235-239.

Chemical Abstract: Ishikawa, H. et al. *Chem. Pharm. Bull.* (1989), 37(8): 2103-2108.

Chemical Abstract: Kawabata, S. et al. *Chemotherapy* (1989), 37(9): 1160-1178.

Abstract of Iwahara, K. et al. *European Journal of Dermatology*, (1999), 9(4): 276-277.

Abstract of Radl, S. *Archiv der Pharmazie*, (1996), 329(3): 115-119.

Abstract of Andriole, V.T. *Drugs*, (1993), 46 (Supp.3): 1-7.

Ball, Peter. "The Quinolones: History and Overview", Chapter 2, pp. 1-28. *The Quinolones*, Second Edition. Academic Press, 1998.

English abstract of WO 98/58923, dated Dec. 30, 1998.

Domagala, John M. "Structure-activity and structure-side effect relationships for the quinolone antibacterials", *J. Antimicrobial Chemotherapy* (1994), 33: 685-706.

Suto, M.J. et al. "Fluoroquinolones: Relationships between Structural Variations, Mammalian Cell Cytotoxicity and Antimicrobial Activity", *J. Med. Chem.*, (1992), 35: 4745-4750.

Abstract of Yamakawa, T. et al. *J. Antimicrobial Chemotherapy*, (2002), 49(3): 455-465.

Hooper, David C. "Mechanisms of fluoroquinolone resistance", *Drug Resistance Update*, (1999), 2: 38-55.

Ince, Dilek and David C. Hooper. "Mechanisms and Frequency of Resistance to Gatifloxacin in Comparison to AM-1121 and Ciprofloxacin in *Staphylococcus aureus*", *Antimicrobial Agents and Chemotherapy*, (2001), 45(10): 2755-2764.

Fournier, B. and David C. Hooper. "Mutations in Topoisomerase IV and DNA Gyrase of *Staphylococcus aureus*: Novel Pleiotropic Effects on Quinolone and Coumarin Activity", *Antimicrobial Agents and Chemotherapy*, (1998), 42(1): 121-128.

Zhao, Xilin et al. "Killing of *Staphylococcus aureus* by C-8-Methoxy Fluoroquinolones", *Antimicrobial Agents and Chemotherapy*, (1998), 42(4): 956-958.

Breines, David M. et al. "Quinolone Resistance Locus *nfxD* of *Escherichia coli* Is a Mutant Allele of the *parE* Gene Encoding a Subunit of Topoisomerase IV", *Antimicrobial Agents and Chemotherapy*, (1997), 41(1): 175-179.

Fournier, B. and David C. Hooper. "Expression of the Multidrug Resistance Transporter NorA from *Staphylococcus aureus* Is Modified by a Two-Component Regulatory System", *J. Bacteriology*, (2000), 182(3): 664-671.

Mandell, Lionel A. et al. "Antimicrobial Safety and Tolerability: Differences and Dilemmas", *CID*, (2001), 32 (Suppl. 1): S72-S79.

Gootz, Thomas D. and Katherine E. Brighty. "Chemistry and Mechanism of Action of the Quinolone Antibacterials", Chapter 2, pp. 29-80. *The Quinolones*, Second Ed. Academic Press, 1998.

Takenouchi, T. et al. "Hydrophilicity of Quinolones Is Not an Exclusive Factor for Decreased Activity in Efflux-Mediated Resistant Mutants of *Staphylococcus aureus*", *Antimicrobial Agents and Chemotherapy*, (1996), 40(8): 1835-1842.

Zhao, Xilin et al. "DNA topoisomerase targets of the fluoroquinolones: A strategy for avoiding bacterial resistance", *Proc. Natl. Acad. Sci. USA*, (1997), 94: 13991-13996.

Takei, M. et al. "Target Preference of 15 Quinolones against *Staphylococcus aureus*, Based on Antibacterial Activities and Target Inhibition", *Antimicrobial Agents and Chemotherapy*, (2001), 45(12): 3544-3547.

Ince, Dilek and David C. Hooper. "Mechanisms and Frequency of Resistance to Premafloxacin in *Staphylococcus aureus*: Novel Mutations Suggestion Novel Drug-Target Interactions", *Antimicrobial Agents and Chemotherapy*, (2000), 44(12): 3344-3350.

Oizumi, Nobuyuki et al. "Relationship between mutations in the DNA gyrase and topoisomerase IV genes and nadifloxacin resistance in clinically isolated quinolone-resistant *Staphylococcus aureus*", *J. Infect. Chemother.*, (20010), 7: 191-194.

Jaén-Oltra, José et al. "Artificial Neural Network Applied to Prediction of Fluoroquinolone Antibacterial Activity by Topological Methods", *J. Med. Chem.*, (2000), 43: 1143-1148.

Chu, Daniel T. W. et al. "Synthesis and Structure-Activity Relationships of Novel Arylfluoroquinolone Antibacterial Agents", *J. Med. Chem.*, (1985), 28: 1558-1564.

Neu, Harold C. et al. "In Vitro Activity of Fleroxacin in Combination with Other Antimicrobial Agents", *The American Journal of Medicine*, (1993), 94 (Suppl. 3A): 3A-15S.

Chin, N. X. and H. C. Neu. "Combination of Ofloxacin and Other Antimicrobial Agents", *Journal of Chemotherapy*, (1990), 2(6):343-347.

Van der Auwera, P. et al. "Comparative In Vitro Activity of Ci 934, A New Fluoroquinolone, Alone and in Combination with Coumermycin Against Gram-Positive Bacteria", *Drugs Exptl. Clin,. Res.*, (1987), XIII(3): 125-132.

Asahina, Y. et al. "Recent advances in structure activity relationships in new quinolones", *Prog. Drug Res.*, (1992): 57-106.

Udo, E. E. et al. "Emergence of high-level mupirocin resistance in methicillin-resistant *Staphylococcus aureus* in Western Australia", *J. Hospital Infection*, (1994), 26: 157-165.

Bundgaard, Hans. "Design of prodrugs:Bioreversible derivatives for various functional groups and chemical entities", Chapter 1, pp. 1-5, *Design of Prodrugs*. Hans Bundgaard, editor. Elsevier Science publishers, 1985.

Mergler, M. et al. "Proceedings of the 12th American Peptide Symposium", reference cited on p. 2 of EPA 09853577.
Takei, CA 136:147733 (2001).
Nishijima, CA 136:2738 (2000).
Yamada, CA 134:141378 (2000).
Yamada, CA 134:141377 (2000).
Kurokawa, CA 135:300896 (2000).
Kurokawa, CA 130:322834 (1999).
Fujio, CQA 129:339430 (1998).
Gollnick, CA 129:310840 (1998).
Cooper, J. Med. Chem., vol. 35 (1992) pp. 1392-1398.
Frank, CA 129:245024 (1998).
Frank, CA 129:239390 (1998).
Xiong, CA 127:358825 (1997).
Klopman, CA 123:164953 (1993).
Sanchez, CA 124:86783 (1995).
Miyamoto, CA 124:170377 (1995).
Hashimoto, CA 124:343084 (1996).
Escribano, CA 127:302924 (1997).
Yang, CA 131:153420 (1999).

* cited by examiner

GENERATION TRIPLE-TARGETING, CHIRAL, BROAD-SPECTRUM ANTIMICROBIAL 7-SUBSTITUTED PIPERIDINO-QUINOLONE CARBOXYLIC ACID DERIVATIVES, THEIR PREPARATION, COMPOSITIONS AND USE AS MEDICAMENTS

This is a divisional of application Ser. No. 10/318,367 filed on Dec. 12, 2002 now U.S. Pat. No. 6,878,713, which is a CIP of application No. 10/128,996 filed Apr. 23, 2002 now U.S. Pat. No. 6,964,966, which claims the benefit of U.S. Provisional Applications Nos. 60/286,291 filed Apr. 25, 2001 and 60/341,165 filed Dec. 13, 2001.

FIELD OF THE INVENTION

The present invention relates to novel antimicrobial 7-substituted piperidino-quinolone carboxylic acid derivatives and pharmaceutically acceptable salts thereof. Methods of preparation of the compounds of the invention, compositions of compounds of the invention and their use are also described.

BACKGROUND OF THE INVENTION

The fluoroquinolone group of antibiotics available since the early 1960s are valuable as antibacterial agents. There have been synthesized, developed and marketed quinolone carboxylic acid derivatives having various chemical structures. Nalidixic acid, the progenitor of the series, was used primarily as a urinary tract antiseptic. Later development provided agents with broader activity, increased potency against selected pathogens and improved pharmacokinetic and pharmacodynamic properties.

From a medical utility viewpoint, the quinolones are classified as first-, second-, and third-generation compounds (Gootz T D et al, Chemistry & Mechanism of Action of the Quinolone Antibacterials. In Andriole VT ed. The Quinolones, San Francisco, Academic Press, 1998, 28-80). First-generation compounds like piromidic acid and pipemidic acid provided coverage for gram negative Enterobacteriaceae. The second-generation compounds are divided into those with enhanced but predominant gram-negative activity, against pathogens like *Escherischia coli* and *Pseudomonas aeruginosa*, and those with balanced broad-spectrum activity (norfloxacin, pefloxacin, enoxacin, fleroxacin, lomefloxacin, ciprofloxacin, ofloxacin, rufloxacin, nadifloxacin). Norfloxacin, ofloxacin and ciprofloxacin have, therefore, been used mainly for treatment of diseases including urinary tract infections, gastrointestinal infections, sexually transmitted diseases and the like. Third-generation drugs (levofloxacin, pazufloxacin, sparfloxacin, clinafloxacin, sitafloxacin, trovafloxacin, tosufloxacin, temafloxacin, grepafloxacin, balofloxacin, moxifloxacin, gatifloxacin) are those with enhanced activity against gram-positive cocci (notably clinafloxacin, sitafloxacin, trovafloxacin for *Streptococcus pneumoniae*) and, for essentially all the third-generation quinolones, activity also against gram-negative *Haemophilus influenzae* and *Legionella pneumophila*, and against anaerobes and atypical pathogens (Ball P, The Quinolone. History and Overview. In Andriole VT ed. The Quinolones, San Francisco, Academic Press, 1998, 1-28). Levofloxacin, moxifloxacin and gatifloxacin have, therefore, found use for community-acquired infections such as those of the upper and lower respiratory tract infections (RTI) like pneumonia, sinusitis and pharyngitis, and for skin and soft tissue infections (SSI) caused by gram-positive strains of staphylococci, pneumococci, streptococci and enterococci.

The improvements seen in most of the third-generation drugs in current use are generally attributed to their uniqueness in inhibiting the bacterial targets, DNA gyrase and topoisomerase IV. Three categories of quinolone inhibition have been suggested. Type I quinolones (norfloxacin, enoxacin, fleroxacin, ciprofloxacin, lomefloxacin, trovafloxacin, grepafloxacin, ofloxacin and levofloxacin) indicated a preference for topoisomerase IV inhibition. Type II quinolones (nadifloxacin and sparfloxacin) indicated a preference for DNA gyrase inhibition. Type III quinolones to which some of the third-generation quinolones belong (gatifloxacin, pazufloxacin, moxifloxacin and clinafloxacin) display, however, a dual-targeting property, and equally influence DNA gyrase inhibition and topoisomerase IV inhibition. (Takei M et al, Antimicrobial Agents and Chemotherapy, 2000; 45:3544-49). DNA gyrase is the primary target in bacteria, and thus is explained the weaker activity in gram-positive bacteria of the preferred topoisomerase IV-targeting second-generation quinolones like norfloxacin, ciprofloxacin, ofloxacin, and levofloxacin. The unusual activity of nadifloxacin described by others, and further significantly elaborated for S-(−)-nadifloxacin by us (cf: our pending U.S. application Ser. Nos. 09/566,875, 09/850,669, WO 00/68229 and WO 01/85728), specially against gram positive *S. aureus*, is now better understood in view of its being shown to be DNA-gyrase targeting, which is the first such report for a quinolone in *S. aureus* (Oizumi N et al, J. Infect. Chemother, 2001; 7: 191-194). Some, but not all, third generation quinolones being primarily topoisomerase IV-targeting in gram-positive staphylococci, and DNA gyrase-targeting in gram-positive *S. pneumoniae*, explains the advantages provided by the dual-targeting third-generation quinolones like moxifloxacin and gatifloxacin.

The evolution of quinolones from first-generation to second-generation to third-generation compounds has also been guided by structure-activity relationship studies. It has been determined by those in the art that certain structures with specific sites on the quinolone ring functionalised have distinct advantages over others. Structure-activity relationships of the quinolones have been the subject of detailed study for more than a decade (Asahina Y et al, Recent Advances in Structure Activity Relationships in New Quinolones, Prog. Drug Res., 1992, 38, 57-106) As a result of these studies, it has been determined by those in the art that certain structures, with specific sites on the quinolone ring functionalised, have distinct advantages over others. The structural feature that remains constant throughout the drug class is the bicyclic aromatic core consisting of 2 fused 6-membered rings. This core can contain a carbon at the 8-position, yielding a true quinolone, or a nitrogen which provides a ring system technically termed a naphthyridone, or an additional fused ring across the N-1 and C-8 positions yielding tricyclic heterocycles, such as pyridobenzoxazines and benzoquinolizidines.

In the context of the current invention, the nature of the amine group at the 7-position takes on special relevance. It is notable that in the cited second-generation quinolones the piperazine ring remains relatively constant and undisturbed as a 7-substituent, except for alkylation on the distal nitrogen, or less frequently on the ring carbons. In the third-generation quinolones, the continuing trend of use of a C-7 cyclic amino group is also almost universal. The presence of a second amine, in addition to the nitrogen bonded to C-7 of the quinolone nucleus has been found to be important. However, amongst these new quinolones, too, the frequent employment of mainly a C-7 piperazino or pyrrolidino variant is to be noted, but with only one example of a C-7 piperidino substituent.

Only two of the above-cited quinolones, the second-generation nadifloxacin and the third-generation balofloxacin, have a C-7 piperidino substituent. Nadifloxacin with a hydroxypiperidine substituent at the C-7 position is notable for its being the sole marketed modern quinolone without a distal amino group, but is merely a topical agent. Balofloxacin has an unusual 3-methylaminopiperidino substituent, which is, however, said to be the contributing element to its lower activity against Enterobacteriaceae and *Mycoplasma pneumoniae*. Among the recent fluoroquinolones which have been introduced commercially are moxifloxacin and gatifloxacin. Both these antibacterial agents have an 8-methoxy substituent in the fluoroquinolone core. As 7-substituents in the core, there is for moxifloxacin a bicyclic pyrollidine as the amino moiety, and for gatifloxacin a substituted pyrollidine as the amino moiety. A more recently described olamufloxacin, which has been shown to have activity in murine models of system infections and urinary tract infections, has an 8-methyl substituent in its fluoroquinolone core in which the C-7 substituent is also a substituted pyrollidine. No commercially introduced fluoroquinolone or one that has commercial potential is known in which a piperidino group, substituted or unsubstituted, is introduced at the 7-position of the quinolone structure also having a methoxy group or methyl group at the 8-position.

Since the 1960s, in an enormous worldwide effort, well more than 10,000 structurally-related fluoroquinolone agents have been described in many hundreds of patents and journal articles. Despite the understanding of the need of a cyclic amine at the C-7 position, the prior art appears to have discounted the value of having a piperidino moiety, unsubstituted or substituted, as a C-7 substituent. For instance, a 1992 review article (Asahina Y et al, vide infra) indicates the comparative low prior art interest in C-7 piperidino substituents, wherein there are only 21 piperidino moieties cited in comparison to 188 piperazino moieties, and 74 pyrollidino moieties out of a total of 578 C-7 amino moieties.

Just as there are structure-activity relationships, there are also structure-side effect relationships that have been determined. Side effects and adverse events related to N-1, C-5, C-8 variants of the quinolone core are generally those that contribute to increase in theophylline interactions, clastogenicity, phototoxicity, hepatotoxicity, cardiotoxicity, arthropathy and tendonitis. Notable is the pattern of (a) the N-1 cyclopropyl and C-8 fluorine, chlorine or methoxy substituted quinolone reported to show heightened cytotoxicity (Domagala J M, J. Antimicrob. Chemother., 1994; 33: 655-706), which can be modulated, however, by further structural manipulation (Gootz T D et al, vide infra), (b) the presence of halogen atoms (fluorine or chlorine) at the C-8 position (sparfloxacin, clinafloxacin) enhancing the tendency to induce photosensitivity, (c) the N-1 difluorophenyl substituent in trovafloxacin and temafloxacin associated with hepatotoxicity and hemolytic anemia and (d) the C-5 methyl (grepafloxacin) and C-8 methoxy substituent (moxifloxacin, gatifloxacin) contributing to prolongation of the QT interval and the development of a form of ventricular tachycardia known as torsade de pointes.

As important, if not more so, than the above-mentioned substituents of the fluoroquinolone core is the amine substituent at the C-7 site. C-7 pyrrolidines tend to show increased cytotoxicity over piperazino substituents, with the combination of 3-substituted pyrrolidines at C-7 and halogens at C-8 providing the most cytotoxic compounds.(Suto N J et al, J Med Chem 1992; 35:4745-50; Mundell L A et al, Clin Infect Dis, 2001; 32(Suppl): S74) In the second most frequently encountered form of quinolone toxicity, namely adverse events involving the CNS, it is the unsubstituted piperazines which correlate best with the degree of GABA-binding inhibition, closely followed by the pyrrolidinyl quinolones.

The incremental improvements that have resulted in moving from first-to second-and third-generation quinolones are a consequence of the understanding of the modulation brought about by a combination of a fluoroquinolone core moiety with a C-7 amino substituent. Although certain substituents can impart improvements, whether on one hand in antibacterial potency or on the other in a minimised potential for adverse effect, it is the overall characteristics of each molecule derived from the interaction of all the substituents with each other and with the specific nucleus employed that brings newer gains. Furthermore, characteristics in addition to those of activity and side effects are central to the development of improved human theraputants such as selective molecular mechanisms of action, broader antibacterial coverage to include anaerobes, atypical and resistant pathogens, improved pharmacokinetics and pharmacodynamics, and devoid of class-identified toxicity features.

It is, thus, clear that the art has focussed on identifying new quinolones to progress from earlier generation compounds to the next generation compounds. Despite the progress made, the full promise of the quinolones has not yet been exploited.

Examples of bacterial infections resistant to antibiotic therapy have been reported in the past; they are now a significant threat to public health in the developed world. The development of microbial resistance is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterials are common. Recent international conferences in 2002 on infectious diseases organised by the Centres for Disease Control and Prevention, USA, World Health Organisation and other groups have highlighted emerging infectious diseases, in which the word "emerging" refers to newly discovered infectious diseases or old ones that have rebounded, turned up in new places, or become drug resistant.

The mechanisms of bacterial resistance to fluoroquinolones is generally believed to function by two principal categories, both resulting from chromosomal mutations (D C Hooper, Drug Resis Updat 1999; 2:38-55). One category is the alterations in drug target enzymes. Fluoroquinolone resistance mutations generally occurring stepwise have been localized to specific regions of the parC and parE genes (grlA and grlB in *S. aureus*) encoding topoisomerase IV, and the gyrA and gyrB genes encoding DNA gyrase. This clustering of mutations has defined the quinolone resistance determining regions (QRDRs) of these genes that are in proximity to the apparent enzyme active site and are thought likely to constitute a domain at which quinolones interact directly with the enzyme-DNA complex. The manner by which the emergence of resistant mutants can be prevented is receiving attention, but is as yet insufficiently understood and continues to be speculative. Studies with the C-8 methoxy fluoroquinolones bearing a C-7 unsubstituted or 3-alkyl substituted piperazino substituent provide support to the concept that attack of both gyrase and topoisomerase IV equally would be ideal. In cases where single point mutation already exists, then a quinolone that would preferably potently inhibit the primary more essential target, whether gyrase or topoisomerase IV, would be better to prevent the resistance (Zhao et al, Proc. Natl. Acad. Sc. 1997; 94: 13991-13996). No similar study, to our knowledge, is available for compounds with a C-7 piperidino substituent, whether unsubstituted or substituted, in any quinolone core. The second category for bacterial resistance to develop is alterations that limit permeation of drug to the target. In *S. aureus* the elevated expression of the norA gene is responsible for efflux-mediated resistance to quinolones. Factors influencing the decrease in activity of quinolones in efflux-mediated resistant mutants of *S. aureus* have been suggested not to be hydrophobicity of the whole quinolone molecule, but rather the bulkiness at the C-7 substituent, and bulkiness and hydrophobicity at the C-8 substituent (Takenouchi T et al, 1996; 40:1835-42). Only two of forty quinolones included in this analysis bore a C-7 amino-substituted piperidino substituent. The effect of efflux was more pronounced with the compound bearing the 4-amino substituted piperidino substituent, its MIC value being 8 times more with an efflux pump-bearing strain than with a non-efflux pump-bearing strain, as compared with a 2 times more value for the 3-amino substituted piperidino substituent. Surprisingly, unlike this precedent, the present invention shows that appropriately substituted 4-amino piperidine substituents on different fluoroquinolone cores display potent efflux pump inhibitory/uptake facilitatory properties.

Stereochemistry-activity relationships are also of importance in considerations regarding the advancement of quinolones that can exist as isomers. For instance, S-(−)-levofloxacin, as an example of a compound in which the chiral centre is close to the quinolone nucleus, is from 8-128 fold as potent as the R-(+)-enantiomer. Earlier work and our pending U.S. patent application Ser. Nos. 09/566,875 and 09/850,669, WO 00/68229 and WO 01/85728 on nadifloxacin, which like levofloxacin has a relatively similar chiral centre, also disclose the superior profile of S-(−)-nadifloxacin over the R-(+)-enantiomer. Chiral centres at C-7 that are at some distance from the quinolone nucleus are said to contribute less significantly to biological activity. However, the relative orientation of the methyl groups on the C-7 piperazine of sparfloxacin is important for bacterial enzymes versus mammalian enzyme selectivity. Sparfloxacin, bearing methyl groups with a cis-stereochemistry essential for its antibacterial activity, displays dramatic differential effects on mammalian topoisomerase-II with no or less interaction with the mammalian enzyme, in contrast to the trans-isomer which does interact with the mammalian enzyme, while however retaining its antibacterial activity (Gootz T D et al., vide infra). Unlike this prior art, the present invention once again surprisingly shows that stereochemical differences of substituents on the C-7 piperidino moiety, while dramatically affecting antibacterial activity, do not significantly influence cytotoxicity of mammalian cell lines, irrespective of whether the differences are enantiomeric or diastereomeric.

Both of the third-generation fluoroquinolone market introductions of moxifloxacin and gatifloxacin with improved activity against gram-positive pathogens, have an 8-methoxy substituent in the core fluoroquinolone nucleus. Even their coverage, however, of staphylococci is considered partial, as they possess weak antibacterial activity against most of the methicillin-resistant strains. Moreover, moxifloxacin and gatifloxacin have failed to show therapeutically relevant potency for recent widely reported ciprofloxacin-resistant and levofloxacin-resistant strains of pneumococci. In addition, the potency of newer fluoroquinolones such as moxifloxacin against gram-negative pathogenic bacteria such as *E. coli* and *P. aeruginosa* has considerably diminished.

Therefore, there is a need for newer orally effective fluoroquinolone antibacterials with superior potency not only against methicillin-resistant, macrolide-resistant and fluoroquinolone-resistant strains, viz. multidrug-resistant strains of gram-positive staphylococci and pneumococci, but also against gram-negative strains with potency comparable to ciprofloxacin and levofloxacin, and against the now so called emerging infectious diseases. Accordingly, numerous studies are being continuously conducted to address the disadvantages of the fluoroquinolones having an 8-methoxy substituent or 8-alkyl substituent or other 8-substituents to make them considerably more potent against bacterial pathogens, to increase their spectrum coverage to include the insufficiently addressed pathogens like mycobacteria, anaerobes, and atypicals, to optimise their action towards bacterial molecular targets, to reduce their efflux or facilitate their cellular uptake, and to improve their oral bioavailability and toxicity profile.

Some 1,4-dihydroquinolone related moieties bearing an 8-methoxy substituent are known in the art to have antimicrobial activity and are described in the following references: U.S. Pat. No. 4,638,067 to Culbertson, et al. on Jan. 20, 1987; U.S. Pat. No. 4,665,079 to Culbertson, et al. on May 12, 1987; European Patent Application 0230295A2 of Kyorin Pharmaceutical Co. pub. Jul. 29, 1987; European Patent Application 0241206A2 of Ube Ind pub. Oct. 14, 1987; U.S. Pat. No. 4,822,801 to Domagala et al. on Apr. 18, 1989; U.S. Pat. No. 5,097,032 to Domagala et al. on Mar. 17, 1992; U.S. Pat. No. 5,051,509 to Nagano et al. on Sep. 24, 1991; European Patent Application 0541086A1 of Kaken Pharmaceutical Co. published May 12, 1993; European Patent Application 0572259A1 of Ube Ind. Published Dec. 1, 1993; WO 1993-JP 1925 of Japan Tobacco, Inc., dated Dec. 28, 1993; European Patent Specification 0342675B1 of Chugai Seiyaku Kabushiki Kaisha published Jan. 25, 1995; Japanese Patent 6-145167 published May 24, 1994; U.S. Pat. No. 5,607,942 of Clive Petersen et al. on Mar. 4, 1997; PCT Patent Application No. PCT/KR94/00005 to Korea Research Institute of Chemical Technology published Jul. 21, 1994; U.S. Pat. No. 5,677,316 to Hideki et al. on Oct. 14, 1997; World Patent WO98/58923A1 to Hagano et al. on Jun. 23, 1998; U.S. Pat. No. 4,777,175 to Warner-Lambert Co. on Oct. 11, 1988; European Patent Application 0919553A1 of Daiichi Pharma Co. published Jun. 2, 1999; U.S. Pat. No. 6,121,285 to Takemura et al., on Sep. 19, 2000; U.S. Pat. No. 6,329,391 B1 to Benoit Ledoussel et al. On Dec. 11, 2001.

Similarly some 1,4-dihydroquinolone related moieties bearing an 8-alkyl substituent, in particular an 8-methyl substituent, are known in the art to have antimicrobial activity and are described in the following references: U.S. Pat. No. 4,874,764 to Hiraki Ueda et al., on Oct. 17, 1989; U.S. Pat. No. 4,935,420 to Hiraki Ueda et al., on Jun. 19, 1990, U.S. Pat. No. 5,859,026 to Ito et al., on Jan. 12, 1999 and European Patent application 0919553A1 of Daichi Pharmaceutical Company published Jun. 2, 1999; U.S. Pat. No. 6,121,285 to Takemura et al., on Sep. 19, 2000.

The methods of producing quinolone carboxylic acids bearing an 8-methoxy substituent are also to be found in the following references:

U.S. Pat. No. 5,639,886 to Zerbes et al. on Jun. 17, 1997; U.S. Pat. No. 5,869,661 to Ochi et al. on Feb. 9, 1999; and PCT Patent Application No. WO 99/26940 to Bayer Aktiergesellschaft published Jun. 3, 1999.

The methods of producing quinolone carboxylic acids bearing an 8-methyl substituent are also to be found in the following references: U.S. Pat. No. 5,859,026 to Ito et al., on Jan. 12, 1999; U.S. Pat. No. 6,121,285 to Takemura et al., on Sep. 19, 2000.

European Patent application 0919553A1 of Daichi Pharmaceutical Company published Jun. 2, 1999.

A number of compounds having a cyclic amino moiety as substituents at the 7-position of these quinolone carboxylic acids are already known. In addition, many attempts have been made to modify the 7-cyclic amino moiety with various substituents to produce superior compounds, and, for example, a cyclic amino substituent such as 4-amino-1-piperidinyl group or 4-hydroxy-1-piperidinyl group wherein the adjacent carbon atom to the amino or hydroxy substituent is further monosubstituted by an alkyl substituent is known, as hereinbelow described in the identified patent applications and patents.

For example PCT Patent Application WO 99/14214 and U.S. Pat. No. 6,329,391B1 discloses a compound having a cyclic amino substituent of the formula

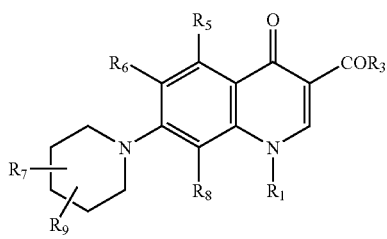

wherein each symbol is as defined in the specification of the above-mentioned publication. For the piperidino substituent at the 7-position of the quinolonecarboxylic acid, the compounds having substituents of 3-amino-4-methyl, 3-amino-4-4-dimethyl, 3-amino-4-spirocyclopropyl, 3-amino-6-cyclopropyl, are included in the preferred examples therein. However, specific examples of compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position, are not disclosed. What is more, compounds with a piperidine substituent at the 7-position as defined in the cited patent application above with a substituent in the 8-position as a methoxy group ($R_8$=$OCH_3$) or as an alkyl group ($R_8$=$CH_3$, $C_2H_5$) and the substituent in the 6-position as a fluoro group ($R_6$=F) are also not disclosed.

European Patent Application 241206A2 discloses a compound having a 7-cyclic amino substituent of the formula

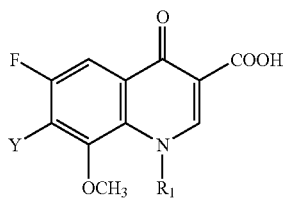

with one meaning of Y being

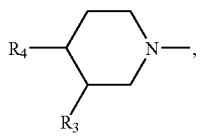

wherein each symbol is as defined in the specification of the above-mentioned publication at the 7-position of quinolonecarboxylic acid and the compounds having substituents of 4-hydroxy-3-methyl, 4-amino-3-methyl, or 4-methylamino-3-methyl are included as specific examples therein. However, specific examples of the compounds having a substituent at the 7-position as piperidine of the present invention with a 4-amino or 4-hydroxy substituent with 2-alkyl or 6-alkyl substituents, or with 3,3-dialkyl substituents, geminally located at a position adjacent to the substituent at the 4-position are not disclosed.

European Patent Application 0394553B1 discloses a compound for the treatment of HIV infections having a 7-cyclic amino substituent of the formula

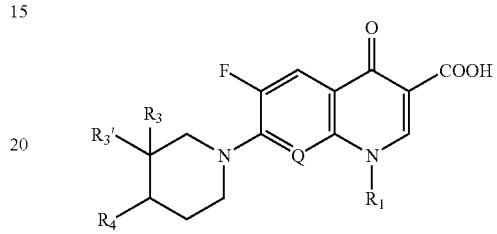

wherein each symbol is as defined in the specification of the above-mentioned publication at the 7-position of the quinolone carboxylic acid with a 4-amino substituent and a single 3-alkyl substituent or a 3-3-dialkyl substituent claimed. However, specific examples of the compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position are not disclosed. What is more, compounds with a piperidine substituent at the 7-position as defined in the cited patent application above with a substituent in the 8-position as a methoxy group (Q=C—$OCH_3$) or as an alkyl group (Q=C—$CH_3$, C—$C_2H_5$) are also not disclosed.

European Patent Application 0304087A2 discloses a compound having a 7-cyclic amino substituent of the formula

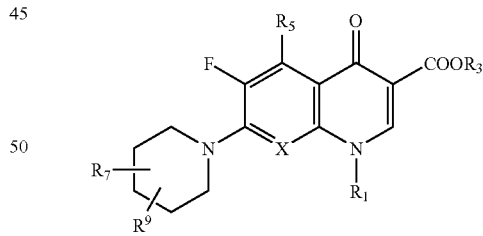

wherein each symbol is as defined in the specification of the above-mentioned publication at the 7-position of the quinolone carboxylic acid with a 4-amino substituent and a single 3-alkyl substituent is claimed. However, specific examples of compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position are not disclosed. What is more, compounds with a piperidine substituent at the 7-position as defined in the cited patent application above with a substituent in the 8-position as a methoxy group (X=C—OCH$_3$) or as an alkyl group (X=C—CH$_3$, C—C$_2$H$_5$) are also not disclosed.

European Patent Application 0572259A1 discloses a compound having a 7-cyclic amino substituent of the formula

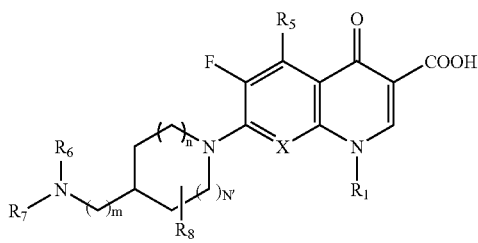

wherein each symbol is as defined in the specification of the above-mentioned publication at the 7-position of the quinolone carboxylic acid with a 4-amino piperidinyl moiety wherein the amino group is substituted with an aryl or aromatic hetero monocyclic group or a fused aromatic group and a single 3-alkyl substituent is disclosed. However, specific examples of compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position are not disclosed. What is more, compounds with a piperidine substituent at the 7-position as defined in the cited patent application above with a substituent in the 8-position as a methoxy group (X=C—OCH$_3$) or as an alkyl group (X=C—CH$_3$, C—C$_2$H$_5$) are also not disclosed.

European Patent Application 0287951A2 discloses a compound having a 7-cyclic amino substituent as in the following formula

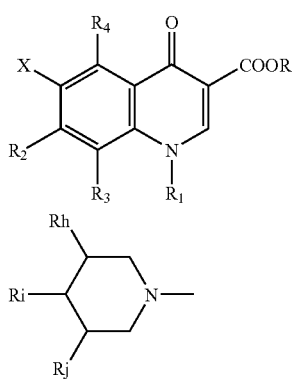

in which one of the meanings of R$_2$ is substituent which is a 5-to 9-membered saturated or unsaturated heterocyclic ring which may be substituted, wherein each symbol is as defined in the specification of the above-mentioned publication at the 7-position of the quinolone carboxylic acid with a 4-hydroxy piperidinyl moiety. However, specific examples of compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position are not disclosed. What is more, compounds with a piperidine substituent at the 7-position as defined in the cited patent application above with a substituent in the 8-position as a methoxy group (R$_3$=OCH$_3$) or as an alkyl group (R$_3$=CH$_3$, C$_2$H$_5$) are also not disclosed.

U.S. Pat. No. 4,382,892 discloses a compound having a cyclic substituted amino group

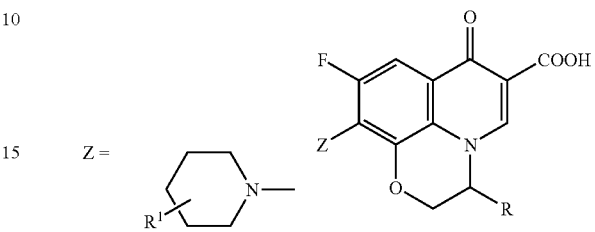

which is a 4-to 7-membered ring which may be substituted, wherein each symbol is as defined in the specification of the above-mentioned publication at the Z substituted position of the quinolone carboxylic acid with a 4-amino 1-piperidinyl moiety, 4-dimethylamino 1-piperidinyl moiety and 4-hydroxy 1-piperidinyl moiety.

However, specific examples of compounds having a substituent at the 7-position as piperidine of the present invention with a 4-amino or 4-hydroxy substituent with 2-alkyl, 3-alkyl, 5-alkyl or 6-alkyl substituents, or with geminal 3,3-dialkyl, or 3,5-dialkyl, or 3,3,5-trialkyl substituents, located at a position adjacent to the substituent at the 4-position are not disclosed.

The feature of the known 7-substituted piperidino derived compounds is that they are said to exhibit antimicrobial properties, but either no biological data is provided or in cases where some data is provided, such piperidino derivatives have been found to be inferior in activity to those derivatives bearing 7-piperazino or 7-pyrrolidino substituents. It is only through our on-going studies in recent years as described in our pending U.S. patent application Ser. Nos. 09/566,875 and 09/850,669, WO 00/68229 and WO 01/85728 that there has begun to be elaborated the full potential of a fluoroquinolone core bearing an unsubstituted or substituted 4-hydroxy piperidino substituent at the 7$^{th}$ position of the core fluoroquinolone for use in clinical development as medicaments for life-threatening old and new emerging infectious diseases.

Thus, the present inventors have extensively studied the subject by introducing various substituted piperidine groups in the 7-position of different fluoroquinolone cores and determining the microbiological/pharmacological properties of the compounds to develop the novel substituted piperidino compounds of the invention, which (a) show a potent hitherto-undescribed antibacterial potency against broad spectrum sensitive and existing/emerging resistant pathogenic strains, including β-lactam-resistant, macrolide-resistant and even fluoroquinolone-resistant strains, mycobacteria, anaerobes and atypical pathogens (b) prevent selection of resistant bacteria by apparently inhibiting both DNA gyrase and topoisomerase IV equally, or by potently inhibiting the enzyme it targets, (c) are not subjected to efflux or have facilitated uptake, (d) do not apparently act to merely form bacteriostatic quinolone-gyrase/topoisomerase-DNA complexes to inhibit cell growth, but also apparently extend the action to release the broken DNA ends to ensure cell death, (d) exhibit high absorption and improved pharmacokinetic properties in a living body, and (e) display a favourable safety profile. As a result, we have identified that the compounds of the general formula I as defined below wherein substituted piperidino groups are introduced into the 7-position of the fluoroquinolone nucleus can satisfy such a purpose.

It is therefore, an aspect of the present invention to provide new non-chiral and chiral 7-substituted piperidino-quinolone carboxylic acid derivatives, of the formula I, as defined below, which show potent antibacterial activity against a broad range of pathogenic microorganisms, including both gram-positive and gram-negative strains with advantages of activity against resistant microorganisms, reduced toxicity, and improved pharmacology and pharmacokinetics.

It is another aspect of the present invention to provide a process for preparing 7-substituted piperidino-quinolone carboxylic acid derivatives of the formula I.

It is a further aspect of the present invention to prepare the intermediates that are necessary to obtain the 7-substituted piperidino-quinolone carboxylic acid derivatives of the formula I.

It is a further aspect of the present invention to provide compositions containing 7-substituted piperidino-quinolone carboxylic acid derivatives of the formula I as an active component.

It is also an aspect of the invention to use the 7-substituted piperidino-quinolone carboxylic acid derivatives of the formula I of the invention and compositions containing them as medicaments for the treatment of infectious diseases.

SUMMARY OF THE INVENTION

This invention describes fluoroquinolones of the formula I

FORMULA I

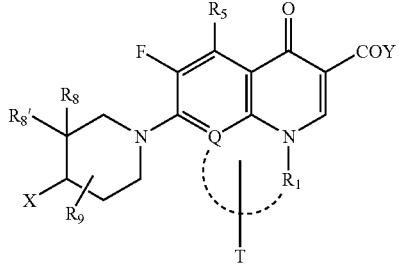

wherein $R_1$ $C_{1-5}$ alkyl, substituted $C_{1-5}$ alkyl, $C_{3-6}$ cycloalkyl, substituted $C_{3-6}$ cycloalkyl, aryl, or substituted aryl;

or when Q is CH and the nitrogen atom to which $R_1$ is linked forms an optionally substituted 5-, 6-or 7-membered ring with the carbon atom of Q, the ring optionally containing one or more hetero atoms selected from nitrogen, oxygen or sulfur atoms, said heteroatom(s) represented by T, preferably $R_1$ is $CH_2CH_2$—, $CH_2T$-, $CH_2CH_2CH_2$—, $CH_2CH_2T$-, $CH_2TCH_2$—, $TCH_2T$-, $TCH_2CH_2CH_2$— $CH_2CH_2CH_2T$-, $CH_2TCH_2CH_2$—, or $TCH_2CH_2T$- where T represents NH, O, or S. If the ring is substituted, the substituent is as defined above for $R_1$.

Y is $OR_3$ where $R_3$ is hydrogen;

$R_3$ is $C_1$-$C_{20}$ alkyl, such as straight chain or branched chain aliphatic residues;

$R_3$ is aralkyl;

$R_3$ is $CH_2CH(NH_2)COOH$;

$R_3$ is $(CH_2)_n$—$CHR_{10}$—$OCOR_{11}$ or $(CH_2)_n$—$CHR_{10}$—$OCO_2R_{11}$ wherein $R_{10}$ is H, or $CH_3$; n is 0-3 and $R_{11}$ is $C_1$-$C_{20}$ alkyl, substituted $C_1$-$C_6$ alkyl or aralkyl or $R_{11}$ is

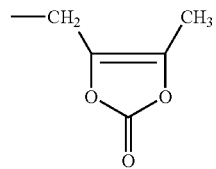

or $R_3$ is α-aminoalkanoyl or an alkanoylalkyl group;

or $R_3$ is

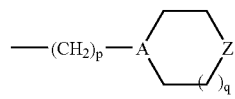

wherein

A is CH or N, and when A is CH, Z is NH or $NCH_3$, and when A is N, Z is CH, O, NH, S, or $NCH_3$; p is 0-2; q is 0-2;

or

Y is $NHR_2$, wherein $R_2$ is H, $C_{1-20}$ alkyl, $C_{3-6}$ cycloalkyl, substituted $C_{3-6}$ cycloalkyl, aryl, substituted aryl, or heteroaryl, all of which heteroaryl residues may be further substituted or unsubstituted;

or $R_2$ is an amino acid residue derived from one of the 20 naturally occurring amino acids, or the optically active isomers thereof, or the racemic mixtures thereof;

$R_5$ is H, $C_{1-5}$ alkyl, $C_{1-5}$ alkoxy, amino, $C_{1-5}$ alkylamino, or $C_{1-5}$ acylamino;

Q is —N—, —C($R_8$)— ($R_8$ being H, F, Cl, bromo, $C_{1-4}$ alkyl or unsubstituted or substituted $C_{1-4}$ alkoxy, wherein when the alkoxy group is substituted it is substituted by one or more halogen atoms such as F, Cl, or Br), or when Q is CH and the nitrogen atom to which $R_1$ is linked forms an optionally substituted 5-, 6-or 7-membered ring with the carbon atom of Q, the ring optionally containing one or more hetero atoms selected from nitrogen, oxygen or sulfur atoms, said heteroatom(s) represented by T, preferably $R_1$ is $CH_2CH_2$—, $CH_2T$-, $CH_2CH_2CH_2$—, $CH_2CH_2T$-, $CH_2TCH_2$—, $TCH_2T$-, $TCH_2CH_2CH_2CH_2$— $CH_2CH_2CH_2T$-, $CH_2TCH_2CH_2$—, or $TCH_2CH_2T$- where T represents NH, O, or S. If the ring is substituted, the substituent is as defined above for $R_1$, X is $OR_4$, wherein $R_4$ is hydrogen, $C_1$-$C_{20}$ alkyl, glycosyl, aralkyl, $C_1$-$C_6$ alkanoyl, aminoalkanoyl or an amino acid residue derived from one of the 20 naturally occurring amino acids, or the optically active isomers thereof, or the racemic mixtures thereof, or $R_4$ is 1-aminocyclohexylcarbonyl or $COOR_{11}$ wherein $R_{11}$ as hereinbefore defined or $R_4$ is —$(CH_2)_n$—$CHR_{10}$—$OCOOR_{11}$ where $R_{10}$ and $R_{11}$ are as hereinbefore defined, or $R_4$ is $C_6H_{11}O_6$, $PO_2(CH_3)H$, $PO_3H_2$, $PO_2(OCH_3)H$ or $SO_3H$ thus giving respectively the gluconic acid, phosphonic acid, phosphoric acid and sulfonic acid ester derivatives of the compounds;

or X is $NR_6R_7$, wherein $R_6$ is H, $C_{1-20}$ alkyl, $C_{3-6}$ cycloalkyl, aralkyl, $C_{1-20}$ alkanoyl, $C_{1-20}$ alkoxycarbonyl, aralkyloxycarbonyl, amino ($C_{1-20}$)alkanoyl, or an amino acid residue derived from one of the 20 naturally occurring amino acids or the optically active isomers thereof, or the racemic mixtures thereof.

The amino acid residue is derived from a single amino acid or from combinations of amino acids that form dipeptide, tripeptide or polypeptide amino acid unit residues, wherein a terminal carboxy group is optionally protected by $C_{1-4}$ alkyl or aralkyl groups and a terminal amino group is optionally protected by a '-Boc (tertiarybutyloxycarbonyl), F-Moc (fluorenylmethoxycarbonyl) or Cbz (benzyloxycarbonyl) group.

$R_6$ may also be $COOR_{11}$ wherein $R_{11}$ as hereinbefore defined or $R_6$ is $C_6H_{11}O_6$ thus giving the gluconic acid ester derivative of the compounds.

$R_7$ is H, $C_{1-6}$ alkyl, $C_{3-6}$ cycloalkyl, aralkyl; $C_{1-6}$ alkanoyl, aralkyloxycarbonyl or amino($C_{1-20}$) alkanoyl; or an amino acid residue derived from one of the 20 naturally occurring amino acids or the optically active isomers thereof, or the racemic mixtures thereof. The amino acid residue is derived from a single amino acid or from combinations of amino acids that form dipeptide, tripeptide or polypeptide amino acid unit residues, wherein a terminal carboxy group is optionally protected by $C_{1-4}$ alkyl or aralkyl groups and a terminal amino group is optionally protected by a '-Boc (tertiarybutyloxycarbonyl), F-Moc (fluorenylmethoxycarbonyl) or Cbz (benzyloxycarbonyl) group or $R_7$ may be $C_6H_{11}O_6$.

$R_8/R_8'$ are substituents at the 3/3-position of the piperidino ring and are the same or different and represent H, $C_{1-6}$ alkyl, substituted $C_{1-6}$ alkyl, alkylamino, or aralkyl.

$R_9$ is a substituent at the 4-position or 5-position of the piperidino ring and represents H, $C_{1-6}$ alkyl, $C_{1-5}$ alkylamino, $C_{1-3}$ dialkylamino, aryl, aralkyl or a trihaloalkyl.

This invention also includes optical isomers, diastereomers, enantiomers, polymorphs, pseudopolymorphs, pharmaceutically acceptable salts, hydrates, or biohydrolyzable esters, amides, or solvates of the fluoroquinolones of formula I and prodrugs of these compounds. In addition, compositions incorporating the compounds of the invention, or using compounds of the invention as starting material are also contemplated in this invention.

The new compounds of the invention have increased potency and bactericidal activity that can be attributed to the combinations of the respective $R_1$, Y, $R_5$, and Q substituents in the fluoroquinolone cores and the respective X, $R_8$, $R_8'$, and $R_9$ substituents on the 7-substituted piperidino moieties introduced in the cores.

The compounds of the invention thus belong to a new generation of dual-targeting, non-effluxed, diastereomeric, enantiomorphic antimicrobial 7-substituted piperidino-quinolone carboxylic acid derivatives. The compounds of the invention may be rightly called new generation triple-targeting, chiral, broad-spectrum antimicrobial agents.

DETAILED DESCRIPTION OF THE INVENTION

The present invention encompasses certain compounds, dosage forms, and methods of administering the compounds, to a human or other animal subject. Specific compounds and compositions to be used in the invention must, accordingly, be pharmaceutically acceptable. As used herein, such a "pharmaceutically-acceptable" compound is one that is suitable for use with humans and/or animals without undue adverse side effects (such as toxicity, irritation, and allergic response) commensurate with a reasonable benefit/risk ratio.

This invention describes fluoroquinolones of the formula I

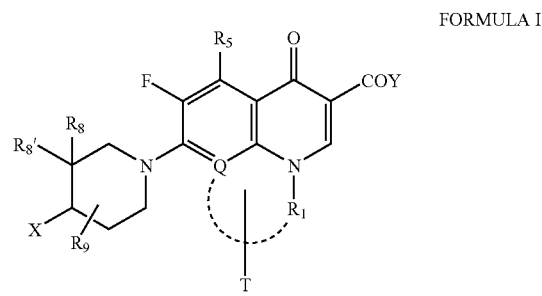

FORMULA I wherein $R_1$ is $C_{1-5}$ alkyl being unsubstituted or substituted with from 1 to 3 fluoro atoms, $C_{3-6}$ cycloalkyl being unsubstituted or substituted with from 1 to 2 fluoro atoms, or aryl being unsubstituted or substituted with from 1 to 3 fluoro atoms;

or when Q is CH and the nitrogen atom to which $R_1$ is linked forms an optionally substituted 5-, 6-or 7-membered ring with the carbon atom of Q, the ring optionally containing one or more hetero atoms selected from nitrogen, oxygen or sulfur atoms, said heteroatom(s) represented by T, preferably $R_1$ is $CH_2CH_2$—, $CH_2T$-, $CH_2CH_2CH_2$—, $CH_2CH_2T$-, $CH_2TCH_2$—, $TCH_2T$-, $TCH_2CH_2CH_2CH_2$— $CH_2CH_2CH_2T$-, $CH_2TCH_2CH_2$—, or $TCH_2CH_2T$- where T represents NH, O, or S. This 5-to 7-membered ring may be substituted with 1 or 2 of the same substituents as those defined above for $R_1$, preferably by one $C_1$-$C_5$ alkyl group.

Y is $OR_3$ where $R_3$ is hydrogen;

$R_3$ is $C_1$-$C_{20}$ alkyl, such as straight chain or branched chain aliphatic residues such as methyl, ethyl, propyl, isopropyl, butyl, isobutyl, tertiary butyl, pentyl, hexyl or their branched chain isomers;

$R_3$ is aralkyl such as benzyl, phenethyl, or phenylpropyl;

$R_3$ is $CH_2CH(NH_2)COOH$;

$R_3$ is $(CH_2)_n$—$CHR_{10}$—$OCOR_{11}$ or $(CH_2)_n$—$CHR_{10}$—$OCO_2R_{11}$ wherein $R_{10}$ is H, or $CH_3$; n is 0-3 and $R_{11}$ is $C_1$-$C_{20}$ alkyl as hereinbefore defined, or substituted $C_1$-$C_6$ alkyl with substituents such as hydroxy, halogen, amino, or mercapto; or aralkyl such as benzyl, phenethyl, phenylpropyl or $R_{11}$ is

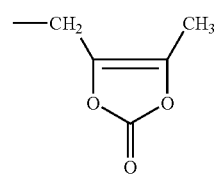

or $R_3$ is α-aminoalkanoyl such as α-aminopropionyl or $R_3$ is alkanoylalkyl group such as acetoxymethyl, acetoxyethyl, pivaloyloxy-methyl, or pivaloyloxyethyl group;

or $R_3$ is

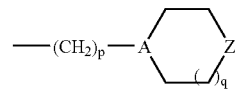

wherein

A is CH or N, and when A is CH, Z is NH or $NCH_3$, and when A is N, Z is CH, O, NH, S, or $NCH_3$ ; p is 0-2 ; q is 0-2, preferably it is a group such as N-methylpiperidin-4-yl, pyrrolidin-2-yl-ethyl, piperidin-2-yl-ethyl, or morpholin-2-yl-ethyl; or Y is $NHR_2$, wherein $R_2$ is H, $C_{1-20}$ alkyl such as straight chain or branched chain aliphatic residues as defined above, $C_{3-6}$ cycloalkyl, substituted $C_{3-6}$ cycloalkyl wherein the substituent is $C_{1-2}$ alkyl such as methyl or ethyl or trifluoroalkyl such as trifluoromethyl or halogen such as fluorine, chlorine, bromine or $R_2$ is aryl such as unsubstituted or substituted phenyl wherein the substituent is $C_{1-3}$ alkyl, $C_{1-3}$ alkoxy, amino, or halogen; heteroaryl such as pyridyl, pyrimidinyl, quinolinyl, isoquinolinyl, furyl, oxazolinyl, thiazolyl, or thiadiazolyl, all of which heteroaryl residues may be further substituted or unsubstituted, wherein the substituent is methyl or ethyl;

or $R_2$ is an amino acid residue derived from one of the 20 naturally occurring amino acids viz. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, or the optically active isomers thereof, or the racemic mixtures thereof;

$R_5$ is H, $C_{1-5}$ alkyl, $C_{1-5}$ alkoxy, amino, $C_{1-5}$ alkylamino such as —$NHCH_3$, $N(CH_3)_2$, and the like; or acylamino such as —$NHCOCH_3$, —$NHCOC(CH_3)_3$, and the like;

Q is —N—, —$C(R_8)$— ($R_8$ being H, F, Cl, bromo, methoxy, $C_{1-4}$ alkyl, or unsubstituted or substituted $C_{1-4}$ alkoxy, wherein when the alkoxy is substituted it is substituted by one or more halogen atoms such as F, Cl, or Br), or when Q is CH and the nitrogen atom to which $R_1$ is linked forms an optionally substituted 5-, 6-or 7-membered ring with the carbon atom of Q, the ring optionally containing one or more hetero atoms selected from nitrogen, oxygen or sulfur atoms, said heteroatom(s) represented by T, preferably $R_1$ is $CH_2CH_2$—, $CH_2T$-, $CH_2CH_2CH_2$—, $CH_2CH_2T$-, $CH_2TCH_2$—, $TCH_2T$-, $TCH_2CH_2CH_2$—$CH_2CH_2CH_2T$-, $CH_2TCH_2CH_2$—, or $TCH_2CH_2T$- where T represents NH, O, or S. If the ring is substituted, the substituent is as defined above for $R_1$. This 5-to 7-membered ring may be substituted with 1 or 2 of the same substituents as those defined above for $R_1$, preferably by one $C_1$-$C_5$ alkyl group.

X is $OR_4$ wherein $R_4$ is hydrogen, $C_1$-$C_{20}$ alkyl as hereinbefore defined, glycosyl, aralkyl such as benzyl; or $C_1$-$C_6$ alkanoyl such as acetyl, propionyl, pivaloyl, stearoyl, or nonadecanoyl or aminoalkanoyl such as aminoacetyl, aminopropionyl and the like or an amino acid residue derived from one of the 20 naturally occurring amino acids viz. alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine, or the optically active isomers thereof, or the racemic mixtures thereof; or $R_4$ is 1-aminocyclohexylcarbonyl or $COOR_{11}$ wherein $R_{11}$ is as hereinbefore defined or $R_4$ is —$(CH_2)_n$—$CHR_{10}$—$OCOOR_{11}$ where $R_{10}$ and $R_{11}$ are as hereinbefore defined, or $R_4$ is $C_6H_{11}O_6$, $PO_2(CH_3)H$, $PO_3H_2$, $PO_2(OCH_3)H$ or $SO_3H$ thus giving respectively the gluconic acid, phosphonic acid, phosphoric acid and sulfonic acid ester derivatives of the compounds;

or X is $NR_6R_7$, wherein $R_6$ is H, $C_{1-20}$ alkyl as hereinbefore defined, $C_{3-6}$ cycloalkyl, aralkyl such as benzyl, phenethyl, or phenylpropyl; $C_{1-20}$ alkanoyl such as $COCH_3$, $COCH_2CH_3$, or $COC(CH_3)_3$, or $C_{1-20}$ alkoxycarbonyl such as $COOCH_3$, $COOCH_2CH_3$, or $COOC(CH_3)_3$; aralkyloxycarbonyl such as benzyloxycarbonyl, or amino($C_{1-20}$)alkanoyl such as aminoacetyl, aminopropionyl and the like, or an amino acid residue derived from one of the 20 naturally occurring amino acids or the optically active isomers thereof, or the racemic mixtures thereof. The amino acid residue is derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. The amino acid residue is derived from a single amino acid or from combinations of amino acids that form dipeptide, tripeptide or polypeptide amino acid unit residues wherein a terminal carboxy group is optionally protected by $C_{1-4}$ alkyl or aralkyl groups and a terminal amino group is optionally protected by a $^t$-Boc (teritarybutyloxycarbonyl), F-Moc (fluorenylmethoxycarbonyl) or Cbz (benzyloxycarbonyl) group or $R_6$ may also be $COOR_{11}$ wherein $R_{11}$ is as hereinbefore defined or $R_6$ is $C_6H_{11}O_6$ thus giving the gluconic acid ester derivative of the compounds.

$R_7$ is H, $C_{1-6}$ alkyl as hereinbefore defined, $C_{3-6}$ cycloalkyl, aralkyl such as benzyl, phenethyl, or phenylpropyl; $C_{1-6}$ alkanoyl such as $COCH_3$, $COCH_2CH_3$, $COC(CH_3)_3$, aralkyloxycarbonyl such as benzyloxycarbonyl or amino ($C_{1-20}$) alkanoyl such as aminoacetyl, aminopropionyl, etc.; or an amino acid residue derived from one of the 20 naturally occurring amino acids or the optically active isomers thereof, or the racemic mixtures thereof. The amino acid residue is derived from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. The amino acid residue is derived from a single amino acid or from combinations of amino acids that form dipeptide, tripeptide or polypeptide amino acid unit residues, wherein a terminal carboxy group is optionally protected by $C_{1-4}$ alkyl or aralkyl groups and a terminal amino group is optionally protected by a $^t$-Boc (teritarybutyloxycarbonyl), F-Moc (fluorenylmethoxycarbonyl) or Cbz (benzyloxycarbonyl) group or $R_7$ may be $C_6H_{11}O_6$ thus giving the gluconic acid ester derivative of the compounds.

$R_8/R_8'$ are substituents at the 3/3-position of the piperidino ring and are the same or different and represent H, $C_{1-6}$ alkyl, substituted $C_{1-6}$ alkyl wherein the substituent is amino, hydroxy, halogen such as one or more fluorine, chlorine, or bromine atoms; alkylamino, or aralkyl such as benzyl.

$R_9$ is a substituent at the 4-position or 5-position of the piperidino ring and represents H, $C_{1-6}$ alkyl, $C_{1-5}$ alkylamino, $C_{1-3}$ dialkylamino or aryl, aralkyl such as benzyl or phenethyl or a trihaloalkyl such as trifluoromethyl.

As used herein aryl is substituted or unsubstituted phenyl. The phenyl, alkyl, and cycloalkyl groups may be substituted at one or more positions by the usual aromatic substituents such as halogen namely F, Cl, or Br; alkyl such as methyl, ethyl, trifluoromethyl, etc. Substituted phenyl groups include such as halophenyl, trifluoromethylphenyl, monofluorophenyl, 2-fluorophenyl, 4-fluorophenyl, or 2,4 difluorophenyl.

This invention also includes optical isomers, diastereomers, enantiomers, polymorphs, pseudopolymorphs, pharmaceutically acceptable salts, hydrates, or biohydrolyzable esters, amides, imides, or solvates of the fluoroquinolones of formula I and prodrugs of these compounds. A pseudopolymorph is a polymorph that differs from a true polymorph by the incorporation of solvent.

It has been found that the compounds of this invention, and composition containing these compounds, are effective antimicrobial agents which are a new generation of antibacterial agents, in particular a new generation of respiratory antibacterials, effective against multidrug-resistant pathogens with broad spectrum coverage of gram-positive and gram-negative microbes, such as sensitive and fluoroquinolone-resistant pneumococci, staphylococci, streptococci, anaerobes, enterococci and atypical pathogens. In addition, the compounds of the invention have potent cidal action for fluoroquinolone-resistant strains. The compounds of the invention have the preferred potential to address the unmet need for orally effective drugs for the treatment of multi-drug-resistant pneumococcal infections like life-threatening pneumoniae and meningitis, to which pediatric and geriatric patients are vulnerable. They are unusually cidal for viridans streptococci, which are the causative groups of strains responsible for bac-teremias, soft tissue infections, abscesses, sepsis and endocarditis. They are potential antitubercular agents against sensitive and resistant mycobacteria. The combination of physicochemical parameters contributed to the fluoroquinolone molecules by the location, hydrogen-acceptor/-donor properties, spatial bulk, hydrophobicity, stereo-chemical orientation of the different contributing substituents at the respective positions surprisingly provide compounds of the invention that are not effluxed by efflux pump bearing strains or have better uptake through bacterial cellular membranes. The above described physicochemical parameters also contribute to their unusually favourable drugability properties. They are orally effective contribute to their unusually favourable drugability properties. They are orally effective with once-a-day potential. They have favourable penetration into tissues like the lung, liver, kidney and heart over serum thus enabling the targeting of organ-specific infections. They are relatively non-phototoxic, with favourable cytotoxicity and cardiotoxicity profiles which are usually the problem toxicities displayed by the fluoroquinolone class of compounds.

Among compounds that fall within the compounds of the aforementioned general formula, optically active compounds and diastereomeric isomers, each having the substituent in a specific stereo and three-dimensional spatial orientation have both excellent antibacterial activity and high safety features.

The compounds of the invention are sufficiently basic to form acid addition salts. The compounds are useful both in the free base form and the form of acid addition salts, and both forms are within the purview of the invention. The acid addition salts are in some cases a more convenient form for use. Examples of appropriate acid addition salts include, but are not limited to acetate, benzenesulfonate, fumarate, hydrochloride, hydrobromide, hydroiodide, hydrogensulfate, isethionate, lactate, malate, maleate, malonate, methanesulfonate, pamoate (embonate), phosphate/diphosphate, stearate, succinate, sulfate, tartrate, trifluoroacetate, trifluoromethanesulfonate, p-toluenesulfonate, and the like. Preferred acid addition salts include halides, sulfonates, carboxylates, phosphates, and the like. However, other appropriate pharmaceutically acceptable salts within the scope of the invention are those derived from other mineral acids, organic acids and amino acids. The amino acid may be selected from one of the 20 naturally occurring amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof. The compounds of the invention are also sufficiently acidic to form alkaline/base addition salts. Preferred alkali/base addition salts include the alkali metal salts (such as sodium and potassium), alkaline earth metal salts (such as magnesium and calcium), inorganic salts, such as ammonium, substituted ammonium, choline and organic base salts from basic amines such as diethanolamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

In practice, the use of the salt form inherently amounts to the use of the base form of the active. Acids used to prepare acid addition salts include preferably those, which produce, when combined with the free base, pharmaceutically acceptable salts. These salts have anions that are relatively innocuous to the animal organism, such as a mammal, in pharmaceutical doses of the salts so that the beneficial property inherent in the free base are not vitiated by any side effects ascribable to the acid's anions.

The pharmaceutically acceptable acid addition salts of compounds of the formula I are prepared in a conventional manner by treating a solution or suspension of the free base of formula I with about one chemical equivalent of a pharmaceutically acceptable acid such as an inorganic acid or organic acid. Conventional concentration and recrystallization techniques are employed in isolating the salts.

For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution.

Although pharmaceutically acceptable salts of the basic compounds are preferred, all acid addition salts are within the scope of the present invention. All acid addition salts are useful as sources of the free base form, even if the particular salt per se is desired only as an intermediate product. For example, when the salt is formed only for purposes of purification or identification, or when it is used as an intermediate in preparing a pharmaceutically acceptable salt by ion exchange procedures, these salts are clearly contemplated to be a part of this invention.

The amino moiety of piperidine is a potential point of formation for the subject compounds of a pharmaceutically acceptable anionic salt; such salts are included in the subject invention compounds. Preferred salts are acid addition salts with, for example, HCl, $CH_3COOH$, $CH_3SO_3H$, HCOOH, $CF_3COOH$, gluconic acid, $C_{1-20}$ straight chain or branched alkanoic acids or one of the 20 naturally occurring amino acids as hereinbefore defined or dipeptide, tripeptide or polypeptide derivatives of the monoaminoacid units thereof.

"Host" is a substrate capable of sustaining a microbe, preferably it is a living organism, and most preferably an animal, more preferably a mammal, and more preferably still a human.

"Biohydrolyzable amides" are aminoacyl, acylamino, or other amides of the compounds of the invention, where the amide does not essentially interfere, preferably does not interfere, with the activity of the compound, or where the amide is readily converted in vivo by a host to yield an active compound.

"Biohydrolyzable imides" are imides of the compounds of the invention, where the imide does not essentially interfere, preferably does not interfere, with the activity of the compound, or where the imide is readily converted in vivo by a host to yield an active compound. Preferred imides are hydroxyimides.

"Biohydrolyzable esters" are esters of the compounds of the invention, where the ester does not essentially interfere, preferably does not interfere, with the antimicrobial activity of the compound, or where the ester is readily converted in a host to yield an active compound. Many such esters are known in the art. Such esters include lower alkyl esters, lower acyloxy-alkyl esters (such as acetoxymethyl, acetoxyethyl, aminocarbonyloxymethyl, pivaloyloxylmethyl and pivaloyloxylethyl esters); lactonyl esters (such as phthalidyl and thiophthalidyl esters) lower alkoxyacyloxyalkyl esters (such as methoxycarbonyloxymethyl, ethoxycarbonyloxyethyl and isopropoxycarbonyloxyethyl esters), alkoxyalkyl esters, choline esters and alkylacylaminoalkyl esters (such as acetamidomethyl esters) and alkyl amino acid esters.

The illustration of specific protected forms and other derivatives of the formula 1 compounds are not intended to be limiting. The application of other useful protecting groups, salt forms, etc. is within the ability of the skilled artisan.

"Optical isomer", "stereoisomer", "diastereomer" "polymorph" "pseudopolymorph", "hydrates" and "solvates" as referred to herein have the standard art recognized meanings. Solvates are generally formed during the process of crystallization when molar or submolar amounts of the solvents get incorporated into the crystal structure of the compound.

The compounds of the invention may contain chiral center(s), thus any such compound includes and contemplates each optical isomer, diastereomer or enantiomer thereof, in purified or substantially purified form, and mixtures thereof, including racemic mixtures.

The compounds of the invention may have one or more chiral centers. As a result, one may selectively prepare one optical isomer, including diastereomer and enantiomer, over another, for example by use of chiral starting materials, catalysts or solvents, one may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers, they may be separated using known methods, such as chiral resolution, chiral chromatography and the like. In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

As used herein, a quinolone derivative includes prodrugs of a quinolone.

The preferred compounds of the invention are those compounds of Formula I which are composed of on one hand the following core fluoroquinolone moieties displayed below minus the respective 7-amino substituent:

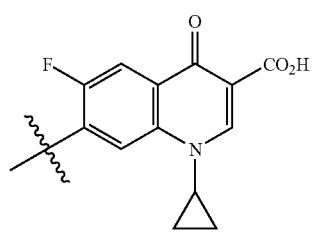

-continued

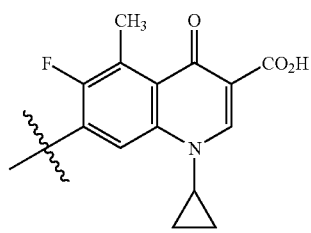

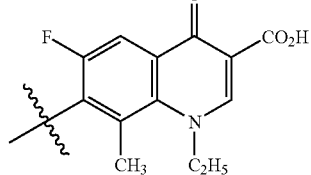

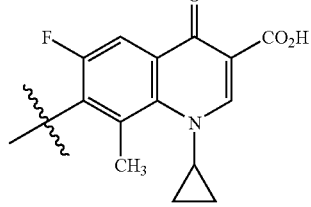

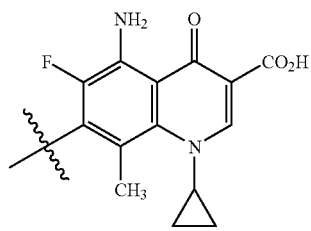

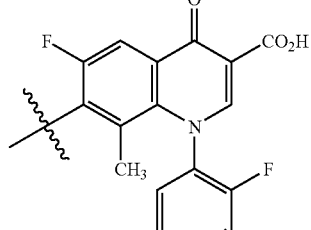

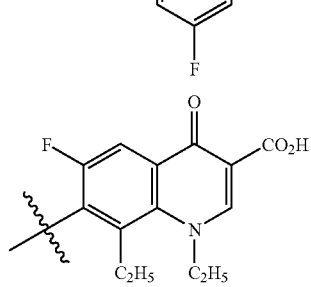

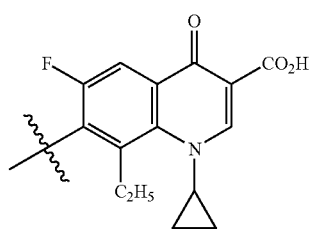

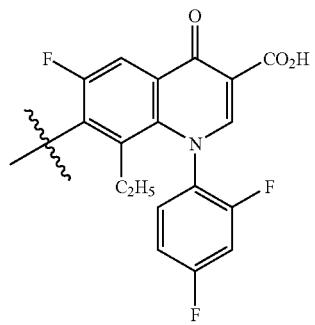
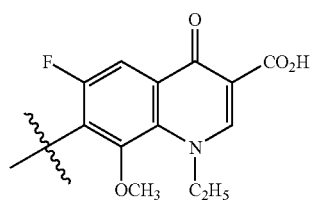
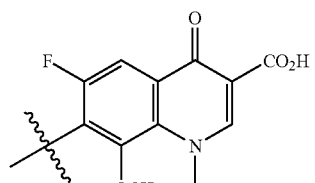
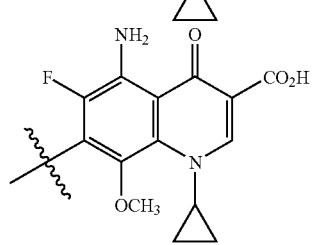
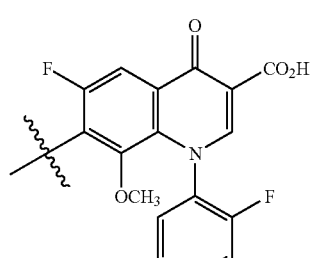
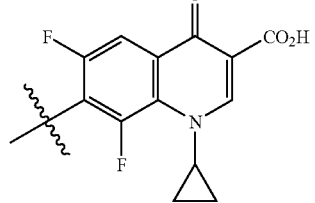
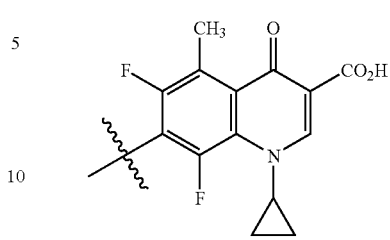
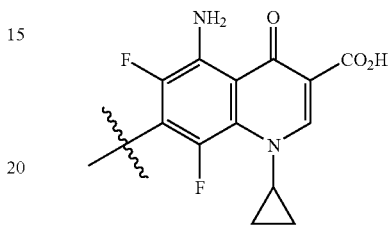
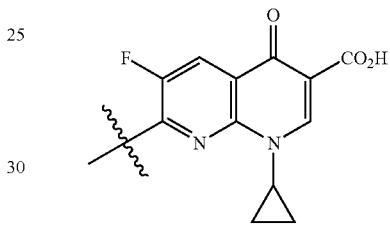
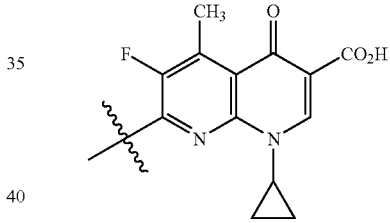
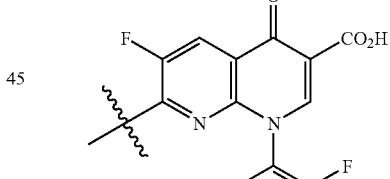
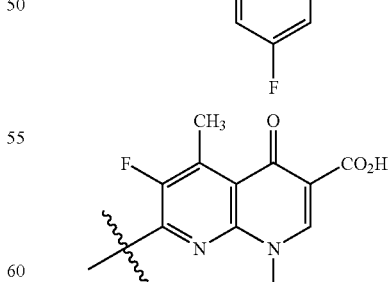
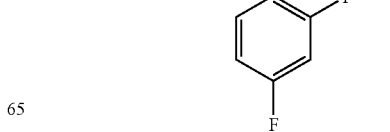

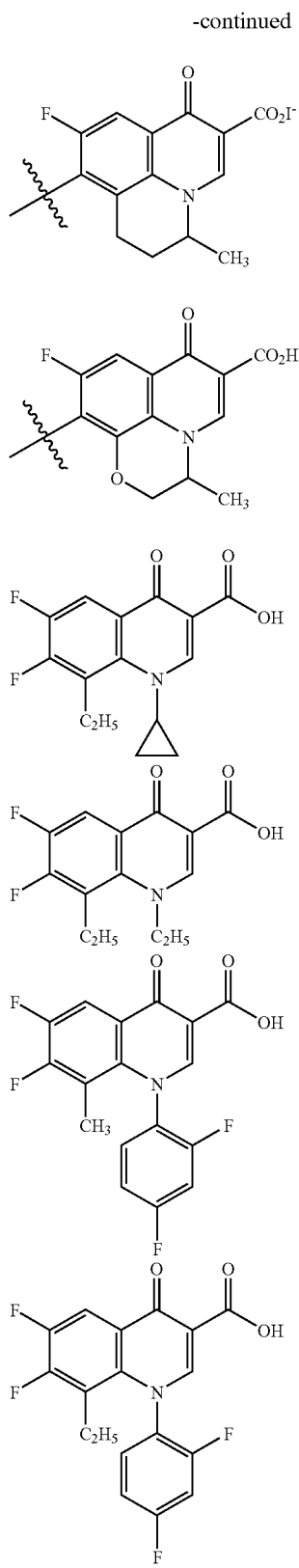
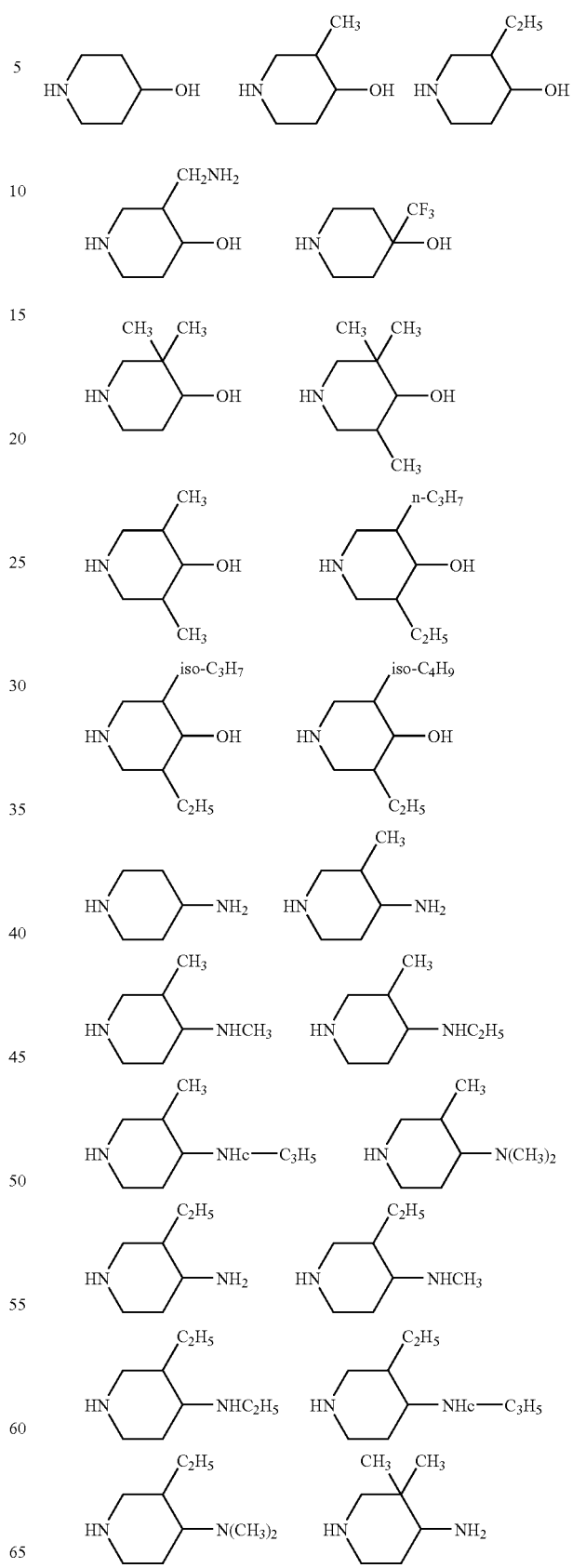
It is preferred that one of the following amines can be combined with the core fluoroquinolone moieties as shown above. The prefix "c" represents cyclo:

-continued

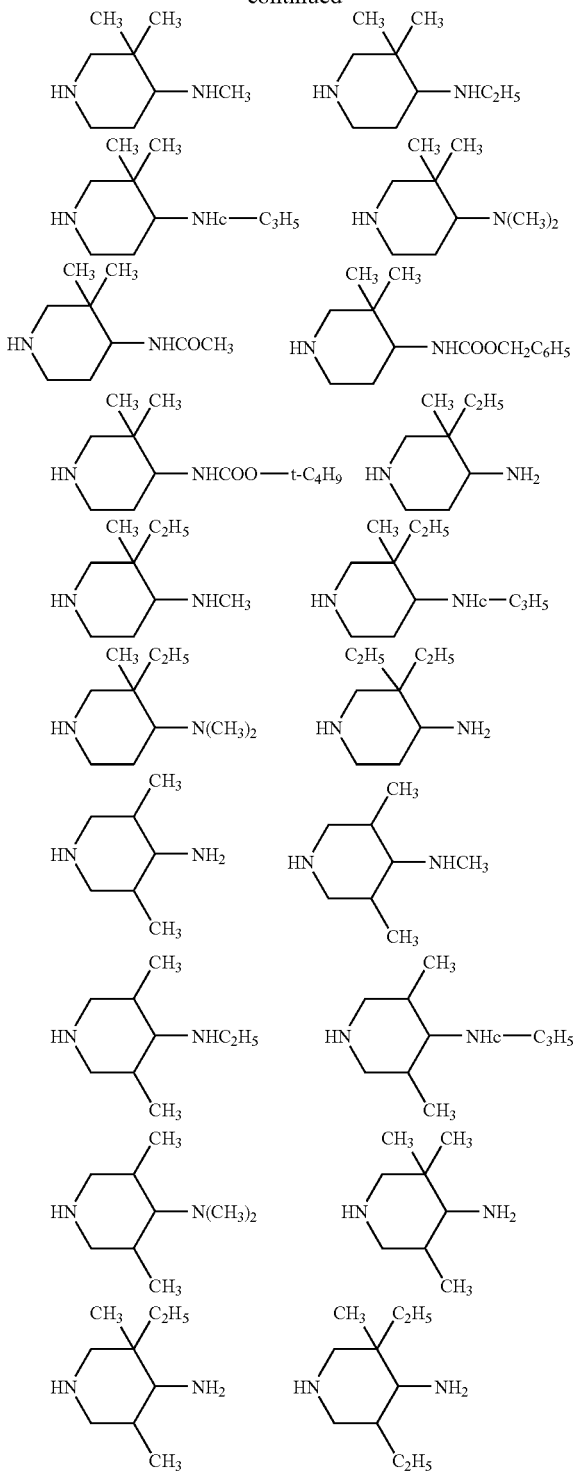

including their optical isomers and diastereomers.

The combinations of the above mentioned cores and the above mentioned amines provide the fluoroquinolone compounds of the invention.

The following exemplary compounds are made using the procedures described herein and variations thereof which are within the purview of the skilled artisan's practice. The examples below do not limit the invention, but rather serve to illustrate some of embodiments of the invention.

In the following tables (Tables 1-16), there are provided some examples of the compounds of the invention. The lower case "c" represents "cyclo".

TABLE 1

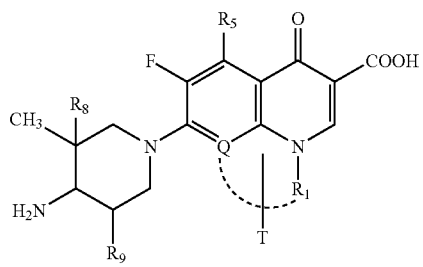

| Q | $R_1$ | $R_5$ | $R_8$ | $R_9$ | Isomer |
|---|---|---|---|---|---|
| C—H | c-$C_3H_5$ | H | H | H | cis + trans |
| C—H | c-$C_3H_5$ | H | H | H | cis |
| C—H | c-$C_3H_5$ | H | H | H | trans |
| C—H | c-$C_3H_5$ | H | $CH_3$ | H | (±) |
| C—H | c-$C_3H_5$ | H | $CH_3$ | H | (+) |
| C—H | c-$C_3H_5$ | H | $CH_3$ | H | (−) |
| C—H | c-$C_3H_5$ | $CH_3$ | H | H | trans |
| C—H | c-$C_3H_5$ | $CH_3$ | $CH_3$ | H | (±) |
| C—H | c-$C_3H_5$ | $CH_3$ | $CH_3$ | H | (+) |
| C—H | c-$C_3H_5$ | $CH_3$ | $CH_3$ | H | (−) |
| C—$CH_3$ | $C_2H_5$ | H | H | H | cis + trans |
| C—$CH_3$ | $C_2H_5$ | H | H | H | cis |
| C—$CH_3$ | $C_2H_5$ | H | H | H | trans |
| C—$CH_3$ | $C_2H_5$ | H | $CH_3$ | H | (±) |
| C—$CH_3$ | $C_2H_5$ | H | $CH_3$ | H | (+) |
| C—$CH_3$ | $C_2H_5$ | H | $CH_3$ | H | (−) |
| C—$CH_3$ | c-$C_3H_5$ | H | H | H | cis + trans |
| C—$CH_3$ | c-$C_3H_5$ | H | H | H | cis |
| C—$CH_3$ | c-$C_3H_5$ | H | H | H | trans |
| C—$CH_3$ | c-$C_3H_5$ | H | $CH_3$ | H | (±) |
| C—$CH_3$ | c-$C_3H_5$ | H | $CH_3$ | H | (+) |
| C—$CH_3$ | c-$C_3H_5$ | H | $CH_3$ | H | (−) |
| C—$CH_3$ | c-$C_3H_5$ | $NH_2$ | H | H | cis + trans |
| C—$CH_3$ | c-$C_3H_5$ | $NH_2$ | H | H | cis |
| C—$CH_3$ | c-$C_3H_5$ | $NH_2$ | H | H | trans |
| C—$CH_3$ | c-$C_3H_5$ | $NH_2$ | $CH_3$ | H | (±) |
| C—$CH_3$ | c-$C_3H_5$ | $NH_2$ | $CH_3$ | H | (+) |
| C—$CH_3$ | c-$C_3H_5$ | $NH_2$ | $CH_3$ | H | (−) |
| C—$CH_3$ | $C_6H_3F_2(2,4)$ | H | H | H | cis + trans |
| C—$CH_3$ | $C_6H_3F_2(2,4)$ | H | H | H | cis |
| C—$CH_3$ | $C_6H_3F_2(2,4)$ | H | H | H | trans |
| C—$CH_3$ | $C_6H_3F_2(2,4)$ | H | $CH_3$ | H | (±) |
| C—$CH_3$ | $C_6H_3F_2(2,4)$ | H | $CH_3$ | H | (+) |
| C—$CH_3$ | $C_6H_3F_2(2,4)$ | H | $CH_3$ | H | (−) |
| C—$C_2H_5$ | $C_2H_5$ | H | H | H | cis + trans |
| C—$C_2H_5$ | $C_2H_5$ | H | H | H | cis |
| C—$C_2H_5$ | $C_2H_5$ | H | H | H | trans |
| C—$C_2H_5$ | $C_2H_5$ | H | $CH_3$ | H | (±) |
| C—$C_2H_5$ | $C_2H_5$ | H | $CH_3$ | H | (+) |
| C—$C_2H_5$ | $C_2H_5$ | H | $CH_3$ | H | (−) |
| C—$C_2H_5$ | c-$C_3H_5$ | H | H | H | cis + trans |
| C—$C_2H_5$ | c-$C_3H_5$ | H | H | H | cis |
| C—$C_2H_5$ | c-$C_3H_5$ | H | H | H | trans |
| C—$C_2H_5$ | c-$C_3H_5$ | H | $CH_3$ | H | (±) |
| C—$C_2H_5$ | c-$C_3H_5$ | H | $CH_3$ | H | (+) |
| C—$C_2H_5$ | c-$C_3H_5$ | H | $CH_3$ | H | (−) |
| C—$C_2H_5$ | $C_6H_3F_2(2,4)$ | H | H | H | cis + trans |
| C—$C_2H_5$ | $C_6H_3F_2(2,4)$ | H | H | H | cis |
| C—$C_2H_5$ | $C_6H_3F_2(2,4)$ | H | H | H | trans |
| C—$C_2H_5$ | $C_6H_3F_2(2,4)$ | H | $CH_3$ | H | (±) |
| C—$C_2H_5$ | $C_6H_3F_2(2,4)$ | H | $CH_3$ | H | (+) |
| C—$C_2H_5$ | $C_6H_3F_2(2,4)$ | H | $CH_3$ | H | (−) |
| C—$OCH_3$ | c-$C_3H_5$ | H | H | $CH_3$ | mixtures A + B |
| C—$OCH_3$ | c-$C_3H_5$ | H | H | $CH_3$ | mixture A of isomers |
| C—$OCH_3$ | c-$C_3H_5$ | H | H | $CH_3$ | mixture B of isomers |
| C—$OCH_3$ | c-$C_3H_5$ | H | $CH_3$ | H | (±) |
| C—$OCH_3$ | c-$C_3H_5$ | H | $CH_3$ | H | (+) |

TABLE 1-continued

| | | | | | |
|---|---|---|---|---|---|
| C—OCH$_3$ | c-C$_3$H$_5$ | H | CH$_3$ | H | (−) |
| C—OCH$_3$ | c-C$_3$H$_5$ | H | CH$_3$ | CH$_3$ | mixtures of isomers |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—OCH$_3$ | c-C$_3$H$_5$ | NH$_2$ | H | CH$_3$ | mixtures A + B |
| C—OCH$_3$ | c-C$_3$H$_5$ | NH$_2$ | CH$_3$ | H | (±) |
| C—OCH$_3$ | c-C$_3$H$_5$ | NH$_2$ | CH$_3$ | H | (+) |
| C—OCH$_3$ | c-C$_3$H$_5$ | NH$_2$ | CH$_3$ | H | (−) |
| C—OCH$_3$ | c-C$_3$H$_5$ | NH$_2$ | CH$_3$ | CH$_3$ | mixtures of isomers |
| C—OCH$_3$ | C$_6$H$_3$F$_2$(2,4) | H | CH$_3$ | H | (±) |
| C—OCH$_3$ | C$_6$H$_3$F$_2$(2,4) | H | CH$_3$ | H | (+) |
| C—OCH$_3$ | C$_6$H$_3$F$_2$(2,4) | H | CH$_3$ | H | (−) |
| C—OCH$_3$ | C$_6$H$_3$F$_2$(2,4) | NH$_2$ | CH$_3$ | H | (±) |
| C—OCH$_3$ | C$_6$H$_3$F$_2$(2,4) | NH$_2$ | CH$_3$ | H | (+) |
| C—OCH$_3$ | C$_6$H$_3$F$_2$(2,4) | NH$_2$ | CH$_3$ | H | (−) |
| C—F | c-C$_3$H$_5$ | H | CH$_3$ | H | (±) |
| C—F | c-C$_3$H$_5$ | H | CH$_3$ | H | (+) |
| C—F | c-C$_3$H$_5$ | H | CH$_3$ | H | (−) |
| C—F | c-C$_3$H$_5$ | CH$_3$ | CH$_3$ | H | (±) |
| C—F | c-C$_3$H$_5$ | CH$_3$ | CH$_3$ | H | (+) |
| C—F | c-C$_3$H$_5$ | CH$_3$ | CH$_3$ | H | (−) |
| C—F | c-C$_3$H$_5$ | NH$_2$ | H | CH$_3$ | mixtures A + B |
| C—F | c-C$_3$H$_5$ | NH$_2$ | H | CH$_3$ | mixture A of isomers |
| C—F | c-C$_3$H$_5$ | NH$_2$ | H | CH$_3$ | mixture B of isomers |
| C—F | c-C$_3$H$_5$ | NH$_2$ | CH$_3$ | H | (±) |
| C—F | c-C$_3$H$_5$ | NH$_2$ | CH$_3$ | H | (+) |
| C—F | c-C$_3$H$_5$ | NH$_2$ | CH$_3$ | H | (−) |
| N | c-C$_3$H$_5$ | H | H | CH$_3$ | mixtures A + B |
| N | c-C$_3$H$_5$ | H | H | CH$_3$ | mixture A of isomers |
| N | c-C$_3$H$_5$ | H | H | CH$_3$ | mixture B of isomers |
| N | c-C$_3$H$_5$ | H | CH$_3$ | H | (±) |
| N | c-C$_3$H$_5$ | H | CH$_3$ | H | (+) |
| N | c-C$_3$H$_5$ | H | CH$_3$ | H | (−) |
| N | c-C$_3$H$_5$ | CH$_3$ | CH$_3$ | H | (±) |
| N | c-C$_3$H$_5$ | CH$_3$ | CH$_3$ | H | (+) |
| N | c-C$_3$H$_5$ | CH$_3$ | CH$_3$ | H | (−) |
| N | C$_6$H$_3$F$_2$(2,4) | H | H | CH$_3$ | mixtures A + B |
| N | C$_6$H$_3$F$_2$(2,4) | H | H | CH$_3$ | mixture A of isomers |
| N | C$_6$H$_3$F$_2$(2,4) | H | H | CH$_3$ | mixture B of isomers |
| N | C$_6$H$_3$F$_2$(2,4) | H | CH$_3$ | H | (±) |
| N | C$_6$H$_3$F$_2$(2,4) | H | CH$_3$ | H | (+) |
| N | C$_6$H$_3$F$_2$(2,4) | H | CH$_3$ | H | (−) |
| N | C$_6$H$_3$F$_2$(2,4) | CH$_3$ | CH$_3$ | H | (±) |
| N | C$_6$H$_3$F$_2$(2,4) | CH$_3$ | CH$_3$ | H | (+) |
| N | C$_6$H$_3$F$_2$(2,4) | CH$_3$ | CH$_3$ | H | (−) |
| C—CH$_2$CH$_2$C*H(CH$_3$) | | H | H | H | cis + trans |
| C—CH$_2$CH$_2$C*H(CH$_3$) | | H | H | H | cis |
| C—CH$_2$CH$_2$C*H(CH$_3$) | | H | H | H | trans |
| C—CH$_2$CH$_2$C*H(CH$_3$) | | H | H | CH$_3$ | mixtures A + B |
| C—CH$_2$CH$_2$C*H(CH$_3$) | | H | CH$_3$ | H | (±) |
| C—CH$_2$CH$_2$C*H(CH$_3$) | | H | CH$_3$ | H | (+) |
| C—CH$_2$CH$_2$C*H(CH$_3$) | | H | CH$_3$ | H | (−) |
| C—OCH$_2$CH(CH$_3$) | | H | H | H | cis + trans |
| C—OCH$_2$CH(CH$_3$) | | H | H | H | cis |
| C—OCH$_2$CH(CH$_3$) | | H | H | H | trans |
| C—OCH$_2$CH(CH$_3$) | | H | H | CH$_3$ | mixtures A + B |
| C—OCH$_2$CH(CH$_3$) | | H | CH$_3$ | H | (±) |
| C—OCH$_2$CH(CH$_3$) | | H | CH$_3$ | H | (+) |
| C—OCH$_2$CH(CH$_3$) | | H | CH$_3$ | H | (−) |

Q = C—H, C—(C$_1$-C$_2$) alkyl, C—OCH$_3$, C—F or N, and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_1$ = C$_2$H$_5$, c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_5$ = H, CH$_3$, or NH$_2$;
R$_8$ = H, or CH$_3$;
R$_9$ = H, or CH$_3$;
and optical isomers, pharmaceutically acceptable salts, hydrates, biohydrolyzable esters, polymorphs and pseudomorphs thereof.

TABLE 2

| Q | R$_1$ | R$_5$ | R$_8$ | R$_9$ | Isomers |
|---|---|---|---|---|---|
| C—H | c-C$_3$H$_5$ | H | H | H | cis + trans |
| C—H | c-C$_3$H$_5$ | H | H | H | cis |
| C—H | c-C$_3$H$_5$ | H | H | H | trans |
| C—H | c-C$_3$H$_5$ | H | CH$_3$ | H | (±) |
| C—H | c-C$_3$H$_5$ | H | CH$_3$ | H | (+) |
| C—H | c-C$_3$H$_5$ | H | CH$_3$ | H | (−) |
| C—H | c-C$_3$H$_5$ | CH$_3$ | H | H | cis + trans |
| C—H | c-C$_3$H$_5$ | CH$_3$ | H | H | cis |
| C—H | c-C$_3$H$_5$ | CH$_3$ | H | H | trans |
| C—H | c-C$_3$H$_5$ | CH$_3$ | CH$_3$ | H | (±) |
| C—H | c-C$_3$H$_5$ | CH$_3$ | CH$_3$ | H | (+) |
| C—H | c-C$_3$H$_5$ | CH$_3$ | CH$_3$ | H | (−) |
| C—CH$_3$ | c-C$_3$H$_5$ | H | H | H | cis + trans |
| C—CH$_3$ | c-C$_3$H$_5$ | H | H | H | cis |
| C—CH$_3$ | c-C$_3$H$_5$ | H | H | H | trans |
| C—OCH$_3$ | C$_2$H$_5$ | H | H | CH$_3$ | mixture A of isomers |
| C—OCH$_3$ | C$_2$H$_5$ | H | H | CH$_3$ | mixture B of isomers |
| C—OCH$_3$ | c-C$_3$H$_5$ | H | H | CH$_3$ | mixture A + B |
| C—OCH$_3$ | c-C$_3$H$_5$ | H | H | CH$_3$ | mixture A of isomers |
| C—OCH$_3$ | c-C$_3$H$_5$ | H | H | CH$_3$ | mixture B of isomers |
| C—OCH$_3$ | c-C$_3$H$_5$ | NH$_2$ | H | CH$_3$ | mixture A + B |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—F | c-C$_3$H$_5$ | NH$_2$ | H | CH$_3$ | mixture A + B |
| C—F | c-C$_3$H$_5$ | NH$_2$ | H | CH$_3$ | mixture A of isomers |
| C—F | c-C$_3$H$_5$ | NH$_2$ | H | CH$_3$ | mixture B of isomers |
| C—F | c-C$_3$H$_5$ | NH$_2$ | CH$_3$ | H | (±) |
| C—F | c-C$_3$H$_5$ | NH$_2$ | CH$_3$ | H | (+) |
| C—F | c-C$_3$H$_5$ | NH$_2$ | CH$_3$ | H | (−) |
| N | c-C$_3$H$_5$ | H | H | H | cis + trans |
| N | c-C$_3$H$_5$ | H | H | H | cis |
| N | c-C$_3$H$_5$ | H | H | H | trans |
| N | c-C$_3$H$_5$ | H | H | CH$_3$ | mixture A + B |
| N | c-C$_3$H$_5$ | H | H | CH$_3$ | mixture A of isomers |
| N | c-C$_3$H$_5$ | H | H | CH$_3$ | mixture B of isomers |
| N | c-C$_3$H$_5$ | H | CH$_3$ | H | (±) |
| N | c-C$_3$H$_5$ | H | CH$_3$ | H | (+) |
| N | c-C$_3$H$_5$ | H | CH$_3$ | H | (−) |
| N | C$_6$H$_3$F$_2$(2,4) | H | H | H | cis + trans |
| N | C$_6$H$_3$F$_2$(2,4) | H | H | H | cis |
| N | C$_6$H$_3$F$_2$(2,4) | H | H | H | Trans |
| N | C$_6$H$_3$F$_2$(2,4) | H | H | CH$_3$ | Mixture A + B |
| N | C$_6$H$_3$F$_2$(2,4) | H | H | CH$_3$ | mixture A of isomers |
| N | C$_6$H$_3$F$_2$(2,4) | H | H | CH$_3$ | mixture B of isomers |
| N | C$_6$H$_3$F$_2$(2,4) | H | CH$_3$ | H | (±) |
| N | C$_6$H$_3$F$_2$(2,4) | H | CH$_3$ | H | (+) |
| N | C$_6$H$_3$F$_2$(2,4) | H | CH$_3$ | H | (−) |
| C—CH$_2$CH$_2$C*H(CH$_3$) | | H | H | H | cis + trans |
| C—CH$_2$CH$_2$C*H(CH$_3$) | | H | H | H | cis |
| C—CH$_2$CH$_2$C*H(CH$_3$) | | H | H | H | trans |
| C—CH$_2$CH$_2$C*H(CH$_3$) | | H | H | CH$_3$ | mixture A + B |
| C—CH$_2$CH$_2$C*H(CH$_3$) | | H | H | CH$_3$ | mixture A of isomers |
| C—CH$_2$CH$_2$C*H(CH$_3$) | | H | H | CH$_3$ | mixture B of isomers |
| C—CH$_2$CH$_2$C*H(CH$_3$) | | H | CH$_3$ | H | (±) |
| C—CH$_2$CH$_2$C*H(CH$_3$) | | H | CH$_3$ | H | (+) |
| C—CH$_2$CH$_2$C*H(CH$_3$) | | H | CH$_3$ | H | (−) |
| C—OCH$_2$CH(CH$_3$) | | H | H | H | cis + trans |
| C—OCH$_2$CH(CH$_3$) | | H | H | H | cis |
| C—OCH$_2$CH(CH$_3$) | | H | H | H | trans |
| C—OCH$_2$CH(CH$_3$) | | H | H | CH$_3$ | mixture A + B |
| C—OCH$_2$CH(CH$_3$) | | H | H | CH$_3$ | mixture A of isomers |
| C—OCH$_2$CH(CH$_3$) | | H | H | CH$_3$ | mixture B of isomers |
| C—OCH$_2$CH(CH$_3$) | | H | CH$_3$ | H | (±) |

TABLE 2-continued

| | | | | |
|---|---|---|---|---|
| C—OCH$_2$CH(CH$_3$) | H | CH$_3$ | H | (+) |
| C—OCH$_2$CH(CH$_3$) | H | CH$_3$ | H | (−) |

Q = C—H, C—CH$_3$, C—OCH$_3$, C—F or N, and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);

R$_1$ =C$_2$H$_5$, c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);

R$_5$ = H, CH$_3$, or NH$_2$;

R$_8$ = H, or CH$_3$;

R$_9$ = H, or CH$_3$;

and optical isomers, pharmaceutically acceptable salts, hydrates, biohydrolyzable esters, polymorphs and pseudomorphs thereof.

TABLE 3

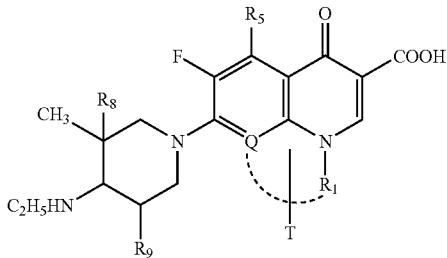

| Q | R$_1$ | R$_5$ | R$_8$ | R$_9$ | Isomers |
|---|---|---|---|---|---|
| C—H | c-C$_3$H$_5$ | H | CH$_3$ | H | (±) |
| C—H | c-C$_3$H$_5$ | H | CH$_3$ | H | (+) |
| C—H | c-C$_3$H$_5$ | H | CH$_3$ | H | (−) |
| C—H | c-C$_3$H$_5$ | CH$_3$ | CH$_3$ | H | (±) |
| C—H | c-C$_3$H$_5$ | CH$_3$ | CH$_3$ | H | (+) |
| C—H | c-C$_3$H$_5$ | CH$_3$ | CH$_3$ | H | (−) |
| C—CH$_3$ | c-C$_3$H$_5$ | H | CH$_3$ | H | (±) |
| C—CH$_3$ | c-C$_3$H$_5$ | H | CH$_3$ | H | (+) |
| C—CH$_3$ | c-C$_3$H$_5$ | H | CH$_3$ | H | (−) |
| C—OCH$_3$ | c-C$_3$H$_5$ | H | H | CH$_3$ | mixture A of isomers |
| C—OCH$_3$ | c-C$_3$H$_5$ | H | H | CH$_3$ | mixture B of isomers |
| C—OCH$_3$ | c-C$_3$H$_5$ | NH$_2$ | H | CH$_3$ | mixture A + B |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—F | c-C$_3$H$_5$ | NH$_2$ | CH$_3$ | H | (±) |
| C—F | c-C$_3$H$_5$ | NH$_2$ | CH$_3$ | H | (+) |
| C—F | c-C$_3$H$_5$ | NH$_2$ | CH$_3$ | H | (−) |
| C—F | c-C$_3$H$_5$ | NH$_2$ | H | CH$_3$ | mixture A + B |
| C—F | c-C$_3$H$_5$ | NH$_2$ | H | CH$_3$ | mixture A of isomers |
| C—F | c-C$_3$H$_5$ | NH$_2$ | H | CH$_3$ | mixture B of isomers |
| N | c-C$_3$H$_5$ | H | H | H | cis + trans |
| N | c-C$_3$H$_5$ | H | H | H | cis |
| N | c-C$_3$H$_5$ | H | H | H | trans |
| N | c-C$_3$H$_5$ | H | CH$_3$ | H | (±) |
| N | c-C$_3$H$_5$ | H | CH$_3$ | H | (+) |
| N | c-C$_3$H$_5$ | H | CH$_3$ | H | (−) |
| N | C$_6$H$_3$F$_2$(2,4) | H | H | H | cis + trans |
| N | C$_6$H$_3$F$_2$(2,4) | H | H | H | cis |
| N | C$_6$H$_3$F$_2$(2,4) | H | H | H | trans |
| N | C$_6$H$_3$F$_2$(2,4) | H | CH$_3$ | H | (±) |
| N | C$_6$H$_3$F$_2$(2,4) | H | CH$_3$ | H | (+) |
| N | C$_6$H$_3$F$_2$(2,4) | H | CH$_3$ | H | (−) |
| C—CH$_2$CH$_2$C*H(CH$_3$) | H | CH$_3$ | H | (±) |
| C—CH$_2$CH$_2$C*H(CH$_3$) | H | CH$_3$ | H | (+) |
| C—CH$_2$CH$_2$C*H(CH$_3$) | H | CH$_3$ | H | (−) |
| C—OCH$_2$CH(CH$_3$) | H | CH$_3$ | H | (±) |

TABLE 3-continued

| | | | | |
|---|---|---|---|---|
| C—OCH$_2$CH(CH$_3$) | H | CH$_3$ | H | (+) |
| C—OCH$_2$CH(CH$_3$) | H | CH$_3$ | H | (−) |

Q = C—H, C—CH$_3$, C—OCH$_3$, C—F or N, and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);

R$_1$ = c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);

R$_5$ = H, CH$_3$, or NH$_2$;

R$_8$ = H, or CH$_3$;

R$_9$ = H, or CH$_3$;

and optical isomers, pharmaceutically acceptable salts, hydrates, biohydrolyzable esters, polymorphs and pseudomorphs thereof.

TABLE 4

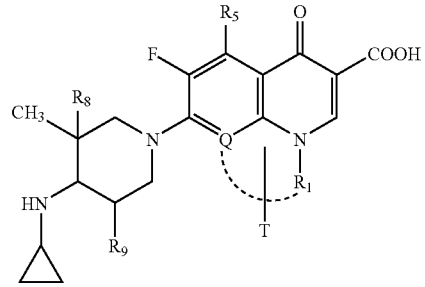

| Q | R$_1$ | R$_5$ | R$_8$ | R$_9$ | Isomer |
|---|---|---|---|---|---|
| C—H | c-C$_3$H$_5$ | H | CH$_3$ | H | (±) |
| C—H | c-C$_3$H$_5$ | H | CH$_3$ | H | (+) |
| C—H | c-C$_3$H$_5$ | H | CH$_3$ | H | (−) |
| C—H | c-C$_3$H$_5$ | CH$_3$ | CH$_3$ | H | (±) |
| C—H | c-C$_3$H$_5$ | CH$_3$ | CH$_3$ | H | (+) |
| C—H | c-C$_3$H$_5$ | CH$_3$ | CH$_3$ | H | (−) |
| C—OCH$_3$ | c-C$_3$H$_5$ | H | H | CH$_3$ | mixture A + B |
| C—OCH$_3$ | c-C$_3$H$_5$ | H | H | CH$_3$ | mixture A of isomers |
| C—OCH$_3$ | c-C$_3$H$_5$ | H | H | CH$_3$ | mixture B of isomers |
| C—OCH$_3$ | c-C$_3$H$_5$ | H | H | CH$_3$ | mixture A + B |
| C—OCH$_3$ | c-C$_3$H$_5$ | H | H | CH$_3$ | mixture A of isomers |
| C—OCH$_3$ | c-C$_3$H$_5$ | H | H | CH$_3$ | mixture B of isomers |
| C—OCH$_3$ | c-C$_3$H$_5$ | NH$_2$ | H | CH$_3$ | mixture A + B |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—OCH$_3$ | c-C$_3$H$_5$ | NH$_2$ | H | CH$_3$ | mixture A + B |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—OCH$_3$ | c-C$_3$H$_5$ | NH$_2$ | CH$_3$ | H | (±) |
| C—OCH$_3$ | c-C$_3$H$_5$ | NH$_2$ | CH$_3$ | H | (+) |
| C—OCH$_3$ | c-C$_3$H$_5$ | NH$_2$ | CH$_3$ | H | (−) |
| C—F | c-C$_3$H$_5$ | NH$_2$ | H | CH$_3$ | mixture A + B |
| C—F | c-C$_3$H$_5$ | NH$_2$ | H | CH$_3$ | mixture A of isomers |
| C—F | c-C$_3$H$_5$ | NH$_2$ | H | CH$_3$ | mixture B of isomers |
| C—F | c-C$_3$H$_5$ | NH$_2$ | CH$_3$ | H | (±) |
| C—F | c-C$_3$H$_5$ | NH$_2$ | CH$_3$ | H | (+) |
| C—F | c-C$_3$H$_5$ | NH$_2$ | CH$_3$ | H | (−) |
| N | c-C$_3$H$_5$ | H | H | H | cis + trans |
| N | c-C$_3$H$_5$ | H | H | H | cis |
| N | c-C$_3$H$_5$ | H | H | H | trans |
| N | c-C$_3$H$_5$ | H | CH$_3$ | H | (±) |
| N | c-C$_3$H$_5$ | H | CH$_3$ | H | (+) |
| N | c-C$_3$H$_5$ | H | CH$_3$ | H | (−) |
| N | C$_6$H$_3$F$_2$(2,4) | H | H | H | cis ± trans |
| N | C$_6$H$_3$F$_2$(2,4) | H | H | H | cis |
| N | C$_6$H$_3$F$_2$(2,4) | H | H | H | trans |
| N | C$_6$H$_3$F$_2$(2,4) | H | CH$_3$ | H | (±) |
| N | C$_6$H$_3$F$_2$(2,4) | H | CH$_3$ | H | (+) |
| N | C$_6$H$_3$F$_2$(2,4) | H | CH$_3$ | H | (−) |
| C—CH$_2$CH$_2$C*H(CH$_3$) | H | CH$_3$ | H | (±) |
| C—CH$_2$CH$_2$C*H(CH$_3$) | H | CH$_3$ | H | (+) |
| C—CH$_2$CH$_2$C*H(CH$_3$) | H | CH$_3$ | H | (−) |
| C—OCH$_2$CH(CH$_3$) | H | CH$_3$ | H | (±) |

TABLE 4-continued

| | | | | |
|---|---|---|---|---|
| C—OCH$_2$CH(CH$_3$) | H | CH$_3$ | H | (+) |
| C—OCH$_2$CH(CH$_3$) | H | CH$_3$ | H | (−) |

Q = C—H, C—OCH$_3$, C—F or N, and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_1$ = c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_5$ = H, CH$_3$, or NH$_2$;
R$_8$ = H, or CH$_3$;
R$_9$ = H, or CH$_3$;
and optical isomers, pharmaceutically acceptable salts, hydrates, biohydrolyzable esters, polymorphs and pseudomorphs thereof.

TABLE 5

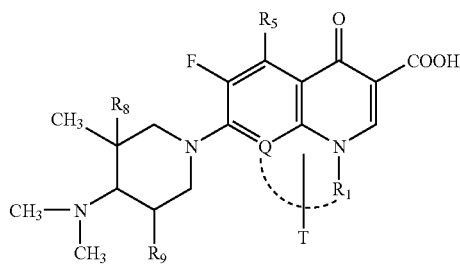

| Q | R$_1$ | R$_5$ | R$_8$ | R$_9$ | Isomers |
|---|---|---|---|---|---|
| C—H | c-C$_3$H$_5$ | H | CH$_3$ | H | (+) |
| C—H | c-C$_3$H$_5$ | H | CH$_3$ | H | (±) |
| C—H | c-C$_3$H$_5$ | H | CH$_3$ | H | (−) |
| C—H | c-C$_3$H$_5$ | CH$_3$ | CH$_3$ | H | (±) |
| C—H | c-C$_3$H$_5$ | CH$_3$ | CH$_3$ | H | (+) |
| C—H | c-C$_3$H$_5$ | CH$_3$ | CH$_3$ | H | (−) |
| C—CH$_3$ | c-C$_3$H$_5$ | H | H | H | cis + trans |
| C—CH$_3$ | c-C$_3$H$_5$ | H | H | H | cis |
| C—CH$_3$ | c-C$_3$H$_5$ | H | H | H | trans |
| C—CH$_3$ | c-C$_3$H$_5$ | H | CH$_3$ | H | (±) |
| C—CH$_3$ | c-C$_3$H$_5$ | H | CH$_3$ | H | (+) |
| C—CH$_3$ | c-C$_3$H$_5$ | H | CH$_3$ | H | (−) |
| C—OCH$_3$ | c-C$_3$H$_5$ | H | H | H | cis + trans |
| C—OCH$_3$ | c-C$_3$H$_5$ | H | H | H | cis |
| C—OCH$_3$ | c-C$_3$H$_5$ | H | H | H | trans |
| C—OCH$_3$ | c-C$_3$H$_5$ | H | H | CH$_3$ | mixtures A + B |
| C—OCH$_3$ | c-C$_3$H$_5$ | H | H | CH$_3$ | mixture A of isomers |
| C—OCH$_3$ | c-C$_3$H$_5$ | H | H | CH$_3$ | mixture B of isomers |
| C—OCH$_3$ | c-C$_3$H$_5$ | H | CH$_3$ | H | (±) |
| C—OCH$_3$ | c-C$_3$H$_5$ | H | CH$_3$ | H | (+) |
| C—OCH$_3$ | c-C$_3$H$_5$ | H | CH$_3$ | H | (−) |
| C—OCH$_3$ | c-C$_3$H$_5$ | NH$_2$ | H | H | cis + trans |
| C—OCH$_3$ | c-C$_3$H$_5$ | NH$_2$ | H | H | cis |
| C—OCH$_3$ | c-C$_3$H$_5$ | NH$_2$ | H | H | trans |
| C—OCH$_3$ | c-C$_3$H$_5$ | NH$_2$ | H | CH$_3$ | mixture A + B |
| C—OCH$_3$ | c-C$_3$H$_5$ | NH$_2$ | H | CH$_3$ | mixture A of isomers |
| C—OCH$_3$ | c-C$_3$H$_5$ | NH$_2$ | H | CH$_3$ | mixture B of isomers |
| C—OCH$_3$ | c-C$_3$H$_5$ | NH$_2$ | CH$_3$ | H | (±) |
| C—OCH$_3$ | c-C$_3$H$_5$ | NH$_2$ | CH$_3$ | H | (+) |
| C—OCH$_3$ | c-C$_3$H$_5$ | NH$_2$ | CH$_3$ | H | (−) |
| C—F | c-C$_3$H$_5$ | CH$_3$ | CH$_3$ | H | (±) |
| C—F | c-C$_3$H$_5$ | CH$_3$ | CH$_3$ | H | (+) |
| C—F | c-C$_3$H$_5$ | CH$_3$ | CH$_3$ | H | (−) |
| C—F | c-C$_3$H$_5$ | NH$_2$ | H | H | cis + trans |
| C—F | c-C$_3$H$_5$ | NH$_2$ | H | H | cis |
| C—F | c-C$_3$H$_5$ | NH$_2$ | H | H | trans |
| C—F | c-C$_3$H$_5$ | NH$_2$ | H | CH$_3$ | mixture A + B |
| C—F | c-C$_3$H$_5$ | NH$_2$ | H | CH$_3$ | mixture A of isomers |
| C—F | c-C$_3$H$_5$ | NH$_2$ | H | CH$_3$ | mixture B of isomers |
| C—F | c-C$_3$H$_5$ | NH$_2$ | CH$_3$ | H | (±) |
| C—F | c-C$_3$H$_5$ | NH$_2$ | CH$_3$ | H | (+) |
| C—F | c-C$_3$H$_5$ | NH$_2$ | CH$_3$ | H | (−) |
| N | c-C$_3$H$_5$ | H | H | H | cis + trans |
| N | c-C$_3$H$_5$ | H | H | H | cis |
| N | c-C$_3$H$_5$ | H | H | H | trans |
| N | c-C$_3$H$_5$ | H | CH$_3$ | H | (±) |
| N | c-C$_3$H$_5$ | H | CH$_3$ | H | (+) |
| N | c-C$_3$H$_5$ | H | CH$_3$ | H | (−) |
| N | C$_6$H$_3$F$_2$(2,4) | H | H | H | cis + trans |
| N | C$_6$H$_3$F$_2$(2,4) | H | H | H | cis |
| N | C$_6$H$_3$F$_2$(2,4) | H | H | H | trans |
| N | C$_6$H$_3$F$_2$(2,4) | H | CH$_3$ | H | (±) |
| N | C$_6$H$_3$F$_2$(2,4) | H | CH$_3$ | H | (+) |
| N | C$_6$H$_3$F$_2$(2,4) | H | CH$_3$ | H | (−) |
| C—CH$_2$CH$_2$C*H(CH$_3$) | H | CH$_3$ | H | (±) |
| C—CH$_2$CH$_2$C*H(CH$_3$) | H | CH$_3$ | H | (+) |
| C—CH$_2$CH$_2$C*H(CH$_3$) | H | CH$_3$ | H | (−) |
| C—OCH$_2$CH(CH$_3$) | H | H | H | cis + trans |
| C—OCH$_2$CH(CH$_3$) | H | H | H | cis |
| C—OCH$_2$CH(CH$_3$) | H | H | H | trans |
| C—OCH$_2$CH(CH$_3$) | H | CH$_3$ | H | (±) |
| C—OCH$_2$CH(CH$_3$) | H | CH$_3$ | H | (+) |
| C—OCH$_2$CH(CH$_3$) | H | CH$_3$ | H | (−) |

Q = C—H, C—CH$_3$, C—OCH$_3$, C—F or N, and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_1$ = c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ are C—CH$_2$CH$_2$C*H(CH$_3$) or C—OCH$_2$CH(CH$_3$);
R$_5$ = H, CH$_3$, or NH$_2$;
R$_8$ = H, or CH$_3$;
R$_9$ = H, or CH$_3$;
and optical isomers, pharmaceutically acceptable salts, hydrates, biohydrolyzable esters, polymorphs and pseudomorphs thereof.

TABLE 6

| Q | R$_1$ | R$_5$ | R$_8$ | R$_9$ | Isomers |
|---|---|---|---|---|---|
| C—CH$_3$ | C$_2$H$_5$ | H | H | H | cis + trans |
| C—CH$_3$ | C$_6$H$_3$F$_2$(2,4) | H | H | H | cis + trans |
| C—C$_2$H$_5$ | C$_2$H$_5$ | H | H | H | cis + trans |
| C—C$_2$H$_5$ | c-C$_3$H$_5$ | H | H | H | cis + trans |
| C—C$_2$H$_5$ | C$_6$H$_3$F$_2$(2,4) | H | H | H | cis + trans |
| C—OCH$_3$ | c-C$_3$H$_5$ | H | H | H | cis + trans |
| C—OCH$_3$ | c-C$_3$H$_5$ | H | H | H | Cis |
| C—OCH$_3$ | c-C$_3$H$_5$ | H | H | H | Trans |
| C—OCH$_3$ | c-C$_3$H$_5$ | H | H | C$_2$H$_5$ | mixture A + B |
| C—OCH$_3$ | c-C$_3$H$_5$ | H | H | C$_2$H$_5$ | mixture A of isomers |
| C—OCH$_3$ | c-C$_3$H$_5$ | H | H | C$_2$H$_5$ | mixture B of isomers |
| C—OCH$_3$ | c-C$_3$H$_5$ | H | CH$_3$ | H | (±) |
| C—OCH$_3$ | c-C$_3$H$_5$ | H | CH$_3$ | H | (+) |
| C—OCH$_3$ | c-C$_3$H$_5$ | H | CH$_3$ | H | (−) |
| C—OCH$_3$ | c-C$_3$H$_5$ | H | CH$_3$ | CH$_3$ | mixture of isomers |
| C—OCH$_3$ | c-C$_3$H$_5$ | H | CH$_3$ | C$_2$H$_5$ | mixture of isomers |
| C—OCH$_3$ | c-C$_3$H$_5$ | H | CH$_3$ | C$_2$H$_5$ | mixture of isomers |
| C—OCH$_3$ | c-C$_3$H$_5$ | H | C$_2$H$_5$ | H | (±) |
| C—OCH$_3$ | c-C$_3$H$_5$ | H | C$_2$H$_5$ | H | (+) |
| C—OCH$_3$ | c-C$_3$H$_5$ | H | C$_2$H$_5$ | H | (−) |
| C—OCH$_3$ | c-C$_3$H$_5$ | H | CH$_3$ | H | (−) |
| C—OCH$_3$ | c-C$_3$H$_5$ | NH$_2$ | H | H | cis + trans |
| C—OCH$_3$ | c-C$_3$H$_5$ | NH$_2$ | H | H | cis |
| C—OCH$_3$ | c-C$_3$H$_5$ | NH$_2$ | H | H | Trans |
| C—OCH$_3$ | c-C$_3$H$_5$ | NH$_2$ | H | C$_2$H$_5$ | mixture A + B |
| C—OCH$_3$ | c-C$_3$H$_5$ | NH$_2$ | H | C$_2$H$_5$ | mixture A of isomers |
| C—OCH$_3$ | c-C$_3$H$_5$ | NH$_2$ | H | C$_2$H$_5$ | mixture B of isomers |
| C—OCH$_3$ | c-C$_3$H$_5$ | NH$_2$ | CH$_3$ | H | (±) |

TABLE 6-continued

| Q | | R₅ | R₈ | R₉ | Isomer |
|---|---|---|---|---|---|
| C—OCH₃ | c-C₃H₅ | NH₂ | CH₃ | H | (+) |
| C—OCH₃ | c-C₃H₅ | NH₂ | CH₃ | H | (−) |
| C—OCH₃ | c-C₃H₅ | NH₂ | CH₃ | CH₃ | mixture of isomers |
| C—OCH₃ | c-C₃H₅ | NH₂ | CH₃ | C₂H₅ | mixture of isomers |
| C—OCH₃ | c-C₃H₅ | NH₂ | C₂H₅ | H | (±) |
| C—OCH₃ | c-C₃H₅ | NH₂ | C₂H₅ | H | (+) |
| C—OCH₃ | c-C₃H₅ | NH₂ | C₂H₅ | H | (−) |
| C—F | c-C₃H₅ | NH₂ | H | H | cis + trans |
| C—F | c-C₃H₅ | NH₂ | H | H | cis |
| C—F | c-C₃H₅ | NH₂ | H | H | trans |
| C—F | c-C₃H₅ | NH₂ | H | C₂H₅ | mixture A + B |
| C—F | c-C₃H₅ | NH₂ | H | C₂H₅ | mixture A of isomers |
| C—F | c-C₃H₅ | NH₂ | H | C₂H₅ | mixture B of isomers |
| C—F | c-C₃H₅ | NH₂ | CH₃ | H | (±) |
| C—F | c-C₃H₅ | NH₂ | CH₃ | H | (+) |
| C—F | c-C₃H₅ | NH₂ | CH₃ | H | (−) |
| C—F | c-C₃H₅ | NH₂ | CH₃ | CH₃ | mixture of isomers |
| C—F | c-C₃H₅ | NH₂ | CH₃ | C₂H₅ | mixture of isomers |
| C—F | c-C₃H₅ | NH₂ | C₂H₅ | H | (±) |
| C—F | c-C₃H₅ | NH₂ | C₂H₅ | H | (+) |
| C—F | c-C₃H₅ | NH₂ | C₂H₅ | H | (−) |
| N | c-C₃H₅ | H | H | H | cis + trans |
| N | c-C₃H₅ | H | H | H | cis |
| N | c-C₃H₅ | H | H | H | trans |
| N | C₆H₃F₂(2,4) | H | H | H | cis + trans |
| N | C₆H₃F₂(2,4) | H | H | H | cis |
| N | C₆H₃F₂(2,4) | H | H | H | trans |

$Q = C—(C_1-C_2)$ alkyl, C—OCH₃, C—F or N;
$R_1 = C_2H_5$, c-C₃H₅, or $C_6H_3F_2(2,4)$;
$R_5 = H$, or NH₂;
$R_8 = H$, CH₃, or C₂H₅;
$R_9 = H$, CH₃, or C₂H₅;
and optical isomers, pharmaceutically acceptable salts, hydrates, biohydrolyzable esters, polymorphs and pseudomorphs thereof.

TABLE 7

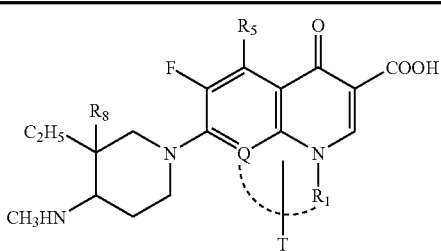

| Q | R₁ | R₅ | R₈ | Isomer |
|---|---|---|---|---|
| C—OCH₃ | c-C₃H₅ | H | H | cis + trans |
| C—OCH₃ | c-C₃H₅ | H | H | cis |
| C—OCH₃ | c-C₃H₅ | H | H | trans |
| C—OCH₃ | c-C₃H₅ | H | CH₃ | (±) |
| C—OCH₃ | c-C₃H₅ | H | CH₃ | (+) |
| C—OCH₃ | c-C₃H₅ | H | CH₃ | (−) |
| C—OCH₃ | c-C₃H₅ | NH₂ | H | cis + trans |
| C—OCH₃ | c-C₃H₅ | NH₂ | H | cis |
| C—OCH₃ | c-C₃H₅ | NH₂ | H | trans |
| C—OCH₃ | c-C₃H₅ | NH₂ | CH₃ | (±) |
| C—OCH₃ | c-C₃H₅ | NH₂ | CH₃ | (+) |
| C—OCH₃ | c-C₃H₅ | NH₂ | CH₃ | (−) |
| C—F | c-C₃H₅ | NH₂ | H | cis + trans |
| C—F | c-C₃H₅ | NH₂ | H | cis |
| C—F | c-C₃H₅ | NH₂ | H | trans |
| C—F | c-C₃H₅ | NH₂ | CH₃ | (±) |
| C—F | c-C₃H₅ | NH₂ | CH₃ | (+) |
| C—F | c-C₃H₅ | NH₂ | CH₃ | (−) |
| C—OCH₂CH(CH₃) | | H | H | cis + trans |
| C—OCH₂CH(CH₃) | | H | H | cis |
| C—OCH₂CH(CH₃) | | H | H | Trans |

$Q = C—OCH_3$, or C—F, and when Q is CH and the nitrogen atom to which $R_1$ is linked forms substituted 6 membered ring with the carbon atom of Q and $R_1$ is $C—OCH_2CH(CH_3)$;
$R_1 = c-C_3H_5$ and when Q is CH and the nitrogen atom to which $R_1$ is linked forms substituted 6 membered ring with the carbon atom of Q and $R_1$ is $C—OCH_2CH(CH_3)$;
$R_5 = H$, or NH₂;
$R_8 = H$, or CH₃;
and optical isomers, pharmaceutically acceptable salts, hydrates, biohydrolyzable esters, polymorphs and pseudomorphs thereof.

TABLE 8

| Q | R₁ | R₅ | R₈ | Isomer |
|---|---|---|---|---|
| C—OCH₃ | c-C₃H₅ | H | H | cis + trans |
| C—OCH₃ | c-C₃H₅ | H | H | cis |
| C—OCH₃ | c-C₃H₅ | H | H | trans |
| C—OCH₃ | c-C₃H₅ | H | CH₃ | (±) |
| C—OCH₃ | c-C₃H₅ | H | CH₃ | (+) |
| C—OCH₃ | c-C₃H₅ | H | CH₃ | (−) |
| C—OCH₃ | c-C₃H₅ | NH₂ | H | cis + trans |
| C—OCH₃ | c-C₃H₅ | NH₂ | H | cis |
| C—OCH₃ | c-C₃H₅ | NH₂ | H | trans |
| C—OCH₃ | c-C₃H₅ | NH₂ | CH₃ | (±) |
| C—OCH₃ | c-C₃H₅ | NH₂ | CH₃ | (+) |
| C—OCH₃ | c-C₃H₅ | NH₂ | CH₃ | (−) |

$Q = C—OCH_3$;
$R_1 = c-C_3H_5$;
$R_5 = H$, or NH₂;
$R_8 = H$, or CH₃;
and optical isomers, pharmaceutically acceptable salts, hydrates, biohydrolyzable esters, polymorphs and pseudomorphs thereof.

TABLE 9

| Q | R₁ | R₅ | R₈ | Isomer |
|---|---|---|---|---|
| C—OCH₃ | c-C₃H₅ | H | H | cis + trans |
| C—OCH₃ | c-C₃H₅ | H | H | cis |
| C—OCH₃ | c-C₃H₅ | H | H | trans |
| C—OCH₃ | c-C₃H₅ | H | CH₃ | (±) |
| C—OCH₃ | c-C₃H₅ | H | CH₃ | (+) |
| C—OCH₃ | c-C₃H₅ | H | CH₃ | (−) |
| C—OCH₃ | c-C₃H₅ | NH₂ | H | cis + trans |

TABLE 9-continued

| C—OCH$_3$ | c-C$_3$H$_5$ | NH$_2$ | H | cis |
| C—OCH$_3$ | c-C$_3$H$_5$ | NH$_2$ | H | trans |
| C—OCH$_3$ | c-C$_3$H$_5$ | NH$_2$ | CH$_3$ | (±) |
| C—OCH$_3$ | c-C$_3$H$_5$ | NH$_2$ | CH$_3$ | (+) |
| C—OCH$_3$ | c-C$_3$H$_5$ | NH$_2$ | CH$_3$ | (−) |

Q = C—OCH$_3$;
R$_1$ = c-C$_3$H$_5$;
R$_5$ = H, or NH$_2$;
R$_8$ = H, or CH$_3$;
and optical isomers, pharmaceutically acceptable salts, hydrates, biohydrolyzable esters, polymorphs and pseudomorphs thereof.

TABLE 10

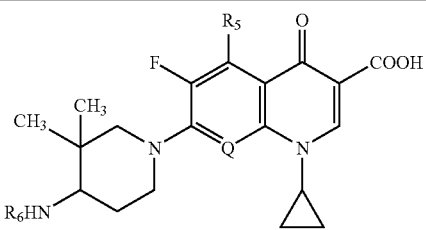

| Q | R$_5$ | R$_6$ | Isomer |
|---|---|---|---|
| C—OCH$_3$ | H | COCH$_3$ | (±) |
| C—OCH$_3$ | H | COOC$_2$H$_5$ | (±) |
| C—OCH$_3$ | H | COOC$_2$H$_5$ | (+) |
| C—OCH$_3$ | H | COOC$_2$H$_5$ | (−) |
| C—OCH$_3$ | H | COOC(CH$_3$)$_3$ | (±) |
| C—OCH$_3$ | H | COOC(CH$_3$)$_3$ | (+) |
| C—OCH$_3$ | H | COOC(CH$_3$)$_3$ | (−) |
| C—OCH$_3$ | H | COOCH$_2$C$_6$H$_5$ | (±) |
| C—OCH$_3$ | H | COOCH$_2$C$_6$H$_5$ | (+) |
| C—OCH$_3$ | H | COOCH$_2$C$_6$H$_5$ | (−) |
| C—OCH$_3$ | H | COC*H(CH$_3$)NH$_2$ | mixture |
| C—OCH$_3$ | H | COC*H(NH$_2$)CH(CH$_3$)$_2$ | mixture |
| C—OCH$_3$ | H | COCH$_2$CH(NH$_2$)COOH | mixture |
| C—OCH$_3$ | H | COC*H(CH$_3$)NHCOC*H(CH$_3$)NH-$^t$-Boc | mixture |
| C—OCH$_3$ | H | COC*H(CH$_3$)NHCOC*H(CH$_3$)NH$_2$ | mixture |
| C—F | NH$_2$ | COCH$_3$ | mixture |

Q = C—OCH$_3$, or C—F;
R$_3$ = H, or NH$_2$;
R$_6$ = COCH$_3$, CO—(O—C$_2$-C$_4$ alkyl), COOCH$_2$C$_6$H$_5$, amino C$_{1-4}$ alkanoyl, carboxy amino C$_{1-4}$ alkanoyl, dipeptidoalkanoyl wherein the terminal amino group is unprotected or protected with a $^t$-Boc-protecting group.

TABLE 11

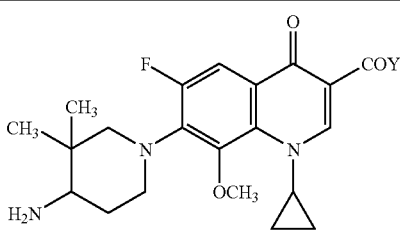

| Y | Isomers |
|---|---|
| NH$_2$ | (±) |
| NHCH$_3$ | (±) |
| NHC$_2$H$_5$ | (±) |
| NHCH(CH$_3$)COOH | (±) |
| OCH$_3$ | (±) |
| OC$_2$H$_5$ | (±) |
| OC$_3$H$_7$(n) | (±) |
| OC$_3$H$_7$(i) | (±) |
| OC$_4$H$_9$(n) | (±) |
| OCH$_2$C$_6$H$_5$ | (±) |
| OCH$_2$COOH | (±) |
| OCH$_2$OCOCH$_3$ | (±) |
| OCH$_2$OCOCH(CH$_3$)$_2$ | (±) |
| OCH$_2$OCOC(CH$_3$)$_3$ | (±) |
| OCH$_2$CH$_2$OCOCH$_3$ | (±) |
| OCH$_2$CH$_2$OCOC(CH$_3$)$_3$ | (±) |
| O-(N-methyl-4-piperidinyl) | (±) |
| 1-pyrrolidinyl | (±) |
| 1-piperidinyl | (±) |
| 1-piperazinyl | (±) |
| 1-morpholinyl | (±) |
| OCH$_2$CH(NH$_2$)COOH | (±) |

Y = NH$_2$, NHR$_2$, wherein R$_2$ is H, C$_{1-2}$ alkyl; or Y is OR$_3$ where R$_3$ is C$_{1-4}$ alkyl (branched or unbranched); CH$_2$C$_6$H$_5$; C$_2$C$_3$ carboxylic acid and their C$_1$C$_4$ alkyl esters (unbranched or branched); or five or six member heterocycle (unsubstituted or substituted) or ∝-aminoalkanoyl such as ∝-aminopropionyl; and optical isomers, pharmaceutically acceptable salts, hydrates, biohydrolyzable esters, polymorphs and pseudomorphs thereof.

TABLE 12

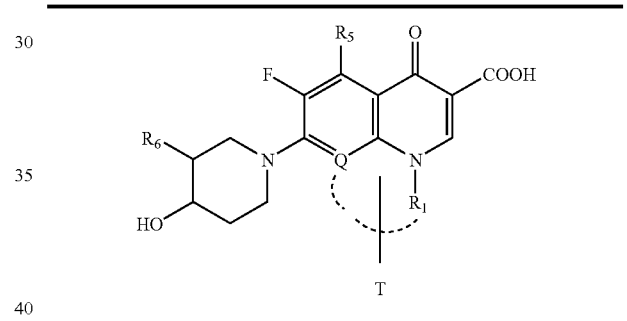

| Q | R$_1$ | R$_5$ | R$_8$ | Isomers |
|---|---|---|---|---|
| C—CH$_3$ | C$_2$H$_5$ | H | H | — |
| C—CH$_3$ | C$_6$H$_3$F$_2$(2,4) | H | H | — |
| C—C$_2$H$_5$ | C$_2$H$_5$ | H | H | — |
| C—C$_2$H$_5$ | c-C$_3$H$_5$ | H | H | — |
| C—C$_2$H$_5$ | C$_6$H$_3$F$_2$(2,4) | H | H | — |
| C—OCH$_3$ | c-C$_3$H$_5$ | H | n-C$_3$H$_7$ | cis + trans |
| C—OCH$_3$ | c-C$_3$H$_5$ | H | i-C$_3$H$_7$ | cis + trans |
| C—OCH$_3$ | c-C$_3$H$_5$ | H | n-C$_4$H$_9$ | cis + trans |
| C—OCH$_3$ | c-C$_3$H$_5$ | H | i-C$_4$H$_9$ | cis + trans |
| C—OCH$_3$ | c-C$_3$H$_5$ | H | CH$_2$C$_6$H$_5$ | cis + trans |
| C—OCH$_3$ | c-C$_3$H$_5$ | H | CF$_3$ | cis + trans |
| C—OCH$_3$ | c-C$_3$H$_5$ | NH$_2$ | CF$_3$ | cis + trans |
| C—F | c-C$_3$H$_5$ | NH$_2$ | CF$_3$ | cis + trans |
| N | C$_6$H$_3$F$_2$(2,4) | H | CF$_3$ | cis + trans |

Q = C—(C$_1$-C$_2$) alkyl, C—OCH$_3$, C13 F or N, and when Q is CH and the nitrogen atom to which R$_1$ is linked forms substituted 6 membered ring with the carbon atom of Q and R$_1$ is C-CH$_2$CH$_2$C*H(CH$_3$);
R$_1$ = C$_2$H$_5$, c-C$_3$H$_5$, or C$_6$H$_3$F$_2$(2,4), and when Q is CH and the nitrogen atom to which R$_1$ is linked forms substituted 6 membered ring with the carbon atom of Q and R$_1$ is C—CH$_2$CH$_2$C*H(CH$_3$);
R$_5$ = H, or NH$_2$;
R$_8$ H, C$_3$-C$_4$ alkyl (unbranched or branched), CH$_2$C$_6$H$_5$, or CF$_3$;
and optical isomers, pharmaceutically acceptable salts, hydrates, biohydrolyzable esters, polymorphs and pseudomorphs thereof.

TABLE 13

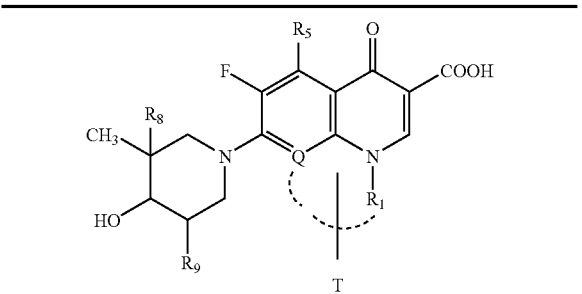

| Q | R₁ | R₅ | R₈ | R₉ | Isomer |
|---|---|---|---|---|---|
| C—H | c-C₃H₅ | H | H | H | cis + trans |
| C—H | c-C₃H₅ | H | H | H | cis |
| C—H | c-C₃H₅ | H | H | H | trans |
| C—H | c-C₃H₅ | H | H | CH₃ | mixture |
| C—H | c-C₃H₅ | H | CH₃ | H | ± |
| C—CH₃ | C₂H₅ | H | H | H | cis + trans |
| C—CH₃ | C₂H₅ | H | H | H | cis |
| C—CH₃ | C₂H₅ | H | H | H | trans |
| C—CH₃ | C₂H₅ | H | CH₃ | H | cis + trans |
| C—CH₃ | c-C₃H₅ | H | H | H | cis + trans |
| C—CH₃ | c-C₃H₅ | H | H | H | cis |
| C—CH₃ | c-C₃H₅ | H | H | H | trans |
| C—CH₃ | c-C₃H₅ | H | CH₃ | H | cis + trans |
| C—CH₃ | c-C₃H₅ | NH₂ | H | H | cis + trans |
| C—CH₃ | c-C₃H₅ | NH₂ | H | H | cis |
| C—CH₃ | c-C₃H₅ | NH₂ | H | H | trans |
| C—CH₃ | C₆H₃F₂(2,4) | H | H | H | cis + trans |
| C—CH₃ | C₆H₃F₂(2,4) | H | H | H | cis |
| C—CH₃ | C₆H₃F₂(2,4) | H | H | H | trans |
| C—CH₃ | C₆H₃F₂(2,4) | H | CH₃ | H | cis + trans |
| C—C₂H₅ | C₂H₅ | H | H | H | cis + trans |
| C—C₂H₅ | C₂H₅ | H | H | H | cis |
| C—C₂H₅ | C₂H₅ | H | H | H | trans |
| C—C₂H₅ | C₂H₅ | H | CH₃ | H | cis + trans |
| C—C₂H₅ | c-C₃H₅ | H | H | H | cis + trans |
| C—C₂H₅ | c-C₃H₅ | H | H | H | cis |
| C—C₂H₅ | c-C₃H₅ | H | H | H | trans |
| C—C₂H₅ | c-C₃H₅ | H | CH₃ | H | ± |
| C—C₂H₅ | C₆H₃F₂(2,4) | H | H | H | cis + trans |
| C—C₂H₅ | C₆H₃F₂(2,4) | H | H | H | Cis |
| C—C₂H₅ | C₆H₃F₂(2,4) | H | H | H | Trans |
| C—C₂H₅ | C₆H₃F₂(2,4) | H | CH₃ | H | ± |
| C—OCH₃ | c-C₃H₅ | H | H | H | cis + trans |
| C—OCH₃ | c-C₃H₅ | H | H | H | Cis |
| C—OCH₃ | c-C₃H₅ | H | H | H | Trans |
| C—OCH₃ | c-C₃H₅ | H | H | CH₃ | mixtures |
| C—OCH₃ | c-C₃H₅ | H | H | CH₃ | mixtures |
| C—OCH₃ | c-C₃H₅ | H | H | CH₃ | mixtures |
| C—OCH₃ | c-C₃H₅ | H | CH₃ | H | ± |
| C—OCH₃ | c-C₃H₅ | H | CH₃ | CH₃ | mixtures |
| C—OCH₃ | c-C₃H₅ | H | C₂H₅ | H | ± |
| C—OCH₃ | c-C₃H₅ | H | C₂H₅ | CH₃ | mixtures |
| C—OCH₃ | c-C₃H₅ | H | C₂H₅ | C₂H₅ | mixtures |
| C—OCH₃ | c-C₃H₅ | NH₂ | H | H | cis + trans |
| C—OCH₃ | c-C₃H₅ | NH₂ | H | H | cis |
| C—OCH₃ | c-C₃H₅ | NH₂ | H | H | trans |
| C—OCH₃ | c-C₃H₅ | NH₂ | H | CH₃ | mixtures |
| C—OCH₃ | c-C₃H₅ | NH₂ | CH₃ | H | ± |
| C—OCH₃ | c-C₃H₅ | NH₂ | CH₃ | CH₃ | mixtures |
| C—OCH₃ | c-C₃H₅ | NH₂ | C₂H₅ | H | ± |
| C—OCH₃ | c-C₃H₅ | NH₂ | C₂H₅ | CH₃ | mixtures |
| C—OCH₃ | c-C₃H₅ | NH₂ | C₂H₅ | C₂H₅ | mixtures |
| C—F | c-C₃H₅ | H | H | CH₃ | mixtures |
| C—F | c-C₃H₅ | H | H | H | ± |
| C—F | c-C₃H₅ | H | CH₃ | H | ± |
| C—F | c-C₃H₅ | NH₂ | H | H | cis + trans |
| C—F | c-C₃H₅ | NH₂ | H | CH₃ | mixture |
| C—F | c-C₃H₅ | NH₂ | CH₃ | H | ± |
| C—F | c-C₃H₅ | NH₂ | C₂H₅ | H | ± |
| N | c-C₃H₅ | H | H | H | cis + trans |
| N | c-C₃H₅ | H | H | H | cis |
| N | c-C₃H₅ | H | H | H | trans |
| N | c-C₃H₅ | H | H | CH₃ | mixtures |
| N | c-C₃H₅ | H | CH₃ | H | ± |
| N | C₆H₃F₂(2,4) | H | H | H | cis + trans |
| N | C₆H₃F₂(2,4) | H | H | H | cis |
| N | C₆H₃F₂(2,4) | H | H | H | trans |
| N | C₆H₃F₂(2,4) | H | H | CH₃ | mixtures |
| N | C₆H₃F₂(2,4) | H | CH₃ | H | ± |
| C-OCH₂CH(CH₃) | H | H | H | | cis + trans |
| C-OCH₂CH(CH₃) | H | H | CH₃ | | mixtures |
| C-OCH₂CH(CH₃) | H | CH₃ | H | | ± |

Q = C—H, C—(C₁-C₂) alkyl, C—OCH₃, C—F or N, and when Q is CH and the nitrogen atom to which R₁ is linked forms substituted 6 membered ring with the carbon atom of Q and R₁ are C—CH₂CH₂C*H(CH₃) or C—OCH₂CH(CH₃);

R₁ = C₂H₅, c-C₃H₅, or C₆H₃F₂(2,4), and when Q is CH and the nitrogen atom to which R₁ is linked forms substituted 6 membered ring with the carbon atom of Q and R₁ are C—CH₂CH₂C*H(CH₃) or C—OCH₂CH(CH₃);

R₅ = H, or NH₂;

R₈ = H, CH₃, or C₂H₅;

R₉ = H, CH₃, or C₂H₅;

and optical isomers, pharmaceutically acceptable salts, hydrates, biohydrolyzable esters, polymorphs and pseudomorphs thereof.

TABLE 14

| Q | R₁ | R₅ | R₉ | Isomers |
|---|---|---|---|---|
| C—H | CH₃ | H | H | cis + trans |
| C—CH₃ | c-C₃H₅ | H | H | cis + trans |
| C—CH₃ | c-C₃H₅ | NH₂ | H | cis + trans |
| C—CH₃ | C₂H₅ | H | H | cis + trans |
| C—CH₃ | C₆H₃F₂(2,4) | H | H | cis + trans |
| C—C₂H₅ | C₂H₅ | H | H | cis + trans |
| C—C₂H₅ | c-C₃H₅ | H | H | cis + trans |
| C—C₂H₅ | C₆H₃F₂(2,4) | H | H | cis + trans |
| C—OCH₃ | c-C₃H₅ | H | H | cis + trans |
| C—OCH₃ | c-C₃H₅ | H | C₂H₅ | Mixture |
| C—OCH₃ | c-C₃H₅ | NH₂ | H | cis + trans |
| C—OCH₃ | c-C₃H₅ | NH₂ | C₂H₅ | Mixture |
| C—F | c-C₃H₅ | NH₂ | H | cis + trans |
| N | c-C₃H₅ | H | H | cis + trans |
| N | C₆H₃F₂(2,4) | H | H | cis + trans |
| C-OCH₂CH(CH₃) | H | H | | cis + trans |

Q = C—H, C—(C₁-C₂) alkyl, C—OCH₃, C—F or N, and when Q is CH and the nitrogen atom to which R₁ is linked forms substituted 6 membered ring with the carbon atom of Q and R₁ is C—OCH₂CH(CH₃);

R₁ = C₁₋₂ alkyl, c-C₃H₅, or C₆H₃F₂(2,4), and when Q is CH and the nitrogen atom to which R₁ is linked forms substituted 6 membered ring with the carbon atom of Q and R₁ is C—OCH₂CH(CH₃);

R₅ = H, or NH₂;

R₉ = H, or C₂H₅;

and optical isomers, pharmaceutically acceptable salts, hydrates, biohydrolyzable esters, polymorphs and pseudomorphs thereof.

TABLE 15

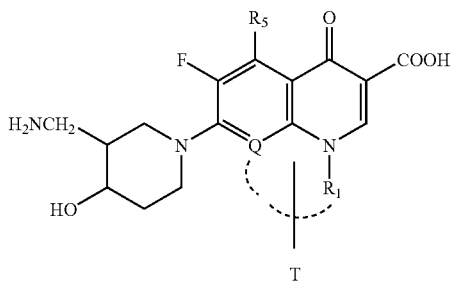

| Q | $R_1$ | $R_5$ | Isomers |
|---|---|---|---|
| C—H | c-$C_3H_5$ | H | cis + trans |
| C—H | c-$C_3H_5$ | $CH_3$ | cis + trans |
| C—$OCH_3$ | c-$C_3H_5$ | H | cis + trans |
| C—F | c-$C_3H_5$ | $CH_3$ | cis + trans |
| C—F | c-$C_3H_5$ | $NH_2$ | cis + trans |
| N | c-$C_3H_5$ | H | cis + trans |
| N | $C_6H_3F_2(2,4)$ | H | cis + trans |
| C-$OCH_2CH(CH_3)$ | | H | cis + trans |

Q = C—H, C—($C_1$-$C_2$) alkyl, C—$OCH_3$, C—F or N, and when Q is CH and the nitrogen atom to which $R_1$ is linked forms substituted 6 membered ring with the carbon atom of Q and $R_1$ is C—$OCH_2CH(CH_3)$;
$R_1$ = c-$C_3H_5$, or $C_6H_3F_2(2,4)$, and when Q is CH and the nitrogen atom to which $R_1$ is linked forms substituted 6 membered ring with the carbon atom of Q and $R_1$ is C—$OCH_2CH(CH_3)$;
$R_5$ = H, $CH_3$, or $NH_2$;
and optical isomers, pharmaceutically acceptable salts, hydrates, biohydrolyzable esters, polymorphs and pseudomorphs thereof.

TABLE 16

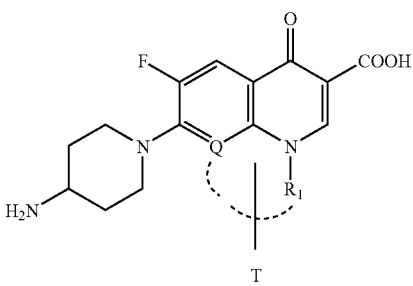

| Q | $R_1$ |
|---|---|
| C—$CH_3$ | $C_2H_5$ |
| C—$CH_3$ | c-$C_3H_5$ |
| C—$CH_3$ | $C_6H_3F_2(2,4)$ |
| C—$C_2H_5$ | $C_2H_5$ |
| C—$C_2H_5$ | c-$C_3H_5$ |
| C—$C_2H_5$ | $C_6H_3F_2(2,4)$ |

Q = C—$CH_3$, or C—$C_2H_5$;
$R_1$ = $C_2H_5$, c-$C_3H_5$, or C—$C_6H_3F_2(2,4)$;
and pharmaceutically acceptable salts, hydrates, biohydrolyzable esters, polymorphs and pseudomorphs thereof.

Particularly preferred compounds of the invention are those where Q is C—$OCH_3$ and C—$CH_3$. A list of these preferred compounds are given below under the heading of specific compounds of the invention.

Specific Compounds of the Invention 1. 1-Cyclopropyl-6-fluoro-1,4-dihydro-8-methoxy-7-(4-amino-3-methyl-1-piperidinyl)-4-oxo-quinoline-3-carboxylic acid (mixture of cis and trans isomers) and its salts;
2. trans-1-Cyclopropyl-6-fluoro-1,4-dihydro-8-methoxy-7-(4-amino-3-methyl-1-piperidinyl)-4-oxo-quinoline-3-carboxylic acid (racemic mixture of 4R, 3R and 4S, 3S) and its salts;
3. trans-1-Cyclopropyl-6-fluoro-1,4-dihydro-8-methoxy-7-(4-amino-3-methyl-1-piperidinyl)-4-oxo-quinoline-3-carboxylic acid (4R, 3R) and its salts;
4. trans-1-Cyclopropyl-6-fluoro-1,4-dihydro-8-methoxy-7-(4-amino-3-methyl-1-piperidinyl)-4-oxo-quinoline-3-carboxylic acid (4S, 3S) and its salts;
5. cis-1-Cyclopropyl-6-fluoro-1,4-dihydro-8-methoxy-7-(4-amino-3-methyl-1-piperidinyl)-4-oxo-quinoline-3-carboxylic acid (racemic mixture of 4S, 3R and 4R, 3S) and its salts;
6. cis-1-Cyclopropyl-6-fluoro-1,4-dihydro-8-methoxy-7-(4-amino-3-methyl-1-piperidinyl)-4-oxo-quinoline-3-carboxylic acid (4S, 3R) and its salts;
7. 1-Cyclopropyl-6-fluoro-1,4-dihydro-8-methoxy-7-(4-amino-3-ethyl-1-piperidinyl)-4-oxo-quinoline-3-carboxylic acid (mixture of cis and trans isomers) and its salts;
8. 1-Cyclopropyl-6-fluoro-1,4-dihydro-8-methoxy-7-(4-methylamino-3-methyl-1-piperidinyl)-4-oxo-quinoline-3-carboxylic acid and its isomers and its salts;
9. 1-Cyclopropyl-6-fluoro-1,4-dihydro-8-methoxy-7-(4-methylamino-3-ethyl-1-piperidinyl)-4-oxo-quinoline-3-carboxylic acid and its isomers and its salts;
10. 1-Cyclopropyl-6-fluoro-1,4-dihydro-8-methoxy-7-(4-ethylamino-3-methyl-1-piperidinyl)-4-oxo-quinoline-3-carboxylic acid and its isomers and its salts;
11. 1-Cyclopropyl-6-fluoro-1,4-dihydro-8-methoxy-7-(4-cyclopropylamino-3-methyl-1-piperidinyl)-4-oxo-quinoline-3-carboxylic acid and its isomers and its salts;
12. 1-Cyclopropyl-6-fluoro-1,4-dihydro-8-methoxy-7-(4-cyclopropylamino-3-ethyl-1-piperidinyl)-4-oxo-quinoline-3-carboxylic acid and its isomers and its salts;
13. 1-Cyclopropyl-6-fluoro-1,4-dihydro-8-methoxy-7-(4-dimethylamino-3-methyl-1-piperidinyl)-4-oxo-quinoline-3-carboxylic acid and its isomers and its salts;
14. 1-Cyclopropyl-6-fluoro-1,4-dihydro-8-methoxy-7-(4-dimethylamino-3-ethyl-1-piperidinyl)-4-oxo-quinoline-3-carboxylic acid and its isomers and its salts;
15. 1-Ethyl-6-fluoro-1,4-dihydro-8-methoxy-7-(4-amino-3,3-dimethyl-1-piperidinyl)-4-oxo-quinoline-3-carboxylic acid and its isomers and its salts;
16. 1-(2,4-Difluorophenyl)-6-fluoro-1,4-dihydro-8-methoxy-7-(4-amino-3,3-dimethyl-1-piperidinyl)-4-oxo-quinoline-3-carboxylic acid and its isomers and its salts;
17. (±)-1-Cyclopropyl-6-fluoro-1,4-dihydro-8-methoxy-7-(4-amino-3,3-dimethyl-1-piperidinyl)-4-oxo-quinoline-3-carboxylic acid, its salts and its polymorphs;
18. (±)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs;
19. (±)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs;
20. (±)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs;
21. (+)-1-Cyclopropyl-6-fluoro-1,4-dihydro-8-methoxy-7-(4-amino-3,3-dimethyl-1-piperidinyl)-4-oxo-quinoline-3-carboxylic acid, its salts and its polymoprhs;
22. (+)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs;

23. (+)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs;
24. (+)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs;
25. (−)-1-Cyclopropyl-6-fluoro-1,4-dihydro-8-methoxy-7-(4-amino-3,3-dimethyl-1-piperidinyl)-4-oxo-quinoline-3-carboxylic acid, its salts and its polymorphs;
26. (−)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs;
27. (−)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs;
28. (−)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs;
29. 1-Cyclopropyl-6-fluoro-1,4-dihydro-8-methoxy-7-(4-acetylamino-3,3-dimethyl-1-piperidinyl)-4-oxo-quinoline-3-carboxylic acid and its isomers and its salts;
30. 1-Cyclopropyl-6-fluoro-1,4-dihydro-8-methoxy-7-(4-carbethoxyamino-3,3-dimethyl-1-piperidinyl)-4-oxo-quinoline-3-carboxylic acid and its isomers and its salts;
31. 1-Cyclopropyl-6-fluoro-1,4-dihydro-8-methoxy-7-(4-$^t$-butyloxycarbonylamino-3,3-dimethyl-1-piperidinyl)-4-oxo-quinoline-3-carboxylic acid and its isomers and its salts;
32. (±)-1-Cyclopropyl-6-fluoro-1,4-dihydro-8-methoxy-7-(4-benzyloxycarbonylamino-3,3-dimethyl-1-piperidinyl)-4-oxo-quinoline-3-carboxylic acid and its salts;
33. (+)-1-Cyclopropyl-6-fluoro-1,4-dihydro-8-methoxy-7-(4-benzyloxycarbonylamino-3,3-dimethyl-1-piperidinyl)-4-oxo-quinoline-3-carboxylic acid and its salts;
34. (−)-1-Cyclopropyl-6-fluoro-1,4-dihydro-8-methoxy-7-(4-benzyloxycarbonylamino-3,3-dimethyl-1-piperidinyl)-4-oxo-quinoline-3-carboxylic acid and its salts;
35. 1-Cyclopropyl-6-fluoro-1,4-dihydro-8-methoxy-7-(4-methylamino-3,3-dimethyl-1-piperidinyl)-4-oxo-quinoline-3-carboxylic acid and its isomers and its salts;
36. 1-Cyclopropyl-6-fluoro-1,4-dihydro-8-methoxy-7-(4-ethylamino-3,3-dimethyl-1-piperidinyl)-4-oxo-quinoline-3-carboxylic acid and its isomers and its salts;
37. 1-Cyclopropyl-6-fluoro-1,4-dihydro-8-methoxy-7-(4-cyclopropylamino-3,3-dimethyl-1-piperidinyl)-4-oxo-quinoline-3-carboxylic acid and its isomers and its salts;
38. 1-Cyclopropyl-6-fluoro-1,4-dihydro-8-methoxy-7-(4-dimethylamino-3,3-dimethyl-1-piperidinyl)-4-oxo-quinoline-3-carboxylic acid and its isomers and its salts;
39. 1-Cyclopropyl-6-fluoro-1,4-dihydro-8-methoxy-7-(4-amino-3-ethyl-3-methyl-1-piperidinyl)-4-oxo-quinoline-3-carboxylic acid, its isomers, and its salts;
40. 1-Cyclopropyl-6-fluoro-1,4-dihydro-8-methoxy-7-(4-methylamino-3-ethyl-3-methyl-1-piperidinyl)-4-oxo-quinoline-3-carboxylic acid, its isomers, and its salts;
41. 1-Cyclopropyl-6-fluoro-1,4-dihydro-8-methoxy-7-(4-cyclopropylamino-3-ethyl-3-methyl-1-piperidinyl)-4-oxo-quinoline-3-carboxylic acid, its isomers, and its salts;
42. 1-Cyclopropyl-6-fluoro-1,4-dihydro-8-methoxy-7-(4-dimethyamino-3-ethyl-3-methyl-1-piperidinyl)-4-oxo-quinoline-3-carboxylic acid and its isomers and its salts;
43. 1-Cyclopropyl-6-fluoro-1,4-dihydro-8-methoxy-7-(4-amino-3,3-diethyl-1-piperidinyl)-4-oxo-quinoline-3-carboxylic acid and its isomers and its salts;
44. 1-Cyclopropyl-6-fluoro-1,4-dihydro-8-methoxy-7-(4-amino-3,5-dimethyl-1-piperidinyl)-4-oxo-quinoline-3-carboxylic acid and its isomers and its salts;
45. 1-Cyclopropyl-6-fluoro-1,4-dihydro-8-methoxy-7-(4-methylamino-3,5-dimethyl-1-piperidinyl)-4-oxo-quinoline-3-carboxylic acid and its isomers and its salts;
46. 1-Ethyl-6-fluoro-1,4-dihydro-8-methoxy-7-(4-methylamino-3,5-dimethyl-1-piperidinyl)-4-oxo-quinoline-3-carboxylic acid and its isomers and its salts;
47. 1-Cyclopropyl-6-fluoro-1,4-dihydro-8-methoxy-7-(4-ethylamino-3,5-dimethyl-1-piperidinyl)-4-oxo-quinoline-3-carboxylic acid and its isomers and its salts;
48. 1-Cyclopropyl-6-fluoro-1,4-dihydro-8-methoxy-7-(4-cyclopropylamino-3,5-dimethyl-1-piperidinyl)-4-oxo-quinoline-3-carboxylic acid and its isomers and its salts;
49. 1-Cyclopropyl-6-fluoro-1,4-dihydro-8-methoxy-7-(4-dimethylamino-3,5-dimethyl-1-piperidinyl)-4-oxo-quinoline-3-carboxylic acid and its isomers and its salts;
50. 1-Cyclopropyl-6-fluoro-1,4-dihydro-8-methoxy-7-(4-amino-3,3,5-trimethyl-1-piperidinyl)-4-oxo-quinoline-3-carboxylic acid and its isomers and its salts;
51. 1-Cyclopropyl-6-fluoro-1,4-dihydro-8-methoxy-7-(4-amino-3-ethyl-3,5-dimethyl-1-piperidinyl)-4-oxo-quinoline-3-carboxylic acid and its isomers and its salts;
52. 1-Cyclopropyl-6-fluoro-1,4-dihydro-8-methoxy-7-(4-amino-3-methyl-3,5-diethyl-1-piperidinyl)-4-oxo-quinoline-3-carboxylic acid, its isomers, and its salts;
53. 5-Amino-1-cyclopropyl-6-fluoro-1,4-dihydro-8-methoxy-7-(4-amino-3-methyl-1-piperidinyl)-4-oxo-quinoline-3-carboxylic acid (mixture of cis and trans isomers) and its salts;
54. trans-5-Amino-1-cyclopropyl-6-fluoro-1,4-dihydro-8-methoxy-7-(4-amino-3-methyl-1-piperidinyl)-4-oxo-quinoline-3-carboxylic acid (racemic mixture of 4R, 3R and 4S, 3S) and its salts;
55. trans-5-Amino-1-cyclopropyl-6-fluoro-1,4-dihydro-8-methoxy-7-(4-amino-3-methyl-1-piperidinyl)-4-oxo-quinoline-3-carboxylic acid (4R, 3R) and its salts;
56. trans-5-Amino-1-cyclopropyl-6-fluoro-1,4-dihydro-8-methoxy-7-(4-amino-3-methyl-1-piperidinyl)-4-oxo-quinoline-3-carboxylic acid (4S, 3S) and its salts;
57. cis-5-Amino-1-cyclopropyl-6-fluoro-1,4-dihydro-8-methoxy-7-(4-amino-3-methyl-1-piperidinyl)-4-oxo-quinoline-3-carboxylic acid (racemic mixture of 4S, 3R and 4R, 3S) and its salts;
58. cis-5-Amino-1-cyclopropyl-6-fluoro-1,4-dihydro-8-methoxy-7-(4-amino-3-methyl-1-piperidinyl)-4-oxo-quinoline-3-carboxylic acid (4S, 3R) and its salts;
59. cis-5-Amino-1-cyclopropyl-6-fluoro-1,4-dihydro-8-methoxy-7-(4-amino-3-methyl-1-piperidinyl)-4-oxo-quinoline-3-carboxylic acid (4R, 3S) and its salts;
60. 5-Amino-1-cyclopropyl-6-fluoro-1,4-dihydro-8-methoxy-7-(4-methylamino-3-methyl-1-piperidinyl)-4-oxo-quinoline-3-carboxylic acid and its isomers and its salts;
61. 5-Amino-1-cyclopropyl-6-fluoro-1,4-dihydro-8-methoxy-7-(4-ethylamino-3-methyl-1-piperidinyl)-4-oxo-quinoline-3-carboxylic acid and its isomers and its salts;
62. 5-Amino-1-cyclopropyl-6-fluoro-1,4-dihydro-8-methoxy-7-(4-cyclopropylamino-3-methyl-1-piperidinyl)-4-oxo-quinoline-3-carboxylic acid and its isomers and its salts;
63. 5-Amino-1-cyclopropyl-6-fluoro-1,4-dihydro-8-methoxy-7-(4-dimethylamino-3-methyl-1-piperidinyl)-4-oxo-quinoline-3-carboxylic acid and its isomers and its salts;
64. 5-Amino-1-cyclopropyl-6-fluoro-1,4-dihydro-8-methoxy-7-(4-amino-3-ethyl-1-piperidinyl)-4-oxo-quinoline-3-carboxylic acid and its isomers and its salts;
65. 5-Amino-1-cyclopropyl-6-fluoro-1,4-dihydro-8-methoxy-7-(4-methylamino-3-ethyl-1-piperidinyl)-4-oxo-quinoline-3-carboxylic acid and its isomers and its salts;

66. 5-Amino-1-cyclopropyl-6-fluoro-1,4-dihydro-8-methoxy-7-(4-cyclopropylamino-3-ethyl-1-piperidinyl)-4-oxo-quinoline-3-carboxylic acid and its isomers and its salts;
67. 5-Amino-1-cyclopropyl-6-fluoro-1,4-dihydro-8-methoxy-7-(4-dimethylamino-3-ethyl-1-piperidinyl)-4-oxo-quinoline-3-carboxylic acid and its isomers and its salts;
68. 5-Amino-1-cyclopropyl-6-fluoro-1,4-dihydro-8-methoxy-7-(4-amino-3,3-dimethyl-1-piperidinyl)-4-oxo-quinoline-3-carboxylic acid and its isomers and its salts;
69. 5-Amino-1-cyclopropyl-6-fluoro-1,4-dihydro-8-methoxy-7-(4-acetylamino-3,3-dimethyl-1-piperidinyl)-4-oxo-quinoline-3-carboxylic acid and its isomers and its salts;
70. 5-Amino-1-cyclopropyl-6-fluoro-1,4-dihydro-8-methoxy-7-(4-ethoxycarbonylamino-3,3-dimethyl-1-piperidinyl)-4-oxo-quinoline-3-carboxylic acid and its isomers and its salts;
71. 5-Amino-1-cyclopropyl-6-fluoro-1,4-dihydro-8-methoxy-7-(4-t-butoxycarbonyl amino-3,3-dimethyl-1-piperidinyl)-4-oxo-quinoline-3-carboxylic acid and its isomers and its salts;
72. 5-Amino-1-cyclopropyl-6-fluoro-1,4-dihydro-8-methoxy-7-(4-benzyloxycarbonyl amino-3,3-dimethyl-1-piperidinyl)-4-oxo-quinoline-3-carboxylic acid and its isomers and its salts;
73. 5-Amino-1-cyclopropyl-6-fluoro-1,4-dihydro-8-methoxy-7-(4-methylamino-3,3-dimethyl-1-piperidinyl)-4-oxo-quinoline-3-carboxylic acid and its isomers and its salts;
74. 5-Amino-1-cyclopropyl-6-fluoro-1,4-dihydro-8-methoxy-7-(4-ethylamino-3,3-dimethyl-1-piperidinyl)-4-oxo-quinoline-3-carboxylic acid and its isomers and its salts;
75. 5-Amino-1-cyclopropyl-6-fluoro-1,4-dihydro-8-methoxy-7-(4-cyclopropylamino-3,3-dimethyl-1-piperidinyl)-4-oxo-quinoline-3-carboxylic acid and its isomers and its salts;
76. 5-Amino-1-cyclopropyl-6-fluoro-1,4-dihydro-8-methoxy-7-(4-dimethylamino-3,3-dimethyl-1-piperidinyl)-4-oxo-quinoline-3-carboxylic acid and its isomers and its salts;
77. 5-Amino-1-cyclopropyl-6-fluoro-1,4-dihydro-8-methoxy-7-(4-amino-3-ethyl-3-methyl-1-piperidinyl)-4-oxo-quinoline-3-carboxylic acid, its isomers, and its salts;
78. 5-Amino-1-cyclopropyl-6-fluoro-1,4-dihydro-8-methoxy-7-(4-methylamino-3-ethyl-3-methyl-1-piperidinyl)-4-oxo-quinoline-3-carboxylic acid, its isomers, and its salts;
79. 5-Amino-1-cyclopropyl-6-fluoro-1,4-dihydro-8-methoxy-7-(4-cyclopropylamino-3-methyl-3-ethyl-1-piperidinyl)-4-oxo-quinoline-3-carboxylic acid, its isomers, and its salts;
80. 5-Amino-1-cyclopropyl-6-fluoro-1,4-dihydro-8-methoxy-7-(4-dimethylamino-3-methyl-3-ethyl-1-piperidinyl)-4-oxo-quinoline-3-carboxylic acid and its isomers and its salts;
81. 5-Amino-1-cyclopropyl-6-fluoro-1,4-dihydro-8-methoxy-7-(4-amino-3,3-diethyl-1-piperidinyl)-4-oxo-quinoline-3-carboxylic acid and its isomers and its salts;
82. 5-Amino-1-cyclopropyl-6-fluoro-1,4-dihydro-8-methoxy-7-(4-amino-3,5-dimethyl-1-piperidinyl)-4-oxo-quinoline-3-carboxylic acid and its isomers and its salts;
83. 5-Amino-1-cyclopropyl-6-fluoro-1,4-dihydro-8-methoxy-7-(4-methylamino-3,5-dimethyl-1-piperidinyl)-4-oxo-quinoline-3-carboxylic acid and its isomers and its salts;
84. 5-Amino-1-cyclopropyl-6-fluoro-1,4-dihydro-8-methoxy-7-(4-ethylamino-3,5-dimethyl-1-piperidinyl)-4-oxo-quinoline-3-carboxylic acid and its isomers and its salts;
85. 5-Amino-1-cyclopropyl-6-fluoro-1,4-dihydro-8-methoxy-7-(4-cyclopropylamino-3,5-dimethyl-1-piperidinyl)-4-oxo-quinoline-3-carboxylic acid and its isomers and its salts;
86. 5-Amino-1-cyclopropyl-6-fluoro-1,4-dihydro-8-methoxy-7-(4-dimethylamino-3,5-dimethyl-1-piperidinyl)-4-oxo-quinoline-3-carboxylic acid and its isomers and its salts;
87. 5-Amino-1-cyclopropyl-6-fluoro-1,4-dihydro-8-methoxy-7-(4-amino-3,3,5-trimethyl-1-piperidinyl)-4-oxo-quinoline-3-carboxylic acid and its isomers and its salts;
88. 5-Amino-1-cyclopropyl-6-fluoro-1,4-dihydro-8-methoxy-7-(4-amino-3-ethyl-3,5-dimethyl-1-piperidinyl)-4-oxo-quinoline-3-carboxylic acid and its isomers and its salts;
89. 5-Amino-1-cyclopropyl-6-fluoro-1,4-dihydro-8-methoxy-7-(4-amino-3-methyl-3,5-diethyl-1-piperidinyl)-4-oxo-quinoline-3-carboxylic acid and its isomers and its salts;
90. 1-Cyclopropyl-6-fluoro-1,4-dihydro-8-methyl-7-(4-amino-1-piperidinyl)-4-oxo-quinoline-3-carboxylic acid and its salts;
91. 1-Cyclopropyl-6-fluoro-8-methyl-7-(4-hydroxy-1-piperidinyl)-1,4-dihydro-4-oxo-quinoline-3-carboxylic acid and its isomers and its salts;
92. cis/trans-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts;
93. cis-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts;
94. trans-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts;
95. (±)-1-Cyclopropyl-6-fluoro-8-methyl-7-(4-hydroxy-3,3-dimethyl-1-piperidinyl)-1,4-dihydro-4-oxo-quinoline-3-carboxylic acid and its isomers and its salts;
96. cis/trans-1-Cyclopropyl-6-fluoro-8-methyl-7-(4-hydroxy-3-ethyl-1-piperidinyl)-1,4-dihydro-4-oxo-quinoline-3-carboxylic acid and its isomers and its salts;
97. trans-1-Cyclopropyl-6-fluoro-1,4-dihydro-8-methyl-7-(4-amino-3-methyl-1-piperidinyl)-4-oxo-quinoline-3-carboxylic acid and its isomers, its salts and its polymorphs;
98. trans-1-Cyclopropyl-6-fluoro-1,4-dihydro-8-methyl-7-(4-amino-3-methyl-1-piperidinyl)-4-oxo-quinoline-3-carboxylic acid hydrochloride and its polymorphs;
99. cis-1-Cyclopropyl-6-fluoro-1,4-dihydro-8-methyl-7-(4-amino-3-methyl-1-piperidinyl)-4-oxo-quinoline-3-carboxylic acid and its isomers and its salts;
100. cis-1-Cyclopropyl-6-fluoro-1,4-dihydro-8-methyl-7-(4-amino-3-methyl-1-piperidinyl)-4-oxo-quinoline-3-carboxylic acid hydrochloride and its polymorphs;
101. (±)-1-Cyclopropyl-6-fluoro-1,4-dihydro-8-methyl-7-(4-amino-3,3-dimethyl-1-piperidinyl)-4-oxo-quinoline-3-carboxylic acid, its salts and its polymorphs;
102. (±)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs;
103. (±)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs;
104. (±)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs;

105. (+)-1-Cyclopropyl-6-fluoro-1,4-dihydro-8-methyl-7-(4-amino-3,3-dimethyl-1-piperidinyl)-4-oxo-quinoline-3-carboxylic acid, its salts and its polymorphs;

106. (+)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs;

107. (+)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs;

108. (+)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs;

109. (−)-1-Cyclopropyl-6-fluoro-1,4-dihydro-8-methyl-7-(4-amino-3,3-dimethyl-1-piperidinyl)-4-oxo-quinoline-3-carboxylic acid and its salts;

110. (−)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs;

111. (−)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs;

112. (−)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs;

113. 1-Cyclopropyl-6-fluoro-1,4-dihydro 8-methyl-7-(4-methylamino-3-methyl-1-piperidinyl)-4-oxo-quinoline-3-carboxylic acid and its isomers and its salts;

114. 1-Cyclopropyl-6-fluoro-1,4-dihydro-8-methyl-7-(4-dimethylamino-3-methyl-1-piperidinyl)-4-oxo-quinoline-3-carboxylic acid and its isomers and its salts;

115. 1-Cyclopropyl-6-fluoro-1,4-dihydro-8-methyl-7-(4-ethylamino-3,3-dimethyl-1-piperidinyl)-4-oxo-quinoline-3-carboxylic acid and its isomers and its salts;

116. 1-Cyclopropyl-6-fluoro-1,4-dihydro-8-methyl-7-(4-dimethylamino-3,3-dimethyl-1-piperidinyl)-4-oxo-quinoline-3-carboxylic acid and its isomers and its salts;

117. 1-Cyclopropyl-6-fluoro-8-ethyl-7-(4-amino-1-piperidinyl)-1,4-dihydro-4-oxo-quinoline-3-carboxylic acid and its isomers and its salts;

118. 1-Cyclopropyl-6-fluoro-8-ethyl-7-(4-hydroxy-1-piperidinyl)-1,4-dihydro-4-oxo-quinoline-3-carboxylic acid and its isomers and its salts;

119. cis/trans-1-Cyclopropyl-6-fluoro-8-ethyl-7-(4-hydroxy-3-methyl-1-piperidinyl)-1,4-dihydro-4-oxo-quinoline-3-carboxylic acid and its isomers and its salts;

120. cis-1-Cyclopropyl-6-fluoro-8-ethyl-7-(4-hydroxy-3-methyl-1-piperidinyl)-1,4-dihydro-4-oxo-quinoline-3-carboxylic acid and its isomers and its salts;

121. trans-1-Cyclopropyl-6-fluoro-8-ethyl-7-(4-hydroxy-3-methyl-1-piperidinyl)-1,4-dihydro-4-oxo-quinoline-3-carboxylic acid and its isomers and its salts;

122. (±)-1-Cyclopropyl-6-fluoro-8-ethyl-7-(4-hydroxy-3,3-dimethyl-1-piperidinyl)-1,4-dihydro-4-oxo-quinoline-3-carboxylic acid and its isomers and its salts;

123. cis/trans-1-Cyclopropyl-6-fluoro-8-ethyl-7-(4-hydroxy-3-ethyl-1-piperidinyl)-1,4-dihydro-4-oxo-quinoline-3-carboxylic acid and its isomers and its salts;

124. trans-1-Cyclopropyl-6-fluoro-1,4-dihydro-8-ethyl-7-(4-amino-3-methyl-1-piperidinyl)-4-oxo-quinoline-3-carboxylic acid and its isomers and its salts;

125. cis-1-Cyclopropyl-6-fluoro-1,4-dihydro-8-ethyl-7-(4-amino-3-methyl-1-piperidinyl)-4-oxo-quinoline-3-carboxylic acid and its isomers and its salts;

126. (±)-1-Cyclopropyl-6-fluoro-1,4-dihydro-8-ethyl-7-(4-amino-3,3-dimethyl-1-piperidinyl)-4-oxo-quinoline-3-carboxylic acid and its salts;

127. (+)-1-Cyclopropyl-6-fluoro-1,4-dihydro-8-ethyl-7-(4-amino-3,3-dimethyl-1-piperidinyl)-4-oxo-quinoline-3-carboxylic acid and its salts;

128. (−)-1-Cyclopropyl-6-fluoro-1,4-dihydro-8-ethyl-7-(4-amino-3,3-dimethyl-1-piperidinyl)-4-oxo-quinoline-3-carboxylic acid and its salts;

129. trans-5-Amino-1-cyclopropyl-6-fluoro-1,4-dihydro-8-methyl-7-(4-amino-3-methyl-1-piperidinyl)-4-oxo-quinoline-3-carboxylic acid and its isomers and its salts;

130. cis-1-5-Amino-1-cyclopropyl-6-fluoro-1,4-dihydro-8-methyl-7-(4-amino-3-methyl-1-piperidinyl)-4-oxo-quinoline-3-carboxylic acid and its isomers and its salts;

131. (±)-5-Amino-1-cyclopropyl-6-fluoro-1,4-dihydro-8-methyl-7-(4-amino-3,3-dimethyl-1-piperidinyl)-4-oxo-quinoline-3-carboxylic acid and its salts;

132. (+)-5-Amino-1-cyclopropyl-6-fluoro-1,4-dihydro-8-methyl-7-(4-amino-3,3-dimethyl-1-piperidinyl)-4-oxo-quinoline-3-carboxylic acid and its salts;

133. (−)-5-Amino-1-cyclopropyl-6-fluoro-1,4-dihydro-8-methyl-7-(4-amino-3,3-dimethyl-1-piperidinyl)-4-oxo-quinoline-3-carboxylic acid and its salts;

134. 1-Cyclopropyl-6-fluoro-1,4-dihydro-8-methoxy-7-(4-hydroxy-3-methyl-1-piperidinyl)-4-oxo-quinoline-3-carboxylic acid and its isomers and its salts;

135. 5-Amino-1-cyclopropyl-6-fluoro-1,4-dihydro-8-methoxy-7-(4-hydroxy-3-methyl-1-piperidinyl)-4-oxo-quinoline-3-carboxylic acid and its isomers and its salts;

136. 1-Cyclopropyl-6-fluoro-1,4-dihydro-8-methoxy-7-(4-hydroxy-3-ethyl-1-piperidinyl)-4-oxo-quinoline-3-carboxylic acid and its isomers and its salts;

137. 5-Amino-1-cyclopropyl-6-fluoro-1,4-dihydro-8-methoxy-7-(4-hydroxy-3-ethyl-1-piperidinyl)-4-oxo-quinoline-3-carboxylic acid and its isomers and its salts;

138. 1-Cyclopropyl-6-fluoro-1,4-dihydro-8-methoxy-7-(4-hydroxy-3-n-propyl-1-piperidinyl)-4-oxo-quinoline-3-carboxylic acid and its isomers and its salts;

139. 5-Amino-1-cyclopropyl-6-fluoro-1,4-dihydro-8-methoxy-7-(4-hydroxy-3-isopropyl 1-1-piperidinyl)-4-oxo-quinoline-3-carboxylic acid and its isomers and its salts;

140. 5-Amino-1-cyclopropyl-6-fluoro-1,4-dihydro-8-methoxy-7-(4-hydroxy-3-isobutyl 1-1-piperidinyl)-4-oxo-quinoline-3-carboxylic acid and its isomers and its salts;

141. 1-Cyclopropyl-6-fluoro-1,4-dihydro-8-methoxy-7-(4-hydroxy-3-aminomethyl-1-piperidinyl)-4-oxo-quinoline-3-carboxylic acid and its isomers and its salts;

142. 5-Amino-1-cyclopropyl-6-fluoro-1,4-dihydro-8-methoxy-7-(4-hydroxy-3-aminomethyl-1-piperidinyl)-4-oxo-quinoline-3-carboxylic acid and its isomers and its salts;

143. 1-Cyclopropyl-6-fluoro-1,4-dihydro-8-methoxy-7-(4-hydroxy-3,3-dimethyl-1-piperidinyl)-4-oxo-quinoline-3-carboxylic acid and its isomers and its salts;

144. 5-Amino-1-cyclopropyl-6-fluoro-1,4-dihydro-8-methoxy-7-(4-hydroxy-3,3-dimethyl-1-piperidinyl)-4-oxo-quinoline-3-carboxylic acid and its isomers and its salts;

145. 1-Cyclopropyl-6-fluoro-1,4-dihydro-8-methoxy-7-(4-hydroxy-3,5-dimethyl-1-piperidinyl)-4-oxo-quinoline-3-carboxylic acid and its isomers and its salts;

146. 5-Amino-1-cyclopropyl-6-fluoro-1,4-dihydro-8-methoxy-7-(4-hydroxy-3,5-dimethyl-1-piperidinyl)-4-oxo-quinoline-3-carboxylic acid and its isomers and its salts;

147. 1-Cyclopropyl-6-fluoro-1,4-dihydro-8-methoxy-7-(4-hydroxy-3,3,5-trimethyl-1-piperidinyl)-4-oxo-quinoline-3-carboxylic acid and its isomers and its salts;

148. 5-Amino-1-cyclopropyl-6-fluoro-1,4-dihydro-8-methoxy-7-(4-hydroxy-3,3,5-trimethyl-1-piperidinyl)-4-oxo-quinoline-3-carboxylic acid and its isomers and its salts;

149. 1-Cyclopropyl-6-fluoro-1,4-dihydro-8-methoxy-7-(4-hydroxy-4-methyl-1-piperidinyl)-4-oxo-quinoline-3-carboxylic acid and isomers and its salts;
150. 5-Amino-1-cyclopropyl-6-fluoro-1,4-dihydro-8-methoxy-7-(4-hydroxy-4-methyl-1-piperidinyl)-4-oxo-quinoline-3-carboxylic acid and its isomers and its salts;
151. 1-Cyclopropyl-6-fluoro-1,4-dihydro-8-methoxy-7-(4-hydroxy-4-trifluoro methyl-1-piperidinyl)-4-oxo-quinoline-3-carboxylic acid and its isomers and its salts;
152. 5-Amino-1-cyclopropyl-6-fluoro-1,4-dihydro-8-methoxy-7-(4-hydroxy-4-trifluoro methyl-1-piperidinyl)-4-oxo-quinoline-3-carboxylic acid and its isomers and its salts;
153. 1-Ethyl-6-fluoro-8-methyl-7-(4-amino-1-piperidinyl)-1,4-dihydro-4-oxo-quinoline-3-carboxylic acid and its isomers and its salts;
154. 1-Ethyl-6-fluoro-8-methyl-7-(4-hydroxy-1-piperidinyl)-1,4-dihydro-4-oxo-quinoline-3-carboxylic acid and its isomers and its salts;
155. cis/trans-1-Ethyl-6-fluoro-8-methyl-7-(4-amino-3-methyl-1-piperidinyl)-1,4-dihydro-4-oxo-quinoline-3-carboxylic acid and its isomers and its salts;
156. cis-1-Ethyl-6-fluoro-8-methyl-7-(4-amino-3-methyl-1-piperidinyl)-1,4-dihydro-4-oxo-quinoline-3-carboxylic acid and its isomers and its salts;
157. trans-1-Ethyl-6-fluoro-8-methyl-7-(4-amino-3-methyl-1-piperidinyl)-1,4-dihydro-4-oxo-quinoline-3-carboxylic acid and its isomers and its salts;
158. cis/trans-1-Ethyl-6-fluoro-8-methyl-7-(4-hydroxy-3-methyl-1-piperidinyl)-1,4-dihydro-4-oxo-quinoline-3-carboxylic acid and its isomers and its salts;
159. cis-1-Ethyl-6-fluoro-8-methyl-7-(4-hydroxy-3-methyl-1-piperidinyl)-1,4-dihydro-4-oxo-quinoline-3-carboxylic acid and its isomers and its salts;
160. trans-1-Ethyl-6-fluoro-8-methyl-7-(4-hydroxy-3-methyl-1-piperidinyl)-1,4-dihydro-4-oxo-quinoline-3-carboxylic acid and its isomers and its salts;
161. (±)-1-Ethyl-6-fluoro-8-methyl-7-(4-amino-3,3-dimethyl-1-piperidinyl)-1,4-dihydro-4-oxo-quinoline-3-carboxylic acid and its salts;
162. (+)-1-Ethyl-6-fluoro-8-methyl-7-(4-amino-3,3-dimethyl-1-piperidinyl)-1,4-dihydro-4-oxo-quinoline-3-carboxylic acid and its salts;
163. (−)-1-Ethyl-6-fluoro-8-methyl-7-(4-amino-3,3-dimethyl-1-piperidinyl)-1,4-dihydro-4-oxo-quinoline-3-carboxylic acid and its salts;
164. (±)-1-Ethyl-6-fluoro-8-methyl-7-(4-hydroxy-3,3-dimethyl-1-piperidinyl)-1,4-dihydro-4-oxo-quinoline-3-carboxylic acid and its salts;
165. cis/trans-1-Ethyl-6-fluoro-8-methyl-7-(4-hydroxy-3-ethyl-1-piperidinyl)-1,4-dihydro-4-oxo-quinoline-3-carboxylic acid and its isomers and its salts;
166. cis/trans-1-Ethyl-6-fluoro-8-methyl-7-(4-amino-3-ethyl-1-piperidinyl)-1,4-dihydro-4-oxo-quinoline-3-carboxylic acid and its isomers and its salts;
167. 1-(2,4-Difluorophenyl)-6-fluoro-8-methyl-7-(4-amino-1-piperidinyl)-1,4-dihydro-4-oxo-quinoline-3-carboxylic acid and its isomers and its salts;
168. 1-(2,4-Difluorophenyl)-6-fluoro-8-methyl-7-(4-hydroxy-1-piperidinyl)-1,4-dihydro-4-oxo-quinoline-3-carboxylic acid and its isomers and its salts;
169. cis/trans-1-(2,4-Difluorophenyl)-6-fluoro-8-methyl-7-(4-amino-3-methyl-1-piperidinyl)-1,4-dihydro-4-oxo-quinoline-3-carboxylic acid and its isomers and its salts;
170. cis-1-(2,4-Difluorophenyl)-6-fluoro-8-methyl-7-(4-amino-3-methyl-1-piperidinyl)-1,4-dihydro-4-oxo-quinoline-3-carboxylic acid and its isomers and its salts;
171. trans-1-(2,4-Difluorophenyl)-6-fluoro-8-methyl-7-(4-amino-3-methyl-1-piperidinyl)-1,4-dihydro-4-oxo-quinoline-3-carboxylic acid and its isomers and its salts;
172. cis/trans-1-(2,4-Difluorophenyl)-6-fluoro-8-methyl-7-(4-hydroxy-3-methyl-1-piperidinyl)-1,4-dihydro-4-oxo-quinoline-3-carboxylic acid and its isomers and its salts;
173. cis-1-(2,4-Difluorophenyl)-6-fluoro-8-methyl-7-(4-hydroxy-3-methyl-1-piperidinyl)-1,4-dihydro-4-oxo-quinoline-3-carboxylic acid and its isomers and its salts;
174. trans-1-(2,4-Difluorophenyl)-6-fluoro-8-methyl-7-(4-hydroxy-3-methyl-1-piperidinyl)-1,4-dihydro-4-oxo-quinoline-3-carboxylic acid and its isomers and its salts;
175. (±)-1-(2,4-Difluorophenyl)-6-fluoro-8-methyl-7-(4-amino-3,3-dimethyl-1-piperidinyl)-1,4-dihydro-4-oxo-quinoline-3-carboxylic acid and its salts;
176. (+)-1-(2,4-Difluorophenyl)-6-fluoro-8-methyl-7-(4-amino-3,3-dimethyl-1-piperidinyl)-1,4-dihydro-4-oxo-quinoline-3-carboxylic acid and its salts;
177. (−)-1-(2,4-Difluorophenyl)-6-fluoro-8-methyl-7-(4-amino-3,3-dimethyl-1-piperidinyl)-1,4-dihydro-4-oxo-quinoline-3-carboxylic acid and its salts;
178. (±)-1-(2,4-Difluorophenyl)-6-fluoro-8-methyl-7-(4-hydroxy-3,3-dimethyl-1-piperidinyl)-1,4-dihydro-4-oxo-quinoline-3-carboxylic acid and its salts;
179. cis/trans-1-(2,4-Difluorophenyl)-6-fluoro-8-methyl-7-(4-hydroxy-3-ethyl-1-piperidinyl)-1,4-dihydro-4-oxo-quinoline-3-carboxylic acid and its isomers and its salts;
180. cis/trans-1-(2,4-Difluorophenyl)-6-fluoro-8-methyl-7-(4-amino-3-ethyl-1-piperidinyl)-1,4-dihydro-4-oxo-quinoline-3-carboxylic acid and its isomers and its salts;
181. 1,8-Diethyl-6-fluoro-7-(4-amino-1-piperidinyl)-1,4-dihydro-4-oxo-quinoline-3-carboxylic acid and its isomers and its salts;
182. 1,8-Diethyl-6-fluoro-7-(4-hydroxy-1-piperidinyl)-1,4-dihydro-4-oxo-quinoline-3-carboxylic acid and its isomers and its salts;
183. cis/trans-1,8-Diethyl-6-fluoro-7-(4-amino-3-methyl-1-piperidinyl)-1,4-dihydro-4-oxo-quinoline-3-carboxylic acid and its isomers and its salts;
184. cis-1,8-Diethyl-6-fluoro-7-(4-amino-3-methyl-1-piperidinyl)-1,4-dihydro-4-oxo-quinoline-3-carboxylic acid and its isomers and its salts;
185. trans-1,8-Diethyl-6-fluoro-7-(4-amino-3-methyl-1-piperidinyl)-1,4-dihydro-4-oxo-quinoline-3-carboxylic acid and its isomers and its salts;
186. cis/trans-1,8-Diethyl-6-fluoro-7-(4-hydroxy-3-methyl-1-piperidinyl)-1,4-dihydro-4-oxo-quinoline-3-carboxylic acid and its isomers and its salts;
187. cis-1,8-Diethyl-6-fluoro-7-(4-hydroxy-3-methyl-1-piperidinyl)-1,4-dihydro-4-oxo-quinoline-3-carboxylic acid and its isomers and its salts;
188. trans-1,8-Diethyl-6-fluoro-7-(4-hydroxy-3-methyl-1-piperidinyl)-1,4-dihydro-4-oxo-quinoline-3-carboxylic acid and its isomers and its salts;
189. (±)-1,8-Diethyl-6-fluoro-7-(4-amino-3,3-dimethyl-1-piperidinyl)-1,4-dihydro-4-oxo-quinoline-3-carboxylic acid and its salts;
190. (+)-1,8-Diethyl-6-fluoro-7-(4-amino-3,3-dimethyl-1-piperidinyl)-1,4-dihydro-4-oxo-quinoline-3-carboxylic acid and its salts;
191. (−)-1,8-Diethyl-6-fluoro-7-(4-amino-3,3-dimethyl-1-piperidinyl)-1,4-dihydro-4-oxo-quinoline-3-carboxylic acid and its salts;
192. (±)-1,8-Diethyl-6-fluoro-7-(4-hydroxy-3,3-dimethyl-1-piperidinyl)-1,4-dihydro-4-oxo-quinoline-3-carboxylic acid and its isomers and its salts;

193. cis/trans-1,8-Diethyl-6-fluoro-7-(4-hydroxy-3-ethyl-1-piperidinyl)-1,4-dihydro-4-oxo-quinoline-3-carboxylic acid and its isomers and its salts;
194. cis/trans-1,8-Diethyl-6-fluoro-7-(4-amino-3-ethyl-1-piperidinyl)-1,4-dihydro-4-oxo-quinoline-3-carboxylic acid and its isomers and its salts;
195. 1-(2,4-Difluorophenyl)-6-fluoro-8-ethyl-7-(4-amino-1-piperidinyl)-1,4-dihydro-4-oxo-quinoline-3-carboxylic acid and its isomers and its salts;
196. 1-(2,4-Difluorophenyl)-6-fluoro-8-ethyl-7-(4-hydroxy-1-piperidinyl)-1,4-dihydro-4-oxo-quinoline-3-carboxylic acid and its isomers and its salts;
197. cis/trans-1-(2,4-Difluorophenyl)-6-fluoro-8-ethyl-7-(4-amino-3-methyl-1-piperidinyl)-1,4-dihydro-4-oxo-quinoline-3-carboxylic acid and its isomers and its salts;
198. cis-1-(2,4-Difluorophenyl)-6-fluoro-8-ethyl-7-(4-amino-3-methyl-1-piperidinyl)-1,4-dihydro-4-oxo-quinoline-3-carboxylic acid and its isomers and its salts;
199. trans-1-(2,4-Difluorophenyl)-6-fluoro-8-ethyl-7-(4-amino-3-methyl-1-piperidinyl)-1,4-dihydro-4-oxo-quinoline-3-carboxylic acid and its isomers and its salts;
200. cis/trans-1-(2,4-Difluorophenyl)-6-fluoro-8-ethyl-7-(4-hydroxy-3-methyl-1-piperidinyl)-1,4-dihydro-4-oxo-quinoline-3-carboxylic acid and its isomers and its salts;
201. cis-1-(2,4-Difluorophenyl)-6-fluoro-8-ethyl-7-(4-hydroxy-3-methyl-1-piperidinyl)-1,4-dihydro-4-oxo-quinoline-3-carboxylic acid and its isomers and its salts;
202. trans-1-(2,4-Difluorophenyl)-6-fluoro-8-ethyl-7-(4-hydroxy-3-methyl-1-piperidinyl)-1,4-dihydro-4-oxo-quinoline-3-carboxylic acid and its isomers and its salts;
203. (±)-1-(2,4-Difluorophenyl)-6-fluoro-8-ethyl-7-(4-amino-3,3-dimethyl-1-piperidinyl)-1,4-dihydro-4-oxo-quinoline-3-carboxylic acid and its salts;
204. (+)-1-(2,4-Difluorophenyl)-6-fluoro-8-ethyl-7-(4-amino-3,3-dimethyl-1-piperidinyl)-1,4-dihydro-4-oxo-quinoline-3-carboxylic acid and its salts;
205. (−)-1-(2,4-Difluorophenyl)-6-fluoro-8-ethyl-7-(4-amino-3,3-dimethyl-1-piperidinyl)-1,4-dihydro-4-oxo-quinoline-3-carboxylic acid and its salts;
206. (±)-1-(2,4-Difluorophenyl)-6-fluoro-8-ethyl-7-(4-hydroxy-3,3-dimethyl-1-piperidinyl)-1,4-dihydro-4-oxo-quinoline-3-carboxylic acid and its isomers and its salts;
207. cis/trans-1-(2,4-Difluorophenyl)-6-fluoro-8-ethyl-7-(4-hydroxy-3-ethyl-1-piperidinyl)-1,4-dihydro-4-oxo-quinoline-3-carboxylic acid and its isomers and its salts;
208. cis/trans-1-(2,4-Difluorophenyl)-6-fluoro-8-ethyl-7-(4-amino-3-ethyl-1-piperidinyl)-1,4-dihydro-4-oxo-quinoline-3-carboxylic acid and its isomers and its salts;

Some preferred compounds of the invention are:

(±)-1-Cyclopropyl-6-fluoro-1,4-dihydro-8-methoxy-7-(4-amino-3,3-dimethyl-1-piperidinyl)-4-oxo-quinoline-3-carboxylic acid and its polymorphs.

(±)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs.

(±)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs.

(±)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs.

(+)-1-Cyclopropyl-6-fluoro-1,4-dihydro-8-methoxy-7-(4-amino-3,3-dimethyl-1-piperidinyl)-4-oxo-quinoline-3-carboxylic acid and its polymorphs.

(+)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs.

(+)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs.

(+)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs.

(−)-1-Cyclopropyl-6-fluoro-1,4-dihydro-8-methoxy-7-(4-amino-3,3-dimethyl-1-piperidinyl)-4-oxo-quinoline-3-carboxylic acid and its polymorphs.

(−)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride and its polymorphs.

(−)-1-Cyclopropyl-6-fluoro-1,4-dihydro-8-methoxy-7-(4-amino-3,3-dimethyl-1-piperidinyl)-4-oxo-quinoline-3-carboxylic acid methane sulfonate and its polymorphs.

(−)-1-Cyclopropyl-6-fluoro-1,4-dihydro-8-methoxy-7-(4-amino-3,3-dimethyl-1-piperidinyl)-4-oxo-quinoline-3-carboxylic acid gluconate and its polymorphs.

cis/trans-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts.

cis-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts.

trans-1-Cyclopropyl-6-fluoro-8-methyl-7-(4-hydroxy-3-methyl-1-piperidinyl)-1,4-dihydro-4-oxo-quinoline-3-carboxylic acid and its isomers and its salts.

cis/trans-1-Cyclopropyl-6-fluoro-8-methyl-7-(4-hydroxy-3-ethyl-1-piperidinyl)-1,4-dihydro-4-oxo-quinoline-3-carboxylic acid and its isomers and its salts.

trans-1-Cyclopropyl-6-fluoro-1,4-dihydro-8-methyl-7-(4-amino-3-methyl-1-piperidinyl)-4-oxo-quinoline-3-carboxylic acid and its isomers and its salts.

trans-1-Cyclopropyl-6-fluoro-1,4-dihydro-8-methyl-7-(4-amino-3-methyl-1-piperidinyl)-4-oxo-quinoline-3-carboxylic acid hydrochloride and its polymorphs.

cis-1-Cyclopropyl-6-fluoro-1,4-dihydro-8-methyl-7-(4-amino-3-methyl-1-piperidinyl)-4-oxo-quinoline-3-carboxylic acid and its isomers and its salts.

cis-1-Cyclopropyl-6-fluoro-1,4-dihydro-8-methyl-7-(4-amino-3-methyl-1-piperidinyl)-4-oxo-quinoline-3-carboxylic acid hydrochloride and its polymorphs.

(±)-1-Cyclopropyl-6-fluoro-1,4-dihydro-8-methyl-7-(4-amino-3,3-dimethyl-1-piperidinyl)-4-oxo-quinoline-3-carboxylic acid and its polymorphs.

(±)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs.

(±)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs.

(±)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs.

(+)-1-Cyclopropyl-6-fluoro-1,4-dihydro-8-methyl-7-(4-amino-3,3-dimethyl-1-piperidinyl)-4-oxo-quinoline-3-carboxylic acid and its polymorphs.

(+)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs.

(+)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs.

(+)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs.

(−)-1-Cyclopropyl-6-fluoro-1,4-dihydro-8-methyl-7-(4-amino-3,3-dimethyl-1-piperidinyl)-4-oxo-quinoline-3-carboxylic acid and its polymorphs.

(−)-1-Cyclopropyl-6-fluoro-1,4-dihydro-8-methyl-7-(4-amino-3,3-dimethyl-1-piperidinyl)-4-oxo-quinoline-3-carboxylic acid hydrochloride and its polymorphs.

(−)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate and its polymorphs.

(−)-1-Cyclopropyl-6-fluoro-1,4-dihydro-8-methyl-7-(4-amino-3,3-dimethyl-1-piperidinyl)-4-oxo-quinoline-3-carboxylic acid gluconate and its polymorphs.

1-Cyclopropyl-6-fluoro-1,4-dihydro-8-methyl-7-(4-dimethylamino-3-methyl-1-piperidinyl)-4-oxo-quinoline-3-carboxylic acid and its isomers and its salts.

Other preferred compounds of the invention include:

Crystalline polymorphic form of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1:

Crystalline polymorphic form of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride -Polymorph A2:

Crystalline polymorphic form of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1:

Crystalline polymorphic form of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A2:

Crystalline polymorphic form of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1:

Crystalline polymorphic form of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A2:

Another embodiment of the invention encompasses a process to make the compounds of the invention, which comprises the following general methods.

General Methods

In general, the fluoroquinolone compounds were prepared by heating the appropriate 6,7-dihalo fluoroquinolone core moiety (bearing either a free 3 carboxylic acid or a 3 carboxylic acid ester or an $O^3O^4$ borane chelate) or the appropriate 8,9-dihalo fluoroquinolone core moiety (bearing an O—B-diacetoxy borane) with the appropriate, 4-substituted/unsubstituted amino/hydroxy-3-substituted/unsubstituted piperidine moiety in an organic solvent, optionally in the presence of a base at 50°-120° C., preferably 50-90° C. for 4-72 hr preferably 16-24 hr and isolating the product. Suitable solvents include acetone, alcohol, acetonitrile, dimethyl sulphoxide, N,N-dimethylformamide, preferably acetonitrile or dimethyl sulphoxide. Suitable bases include triethylamine, pyridine, 1,5-diazabicyclo[4.3.0]non-5-ene (DBN), 1,7-diazabicyclo[5.4.0]undec-7-ene (DBU), preferably triethylamine. When the amino function of the 7 piperidino substituent bears an alkoxycarbonyl or aralkyloxycarbonyl as a protecting group, the protecting group is removed by treatment with aqueous alkali or inorganic acid at 30-120° C., preferably 30-80° C. for 4-12 hours, preferably 4-6 hours and isolating the product.

Method 1

1-Cyclopropyl-6-fluoro-7-{(4-amino/substituted amino/disubstituted amino/hydroxy-3-alkyl/3,3-dialkyl/3,5-dialkyl)-1-1-piperidinyl)-1,4-dihydro-4-oxo-quinoline-3-carboxylic acid and isomers were prepared by heating a mixture of 1-cyclopropyl-6-fluoro-7-chloro-1,4-dihydro-4-oxo-quinoline-3-carboxylic acid with appropriate {4-(amino/substituted amino/disubstituted amino/hydroxy-3-alkyl/3,3-dialkyl/3,5-dialkyl/3,3,5-trialkyl)}piperidine in an organic solvent optionally in the presence of a base at 50°-120° C., preferably 90° C. for 4-72 hr. The solvent may be selected from acetone, alcohol, acetonitrile, dimethyl sulphoxide, N,N-dimethylformamide preferably acetonitrile or dimethyl sulphoxide. The base may be selected from triethylamine, pyridine, 1,5-diazabicyclo[4.3.0]non-5-ene (DBN), or 1,7-diazabicyclo[5.4.0]undec-7-ene (DBU), preferably triethylamine.

Method 2

1-Cyclopropyl-6-fluoro-8-methoxy-7-{(4-amino/substituted amino/disubstituted amino/hydroxy-3-alkyl/3,3-dialkyl/3,5-dialkyl/3,3,5-trialkyl)-1-piperidinyl)-1,4-dihydro-4-oxo-quinoline-3-carboxylic acid and isomers were prepared by a procedure described in Method 1 by using [1-cyclopropyl-6,7-difluoro-8-methoxy-1,4-dihydro-4-oxo-quinoline-3-carboxylate-$O^3,O^4$]difluoroboron chelate and appropriate {4-(amino/substituted amino/disubstituted amino/hydroxy-3-alkyl/3,3-dialkyl/3,5-dialkyl)}piperidine followed by hydrolysis of the obtained boron complex in presence of base such as aqueous sodium hydroxide, aqueous potassium hydroxide, triethylamine, diisopropylethylamine in solvents such as acetonitrile, methyl alcohol, ethyl alcohol.

Method 3

5-Amino-1-cyclopropyl-6-fluoro-8-methoxy-7-{(4-amino/substituted amino/disubstituted amino/hydroxy-3-alkyl/3,3-dialkyl/3,5-dialkyl/3,3,5-trialkyl)1-1-piperidinyl)-1,4-dihydro-4-oxo-quinoline-3-carboxylic acid and isomers were prepared by a procedure described in Method 1 by using 5-amino-1-cyclopropyl-6,7-difluoro-8-methoxy-1,4-dihydro-4-oxo-quinoline-3-carboxylic acid and appropriate {4-(amino/substituted amino/disubstituted amino/hydroxy-3-alkyl/3,3-dialkyl/3,5-dialkyl/3,3,5-trialkyl)} piperidine.

Method 4

9-Fluoro-5-methyl-6,7-dihydro-8-(3/4/5-substituted-4-hydroxyl-1-piperidinyl)-1-oxo-1H,5H-benzo[i,j]quinolizine-2-carboxylic acid its isomers were prepared by a procedure described in Method 1 by using (O—B)-diacetoxy-{S-(−)-8,9-difluoro-5-methyl-6,7-dihydro-1-oxo-1H,5H-benzo[i,j] quinolizine-2-carboxy}borane and appropriate 3/4/5-substituted-4-hydroxy piperidine and optionally hydrolyzing the obtained boron complex in the presence of a base.

Method 5

1-Cyclopropyl-6-fluoro-7-{(4-amino/substituted amino/disubstituted amino/hydroxy-3-alkyl/3,3-dialkyl/3,5-dialkyl)1-1-piperidinyl)-1,4-dihydro-4-oxo-1,8-naphthyridone-3-carboxylic acid and isomers were prepared by a procedure described in Method 1 by using 1-cyclopropyl-7-chloro-6-fluoro-1,4-dihydro-4-oxo-1,8-naphthyridone-3- carboxylic acid and appropriate {4-amino/substituted amino/disubstituted amino/hydroxy-3-alkyl/3,3-dialkyl/3,5-dialkyl)}piperidine.

Method 6

1-(2,4-Difluorophenyl)-6-fluoro-7-{(4-amino/substituted amino/disubstituted amino/hydroxy-3-alkyl/3,3-dialkyl/3,5-dialkyl)1-1-piperidinyl)-1,4-dihydro-4-oxo-1,8-naphthyridone-3-carboxylic acid and isomers were prepared by a procedure described in Method 1 by using ethyl-1-(difluorophenyl)-7-chloro-6-fluoro-1,4-dihydro-4-oxo-1,8-naphthyridone-3-carboxylate and appropriate {4-amino/substituted amino/disubstituted amino/hydroxy-3-alkyl/3,3-dialkyl/3,5-dialkyl}piperidine.

Method 7

1-Cyclopropyl-6-fluoro-8-methoxy-7-{4-amino-3-alkyl/3,3-dialkyl/3,5-dialkyl-1-piperidinyl}-1,4-dihydro-4-oxo-quinoline-3-carboxylic acid and enantiomers were prepared by hydrolysis of racemic or optically active 1-cyclopropyl-6-fluoro-1,4-dihydro-8-methoxy-7-{4-benzyloxycarbonylamino/$^t$-butyloxycarbonylamino/ethoxycarbonylamino-3-alkyl/3,3-dialkyl/3,5-dialkyl-1-piperidinyl)-4-oxo-quinoline-3 acid with aqueous alkali preferably aqueous sodium hydroxide or inorganic acid such as hydrochloric acid at ambient temperature for 2-12 hr.

Method 8

1-Cyclopropyl-6-fluoro-8-methyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1-cyclopropyl-6,7-difluoro-8-methyl-1,4-dihydro-4-oxo-quinoline-3-carboxylate-$O^3,O^4$] difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Method 9

1-Cyclopropyl-6-fluoro-8-ethyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1-cyclopropyl-6,7-difluoro-8-ethyl-1,4-dihydro-4-oxo-quinoline-3-carboxylate-$O^3,O^4$] difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Method 10

5-Amino-1-cyclopropyl-6-fluoro-8-methyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [5-amino-1-cyclopropyl-6,7-difluoro-8-methyl-1,4-dihydro-4-oxo-quinoline-3-carboxylate-$O^3,O^4$]difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Method 11

1-Ethyl-6-fluoro-8-methyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1-ethyl-6,7-difluoro-8-methyl-1,4-dihydro-4-oxo-quinoline-3-carboxylate-$O^3,O^4$]difluoroboron chelate and appropriate {4-amino/substituted amino/disubstituted amino/hydroxy -3-alkyl/3,3-dialkyl}piperidine and optionally hydrolyzing the obtained boron complex in the presence of a base.

Method 12

1,8-Diethyl-6-fluoro-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1,8-diethyl-6,7-difluoro-1,4-dihydro-4-oxo-quinoline-3-carboxylate-$O^3,O^4$]difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Method 13

1-(2,4-Difluorophenyl)-6-fluoro-8-methyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1-(2,4-Difluorophenyl)-6,7-difluoro-8-methyl-1,4-dihydro-4-oxo-quinoline-3-carboxylate-O3,O4]difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Method 14

1-(2,4-Difluorophenyl)-6-fluoro-8-ethyl-7-{4-amino/substituted amino/disubstituted amino/hydroxy-3-alkyl/3,3-dialkyl-1-piperidinyl}-1,4-dihydro-4-oxo-quinoline-3-carboxylic acid and isomers were prepared by a procedure described in Method 1 by using [1-(2,4-Difluorophenyl)-6,7-difluoro-8-ethyl-1,4-dihydro-4-oxo-quinoline-3-carboxylate-O3,O4] difluoroboron chelate and appropriate {4-amino/substituted amino/disubstituted amino/hydroxy-3-alkyl/3,3-dialkyl}piperidine and optionally hydrolyzing the obtained boron complex in the presence of a base.

Another aspect of the invention are novel amines that can be used to prepare the compounds of formula 1. The amines are listed below and the methods for their preparation are included in parenthesis alongside each one of them as follows:

4-Amino-3,3-dimethylpiperidine (prepared as in Preparation 10, step 2) and optical enantiomers thereof (prepared as in Preparation 37 and Preparation 38);

4-Methylamino-3,3-dimethylpiperidine (prepared as in Preparation 11) and optical enantiomers thereof (can be prepared by methods known to those skilled in the art);

4-Ethylamino-3,3-dimethylpiperidine (prepared as in Preparation 12) and optical enantiomers thereof (can be prepared by methods known to those skilled in the art);

4-Cyclopropylamino-3,3-dimethylpiperidine (prepared as in Preparation 13) and optical enantiomers thereof (can be prepared by methods known to those skilled in the art);

4-Dimethylamino-3,3-dimethylpiperidine (prepared as in Preparation 14) and optical enantiomers thereof (can be prepared by methods known to those skilled in the art);

4-Benzylamino-3,3-dimethylpiperidine and optical enantiomers thereof (can be prepared by methods known to those skilled in the art);

4-Acetylamino-3,3-dimethylpiperidine (prepared as in Preparation 16) and optical enantiomers thereof (can be prepared by methods known to those skilled in the art);

4-Carbethoxyamino-3,3-dimethylpiperidine (prepared as in Preparation 15) and optical enantiomers thereof (can be prepared by methods known to those skilled in the art);

(±)-4-$^t$-Butyloxycarbonylaamino-3,3-dimethylpiperidine (can be prepared according to Preparation 19, step 7 using the racemic mixture of isomers in place of the optical enantiomer);

(+)-4-$^t$-Butyloxycarbonylamino-3,3-dimethylpiperidine (prepared according to Preparation 19, step 7);

(−)-4-$^t$-Butyloxycarbonylamino-3,3-dimethylpiperidine (prepared according to Preparation 19, step 7);

4-Benzyloxycarbonylamino-3,3-dimethylpiperidine (prepared as in Preparation 18) and optical enantiomrers thereof (can be prepared by methods known to those skilled in the art);

4-Amino-1-benzyl-3,3-dimethylpiperidine (prepared as in Preparation 10, step 2)and optical enantiomers thereof (can be prepared by methods known to those skilled in the art);

4-Amino-1-carbethoxy-3,3-dimethylpiperidine and optical enantiomers thereof (can be prepared by methods known to those skilled in the art);

4-Amino-1-$^t$butyloxycarbonyl-3,3-dimethylpiperidine (prepared as in Preparation 18, step 2) and optical enantiomers thereof (can be prepared by methods known to those skilled in the art);

(±)-4-Amino-1-benzyloxycarbonyl-3,3-dimethylpiperidine (prepared as in Preparation 19, step 2);

(+)-4-Amino-1-benzyloxycarbonyl-3,3-dimethylpiperidine (prepared as in Preparation 19, step 3); and (−)-4-Amino-1-benzyloxycarbonyl-3,3-dimethylpiperidine (prepared as in Preparation 19, step 4);

4-Amino-1-carbethoxy-3-methylpiperidine (prepared as in Preparation 1, step 1);

4-Amino-3,5-diethyl-3-methylpiperidine (prepared as in Preparation 32);

4-Amino-1-carbethoxy-3,5-dimethylpiperidine (prepared as in Preparation 25, step 2);

4-Amino-1-benzyl-3,5-diethyl-3-methylpiperidine (prepared as in Preparation 32);

4-Amino-3,5-dimethyl-3-ethylpiperidine (prepared as in Preparation 33);

4-Amino-1-benzyl-3,5-dimethyl-3-ethylpiperidine (prepared as in Preparation 33);

4-Amino-3,5-diethylpiperidine (prepared as in Preparation 30);

4-Amino-1-benzyl-3,5-diethylpiperidine (prepared as in Preparation 30);

4-Amino-3,3,5-trimethylpiperidine (prepared as in Preparation 31);

4-Amino-3,3-diethylpiperidine (prepared as in Preparation 24);

4-Amino-1-benzyl-3,3-diethylpiperidine (prepared as in Preparation 24);

4-Amino-3,5-dimethylpiperidine (prepared as in Preparation 25);

Mixture of isomers of 4-amino-1-carbethoxy-3,5-dimethylpiperidine (prepared as in Preparation 25, step 1);

4-Amino-3-ethyl-3-methylpiperidine (prepared as in Preparation 20);

4-Amino-1-benzyl-3-ethyl-3-methylpiperidine (prepared as in Preparation 20);

4-Acetylamino-1-benzyl-3,3-dimethyl piperidine (prepared as in Preparation 16);

cis or trans-4-t-Butyloxycarbonylamino-1-benzyl-3-methylpiperidine (prepared as in Preparation 34, step 4);

cis-4-t-Butyloxycarbonylamino-3-methylpiperidine (prepared as in Preparation 35);

trans-4-t-Butyloxycarbonylamino-3-methylpiperidine (prepared as in Preparation 36);

1-Benzyl-4-carbethoxyamino-3,3-dimethyl piperidine (prepared as in Preparation 15);

1-Benzyl-4-cyclopropylamino-3-ethyl-3-methylpiperidine (prepared as in Preparation 22);

1-Benzyl-4-methylamino-3-ethyl-3-methylpiperidine (prepared as in Preparation 21);

1-Benzyl-4-dimethylamino-3-ethyl-3-methylpiperidine (prepared as in Preparation 23);

1-Carbethoxy-4-ethylamino-3-methylpiperidine (prepared as in Preparation 3, step 1);

4-Cyclopropylamino-3-methylpiperidine (prepared as in Preparation 4, step 2);

1-Carbethoxy-4-cyclopropylamino-3-methylpiperidine (prepared as in Preparation 4, step 2);

1-Carbethoxy-4-dimethylamino-3-methylpiperidine (prepared as in Preparation 5, step 1);

4-Cyclopropylamino-3-ethylpiperidine (prepared as in Preparation 8);

4-Cyclopropylamino-3-ethyl-3-methylpiperidine (prepared as in Preparation 22);

4-Cyclopropylamino-3,5-dimethylpiperidine (prepared as in Preparation 28);

4-Dimethylamino-3-ethylpiperidine (prepared as in Preparation 9);

4-Dimethylamino-3-methylpiperidine (prepared as in Preparation 5, step 2);

4-Dimethylamino-3,5-dimethylpiperidine (prepared as in Preparation 29);

4-Dimethylamino-3-ethyl-3-Methylpiperidine (prepared as in Preparation 23);

4-Methylamino-3-methylpiperidine (prepared as in Preparation 2, step 2);

4-Ethylamino-3-methylpiperidine (prepared as in Preparation 3, step 2);

4-Methylamino-3-ethylpiperidine (prepared as in Preparation 7);

4-Methylamino-3-ethyl-3-methylpiperidine (prepared as in Preparation 21);

4-Methylamino-3,5-dimethylpiperidine (prepared as in Preparation 26);

4-Ethylamino-3,5-dimethylpiperidine (prepared as in Preparation 27);

In addition, the invention also provides novel intermediate amines that can be used to prepare the amines listed above. The novel intermediate amines are listed below and the methods for their preparation are included in parenthesis alongside each one of them as follows:

3,3-Dimethyl-4-piperidone (prepared as in Preparation 17);

$^t$-Butyloxycarbonyl-3,3-dimethyl-4-piperidone (prepared as in Preparation 18, step 1);

1-Benzyloxycarbonyl-3,3-dimethyl-4-piperidone (prepared as in Preparation 19, step 1);

(±)-4-Benzyloxycarbonylamino-1-$^t$butyloxycarbonyl-3,3-dimethylpiperidine (prepared as in Preparation 18, step 3);

(+)-1-Benzyloxycarbonyl-4-$^t$butyloxycarbonylamino-3,3-dimethylpiperidine (prepared as in Preparation 19, step 5);

(−)-1-Benzyloxycarbonyl-4-$^t$butyloxycarbonylamino-3,3-dimethylpiperidine (prepared as in Preparation 19, step 6);

1-Carbethoxy-3,5-dimethyl-4-piperidone (prepared as in Preparation 25, step 1);

3,3,5-Trimethyl-4-piperidone (prepared as in Preparation 31);

Ethyl-1-benzyl-3-methyl-4-oxo-piperidine-3-carboxylate (prepared as in Preparation 34, step 1);

The above mentioned novel intermediates are used to prepare the novel amines of the invention. The intermediates can be classified as (a) the unprotected dialkyl or trialkyl 4-piperidones, (b) the dialkyl or trialkyl 1-N protected 4-piperidones and (c) the dialkyl 1-N protected, 4-protected amino piperidines.

The unprotected dialkyl or trialkyl 4-piperidone intermediates can be used to prepare the corresponding amines by using the known art of transforming a carbonyl functionality to an amine functionality by using reagents such as ammonium acetate, methyl amine hydrocholide, ethyl amine hydrochloride, cyclopropyl amine etc to form an imino functionality which upon subsequent reduction can produce desired amine after reduction. The reducing agents can be selected from sodium cyano borohydride or palladium on carbon in a solvent such as methanol, ethanol, ethyl acetate etc.

The dialkyl or trialkyl 1-N protected 4-piperidones are used to prepare the corresponding deprotected amines by using the known art of deprotection such as hydrogenolysis to deprotect a benzyloxycarbonyl moiety or a benzyl moiety by stirring the intermediate in the presence of catalysts and a hydrogen source. The catalyst can be selected from palladium on carbon, palladium hydroxide on carbon and hydrogen source can be selected from hydrogen gas or ammonium formate, cyclohexene, in solvents such as methanol ethanol, ethyl acetate etc.

The dialkyl 1-N protected, 4-protected amino piperidines can be used to prepare the corresponding deprotected amines by using the known art of deprotection as described in the previous paragraph to remove a benzyloxycarbonyl or a benzyl moiety and the known art of removing a butyloxycarbonyl group by stirring the intermediate, in the presence of inorganic acids such as concentrated hydrochloric acid or organic acids such as trifluoro acetic acid in solvents such as tetrahydrofuran, dioxane etc.

The preparations 1-38 include examples of the specific preparative methods used of how to use the described amine intermediates for the preparation of the corresponding novel amines of the invention.

The pharmaceutically acceptable acid addition salts of compounds of the formula I are prepared in a conventional manner by treating a solution or suspension of the free base of the formula I with about one chemical equivalent of a pharmaceutically acceptable acid such as an inorganic acid or organic acid. Conventional concentration and recrystallization techniques are employed in isolating the salts. For example, the free base can be dissolved in an aqueous alcohol solution containing the appropriate acid and the salt is isolated by evaporation of the solution. Alternatively, they may be prepared by reacting the free base with an acid in an organic solvent so that the salt separates directly. Where separation of the salt is difficult, it can be precipitated with a second organic solvent, or can be obtained by concentration of the solution. Examples of appropriate acid addition salts include, but are not limited to acetate, benzenesulfonate, fumarate, hydrochloride, hydrobromide, hydroiodide, hydrogensulfate, isethionate, lactate, malate, maleate, malonate, methanesulfonate, pamoate (embonate), phosphate/diphosphate, stearate, succinate, sulfate, tartrate, trifluoroacetate, trifluoromethanesulfonate, p-toluenesulfonate, and the like. Preferred acid addition salts include halides, sulfonates, carboxylates, phosphates, and the like. However, other appropriate pharmaceutically acceptable salts within the scope of the invention are those derived from other mineral acids, organic acids and amino acids. The amino acid may be selected from one of the 20 naturally occurring amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

The pharmaceutically acceptable alkali/base addition salts of compounds of formula I may be prepared by conventional methods from the corresponding acids e.g. by reaction with about one equimolar amount of an alkali/base. Preferred alkali/base addition salts include the alkali metal salts (such as sodium and potassium), alkaline earth metal salts (such as magnesium and calcium), inorganic salts, such as ammonium, substituted ammonium, choline and organic base salts from basic amines such as diethanolamine, N-methyl glucamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

The hydrates, pseudopolymorphs, polymorphs and solvates of all the compounds of the invention are also included and are prepared by conventional methods.

The present invention also encompasses the process of making the intermediate amines, as illustrated in the detailed preparations that are used in the condensation with the fluoroquinolone nucleus. For instance, the 3-substituted-4-aminopiperidine intermediates can exist as a mixture of cis and trans isomers and the mixture was prepared by the procedure described in Preparation 1. The mixture of cis and trans isomers of 4-amino-3-methylpiperidine was prepared by a sequence as described in Preparation 34. Each cis and trans isomer is a racemic mixture and can be resolved into optically active enantiomeric forms by the usual methods of optical resolution of amines known to those skilled in the art. Other 3-substituted-4-aminopiperidines were synthesised using a similar method.

The 4-amino-3,5-dimethylpiperidine intermediate was obtained in the following manner. 4-Amino-1-carbethoxy-3,5-dimethylpiperidine (a mixture of isomers) was prepared according to the procedure described in Preparation 25 and separated by silica gel column chromatography into the two major mixtures of isomers, one mixture designated as upper mixture A and the other designated as lower mixture B of isomers. Conformations of these mixtures of isomers were not assigned. Using any one of the mixtures of isomers of 4-amino-3,5-dimethylpiperidine, some compounds of the invention can be prepared by condensing the respective mixture of isomers of 4-amino-3,5-dimethyl-piperidine with [1-cyclopropyl-6,7-difluoro-1,4-dihydro-8-methoxy-4-oxo-quinoline-3-carboxylate-$O^3,O^4$]difluoroboron chelate, as exemplified in the section on examples described later in this specification.

The present invention also encompasses an antiinfective composition for the treatment of humans and animals in need of prophylaxix and/or therapy for systemic or topical infections especially resistant gram-positive organism infections, gram-negative organism infections, mycobacterial infections and nosocomial pathogen infections, which composition comprises an amount of a compound of the invention, the derivatives, isomers, salts, polymorphs, pseudopolymorphs, and hydrates thereof, substantially sufficient to eradicate said infection, but not to cause any undue side effects. Compounds and compositions of this invention can be administered to humans and animals who are at risk of being infected, for example a compound or composition of this invention can be administered to a patient prior to and/or after surgery.

In addition the compounds of the invention have superior bactericidal activity against pneumococci and streptococci of various groups. Cidal features available in such molecules add to their clinical attractiveness as it would offer clinicians a valuable treatment option to treat a broader range of infections caused by staphylococci, MRSA, MRSE, pneumococci, streptococci, mycobacteria and diverse range of anaerobic bacteria of clinical importance in a situation such as patients allergic to β-lactam or possibility of infections due to macrolide resistant strains of streptococci and pneumococci or MRSA/QRSA. For anaerobic bacterial infections, currently available treatment options are rather limited due to reasons such as inadequate potency or gaps in the spectrum of anaerobic pathogens covered. Such is the case with macrolides. With β-lactam antibacterials, the major shortcoming is their liability to a variety of β-lactamases, the drug inactivating enzymes elaborated by commonly encountered anaerobic pathogens. Older fluoroquinolones such as ciprofloxacin, levofloxacin, pefloxacin also suffered due to inadequate anti-anaerobic potency. The molecules of invention demonstrate several distinct gains in antimicrobial properties against anaerobic pathogens vis-à-vis earlier antibacterial agents of the β-lactam, macrolide and fluoroquinolone classes.

It has been found that the compounds of this invention, and compositions containing these compounds, are effective antimicrobial agents against a broad range of pathogenic microorganisms with advantages in low susceptibility to microbial resistance, reduced toxicity, and improved pharmacology.

Moreover, the molecules of the invention, chiral compounds, salts, polymorphs, pseudopolymorphs and hydrates thereof, also retain the other valuable features, of being bactericidal to fluoroquinolone resistant staphylococci (QRSA with resistant gyrase) and even to staphylococcal and pneumococcal isolates possessing Nor A efflux pumps and other efflux pumps. The compounds of the invention also display efflux pump inhibitory activity. A combination of all these properties coupled with overall good safety and tolerability observed in a new molecule renders them worthy of therapeutic use in humans and animals. By virtue of such features, they have considerable advantages over existing fluoroquinolone antibacterials, in particular in the treatment of respiratory diseases and infections of skin and soft tissue.

The above list of pathogens is merely by way of example and is in no way to be interpreted as limiting. Streptococci are implicated as one of the most common pathogens, in both the pediatric and adult population in diverse infections/diseases. Examples which may be mentioned of diseases, which can thus be prevented, alleviated and/or cured by the formulations according to the invention include but are not limited to are meningitis, otitis externa, otitis media; pharyngitis; pneumonia; life-threatening bacteremia, peritonitis; pyelonephritis; cystitis; endocarditis; systemic infections; bronchitis; arthritis; local infections; and septic diseases. Several molecules of the present inventions also exhibit impressive gains in potency against *Mycobacterium tuberculosis* and therefore of potential value in the treatment of latent and recalcitrant mycobacterial infections such as tuberculosis.

These findings have an important implication from the point of view of the systemic use of the compounds of the invention in view of their superior potency, superior bactericidal activity, expanded biospectrum, better bioavailability and improved tolerability which are now enabled to be administered systemically in therapeutically effective doses.

Utilizing the compounds of the invention or the substantially optically pure or optically pure isomers, the derivatives and salts thereof, whether in systemic or topical dosage form, results in clearer dose-related definitions of efficacy, diminished toxic effects and accordingly an improved therapeutic index.

The present invention encompasses certain compounds, dosage forms, and methods of administering the compounds to a human or other animal subject. Specific compounds and compositions to be used in the invention must, accordingly, be pharmaceutically acceptable. As used herein, such a "pharmaceutically acceptable" component is one that is suitable for use with humans and/or animals without undue adverse side effects (such as toxicity, irritation, and allergic response) commensurate with a reasonable benefit/risk ratio.

The pharmaceutical compositions are prepared according to conventional procedures used by persons skilled in the art to make stable and effective compositions. In the solid, liquid, parenteral and topical dosage forms, an effective amount of the active compound or the active ingredient is any amount, which produces the desired results.

For the purpose of this invention the pharmaceutical compositions may contain the active compounds of the invention, their derivatives, salts and hydrates thereof, in a form to be administered alone, but generally in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

Any suitable route of administration may be employed for providing the patient with an effective dosage of the compound of the invention their derivatives, salts and hydrates thereof. For example, oral, rectal, parenteral (subcutaneous, intramuscular, intravenous), transdermal, topical and like forms of administration may be employed. Dosage forms include (solutions, suspensions, etc) tablets, pills, powders, troches, dispersions, suspensions, emulsions, solutions, capsules, injectable preparations, patches, ointments, creams, lotions, shampoos and the like.

The prophylactic or therapeutic dose of the compounds of the invention, their derivatives, salts or hydrates thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, the derivatives, salts or hydrates thereof, for the conditions described herein, is from about 200 mg to about 1500 mg, in single or divided doses. Preferably, a daily dose range should be between about 400 mg to 1200 mg, in single or divided dosage, while most preferably a daily dose range should be between about 500 mg to about 1000 mg in divided dosage. While intramuscular administration may be a single dose or up to 3 divided doses, intravenous administration can include a continuous drip. It may be necessary to use dosages outside these ranges in some cases as will be apparent to those skilled in the art. Further, it is noted that the clinician or treating physician will know how and when to interrupt, adjust, or terminate therapy in conjunction with individual patient's response. The term "an amount sufficient to eradicate such infections but insufficient to cause undue side effects" is encompassed by the above-described dosage amount and dose frequency schedule.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. The compositions of the present invention include compositions such as suspensions, solutions, elixirs, aerosols, and solid dosage forms. Carriers as described in general above are commonly used in the case of oral solid preparations (such as powders, capsules and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. Examples of suitable carriers include excipients such as lactose, white sugar, sodium chloride, glucose solution, urea, starch, calcium carbonate, kaolin, crystalline cellulose and silicic acid, binders such as water, ethanol, propanol, simple syrup, glucose, starch solution, gelatin solution, carboxymethyl cellulose, shellac, methyl cellulose, potassium phosphate and polyvinyl pyrrolidone, disintegrants such as dried starch, sodium alginate, agar powder, laminaria powder, sodium hydrogen carbonate, calcium carbonate, Tween (fatty acid ester of polyoxyethylenesorbitan), sodium lauryl sulfate, stearic acid monoglyceride, starch, and lactose, disintegration inhibitors such as white sugar, stearic acid glyceryl ester, cacao butter and hydrogenated oils, absorption promoters such as quaternary ammonium bases and sodium lauryl sulfate, humectants such as glycerol and starch, absorbents such as starch, lactose, kaolin, bentonite and colloidal silicic acid, and lubricants such as purified talc, stearic acid salts, boric acid powder, polyethylene glycol and solid polyethylene glycol.

The tablet, if desired, can be coated, and made into sugar-coated tablets, gelatin-coated tablets, enteric-coated tablets, film-coated tablets, or tablets comprising two or more layers.

If desired, tablets may be coated by standard aqueous or non-aqueous techniques.

In molding the pharmaceutical composition into pills, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, gelatin, and ethanol, and disintegrants such as laminaria and agar. In molding the pharmaceutical composition into a suppository form, a wide variety of carriers known in the art can be used. Examples of suitable carriers include polyethylene glycol, cacao butter, higher alcohols, gelatin, and semi-synthetic glycerides.

A second preferred method is parenterally for intramuscular, intravenous or subcutaneous administration.

A third preferred route of administration is topically, for which creams, ointments, shampoos, lotions, dusting powders and the like are well suited. Generally, an effective amount of the compound according to this invention in a topical form is from about 0.1% w/w to about 10% w/w of the total composition. Preferably, the effective amount of the compound of the invention is 1% w/w of the total composition.

In addition to the common dosage forms set out above, the compounds of the present invention may also be administered by controlled release means and/or delivery devices such as those described in U.S. Pat. Nos. 3,845,770; 3,916,899; 3,536,809; 3,598,123 and 4,008,719; the disclosures of which are hereby incorporated by reference.

Desirably, each tablet contains from about 200 mg to about 1500 mg of the active ingredient. Most preferably, the tablet, cachet or capsule contains either one of three dosages, about 200 mg, about 400 mg, or about 600 mg of the active ingredient.

When the pharmaceutical composition is formulated into an injectable preparation, in formulating the pharmaceutical composition into the form of a solution or suspension, all diluents customarily used in the art can be used. Examples of suitable diluents are water, ethyl alcohol, polypropylene glycol, ethoxylated isostearyl alcohol, polyoxyethylene sorbitol, and sorbitan esters. Sodium chloride, glucose or glycerol may be incorporated into a therapeutic agent.

The antimicrobial pharmaceutical composition may further contain ordinary dissolving aids, buffers, pain-alleviating agents, and preservatives, and optionally coloring agents, perfumes, flavors, sweeteners, and other drugs. For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g. preservatives, antioxidants, stabilizers, wetting agents, buffers or salts for influencing osmotic pressure, etc. For topical application, also suitable are sprayable aerosol preparations wherein the active ingredient preferably in combination with a solid or liquid inert carrier material.

A specific embodiment of the invention is the preparation of storage stable compositions of the compounds of the invention of formula I. Such stable compositions can be advantageously made through the use of selective stabilizers. Different stabilizers are known to those skilled in the art of making pharmaceutical compositions. Of special utility for making storage stable compositions of the compound of the invention of formula I, stabilizers such as disodium ethylenediaminetetraacetic acid (EDTA), tromethamine, cyclodextrins such as gamma-cyclodextrin, hydroxy-propyl-gamma-cyclodextrin have been found to be useful.

In a specific embodiment of the invention, the pharmaceutical compositions contain an effective amount of the active compounds of the invention, its derivatives, salts or hydrates thereof described in this specification as hereinbefore described in admixture with a pharmaceutically acceptable carrier, diluent or excipients, and optionally other therapeutic ingredients.

The invention is further defined by reference to the following examples describing in detail the preparation of the composition of the present invention as well as their utility. It will be apparent to those skilled in the art that many modifications, both to materials and methods may be practiced without departing from the purpose and scope of this invention.

The following preparations and examples illustrate the methods of preparation of the compounds of the invention and are provided only as examples, but not to limit the scope of the compounds of the invention.

General Preparation for Synthesising
1-benzyl-3-alkyl-4-piperidones

A method for preparing a 3-alkyl substituted-1-benzyl-4-piperidone comprising the steps of:
1) treating ethyl-1-benzyl-4-oxo-piperidine-3-carboxylate hydrochloride with a base such as potassium tert-butoxide, potassium hydroxide, preferably potassium hydroxide in an organic solvent ; such as diethyl ether, dioxane, tetrahydrofuran, N,N-dimethylformamide or mixtures thereof, preferably 1:1 mixture of tetrahydrafuran and N,N-dimethylformamide,
2) adding alkyl halide under stirring at a temperature between 25° C.-65° C., preferably 25° C.-40° C. for 1-12 hrs, preferably 2-3 hrs; and
3) heating with inorganic acid such as hydrochloric acid, sulfuric acid, preferably hydrochloric acid, in the presence of solvent such as water, dioxane, N, N-dimethylformamide, preferably water or dioxane at 80° C.-120° C., preferably 90° C.-110° C. for 5-36 hrs, preferably 24-36 hrs, and isolating the product.

General Preparation for Synthesising 1-benzyl-3,3-dialkyl/3,5-dialkyl/3,3,5-trialkyl-4-piperidones A method for preparing a 3,3-dialkyl/3,5-dialkyl/3,3,5-trialkyl substituted-1-benzyl-4-piperidone comprising the steps of:
1) treating 1-benzyl-4-piperidone or ethyl-3-alkyl-1-benzyl-4-oxo-piperidine-3-carboxylate or 3,3-dialkyl-1-benzyl-4-piperidones in an organic solvent such as dioxane, N, N-dimethylformamide, tetrahydrofuran, preferably tetrahydrofuran or dioxane with a base such as potassium tert-butoxide, sodium hydride, n-butyl lithium, preferably sodium hydride or potassium tert-butoxide;
2) adding an alkyl halide selected from C1-C6 lower alkyl/alkenyl iodides/bromides such as methyl iodide, ethyl iodides, allyl bromide, propargyl bromide etc or C1-C6 aralkyl iodides/bromides/chlorides such as benzyl bromide, benzyl chloride etc under stirring at temperature a between –10° C. to 45° C., preferably –10° C. to 35° C. for 12-24 hrs, preferably 12-16 hrs, and isolating the product.

General Preparation for Synthesising 3-alkyl/3,3-dialkyl/3,5-dialkyl/3,3,5-trialkyl-4-aminopiperidines A method for preparing a 3-alkyl/3,3-dialkyl/3,5-dialkyl/3,3,5-trialkyl substituted-4-amino/methylamino/ethylamino/cyclopropylamino/dimethylamino-piperidine comprising the steps of:
1) treating a 3-alkyl 3,3-dialkyl/3,5-dialkyl/3,3,5-trialkyl substituted-1-benzyl-4-piperidone with an amine such as ammonium acetate (ammonia source), methylamine hydrochloride, ethylamine hydrochloride, cyclopropylamine, dimethylamine hydrochloride in an organic solvent such as methanol, ethanol, preferably methanol, at a temperature between 10° C. to 35° C., preferably 20° C. to 35° C., for 1-6 hrs, preferably 3-4 hrs;
2) adding sodium cyano borohydride at temperature between 0° C. to 60° C., preferably 0° C. to 35° C. and isolating the product by evaporating the solvent under vacuum;
3) treating the isolated product with a catalyst such as palladium hydroxide, palladium on carbon or platinum, preferably palladium on carbon, in an organic solvent, such as methanol, ethanol, ethyl acetate, preferably methanol in presence of hydrogen or hydrogen sources such as hydrogen gas, ammonium formate, cyclohexene, preferably hydrogen gas, ammonium formate, at temperature between 30° C. to 60° C., preferably 30° C. to 45° C. and isolating the product.

Preparation 1

4-Amino-3-methylpiperidine

Step-1

4-Amino-1-carbethoxy-3-methylpiperidine

Ethyl chloroformate (3.0 g, 26.7 mmol) was added to a stirred solution of 1-benzyl-3-methyl-4-piperidinone (2.0 g, 9.85 mmol) in benzene (30 ml) at ambient temperature. The obtained reaction mixture was refluxed with stirring for 6 hr and concentrated to dryness to give 1-carbethoxy-3-methyl-4-piperidone as oil. Yield 1.4 g (77%), $C_9H_{15}NO_3$, m/z 186 (M+1).

Ammonium acetate (5 g, 64.93 mmol) was added to the stirred solution of 1-carbethoxy-3-methyl-4-piperidone (1.4 g, 7.56 mmol) in methanol (25 ml) and stirring was continued for 3 hr at ambient temperature. The resulting mixture was cooled at 0° C. and sodium cyanoborohydride (0.5 g, 7.93 mmol) was added to it. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to furnish 4-amino-1-carbethoxy-3-methylpiperidine. Yield 1.0 g (72%), $C_9H_{18}N_2O_2$, m/z 187 (M+1), PMR (CDCl$_3$): 0.94 (dd, 3H), 1.22 (m, 1H), 1.26 (t, 3H), 1.6 (m, 1H), 1.82 (m, 1H), 2.4 (m, 1H), 2.82 (m, 1H), 3.34 (m, 2H), 3.64 (m, 1H) 4.14 (q, 2H).

Step-2

4-Amino-3-methylpiperidine

4-Amino-1-carbethoxy-3-methylpiperidine (1.0 g, 5.73 mmol) was suspended in 5 M NaOH solution (10 ml), stirred at 120° C. for 6 hr, cooled, extracted with ethyl acetate, dried ($Na_2SO_4$) and concentrated to dryness to afford 4-amino-3-methylpiperidine. Yield 0.2 g (34%), $C_6H_{14}N_2$, m/z 115 (M+1), PMR (CDCl$_3$): 0.94 (m, 3H), 1.22-1.8 (m, 3H), 1.88 (m, 1H), 2.22 (m, 1H), 2.7 (m, 1H), 3.0 (m, 2H).

Preparation 2

4-Methylamino-3-methylpiperidine

Step-1

1-Carbethoxy-4-methylamino-3-methylpiperidine

Methylamine hydrochloride (10 g, 148 mmol) was added to the stirred solution of 1-carbethoxy-3-methyl-4-piperidone (7 g, 37.83 mmol) obtained as described in Preparation 1, in methanol (50 ml) followed by 8.3 g (148 mmol) KOH.

Stirring was continued for 3 hr at ambient temperature. The resulting mixture was cooled at 0° C. and sodium cyanoborohydride (3.0 g, 46.0 mmol) was added to it. Cooling was removed after 10 min. and resulting mixture was stirred for 12 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to give 1-carbethoxy-4-methylamino-3-methylpiperidine. Yield 4.0 g (50%), $C_{10}H_{20}N_2O_2$, m/z 201 (M+1), PMR ($CDCl_3$): 0.92 (dd, 3H), 1.26 (t, 3H), 1.54 (m, 1H), 2.1 (m, 2H), 2.34 (s, 3H), 2.62 (m, 1H), 2.86 (m, 1H), 3.06 (m, 1H), 3.46 (m, 1H), 3.72 (m, 1H), 4.1 (q, 2H).

Step-2

4-Methylamino-3-methylpiperidine

1-Carbethoxy-4-methylamino-3-methylpiperidine (4.0 g, 18.34 mmol) was suspended in 5 M NaOH solution (15 ml), stirred at 110° C. for 24 hr, cooled, extracted with ethyl acetate, dried ($Na_2SO_4$) and concentrated to dryness to afford 4-methylamino-3-methyl-piperidine. Yield 1.8 g (77%), $C_7H_{16}N_2$, m/z 129 (M+1), PMR ($CDCl_3$): 0.92 (dd, 3H), 1.54 (m, 1H), 2.12 (m, 2H), 2.38 (s, 3H), 2.6 (m, 1H), 2.8 (m, 1H), 3.02 (m, 1H), 3.42 (m, 1H), 3.68 (m, 1H).

Preparation 3

4-Ethylamino-3-methylpiperidine

Step-1

1-Carbethoxy-4-ethylamino-3-methylpiperidine

Ethylamine hydrochloride (5 g, 61.34 mmol) was added to the stirred solution of 1-carbethoxy-3-methyl-4-piperidone (3.5 g, 18.9 mmol) obtained as described in Preparation 1, in methanol (30 ml) followed by 3.43 g (61.34 mmol) KOH. Stirring was continued for 3 hr at ambient temperature. The resulting mixture was cooled at 0° C. and sodium cyanoborohydride (1.4 g, 22.22 mmol) was added to it. Cooling was removed after 10 min. and resulting mixture was stirred for 16 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to give 1-carbethoxy-4-ethylamino-3-methylpiperidine. Yield 2.3 g (54%), $C_{11}H_{22}N_2O_2$, m/z 215 (M+1).

Step-2

4-Ethylamino-3-methylpiperidine

1-Carbethoxy-4-ethylamino-3-methylpiperidine (2.3 g, 10.74 mmol) was suspended in 5 M NaOH solution (15 ml), stirred at 110° C. for 120 hr, cooled, extracted with ethyl acetate, dried ($Na_2SO_4$) and concentrated to dryness to afford 4-ethylamino-3-methylpiperidine. Yield 0.7 g (46%), $C_8H_{18}N_2$, m/z 143, (M+1).

Preparation 4

4-Cyclopropylamino-3-methylpiperidine

Step-1

1-Carbethoxy-4-cyclopropylamino-3-methylpiperidine

Cyclopropylamine (10 g, 169.5 mmol) was added to the stirred solution of 1-carbethoxy-3-methyl-4-piperidone (7.0 g, 37.83 mmol) obtained as described in Preparation 1, in methanol (50 ml) and stirring was continued for 12 hr at ambient temperature. The resulting mixture was cooled at 0° C. and sodium cyanoborohydride (3.0 g, 46.0 mmol) was added to it. Cooling was removed after 10 min. and stirring was continued for 12 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to afford 1-carbethoxy-4-cyclopropylamino-3-methylpiperidine. Yield 6.0 g (70%), $C_{12}H_{22}N_2O_2$, m/z 227 (M+1), PMR ($CDCl_3$): 0.38 (m, 4H), 0.88 (dd, 3H), 1.28 (t, 3H), 1.54 (m, 1H), 2.06 (m, 2H), 2.32 (m, 1H), 2.48 (m, 1H), 2.84 (m, 1H), 3.06 (m, 1H), 3.72 (m, 1H), 3.88-4.24 (m, 2H).

Step-2

4-Cyclopropylamino-3-methylpiperidine

1-Carbethoxy-4-cyclopropylamino-3-methylpiperidine (6.0 g, 26.66 mmol) was suspended in 5 M NaOH solution (20 ml), stirred at 130° C. for 120 hr, cooled and extracted with ethyl acetate. Ethyl acetate extract was dried ($Na_2SO_4$) and concentrated to dryness to afford a mixture of starting material (3.0 g) and 4-cyclopropylamino-3-methylpiperidine, which were separated by silica column chromatography. Yield 1.0 g (35%), $C_9H_{18}N_2$, m/z 155, (M+1).

Preparation 5

4-Dimethylamino-3-methylpiperidine

Step-1

1-Carbethoxy-4-dimethylamino-3-methylpiperidine

Paraformaldehyde (5.1 g) was added to the stirred solution of 4-amino-1-carbethoxy-3-methylpiperidine (3.5 g, 18.8 mmol) in methanol (100 ml) at 0° C. and sodium cyanoborohydride (1.7 g, 27.0 mmol) was added to it. Then, acetic acid (1 ml) was added to the resulting mixture and stirring was continued for 96 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to give 1-carbethoxy-4-dimethylamino-3-methylpiperidine. Yield 3.5 g (88%), $C_{11}H_{22}N_2O_2$, m/z 215 (M+1).

Step-2

4-Dimethylamino-3-methylpiperidine

1-Carbethoxy-4-dimethylamino-3-methylpiperidine (3.5 g, 16.3 mmol) was suspended in 5 M NaOH solution (20 ml), stirred at 110° C. for 48 hr, cooled, extracted with ethyl acetate, dried (Na$_2$SO$_4$) and concentrated to dryness to afford 4-dimethylamino-3-methylpiperidine. Yield 1.0 g (43%), C$_8$H$_{18}$N$_2$, m/z 143 (M+1), PMR (CDCl$_3$): 0.96 (dd, 3H), 1.3 (m, 1H), 1.5 (m, 1H), 1.74 (m, 1H), 2.08 (m, 1H), 2.24 (s, 6H), 2.38 (m, 1H), 2.61 (bs, 1H, D$_2$O exchangeable), 2.86 (m, 1H), 3.16 (m, 1H), 3.68 (m, 1H).

Preparation 6

4-Amino-3-ethylpiperidine

Ethyl chloroformate (37.49 g, 346 mmol) was added to a stirred solution of 1-benzyl-3-ethyl-4-piperidone (24.0 g, 110 mmol) in benzene (200 ml) at ambient temperature. The obtained reaction mixture was refluxed with stirring for 16 hr and concentrated to dryness to give 1-carbethoxy-3-ethylpiperidin-4-one as oil. Yield 21 g (96%), C$_{10}$H$_{17}$NO$_3$, m/z 200 (M+1).

Ammonium acetate (33 g) was added to the stirred solution of 1-carbethoxy-3-ethyl-4-piperidinone (8.2 g, 41 mmol) in methanol (125 ml) and stirring was continued for 3 hr at ambient temperature. The resulting mixture was cooled at 0° C. and sodium cyanoborohydride (2.5 g, 39 mmol) was added to it. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to furnish crude 4-amino-1-carbethoxy-3-ethylpiperidine, which was used as such in the next step. 4-Amino-1-carbethoxy-3-ethylpiperidine was suspended in 5 M NaOH solution (36 ml), stirred at 120° C. for 120 hr, cooled, extracted with ethyl acetate, dried (Na$_2$SO$_4$) and concentrated to dryness to afford 4-amino-3-ethylpiperidine. Yield 3.1 g (59.6%), C$_7$H$_{16}$N$_2$, m/z 129 (M+1).

Preparation 7

4-Methylamino-3-ethylpiperidine

Methylamine hydrochloride (17 g, 252 mmol) was added to the stirred solution of 1-carbethoxy-3-ethyl-4-piperidone (10 g, 50 mmol) in methanol (150 ml) followed by 14.1 g (252 mmol) KOH. Stirring was continued for 3 hr at ambient temperature. The resulting mixture was cooled at 0° C. and sodium cyanoborohydride (4.72 g, 75 mmol) was added to it. Cooling was removed after 10 min. and resulting mixture was stirred for 12 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to give crude 1-carbethoxy-4-methylamino-3-ethylpiperidine. The obtained crude 1-carbethoxy-4-methylamino-3-ethylpiperidine was suspended in 7 M NaOH solution (50 ml), stirred at 110° C. for 230 hr, cooled, extracted with ethyl acetate, dried (Na$_2$SO$_4$) and concentrated to dryness to afford 4-methylamino-3-ethyl-piperidine. Yield 3.5 g (50%), C$_8$H$_{18}$N$_2$, m/z 142 (M+1).

Preparation 8

4-Cyclopropylamino-3-ethylpiperidine

Cyclopropylamine (14.25 g, 250 mmol) was added to the stirred solution of 1-carbethoxy-3-ethyl-4-piperidone (10 g, 50 mmol) in methanol (100 ml) and stirring was continued for 12 hr at ambient temperature. The resulting mixture was cooled at 0° C. and sodium cyanoborohydride (3.9 g, 62 mmol) was added to it. Cooling was removed after 10 min. and stirring was continued for 12 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to afford crude 1-carbethoxy-4-cyclopropylamino-3-ethyl piperidine. The obtained crude 1-carbethoxy-4-cyclopropylamino-3-ethylpiperidine was suspended in 7 M NaOH solution (30 ml), stirred at 130° C. for 160 hr, cooled and extracted with ethyl acetate. Ethyl acetate extract was dried (Na$_2$SO$_4$) and concentrated to dryness to afford 4-cyclopropylamino-3-ethylpiperidine. Yield 5.7 g (67%), C$_{10}$H$_{20}$N$_2$, m/z 169, (M+1).

Preparation 9

4-Dimethylamino-3-ethylpiperidine

Sodium cyanoborohydride (3.2 g, 50.8 mmol) was added to the stirred suspension of N-tert.-butoxycarbonyl-3-ethyl-4-piperidone (8 g, 35 mmol), N,N-dimethylamine hydrochloride (14 g, 172 mmol) and KOH (9.6 g, 172 mmol) in methanol (50 ml) at 0° C. The resulting mixture was stirred for 4 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to give 4-dimethylamino-3-ethylpiperidine. Yield 2.3 g (37%), C$_9$H$_{20}$N$_2$, m/z 157 (M+1).

Preparation 10

4-Amino-3,3-dimethylpiperidine

Step-1

1-Benzyl-3,3-dimethyl-4-piperidone

Method -A

To a solution of 1-benzyl-4-piperidone (1 kg, 5.3 mol) in 7 liter THF, was added simultaneously potassium tert-butoxide (1.25 kg, 11.16 mol) in eight equal lots, and methyl iodide (1.5 kg, 10.56 mol) diluted with 1 liter THF, over a period of four hours between temperature 0 to 10° C. The reaction mixture was slowly allowed to warm upto to 35° C. and maintained for 4 hours. The reaction mixture was diluted with 4 liter saturated aqueous sodium chloride solution. The organic layer was separated. The aqueous layer was washed with 2.0 liter chloroform. Combined organic layer was concentrated to provide a crude product in 1.23 kg quantity.

The crude product was distilled at 3 mm vacuum, and 160° C. fraction distillate was collected in a quantity of 800 gm. To the distillate, 1 liter concentrated HCl was added to provide a clear solution. The solution obtained was concentrated to dryness. The solid obtained was recrystallised from 2 liter isopropanol to afford hydrochloride salt of 1-benzyl-3,3-dimethyl-4-piperidone (720 gm).

The solid was dissolved in 2 liter water and treated with 800 ml aqueous ammonia. The basic solution obtained was extracted with 2×2 liter $CHCl_3$. Concentration of the combined organic layer afforded 1-benzyl-3,3-dimethyl-4-piperidone (490 gm, 42% yield) having spectral data as given below:

C14H19NO m/z=218 (ES+1)

PMR ($CDCl_3$): 1.18 (s, 6H); 2.40 (s, 2H); 2.45 (t, 2H); 2.65 (t, 2H); 3.60 (s, 2H); 7.38 (m, 5H).

Method-B

1-Benzyl-4-piperidone (100 gm, 0.53 mol) diluted with 100 ml THF was added to a suspension of 60% NaH (42 g, 1.05 mol) in 700 ml THF at −10 to −5° C. The mixture was stirred for 1 hour and methyl iodide (150 gm, 1.06 mol) diluted in 50 ml THF was added, maintaining the temperature between −3 to −10° C. The resultant mixture was stirred. Ethyl acetate (800 ml) was added to the reaction mixture followed addition of 300 ml water. The organic layer was separated washed with 2×300 ml water and concentrated under vacuum to obtain a syrup. The syrup was triturated with 200 ml hexane. the mass was filtered at room temperature over celite and the filtrate concentrated to afford a 121 gm of crude compound. The crude compound upon high vacuum distillation afforded 85 g distillate. To the distillate (50 gm) was charged 50 ml of concentrated hydrochloric acid. The suspension was stirred for 15 minutes and hydrochloric acid was evaporated under vacuum to obtain a thick residue. Isopropanol (50 ml) was added to this residue and was evaporated under vacuum to obtain a solid. The solid was dissolved in 200 ml isopropanol under reflux and stirring, and cooled under stirring to effect crystallization. The crystalline solid was filtered under suction at 20-30° C. to give a white crystalline compound as hydrochloride salt of 1-benzyl-3,3-dimethyl-4-piperidone. The solid was dissolved in 100 ml water and made alkaline with aqueous ammonia solution to pH 10-11. Alkaline aqueous phase was extracted with 50 ml chloroform thrice. Combined organic extract was washed with water, dried over sodium sulfate and then evaporated under vacuum to afford 28 g (80%) compound as an oil.

m/z (M+1) 218.

NMR ($CDCl_3$): 1.18 (s, 6H,); 2.40 (s, 2H); 2.45(t, 2H); 2.65 (t, 2H); 3.60 (s, 2H); 7.38 (m, 5H).

Step-2

4-Amino-3,3-dimethylpiperidine

Ammonium acetate (3.5 g, 45.45 mmol) was added to the stirred solution of 1-benzyl-3,3-dimethyl-4-piperidone (2.0 g, 9.2 mmol), in methanol (20 ml) and stirring was continued for 3 hr at ambient temperature. The resulting mixture was cooled at 0° C. and sodium cyanoborohydride (0.58 g, 9.2 mmol) was added. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to dryness to furnish 4-amino-1-benzyl-3,3-dimethyl piperidine. Yield 1.6 g (77%), $C_{14}H_{22}N_2$, m/z 219 (M+1), PMR ($CDCl_3$): 0.84 (s, 3H), 0.98 (s, 3H), 1.48 (bs, 2H, $D_2O$ exchangeable), 1.66 (m, 2H), 2.04 (m, 2H), 2.42 (m, 2H), 2.86 (m, 1H), 3.46 (dd, 2H), 7.32 (m, 5H).

A mixture of 20% $Pd(OH)_2$ on carbon (0.3 g) and 4-amino-1-benzyl-3,3-dimethylpiperidine (1.6 g, 7.33 mmol) in methanol (25 ml) was stirred in hydrogen atmosphere (1 atm.) at 30° C. for 6 hr. The catalyst was filtered off, washed with methanol and filtrate was concentrated to dryness to afford 4-amino-3,3-dimethylpiperidine. Yield 0.7 g (75%), $C_7H_{16}N_2$, m/z 129 (M+1), PMR ($CDCl_3$): 0.9 (s, 6H), 1.5 (m, 2H), 1.58 (bs, 2H, $D_2O$ exchangeable), 2.26-2.68 (m, 4H), 3.06 (m, 1H), 3.52 (bs, 1H, $D_2O$ exchangeable).

Preparation 11

4-Methylamino-3,3-dimethylpiperidine

Potassium hydroxide (12.85 g, 230 mmol) was added to the stirred solution of methylamine hydrochloride (15.5 g, 230.0 mmol) in methanol (100 ml) and stirring was continued for 30 min at 30° C. 1-Benzyl-3,3-dimethyl-4-piperidone (5 g, 23.0 mmol), was added to the resulting mixture and stirred for 6 hr. Sodium cyanoborohydride (1.45 g, 23.0 mmol) was added to it and reaction mixture was stirred for 15 hr. The reaction mixture was concentrated to dryness, triturated with water, extracted with chloroform, dried ($Na_2SO_4$) and concentrated to give 1-benzyl-4-methylamino-3,3-dimethylpiperidine. Yield 5.3 g (99%), $C_{15}H_{24}N_2$, m/z 233 (M+1), PMR ($CDCl_3$): 0.9 (s, 3H), 1.0 (s, 3H), 1.38 (m, 2H), 1.54 (bs, 1H, $D_2O$ exchangeable), 1.68-2.1 (m, 4H), 2.4 (s, 3H), 2.86 (m, 1H), 3.4 (dd, 2H), 7.3 (m, 5H).

A mixture of 20% $Pd(OH)_2$ on carbon (0.15 g) and 1-benzyl-4-methylamino-3,3-dimethylpiperidine (0.5 g, 2.1 mmol) in methanol (10 ml) was stirred in hydrogen atmosphere (1 atm.) at 60° C. for 6 hr. The catalyst was filtered off, washed with methanol and filtrate was concentrated to dryness to afford 4-methylamino-3,3-dimethyl-piperidine. Yield 0.3 g (99%), $C_8H_{18}N_2$, m/z 143 (M+1), PMR ($CDCl_3$): 0.88 (s, 6H), 1.24 (m, 2H), 1.8 (bs, 2H, $D_2O$ exchangeable), 1.8 (m, 1H), 2.1 (m, 1H), 2.4 (s, 3H), 2.6 (d, 2H), 2.86 (m, 1H).

Preparation 12

4-Ethylamino-3.3-dimethylpiperidine

Potassium hydroxide (4.6 g, 83.0 mmol) was added to the stirred solution of ethylamine hydrochloride (6.8 g, 83.0 mmol) in methanol (70 ml) and stirring was continued for 30 min at 30° C. 1-benzyl-3,3-dimethyl-4-piperidone (3.5 g, 16.6 mmol)), was added to the resulting mixture and stirred for 6 hr. Sodium cyanoborohydride (1.0 g, 16.6 mmol) was added to it and reaction mixture was stirred for 15 hr. The reaction mixture was concentrated to dryness, triturated with water, extracted with chloroform, dried ($Na_2SO_4$) and concentrated to give 1-benzyl-4-ethylamino-3,3-dimethylpiperidine. Yield 3.8 g (88%), $C_{16}H_{26}N_2$, m/z 247 (M+1), PMR ($CDCl_3$): 0.9 (s, 3H), 1.06 (s, 3H), 1.18-1.38 (m, 5H), 1.64-2.8 (m, 6H), 2.94 (m, 1H), 3.44 (dd, 2H), 7.2 (m, 5H).

A mixture of 20% $Pd(OH)_2$ on carbon (0.4 g) and 1-benzyl-4-ethylamino-3,3-dimethylpiperidine (1.3 g, 5.3 mmol) in methanol (10 ml) was stirred in hydrogen atmosphere (1 atm.) at ambient temperature for 15 hr. The catalyst was filtered off, washed with methanol and filtrate was concentrated to dryness to afford 4-ethylamino-3,3-dimethylpiperidine. Yield 0.8 g (97%), $C_9H_{20}N_2$, m/z 157 (M+1), PMR ($CDCl_3$): 0.9 (s, 3H), 1.06 (s, 3H), 1.18-1.38 (m, 5H), 1.85 (bs, 2H, $D_2O$ exchangeable), 1.64-2.8 (m, 6H), 2.94 (m, 1H).

Preparation 13

4-Cyclopropylamino-3,3-dimethylpiperidine

1-Benzyl-3,3-dimethyl-4-piperidone (10.0 g, 46.0 mmol), was added to the stirred solution cyclopropylamine (13.1 g, 230.0 mmol) in methanol (150 ml) and stirred for 6 hr. Sodium cyanoborohydride (2.9 g, 46.0 mmol) was added to it and reaction mixture was stirred for 15 hr. The reaction mixture was concentrated to dryness, triturated with water, extracted with chloroform, dried ($Na_2SO_4$) and concentrated. The obtained crude product was purified over silica gel column. Eluted from 5% ethyl acetate in hexane gave 1-benzyl-4-cyclopropylamino-3,3-dimethyl piperidine. Yield 8.0 g (67.3%), $C_{17}H_{26}N_2$, m/z 259 (M+1), PMR ($CDCl_3$): 0.4 (m, 2H), 0.82 (s, 3H), 1.06 (s, 3H), 1.16 (m, 2H), 1.5 (bs, 1H, $D_2O$ exchangeable), 1.7 (m, 2H), 1.9-2.95 (m, 5H), 3.3-3.6 (m, 3H), 7.22 (m, 5H).

A mixture of 20% $Pd(OH)_2$ on carbon (0.5 g) and 1-benzyl-4-cyclopropyl-amino-3,3-dimethylpiperidine (2.0 g, 7.7 mmol) in methanol (20 ml) was stirred in hydrogen atmosphere (1 atm.) at 60° C. for 48 hr. The catalyst was filtered off, washed with methanol and filtrate was concentrated to dryness to afford 4-cyclopropylamino-3,3-dimethylpiperidine. Yield 1.2 g (92%), $C_{10}H_{20}N_2$, m/z 169 (M+1), PMR ($CDCl_3$): 0.42 (m, 2H), 0.84 (s, 3H), 0.9 (s, 3H), 1.22 (m, 2H), 1.7 (bs, 2H, $D_2O$ exchangeable), 1.94 (m, 2H), 2.1-2.72 (m, 5H), 3.08 (m, 1H).

Preparation 14

4-Dimethylamino-3,3-dimethylpiperidine

Formaldehyde solution (47%, 10 g) was added to the stirred solution of 4-amino-1-benzyl-3,3-dimethylpiperidine (2.0 g, 9.2 mmol) in methanol (20 ml) at 0° C. and sodium cyanoborohydride (0.5 g, 9.2 mmol) was added to it. Then, acetic acid (2 ml) was added to the resulting mixture and stirring was continued for 24 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried ($Na_2SO_4$) and concentrated to give 1-benzyl-4-dimethylamino-3,3-dimethylpiperidine. Yield 1.9 g (84%), $C_{16}H_{26}N_2$, m/z 247 (M+1).

A mixture of 20% $Pd(OH)_2$ on carbon (0.3 g) and 1-benzyl-4-dimethylamino-3,3-dimethylpiperidine (4.5 g, 6.0 mmol) in methanol (20 ml) was stirred in hydrogen atmosphere (1 atm.) for 48 hr at room temperature. The catalyst was filtered off, washed with methanol and filtrate was concentrated to afford 4-dimethylamino-3,3-dimethylpiperidine. Yield 1.6 g (95%), $C_9H_{20}N_2$, m/z 157 (M+1).

Preparation 15

4-Carbethoxyamino-3,3-dimethylpiperidine

Ethyl chloroformate (2 ml) was added to a stirred solution of 4-amino-1-benzyl-3,3-dimethylpiperidine (1.6 g, 7.33 mmol) and triethylamine (2 ml) in methylene chloride (25 ml) at ambient temperature, stirring was continued for 1 hr concentrated to dryness, triturated with water, extracted with ethyl acetate, dried ($Na_2SO_4$) and concentrated to give 1-benzyl-4-carbethoxyamino-3,3-dimethyl piperidine as oil. Yield 1.3 g (62%), $C_{17}H_{26}N_2O_2$, m/z 291 (M+1), PMR ($CDCl_3$): 0.98 (s, 3H), 1.2 (t, 6H), 1.78 (m, 2H), 2.42 (m, 2H), 2.82 (m, 2H), 3.6 (d, 2H), 3.9 (m, 1H), 4.1 (q, 2H), 4.8 (bs, 1H), 7.54 (m, 5H).

A mixture of 20% $Pd(OH)_2$ on carbon (0.3 g) and 1-benzyl-4-carbethoxyamino-3,3-dimethylpiperidine (1.3 g, 4.48 mmol) in methanol (15 ml) was stirred in hydrogen atmosphere (1 atm.) at 30° C. for 3 hr. The catalyst was filtered off, washed with methanol and filtrate was concentrated to dryness to afford 4-carbethoxyamino-3,3-dimethylpiperidine. Yield 0.8 g (90%), $C_{10}H_{20}N_2O_2$, m/z 201 (M+1).

Preparation 16

4-Acetylamino-3,3-dimethylpiperidine

Acetic anhydride (3 ml) was added to a stirred solution of 4-amino-1-benzyl-3,3-dimethylpiperidine (2.0 g, 9.17 mmol) in pyridine (5 ml) and stirred for 1 hr. The reaction mixture was concentrated to furnish 4-acetylamino-1-benzyl-3,3-dimethyl piperidine as an oil. Yield 1.8 g (76%), $C_{16}H_{24}N_2O$, m/z 261 (M+1), PMR ($CDCl_3$): 0.84 (s, 3H), 0.98 (s, 3H), 1.64 (m, 2H), 2.02 (s, 3H), 2.12 (m, 2H), 2.44 (d, 1H), 2.84 (d, 1H), 3.44 (d, 2H), 3.7 (m, 1H), 5.3 (bs, 1H), 7.31 (m, 5H).

A mixture of 20% $Pd(OH)_2$ on carbon (0.3 g) and 4-acetylamino-1-benzyl-3,3-dimethyl piperidine (1.8 g, 6.92 mmol) in methanol (20 ml) was stirred in hydrogen atmosphere (1 atm.) at 35° C. for 6 hr. The catalyst was filtered off, washed with methanol and filtrate was concentrated to dryness to afford 4-acetylamino-3,3-dimethylpiperidine. Yield 1.0 g (90%), $C_9H_{18}N_2O$, m/z 171 (M+1).

Preparation 17

3.3-Dimethyl-4-piperidone

1-Benzyl-3,3-dimethyl-4-piperidone 275 g (1.26 mol), was dissolved in 1.0 L. methanol. The solution was transferred to a Parr reactor after adding 10% palladium on carbon (25 g). The reaction mixture was stirred under 300 psi hydrogen pressure at 60° C. until chromatography showed complete conversion. The reaction mixture was filtered and the residue washed with methanol (200 ml). The filtrate was concentrated to dryness to afford 3,3-dimethyl-4-piperidone (158 g) which was used as such for the preparation of either 4-benzyloxycarbonylamino-3,3-dimethylpiperidine or 4-t-butyloxycarbonylamino-3,3-dimethylpiperidine.

Preparation 18

(±)-4-Benzyloxycarbonylamino-3,3-dimethylpiperidine

Step-1

1-$^t$Butyloxycarbonyl-3,3-dimethyl-4-piperidone

Di-t-butyldicarbonate (430 g, 1.97 mol) was added to a stirred solution of 3,3-dimethyl-4-piperidone (262 g, 2.06 mol) and triethylamine (175 g, 1.73 mol) in 600 ml dichloromethane at 0-10° C. over a period of 1 hour. Cooling was removed and the reaction mixture was stirred at 20-30° C. for 30 min. The reaction mixture was concentrated to dryness and the residue was triturated with hexane (250 ml) and filtered to give 1-t-butyloxycarbonyl-3,3-dimethyl-4-piperidone (352 g) in 76% yield. m/z (M+1) 228.

NMR(CDCl$_3$): 0.8 (s, 3H); 0.95 (s, 3H); 1.50 (s, 9H); 1.5-1.8 (m, 2H); 2.5-2.9 (m, 2H); 3.4-3.8 (m, 2H); 4.05 (bs, 1H), 4.6 (d, 1H), 5.05(s, 2H), 7.4 (s, 5H).

Step-2

4-Amino 1-$^t$-butyloxycarbonyl-3,3-dimethylpiperidine

Ammonium acetate (700 g, 9.09 mol) was added to a stirred solution of 1-$^t$-butyloxy carbonyl-3,3-dimethyl-4-piperidone (352 g, 1.55 mol) in methanol (1.0 L). The suspension was stirred for 3 hr at 20-30° C. The reaction mixture was cooled to 0° C. and sodiumcyanoborohydride (45 g, 0.71 mol) was added portion wise over 30 minutes. Cooling was removed and the suspension was stirred for 12 hr at 20-30° C. The reaction mixture was concentrated to dryness, stirred with water (2.0 L) and extracted with 1.0 L×3 dichloromethane. Combined organic extract was washed with water and dried over sodium sulfate. Evaporation of organic solvent afforded the product.

Step-3

4-Benzyloxycarbonylamino-1-$^t$-butyloxycarbonyl-3,3-dimethylpiperidine

Benzyl chloroformate (50% in toluene, 450 ml, 1.57 mol) was added to a stirred suspension of 4-amino-1-$^t$-butyloxycarbonyl-3,3-dimethylpiperidine (365 g) as prepared above and NaHCO$_3$ (150 g, 1.78 mol) in dry tetrahydrofuran (1.5 L). The reaction mixture was stirred for 20 hr at 35° C. The reaction mixture was diluted with 3.5 L water and was extracted with 2.0 L×2 ethyl acetate. Combined organic extract was washed with water, dried over Na$_2$SO$_4$ and concentrated to dryness. The residue was subjected to chromatography on a silica gel column to give 4-benzyloxycarbonylamino-1-$^t$-butyloxycarbonyl-3,3-dimethylpiperidine in 63% (350 g) yield. m/z 363 (M+1).

NMR(CDCl$_3$): 0.8 (s, 3H); 0.95 (s, 3H); 1.5 (s, 9H); 1.5-1.8 (m, 2H);2.5-2.9 (m, 2H); 3.4-3.8 (m, 2H); 4.05 (bs, 1H); 4.6 (d, 1H); 5.05 (s, 2H); 7.4 (s, 5H)

Step-4

4-Benzyloxycarbonylamino-3,3-dimethylpiperidine

6 N HCl (200 ml) was added to a stirred solution of 4-benzyloxycarbonylamino-1-$^t$-butyloxycarbonyl-3,3-dimethylpiperidine (350 g, 0.96 mol) in dioxane (200 ml). The resulting mixture was stirred for 1 hr and concentrated to dryness. The resultant residue was treated with water (3.0 L) water and was extracted with 1.0 L×2 ethyl acetate. The aqueous layer was basified with 2 M aqueous NaOH and extracted with 2.5 L×2 dichloromethane. Combined organic extract was washed with water, dried over Na$_2$SO$_4$ and concentrated to afford 4-benzyloxycarbonylamino-3,3-dimethylpiperidine in 89% (224 g) yield.

m/z (M+1) 263.

NMR (CDCl$_3$): 0.88 (s, 6H); 1.2-1.5 (m, 2H); 1.6-1.8 (m, 1H); 2.4-2.7 (m, 3H); 2.9-3.1 (m, 1H); 3.4-3.6 (m, 1H); 4.7 (s, 1H), 5.1 (s, 2H); 7.40 (s, 5H).

Preparation 19

(+) and (−)-4-$^t$-Butyloxycarbonylamino-3,3-dimethylpiperidine

Step-1

1-Benzyloxycarbonyl-3,3-dimethyl-4-piperidone

Method A 3,3-dimethyl-4-piperidone (157 g, 1.24 mol) was dissolved in 750 L. tetrahydrofuran and was charged with solid NaHCO$_3$ (115 g, 1.37 mol). The reaction mixture was stirred and under stirring addition of 50% benzyl chloroformate in toluene (470 ml, 1.37 mol) was made at 0 to 10° C. temperature. To the reaction mixture 1.0 L water was added and the resulting mixture was extracted with 500 ml×3 ethyl acetate. Combined organic extract was washed with water, dried over sodium sulfate and concentrated in vacuo to give a residue which was subjected to silica gel column chromatography to give 272 g titled compound.

m/z (M+1) 262.

NMR(CDCl$_3$): 1.18 (s, 6H); 2.50 (t, 2H); 3.50(s, 2H); 3.80 (t, 2H); 5.20 (s, 2H); 7.40 (s, 5H).

Method B

1-Benzyl-3,3-dimethyl-4-piperidone (255 g, 1.175 mol) was dissolved in 800 ml toluene. To the clear solution was charged 50% benzyl chloroformate in toluene (441 ml, 1.29 mol). The reaction mixture was stirred at temperature between 80-85° C. for 4-5 hrs. The reaction mixture was concentrated under vacuum. Crude product was purified by silica gel column chromatograhy to give 292 g (95%) titled compound. m/z (M+1) 262.

NMR (CDCl$_3$): 1.18 (s, 6H); 2.50 (t, 2H); 3.50(s, 2H); 3.80 (t, 2H); 5.20 (s, 2H); 7.40 (s, 5H).

Step-2

4-Amino-1-benzyloxycarbonyl-3,3-dimethylpiperidine

1-Benzyloxycarbonyl-3,3-dimethyl-4-piperidone (290 g, 1.11 mol) was dissolved in methanol (1.5 L) and under stirring addition of ammonium acetate (600 g, 7.80 mol ) was made at 30-35° C. The reaction mixture was stirred for 5 hrs. Sodium cyanoborohydride (35 g, 0.55 mol) was added portion wise to the suspension. over 0.5 hrs by maintaining temperature between 0-10° C. The reaction mixture was stirred for 6-7 hrs. After completion of reaction, solvent was evaporated under reduced pressure and addition of 3.00 L water was made under stirring. The reaction mixture was stirred for 15 minutes. It was extracted with 1.5 L×2 CHCl$_3$. Combined organic extract was evaporated under vacuum. The residue was dissolved in 3 N HCl till pH 1 and was extracted with 500 ml×2 dichloromethane. The aqueous layer was basified with 300 ml aqueous ammonia solution (23-25%) to pH 10-11 and then was extracted with 1.5 L×3 dichloromethane. Combined organic extract was washed with water and was dried over sodium sulfate. Evaporation of organic solvent afforded 225 g (77%) title compound.

m/z (M+1) 263.

NMR (CDCl$_3$) D$_2$O exchange: 0.80 (s, 3H); 0.98 (s, 3H); 1.40-1.78 (m, 2H); 2.50 (dt, 2H); 2.90 (m, 1H); 3.80 (t, 1H); 4.18 (t, 1H), 5.18 (s, 2H); 7.40 (s, 5H).

Step-3

(+)-4-Amino-1-benzyloxycarbonyl-3,3-dimethylpiperidine

4-Amino-1-benzyloxycarbonyl-3,3-dimethylpiperidine (200 g, 0.76 mol) was dissolved in 2.4 L 2-3% aqueous ethyl alcohol (moisture content 2.6% by Karl Fischer titration) and L-(+)-tartaric acid (110 g, 0.73 mol) was added to the solution at 65-70° C. The reaction mixture was heated under stirring for half an hour at 65-70° C. The reaction mixture was cooled under stirring between 20-30° C. The solid was filtered and the wet cake was washed with additional 675 ml ethyl alcohol.

Resultant 'solid A' was treated separately to obtain (−) isomer of 4-amino-1-benzyloxycarbonyl-3,3-dimethyl-piperidine as described in Step-4.

The filtrate was concentrated under vacuum to obtain a 'solid B'. The 'solid B' was treated with aqueous $K_2CO_3$ solution made by dissolving 112 g $K_2CO_3$ in 1.2 L water and was extracted with 750 ml chloroform thrice. Combined organic extract was washed with 200 ml water and dried over sodium sulfate. Evaporation of organic solvent afforded 71 g (71%) as an oil. The compound was subjected to a second resolution by dissolving it (70 g, 0.267 mol} in 840 ml 2-3% aqueous ethyl alcohol (moisture content, 2.6%) under stirring and resultant solution was treated with (40 g, 0.267 mol) D-(−)-tartaric acid at 60-70° C. The reaction mixture was agitated at 65-70° C. for half an hour. The reaction mass was cooled and was filtered at 20-30° C. The wet cake was washed with 210 ml additional ethyl alcohol to afford a crystalline salt. The resultant wet solid was treated with aqueous $K_2CO_3$ solution made by dissolving 81 g $K_2CO_3$ in 0.81 L water and was extracted with 750 ml×3 chloroform. Combine organic extract was washed with 200 ml water and was dried over sodium sulfate. Evaporation of organic solvent afforded 57 g (86%) as an oil.

m/z (M+1) 263.

NMR(CDCl$_3$) D$_2$O exchange: 0.80 (s, 3H); 0.98 (s, 3H); 1.40-1.78 (m, 2H); 2.50 (dt, 2H); 2.90 (m, 1H); 3.80 (t, 1H); 4.18 (t, 1H), 5.18 (s, 2H); 7.40 (s, 5H).

$[\alpha]_D^{25}$ value +30.60 (c=1, CHCl$_3$), percentage of isomers ratio 98.07:1.93 determined by HPLC of Mosher amide analogue.

The process of the resolution is further repeated on the free base till the unwanted chiral isomer falls below 0.5% limit by HPLC analysis.

Step-4

(−)-4-Amino-1-benzyloxycarbonyl-3,3-dimethylpiperidine

The 'solid A' obtained in Step-3 was treated with aqueous $K_2CO_3$ solution made by dissolving 164 g $K_2CO_3$ in 1.6 L water and was extracted with 750 ml chloroform thrice. Combined organic extract was washed with 200 ml water and dried over sodium sulfate. Evaporation of organic solvent afforded 85 g (85%) as an oil.

The compound was subjected to a second resolution by dissolving it (84 g, 0.32 mol} in 1.0 L 2-3% aqueous ethyl alcohol (moisture content, 2.6%) under stirring and resultant solution was treated with L-(+)-tartaric acid (46 g, 0.307 mol) at 60-70° C. The reaction mixture was agitated at 65-70° C. for half an hour. The reaction mass was cooled and was filtered at 20-30° C. The wet cake was washed with 250 ml additional ethyl alcohol to afford a crystalline salt. The resultant white solid was treated with aqueous $K_2CO_3$ solution made by dissolving 93 g $K_2CO_3$ in 1.0 L water and was extracted with 750 ml×3 chloroform. Combined organic extract was washed with 200 ml water and was dried over sodium sulfate. Evaporation of organic solvent afforded 71 g (83%) as an oil.

$[\alpha]_D^{25}$ value −31.800° (c=1, CHCl$_3$), percentage of isomers ratio 96.37:3.63 determined by HPLC of Mosher amide analogue.

The process of the resolution is further repeated on the free base till the unwanted chiral isomer falls below 0.5% limit by HPLC analysis.

Step-5

(+)-1-Benzyloxycarbonyl-4-$^t$-butyloxycarbonylamino-3,3-dimethylpiperidine To a solution of (+)-4-amino-1-benzyloxycarbonyl-3,3-dimethylpiperidine (55 g, 0.209 mol) was dissolved in 500 L dichloromethane was added triethylamine (22.2 g, 0.209 mol) followed by di-$^t$butyl carbonate (45.8 g, 0.209 mol) dissolved in 200 ml dichloromethane while maintaining temperature between 5-10° C., under stirring. The reaction was maintained at 25-35° C. After completion of reaction the reaction mixture was diluted with 1.0 L water and layers were separated. Combined organic extract was dried over sodium sulfate and was evaporated to dryness to obtain 76 g of product.

m/z (M+1) 363.

NMR(CDCl$_3$) D$_2$O exchange: 0.80 (s, 3H); 0.98 (s, 3H); 1.45 (s, 9H); 1.70 (m, 1H); 2.70 (m, 1H); 2.90 (t, 1H); 3.40 (t, 1H), 3.80 (t, 1H); 4.18 (t, 1H); 4.4 (d, 1H), 5.1 (s, 2H); 7.40 (s, 5H).

$[\alpha]_D^{25}$ value +16.28° (c=1, CHCl$_3$).

Step-6

(−)-1-Benzyloxycarbonyl-4-$^t$-butyloxycarbonylamino-3,3-dimethylpiperidine The compound was prepared as per procedure described for its (+) isomer in quantitative yield.

$[\alpha]_D^{25}$ value −15.86° (c=1, CHCl$_3$).

Step-7

(+)-4-$^t$-Butyloxycarbonylamino-3,3-dimethylpiperidine (+)-1-Benzyloxycarbonyl-4-$^t$butyloxycarbonylamino-3,3-dimethylpiperidine (75 g, 0.207 mol) was dissolved in 500 ml methanol and the solution was transferred to a Parr reactor. Wet 10% palladium on carbon (7.5 g) was added to the solution and was stirred at 200 psi hydrogen pressure. Reaction progress was monitored on TLC and reaction was completed in 3-4 hrs. The reaction mixture was filtered as soon as it was completed. The residue was washed with 100 ml methanol. Filtrate was evaporated to dryness to afford the required product (47 g) in quantitative yield.

m/z (M+1) 229.

NMR(CDCl$_3$): 0.95 (bs, 6H); 1.45-1.6 (m, 10H); 1.6-1.8 (m, 1H); 2.4 (d, 1H); 2.5-2.7 (m, 2H); 3.05 (m, 1H); 3.3-3.5 (m, 1H), 4.4 (m, 1H).

Step-8

(−)-4-*t*-Butyloxycarbonylamino-3,3-dimethylpiperidine

The compound was prepared as per procedure described for its (+) isomer.

m/z (M+1) 229.

NMR(CDCl$_3$): 0.95 (bs, 6H); 1.45-1.6 (m, 10H); 1.6-1.8 (m, 1H); 2.4 (d, 1H); 2.5-2.7 (m, 2H); 3.05 (m, 1H); 3.3-3.5 (m, 1H), 4.4 (m, 1H).

Preparation 20

4-Amino-3-ethyl-3-methylpiperidine

Ammonium acetate (2.5 g, 32.46 mmol) was added to the stirred solution of 1-benzyl-3-ethyl-3-methyl-4-piperidinone (0.9 g, 3.9 mmol) in methanol (20 ml) and stirring was continued for 3 hr at ambient temperature. The resulting mixture was cooled at 0° C. and sodium cyanoborohydride (0.2 g, 3.1 mmol) was added to it. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to furnish 4-amino-1-benzyl-3-ethyl-3-methylpiperidine. Yield 0.6 g (66%), C$_{15}$H$_{24}$N$_2$, m/z 233 (M+1).

A mixture of 20% Pd(OH)$_2$ on carbon (0.2 g) and 4-amino-1-benzyl-3-ethyl-3-methylpiperidine (0.6 g, 2.58 mmol) in methanol (210 ml) was stirred in hydrogen atmosphere (1 atm.) at 30° C. for 6 hr. The catalyst was filtered off, washed with methanol and filtrate was concentrated to dryness to afford 4-amino-3-ethyl-3-methylpiperidine. Yield 0.27 g (74%), C$_8$H$_{18}$N$_2$, m/z 143 (M+1).

Preparation 21

4-Methylamino-3-ethyl-3-methylpiperidine

Potassium hydroxide (15.45 g, 276 mmol) was added to the stirred solution of methylamine hydrochloride (18.54 g, 276 mmol) in methanol (100 ml) and stirring was continued for 30 min at 30° C. 1-benzyl-3-ethyl-3-methyl-4-piperidinone (8 g, 34.6 mmol) was added to the resulting mixture and stirred for 6 hr. Sodium cyanoborohydride (2.18 g, 34.6 mmol) was added to it and reaction mixture was stirred for 15 hr. The reaction mixture was concentrated to dryness, triturated with water, extracted with chloroform, dried (Na$_2$SO$_4$) and concentrated to give 1-benzyl-4-methylamino-3-ethyl-3-methylpiperidine. Yield 6 g (67%), C$_{16}$H$_{26}$N$_2$, m/z 247 (M+1).

A mixture of 20% Pd(OH)$_2$ on carbon (0.7 g) and 1-benzyl-4-methylamino-3-ethyl-3-methyl piperidine (6 g, 24.39 mmol) in methanol (60 ml) was stirred in hydrogen atmosphere (1 atm.) at 60° C. for 6 hr. The catalyst was filtered off, washed with methanol and filtrate was concentrated to dryness to afford 4-methylamino-3-ethyl-3-methylpiperidine. Yield 2.5 g (66%), C$_9$H$_{20}$N$_2$, m/z 157 (M+1).

Preparation 22

4-Cyclopropylamino-3-ethyl-3-methylpiperidine

1-Benzyl-3-ethyl-3-methyl-4-piperidinone (4.2 g, 18.18 mmol) was added to the stirred solution cyclopropylamine (6.5 g, 115 mmol) in methanol (100 ml) and stirred for 6 hr. Sodium cyanoborohydride (1.14 g, 18.18 mmol) was added to it and reaction mixture was stirred for 15 hr. The reaction mixture was concentrated to dryness, triturated with water, extracted with chloroform, dried (Na$_2$SO$_4$) and concentrated to furnish crude 1-benzyl-4-cyclopropylamino-3-ethyl-3-methylpiperidine. Yield 4 g (88%), C$_{18}$H$_{28}$N$_2$, m/z 273 (M+1).

A mixture of 20% Pd(OH)$_2$ on carbon (0.5 g) and 1-benzyl-4-cyclopropylamino-3-ethyl-3-methylpiperidine (3.54 g, 13.00 mmol) in methanol (70 ml) was stirred in hydrogen atmosphere (1 atm.) at 60° C. for 48 hr. The catalyst was filtered off, washed with methanol and filtrate was concentrated to dryness to afford 4-cyclopropylamino-3-ethyl-3-methylpiperidine. Yield 2.3 g (93%), C$_{11}$H$_{22}$N$_2$, m/z 183 (M+1).

Preparation 23

4-Dimethylamino-3-Ethyl-3-Methylpiperidine

Paraformaldehyde (10 g) was added to the stirred solution of 4-amino-1-benzyl-3-ethyl-3-methylpiperidine (8.0 g, 34 mmol) in methanol (100 ml) at 0° C. and sodium cyanoborohydride (2.14 g, 34 mmol) was added to it. Then, acetic acid (2 ml) was added to the resulting mixture and stirring was continued for 24 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to give 1benzyl-4-dimethylamino-3-ethyl-3-methylpiperidine. Yield 6 g (67%), C$_{17}$H$_{28}$N$_2$, m/z 261 (M+1).

A mixture of 20% Pd(OH)$_2$ on carbon (0.7 g) and 1-benzyl-4-dimethylamino-3-ethyl-3-methyl piperidine (6 g, 23 mmol) in methanol (50 ml) was stirred in hydrogen atmosphere (1 atm.) for 48 hr at room temperature. The catalyst was filtered off, washed with methanol and filtrate was concentrated to afford 4-dimethylamino-3-ethyl-3-methylpiperidine. Yield 2.8 g (72%), C$_{10}$H$_{22}$N$_2$, m/z 171 (M+1).

Preparation 24

4-Amino-3,3-diethylpiperidine

Ammonium acetate (7.85 g, 102 mmol) was added to the stirred solution of 1-benzyl-3,3-diethyl piperidin-4-one (5.0 g, 20.40 mmol) in methanol (100 ml) and stirring was continued for 3 hr at ambient temperature. The resulting mixture was cooled at 0° C. and sodium cyanoborohydride (1.3 g, 20.40 mmol) was added to it. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to dryness to furnish 4-amino-1-benzyl-3,3-diethyl piperidine. Yield 8.2 g (82%), $C_{16}H_{26}N_2$, m/z 247 (M+1), PMR (CDCl$_3$): 0.84 (s, 3H), 0.98 (s, 3H), 1.48 (bs, 2H, D$_2$O exchangeable), 1.66 (m, 2H), 2.04(m, 2H), 2.42 (m, 2H), 2.86 (m, 1H), 3.46 (dd, 2H), 7.32 (m, 5H).

A mixture of 20% Pd(OH)$_2$ on carbon (0.8 g) and 4-amino-1-benzyl-3,3-diethylpiperidine (8.0 g, 32.52 mmol) in methanol (100 ml) was stirred in hydrogen atmosphere (1 atm.) at 30° C. for 6 hr. The catalyst was filtered off, washed with methanol and filtrate was concentrated to dryness to afford 4-amino-3,3-diethylpiperidine. Yield 4.8 g (94.60%), $C_9H_{20}N_2$, m/z 157 (M+1), PMR (CDCl$_3$): 0.9 (s, 6H), 1.5 (m, 2H), 1.58 (bs, 2H, D$_2$O exchangeable), 2.26-2.68 (m, 4H), 3.06 (m, 1H), 3.52 (bs, 1H, D$_2$O exchangeable).

Preparation 25

4-Amino-3,5-dimethylpiperidine

Step-1

Mixture of Isomers of
4-amino-1-carbethoxy-3,5-dimethylpiperidine

Ethyl chloroformate (10.0 g, 90 mmol) was added to a stirred solution of 1-benzyl-3,5-dimethyl-4-piperidinone (5.0 g, 24 mmol) in benzene (20 ml), refluxed with stirring for 6 hr and concentrated to dryness to give 1-carbethoxy-3,5-dimethyl-4-piperidinone as oil. Yield 4.51 g (90%), $C_{10}H_{17}NO_3$, m/z 200 (M+1).

Ammonium acetate (20 g) was added to the stirred solution of 1-carbethoxy-3,5-dimethyl-4-piperidinone (4.5 g, 22.5 mmol) in methanol (200 ml) and stirred for 3 hr. The resulting mixture was cooled at 0° C. and sodium cyanoborohydride (1.4 g, 22.5 mmol) was added to it. Cooling was removed and stirring was for 3 hr at 35° C. The reaction mixture was concentrated, triturated with water, acidified with conc. HCl (pH 3~4) and extracted with ethyl acetate to remove impurities. The aqueous layer was basified with 1 M sodium hydroxide solution (pH ~10) and extracted with ethyl acetate. Ethyl acetate extract was dried (Na$_2$SO$_4$) and concentrated to give 4-amino-1-carbethoxy-3,5-dimethylpiperidine. The obtained 4-amino-1-carbethoxy-3,5-dimethylpiperidine was subjected to silica gel column chromatography. Elution with 5% methanol in chloroform furnished a solid, which was a mixture of stereoisomers, conformational analysis of which was not obtained.

Yield 3.5 g (77%), m.p. 218-20° C., $C_{10}H_{18}N_2O_2$, m/z 201 (M+1).

Step-2

Separation of Isomers of
4-amino-1-carbethoxy-3,5-dimethylpiperidine

4-Amino-1-carbethoxy-3,5-dimethylpiperidine obtained as per procedure described in Step-1 was subjected to silica gel column chromatography. Elution with chloroform gave "upper" mixture of isomers of 4-amino-1-carbethoxy-3,5-dimethylpiperidine m.p. 248-50° C., $C_{10}H_{18}N_2O_2$, m/z 201 (M+1), PMR (CDCl$_3$): 0.94 (m, 6H), 1.16 (t, 3H), 1.78 (m, 1H), 2.02 (m, 1H), 2.06 (bs, 2H, D$_2$O exchangeable), 2.72 (m, 2H), 2.86 (m, 1H), 3.74 (m, 2H), 4.12 (q, 2H).

Further elution with 5% methanol in chloroform furnished "lower" mixture of isomers of 4-amino-1-carbethoxy-3,5-dimethylpiperidine m.p. 236-40° C., $C_{10}H_{18}N_2O_2$, m/z 201 (M+1), PMR (CD$_3$OD): 0.88 (m, 6H), 1.16 (t, 3H), 1.82 (m, 1H), 2.1 (m, 1H), 2.5 (m, 2H), 2.94-3.15 (m, 3H), 3.96 (q, 2H).

Step-3

Mixture of Isomers of
4-amino-3,5-dimethylpiperidine (Mixtures A+B)

A mixture of isomers of 4-amino-1-carbethoxy-3,5-dimethylpiperidine (10 g, 51 mmol) obtained by a procedure as described in step-1, was stirred in 5 M NaOH solution (100 ml) at 100° C. for 48 hr, cooled, extracted with ethyl acetate, dried (Na$_2$SO$_4$) and concentrated to afford mixture of isomers of 4-amino-3,5-dimethylpiperidine as oil as "mixture A+B". Yield 5.1 g (80%), $C_7H_{16}N_2$, m/z 129 (M+1).

Step-4

"Upper" Mixture of Isomers of
4-amino-3,5-dimethylpiperidine (Mixture A of Isomers)

A "upper" mixture of isomers of 4-amino-1-carbethoxy-3,5-dimethylpiperidine (1.5 g, 7.5 mmol) obtained as described in Step-2, was stirred in 5 M NaOH solution (10 ml) at 100° C. for 48 hr, cooled, extracted with ethyl acetate, dried (Na$_2$SO$_4$) and concentrated to afford "upper" mixture of isomers of 4-amino-3,5-dimethyl piperidine as oil as mixture A of isomers, of which the conformational analysis was not obtained. Yield 0.72 g (76%), $C_7H_{16}N_2$, m/z 129 (M+1), PMR (CDCl$_3$): 0.94 (m, 6H), 1.7 (bs, 3H, D$_2$O exchangeable), 1.78 (m, 1H), 2.02 (m, 1H), 2.5-2.8 (m, 4H), 2.86 (m, 1H).

Step-5

"Lower" Mixture of Isomers of
4-amino-3,5-dimethylpiperidine (Mixture B of Isomers)

A "lower" mixture of isomers of 4-amino-1-carbethoxy-3,5-dimethylpiperidine (1.0 g, 5.0 mmol) obtained by a procedure as described in step-2, was stirred in 5 M NaOH solution (10 ml) at 100° C. for 48 hr, cooled, extracted with ethyl acetate, dried (Na$_2$SO$_4$) and concentrated to afford "lower" mixture of isomers of 4-amino-3,5-dimethylpiperidine as an oil as mixture B of isomers, of which the conformational analysis was not obtained. Yield 0.51 g (80%), $C_7H_{16}N_2$, m/z 129 (M+1).

Preparation 26

4-Methylamino-3,5-Dimethylpiperidine

Powdered KOH (0.92 g, 16.44 mmol) was added in portions to the stirred solution of methylamine hydrochloride (1.11 g, 16.44 mmol) in methanol (20 ml) at 0-5° C. and 1-carbethoxy-3,5-dimethyl-4-piperidinone (2.2 g, 1.1 mmol), obtained by a procedure as described in Example 25 (Step-1), was added in portions to it. The resulting reaction mixture was stirred for 45 min at 10° C. and a solution of sodium cyanoboro-hydride (0.7 g, 1.1 mmol) in methanol (5 ml) was added dropwise to it. Cooling was removed and stirring was for 24 hr at 30° C. The reaction mixture was basified with 20% KOH solution, filtered (to remove insoluble impurities) and filtrate was concentrated to dryness. The obtained residue was dissolved in water and extracted with chloroform. Chloroform layer was extracted with 50% HCl and acid layer was basified with 20% KOH solution. The separated oil was extracted with chloroform, dried (Na$_2$SO$_4$) and concentrated to give a Mixtures A+B of 4-methylamino- 1-carbethoxy-3,5-dimethylpiperidine. Yield 1.34 g (60%), $C_{11}H_{22}N_2O_2$, m/z 214 (M+1).

Mixtures A+B of 4-methylamino-1-carbethoxy-3,5-dimethylpiperidine (1.3 g, 0.6 mmol) was stirred in a mixture of 10% NaOH solution (20 ml) and ethyl alcohol (10 ml) at 100° C. for 120 hr, cooled, extracted with ethyl acetate, dried ($Na_2SO_4$) and concentrated to afford a Mixtures A+B of 4-methylamino-3,5-dimethylpiperidine. Yield 0.61 g (70%), $C_8H_{18}N_2$, m/z 143 (M+1).

Mixture A of isomers and Mixture B of isomers of 4-methylamino-3,5-dimethylpiperidine were prepared by separation technique at 4-methylamino-1-carbethoxy-3,5-dimethylpiperidine stage by using silica gel column chromatography similar as described in Preparation 25 (Step-2) followed by aqueous sodium hydroxide mediated hydrolysis.

Preparation 27

4-methylamino-3,5-dimethylpiperidine

Powdered KOH (2.8 g, 50 mmol) was added in portions to the stirred solution of ethylamine hydrochloride (4.0 g, 50 mmol) in methanol (50 ml) and 1-carbethoxy-3,5-dimethyl-4-piperidinone (5.0 g, 25.12 mmol) obtained by a procedure as described in Example 25 (Step-1), was added to it. The resulting reaction mixture was stirred for 6 hr. A solution of sodium cyanoborohydride (1.6 g, 25.12 mmol) in methanol (10 ml) was added dropwise to it and stirring was continued for 16 hr. The reaction mixture was concentrated to dryness. The obtained residue was dissolved in water and extracted with chloroform. Chloroform layer was extracted with 50% HCl and acid layer was basified with KOH (20%) solution. The oil thus separated was extracted with chloroform, dried ($Na_2SO_4$) and concentrated to give Mixtures A+B of 4-ethylamino-1-carbethoxy-3,5-dimethylpiperidine as an oil. Yield 5.6 g (97.7%), $C_{12}H_{24}N_2O_2$, m/z 229 (M+1).

The similarly obtained Mixtures A+B of 4-ethylamino-1-carbethoxy-3,5-dimethylpiperidine was separated over silica gel column chromatography. Elution from 5% methanol in chloroform gave Mixture A of isomers of 4-ethylamino-1-carbethoxy-3,5-dimethylpiperidine as oil. Yield 2.1 g (36%), $C_{12}H_{24}N_2O_2$, m/z 229 (M+1), PMR ($CDCl_3$): 0.94 (dd, 6H), 1.25 (t, 3H), 1.5-2.1 (3H, m, $D_2O$ exchangeable), 2.38 (m, 1H), 2.72 (m, 2H), 3.3-3.8 (m, 3H), 3.64 (s, 1H), 4.12 (q, 2H). Further elution from 5% methanol in chloroform furnished Mixture B of isomers of 4-ethylamino-1-carbethoxy-3,5-dimethylpiperidine as oil. Yield 2.1 g (36%), $C_{12}H_{24}N_2O_2$, m/z 229 (M+1), PMR ($CDCl_3$): 0.92 (dd, 6H), 1.18 (t, 3H), 1.48 (bs, 1H, $D_2O$ exchangeable), 1.68 (m, 1H), 2.02 (m, 1H), 2.3 (m, 1H), 2.4-2.68 (m, 3H), 3.0 (dd, 1H), 3.82 (dd, 1H), 3.95 (m, 11H), 4.12 (m, 2H).

The Mixture A of isomers of 4-ethylamino-1-carbethoxy-3,5-dimethylpiperidine (2.1 g, 0.92 mmol) was stirred in 5 N NaOH solution (20 ml) at 100° C. for 96 hr, cooled, extracted with ethyl acetate, dried ($Na_2SO_4$) and concentrated to afford Mixture A of isomers of 4-ethylamino-3,5-dimethyl piperidine as oil. Yield 1.34 g (93.2%), $C_9H_{20}N_2$, m/z 157 (M+1), PMR ($CDCl_3$): 0.94 (dd, 9H), 1.45 (m, 1H), 1.66 (m, 1H), 1.94 (m, 3H, $D_2O$ exchangeable), 2.36 (m, 1H), 2.44-2.74 (m, 3H), 3.0 (dd, 1H), 3.5 (m, 1H).

The Mixture B of isomers of 4-ethylamino-1-carbethoxy-3,5-dimethylpiperidine (2.1 g, 0.92 mmol) was stirred in 5 N NaOH solution (20 ml) at 100° C. for 96 hr, cooled, extracted with ethyl acetate, dried ($Na_2SO_4$) and concentrated to afford Mixture B of isomers 4-ethylamino-3,5-dimethylpiperidine as oil. Yield 1.34 g (93.2%), $C_9H_{20}N_2$, m/z 157 (M+1), PMR ($CDCl_3$): 0.94 (dd, 6H), 1.12 (t, 3H), 1.5-1.8 (m, 3H, $D_2O$ exchangeable), 1.9 (m, 1H), 2.28 (m, 2H), 2.46 (m, 1H), 2.62-3.0 (m, 4H).

Preparation 28

4-Cyclopropylamino-3,5-dimethylpiperidine

A solution of cyclopropylamine (71.6 g, 126 mmol) and 1-carbethoxy-3,5-dimethyl-4-piperidinone (50 g, 26 mmol) obtained by a procedure as described in Example 25 (Step-1), in methanol (500 ml) was stirred for 6 hr at ambient temperature. Sodium cyanoborohydride (16 g, 26 mmol) was added in portions to the resulting mixture and stirring was continued for 16 hr. The reaction mixture was concentrated to dryness. The obtained residue was dissolved in water and extracted with chloroform. Chloroform layer was extracted with 6N HCl and HCl extract was basified with aqueous KOH (20%) solution. The oil thus separated was extracted with chloroform, dried ($Na_2SO_4$) and concentrated to give a mixture of Mixtures A+B of 1-carbethoxy-4-cyclopropylamino-3,5-dimethylpiperidine as oil. Yield 58 g (96%), $C_{13}H_{24}N_2O_2$, m/z 241 (M+1).

The similarly obtained Mixture A+B of 1-carbethoxy-4-cyclopropylamino-3,5-dimethylpiperidine was separated over silica gel column chromatography. Elute from 5% ethyl acetate in hexane gave Mixture A of isomers of 1-carbethoxy-4-cyclopropyamino-3,5-dimethylpiperidine as oil. $C_{13}H_{24}N_2O_2$, m/z 241 (M+1), PMR ($CDCl_3$): 0.88-1.17 (m, 10H), 1.3 (t, 3H), 1.74 (bs, 1H, $D_2O$ exchangeable), 2.48-2.82 (m, 4H), 3.26-3.85 (m, 2H), 4.18 (q, 2H), 4.42 (bm, 2H).

Further elution from 5% ethyl acetate in hexane furnished Mixture B of isomers of 1-carbethoxy-4-cyclopropylamino-3,5-dimethylpiperidine as oil. $C_{13}H_{24}N_2O_2$, m/z 241 (M+1), PMR ($CDCl_3$): 0.78-1.08 (m, 10H), 1.15 (t, 3H), 1.48-2.1 (m, 4H, $D_2O$ exchangeable), 2.32-2.82 (m, 2H), 3.24-3.82 (m, 2H), 4.04-4.25 (m, 3H).

Mixture A of isomers of 1-carbethoxy-4-cyclopropylamino-3,5-dimethylpiperidine (3.5 g, 1.45 mmol) was stirred in 5 N NaOH solution (25 ml) at 100° C. for hr, cooled, extracted with ethyl acetate, dried ($Na_2SO_4$) and concentrated to afford Mixture A of isomers of 4-cyclopropylamino-3,5-dimethyl piperidine as oil. Yield 2.1 g (85%), $C_{10}H_{20}N_2$, m/z 169 (M+1).

The Mixture B of isomers of 1-carbethoxy-4-cyclopropylamino-3,5-dimethylpiperidine (2.8 g, 1.16 mmol) was stirred in a mixture 5 N NaOH solution (20 ml) and ethyl alcohol (5 ml) at 100° C. for 120 hr, cooled, extracted with ethyl acetate, dried ($Na_2SO_4$) and concentrated to afford Mixture B of isomers of 4-cyclopropylamino-3,5-dimethylpiperidine as an oil. Yield 1.6 g (84%), $C_{10}H_{20}N_2$, m/z 169 (M+1) PMR ($CDCl_3$): 0.82-1.05 (m, 10H), 1.5 (m, H), 1.75 (m, H,), 2.16-2.38 (m, 3H), 2.65 (m, 1H), 2.78 (m, 1H), 3.02 (m, 1H), 3.41 (m, 1H), 3.64 (m, 1H).

Preparation 29

4-Dimethylamino-3,5-dimethylpiperidine

Potassium hydroxide (3.86 g) was added to the stirred solution of N,N-dimethylamine hydrochloride (5.63 g, 69.0 mmol) in methanol (20 ml) and stirring was continued for 30 min at 30° C. 1-benzyl-3,5-methyl-4-piperidinone (3 g, 13.8 mmol) was added to the stirred mixture and refluxed for 48 hr. Reaction mixture was cooled at 30° C. and sodium cyanoborohydride (0.87 g, 13.8 mmol) was added. The resulting reaction mixture was stirred for 24 hr at 70° C. The reaction mixture was concentrated to dryness, triturated with water, extracted with chloroform, dried (Na$_2$SO$_4$) and concentrated to give Mixtures A+B of 1-benzyl-4-dimethylamino-3,5-dimethylpiperidine. Yield 2.7 g (79.4%), C$_{16}$H$_{26}$N$_2$, m/z 247 (M+1).

A mixture of 20% Pd(OH)$_2$ on carbon (0.5 g) and Mixtures A+B of 1-benzyl-4-dimethylamino-3,5-dimethylpiperidine (2.7 g, 10.1 mmol) in methanol (50 ml) was stirred in hydrogen atmosphere (1 atm.) at 60° C. for 48 hr. The catalyst was filtered off, washed with methanol and filtrate was concentrated to dryness to afford Mixtures A+B of 4-dimethylamino-3,5-dimethylpiperidine. Yield 0.9 g (52.6%), C$_9$H$_{20}$N$_2$, m/z 157 (M+1).

Mixture A of isomers and Mixture B of isomers of 4-dimethylamino-3,5-dimethylpiperidine were prepared by separation technique at 1-benzyl-4-dimethylamino-3,5-dimethylpiperidine stage by using silica gel column chromatography followed by debenzylation by using catalytic palladium hydroxide on carbon.

Preparation 30

4-Amino-3,5-diethylpiperidine

Ammonium acetate (10 g, 130 mmol) was added to the stirred solution of 1-benzyl-3,5-diethyl-4-piperidone (3.5 g, 14.3 mmol) in methanol (50 ml) and stirring was continued for 4 hr at ambient temperature. The resulting mixture was cooled at 0° C. and sodium cyanoborohydride (0.45 g, 7.14 mmol) was added to it. Cooling was removed after 10 min. and resulting mixture was stirred for 10 hr at ambient temperature. The reaction mixture was concentrated to dryness, triturated with water, acidified with conc. HCl (pH 2) and extracted with ethyl acetate to remove impurities. The aqueous layer was basified with 1M sodium hydroxide solution (pH 10) and extracted with ethyl acetate. Ethyl acetate extract was dried (Na$_2$SO$_4$) and concentrated to dryness to furnish 4-amino-1-benzyl-3,5-diethylpiperidine. Yield 3.4 g (97%), C$_{16}$H$_{26}$N$_2$, m/z 247 (M+1).

A mixture of 5% Pd on carbon (0.5 g) and 4-amino-1-benzyl-3,5-diethylpiperidine (3.4 g, 13.82 mmol) in methanol (25 ml) was stirred in hydrogen atmosphere (3 atm.) at 60° C. for 6 hr. The catalyst was filtered off, washed with methanol and filtrate was concentrated to dryness to afford 4-amino-3,5-diethylpiperidine as an oil. Yield 1.4 g (64.5%), C$_9$H$_{20}$N$_2$, m/z 157 (M+1).

Preparation 31

4-Amino-3,3,5-trimethylpiperidine

A mixture of 20% Pd(OH)$_2$ on carbon (0.3 g) and 1-benzyl-3,3,5-trimethyl-4-piperidone (1.5 g, 6.5 mmol) in methanol (20 ml) was stirred in hydrogen atmosphere (1 atm.) at 30° C. for 6 hr. The catalyst was filtered off, washed with methanol and filtrate was concentrated to dryness to afford 3,3,5-trimethyl-4-piperidinone. Yield 0.8 g (88%), C$_8$H$_{15}$NO, m/z 142 (M+1).

Ammonium acetate (2.5 g, 32.46 mmol) was added to the stirred solution of 3,3,5-trimethyl-4-piperidone (0.8 g, 5.67 mmol) in methanol (20 ml) and stirring was continued for 3 hr at ambient temperature. The resulting mixture was cooled at 0° C. and sodium cyanoborohydride (0.25 g, 3.96 mmol) was added to it. Cooling was removed after 10 min. and resulting mixture was stirred for 6 hr at ambient temperature. The reaction mixture was concentrated to dryness, triturated with water, acidified with conc. HCl (pH 3~4) and extracted with ethyl acetate to remove impurities. The aqueous layer, was basified with 1 M sodium hydroxide solution (pH 10) and extracted with ethyl acetate. Ethyl acetate extract was dried (Na$_2$SO$_4$) and concentrated to dryness to furnish 4-amino-3,3,5-trimethylpiperidine. Yield 0.45 g (54%), C$_8$H$_{18}$N$_2$, m/z 143 (M+1).

Preparation 32

4-Amino-3,5-diethyl-3-methylpiperidine

Ammonium acetate (8.0 g, 104 mmol) was added to the stirred solution of 1-benzyl-3,5-diethyl-3-methyl-4-piperidone (2.5 g, 9.65 mmol) in methanol (25 ml) and stirring was continued for 24 hr at ambient temperature. The resulting mixture was cooled at 0° C. and sodium cyanoborohydride (0.69 g, 11.2 mmol) was added to it. Cooling was removed after 10 min. and resulting mixture was stirred for 20 hr at ambient temperature. The reaction mixture was concentrated to dryness, triturated with water, acidified with conc. HCl (pH 2) and extracted with ethyl acetate to remove impurities. The aqueous layer was basified with 1M sodium hydroxide solution (pH 9) and extracted with ethyl acetate. Ethyl acetate extract was dried (Na$_2$SO$_4$) and concentrated to dryness to furnish 4-amino-1-benzyl-3,5-diethyl-3-methylpiperidine as an oil. Yield 2.1 g (84%), C$_{17}$H$_{28}$N$_2$, m/z 261 (M+1).

A mixture of 20% Pd(OH)$_2$ on carbon (0.3 g) and 4-amino-1-benzyl-3,5-diethyl-3-methylpiperidine (2.1 g, 8.07 mmol) in methanol (50 ml) was stirred in hydrogen atmosphere (4 atm.) at 45° C. for 4 hr. The catalyst was filtered off, washed with methanol and filtrate was concentrated to dryness to afford 4-amino-3,5-diethyl-3-methyl-piperidine as an oil. Yield 1.2 g (88%), C$_{10}$H$_{22}$N$_2$, m/z 171 (M+1).

Preparation 33

4-Amino-3,5-dimethyl-3-ethylpiperidine

Ammonium acetate (2.5 g, 32.46 mmol) was added to the stirred solution of 1-benzyl-3,5-dimethyl-3-ethyl-4-piperidone (3.0 g, 12.25 mmol) in methanol (40 ml) and stirring was continued for 20 hr at ambient temperature. The resulting mixture was cooled at 0° C. and sodium cyanoborohydride (0.8 g, 12.7 mmol) was added to it. Cooling was removed after 10 min. and resulting mixture was stirred for 20 hr at ambient temperature. The reaction mixture was concentrated to dryness, triturated with water, acidified with conc. HCl (pH 2) and extracted with ethyl acetate to remove impurities. The aqueous layer was basified with 1 M sodium hydroxide solution (pH 9) and extracted with ethyl acetate. Ethyl acetate extract was dried (Na$_2$SO$_4$) and concentrated to dryness to furnish 4-amino-1-benzyl-3,5-dimethyl-3-ethylpiperidine. Yield 2.2 g (73%), C$_{16}$H$_{26}$N$_2$, m/z 247 (M+1).

A mixture of 20% Pd(OH)$_2$ on carbon (0.4 g) and 4-amino-1-benzyl-3,5-dimethyl-3-ethylpiperidine (2.2 g, 8.9 mmol) in methanol (15 ml) was stirred in hydrogen atmosphere (1 atm.) at 60° C. for 10 hr. The catalyst was filtered off, washed with methanol and filtrate was concentrated to dryness to afford 4-amino-3,5-dimethyl-3-ethylpiperidine as a semi solid. Yield 1.1 g (79%), C$_9$H$_{20}$N$_2$, m/z 157(M+1).

Preparation 34 cis or trans-4-t-Butyloxycarbonylamino-1-benzyl-3-methylpiperidine

Step-1

Ethyl-1-benzyl-3-methyl-4-oxo-piperidine-3-carboxylate

Ethyl -1-benzyl-4-oxo-piperidine-3-carboxylate hydrochloride (150 g, 0.504 mol) was suspended in a solvent mixture of 750 ml THF and 750 ml DMF at room temperature. Addition of powdered KOH (56 g, 1.0 mol) was made in two equal lots keeping half an hour interval between two additions. To a clear reaction mixture methyl iodide (78 g, 0.55 mol) was added over period of 10 minutes and it was stirred for three hours at room temperature. The reaction was quenched by adding 4 ltr water followed by 1.5 ltr diethyl ether. Layers were separated. Organic layer was washed with water and dried over $Na_2SO_4$. Evaporation of organic solvent afforded a liquid, which was passed through a silica gel column to give 86 g (61%), titled compound.

mass ($ES^+$) 276, Molecular Formula $C_{16}H_{21}NO_3$,
$H^1$NMR ($CDCl_3$) 1.2 (s, 3H), 1.25 (t, 2H), 2.15 (d, 1H), 2.35-2.5 (m, 2H), 2.9 (d, 2H), 3.45 (d, 1H), 3.6 (s, 2H), 4.12-4.3 (m, 2H), 7.3 (s, 5H).

Step-2

1-Benzyl-3-methyl-4-piperidone

Ethyl-1-benzyl-3-methyl-4-oxo-piperidine-3-carboxylate (85 g, 0.31 mol) was dissolved in conc HCl (82 ml, 0.77 mol) and the reaction mixture was heated to 100° C. for 32 hrs. Solvent was removed under reduced pressure and the resulting solid was dissolved in the 300 ml CHCl3 and 400 ml pet ether was added to this under stirring to provide a solid. The solid was filter and was dissolved in 400 ml ethyl acetate and organic layer was washed with 10% NaOH aqueous solution. Layers were separated and concentration of organic layer afforded 48 g (75%) oil as a titled product.

mass ($ES^+$) 204, Molecular Formula $C_{13}H_{17}NO$,
$H^1$NMR ($CDCl_3$) 1.0 (d, 3H), 2.1 (t, 1H), 2.3-2.5 (m, 2H), 2.6-2.8 (m, 2H), 3.0-3.2 (m, 2H), 3.6 (s, 2H), 7.4 (s, 5H).

Step-3

4-Amino-1-benzyl-3-methylpiperidine

Ammonium acetate (178.3 g, 2.31 mol) was charged to a solution of 1-benzyl-3-methyl-4-piperidone (47 g, 0.232 mol) in 500 ml methanol. The suspension was stirred for 4 hours at room temperature. Sodium cyanoborohydride (7.3 g, 0.116 mol) was added in lots at 10° C. and it was stirred for 1 hour.

Solvent was removed under vacuum and resultant solid was suspended in 500 ml water and acidified with dilute aqueous HCl. It was extracted with 200 ml×2 chloroform and layers were separated. Aqueous layer was basified with ammonia solution to pH 9 and extracted with 500 ml×3 $CHCl_3$. Drying of organic layer over $Na_2SO_4$ and evaporation afforded 44 g (92%) titled product as an oil, which was used directly for further reaction.

Step 4 cis or trans-4-t-Butyloxycarbonylamino-1-benzyl-3-methylpiperidine

Di-tert-butyloxydicarbonate (45 g, 0.206 mol) was charged in lots to a solution of 4-amino-1-benzyl-3-methylpiperidine (42 g, 0.206 mol) and 300 ml $CH_2Cl_2$ followed by 5 ml triethylamine. Reaction was worked up after 90 minutes by adding 300 ml water and layers were separated Drying of organic layer over $Na_2SO_4$ and evaporation yielded mixture of cis and trans isomers in unequal proportion which when subjected to silica gel column chromatography with 10% ethyl acetate and hexane yielded 14 g of cis isomer and 11 g trans isomer and 19 gm mixture of both isomers of titled compound.

For cis isomer:
mass ($ES^+$) 305, Molecular Formula $C_{18}H_{28}N_2O_2$,
$H^1$NMR ($CDCl_3$) 0.95 (d, 3H), 1.45 (s, 9H), 1.7-1.8 (m, 2H), 2.0-2.2 (m, 2H), 2.35-2.5 (m, 2H), 3.5 (d, 2H), 3.7-3.8 (bs, 1H), 4.5 (bs, 1H), 7.3 (s, 5H).

For trans isomer:
mass ($ES^+$) 305, Molecular Formula $C_{18}H_{28}N_2O_2$,
$H^1$NMR ($CDCl_3$) 0.90 (d, 3H), 1.45 (s, 9H), 1.7-1.8 (t, 2H), 1.9-2.1 (m, 2H), 2.8-2.9 (m, 2H), 3.1 (m, 1H), 3.45(s, 2H), 4.3 (m, 1H), 7.3 (s, 5H).

Preparation 35 cis-4-t-Butyloxycarbonylamino-3-methylpiperidine cis-4-t-Butyloxycarbonylamino-1-benzyl-3-methylpiperidine (13 g, 0.042 mol) was dissolved in 170 ml methanol and transferred to the Parr pressure reactor after addition of 1.3 g of $Pd(OH)_2$ on carbon. The rqcytoion mixture stirred for 6 hrs at 400 psi pressure at 50° C. Catalyst was removed by filtration and eavaporation of the solvent afforded 8.7 g (95%) of titled compound.

mass ($ES^+$) 215, Molecular Formula $C_{11}H_{22}N_2O_2$,
$H^1$NMR ($CDCl_3$) 0.90 (d, 3H), 1.45 (s, 9H), 1.7 (m, 2H), 2.0 (m, 2H), 2.8 (m, 2H), 3.8 (bs, 1H), 4.7 (bs, 1H).

Preparation 36 trans-4-t-Butyloxycarbonylamino-3-methylpiperidine trans-4-t-Butyloxycarbonylamino-3-methylpiperidine was obtained as per procedure depicted in preparation 000 by using trans-4-t-Butyloxycarbonylamino-1-benzyl-3-methylpiperidine in the place of cis-4-t-Butyloxycarbonylamino-1-benzyl-3-methylpiperidine in 96% yield.

mass ($ES^+$) 215, Molecular Formula $C_{11}H_{22}N_2O_2$,
$H^1$NMR ($CDCl_3$) 0.90 (d, 3H), 1.40 (s, 9H), 1.9 (m, 2H), 2.8 (m, 2H), 3.1 (m, 2H), 3.4 (s, 1H), 4.3 (m, 1H).

Preparation 37

(−)-4-Amino-3,3-dimethylpiperidine

A mixture of 10% palladium on carbon (7.5 g) and (−)-4-amino-1-benzyloxycarbonyl-3,3-dimethylpiperidine (cf. Preparation 19, Step 4, 50 g, 191.0 mmol) in methanol (500 ml) was stirred under hydrogen atmosphere (30 atm.) at 30° C. for 6 hr. The catalyst was filtered off, washed with 100 ml methanol and filtrate was concentrated to dryness to afford (−)-4-amino-3,3-dimethylpiperidine, which was further purified by vacuum distillation to give 16.8 (71%) titled compound.

$C_7H_{16}N_2$, m/z 129 (M+1), PMR (CDCl$_3$): 0.9 (s, 6H), 1.5 (m, 2H), 1.58 (bs, 2H, D$_2$O exchangeable), 2.26-2.68 (m, 4H), 3.06 (m, 1H), 3.52 (bs, 1H, D$_2$O exchangeable). [α]$_D^{25}$ value –31.72 (c=1, CHCl$_3$).

Preparation 38

(+)-4-Amino-3,3-dimethylpiperidine

The titled compound was prepared by the procedure described in Preparation 37, by using (+)-4-amino-1-benzyloxycarbonyl-3,3-dimethylpiperidine (cf. Preparation 19, Step 3, 44 g, 168.0 mmol), to give 15.0 (70%) titled compound. $C_7H_{16}N_2$, m/z 129 (M+1), PMR (CDCl$_3$): 0.9 (s, 6H), 1.5 (m, 2H), 1.58 (bs, 2H, D$_2$O exchangeable), 2.26-2.68 (m, 4H), 3.06 (m, 1H), 3.52 (bs, 1H, D$_2$O exchangeable). [α]$_D^{25}$ value +32.34 (c=1, CHCl$_3$).

EXAMPLE 1

1-Cyclopropyl-6-fluoro-1,4-dihydro-8-methoxy-7-(4-amino-3-methyl-1-piperidinyl)-4-oxo-quinoline-3-carboxylic acid A mixture of [1-cyclopropyl-6,7-difluoro-1,4-dihydro-8-methoxy-4-oxo-quinoline-3-carboxylate-O$^3$, O$^4$]difluoroboron chelate (0.1 g, 0.29 mmol) and 4-amino-3-methylpiperidine (0.2 g, 1.75 mmol) in acetonitrile (20 ml) was refluxed for 6 hr. The reaction mixture was concentrated to dryness. The obtained residue was treated with triethylamine (3 ml) and ethanol (15 ml) and refluxed for 16 hr. The resulting mixture was concentrated to dryness; the solid thus obtained was triturated with water (10 ml), filtered, washed with water, dried and purified by preparative HPLC to furnish the required product. Yield 0.04 g (35%), m.p. 238-40° C., $C_{20}H_{24}FN_3O_4$, m/z 390 (M+1), PMR (CD$_3$OD): 0.84-1.42 (m, 7H), 1.8-2.4 (m, 3H), 3.02 (m, 1H), 3.18-3.72 (m, 4H), 3.8 (s, 3H), 4.18 (m, 1H), 7.82 (d, 1H), 8.9(s, 1H).

EXAMPLE 2 trans-1-Cyclopropyl-6-fluoro-1,4-dihydro-8-methoxy-7-(4-amino-3-methyl-1-piperidinyl)-4-oxo-quinoline-3-carboxylic acid It was prepared in a similar manner as described in Example 1, where trans-4-amino-3-methylpiperidine was used in place of 4-amino-3-methylpiperidine. Yield 35%, m.p. 240-42° C., $C_{20}H_{24}FN_3O_4$, m/z 390 (M+1).

EXAMPLE 3 cis-1-cyclopropyl-6-fluoro-1,4-dihydro-8-methoxy-7-(4-amino-3-methyl-1-piperidinyl)-4-oxo-quinoline-3-carboxylic acid It was prepared in a similar manner as described in Example 1, where cis-4-amino-3-methylpiperidine was used in place of 4-amino-3-methylpiperidine Yield 35%, m.p. 246-50° C., $C_{20}H_{24}N_3O_4F$, m/z 390 (M+1).

EXAMPLE 4

1-Cyclopropyl-6-fluoro-1,4-dihydro-8-methoxy-7-(4-methylamino-3-methyl-1-piperidinyl)-4-oxo-quinoline-3-carboxylic acid It was prepared in a similar manner as described in Example 1, where 4-methylamino-3-methylpiperidine was used in place of 4-amino-3-methylpiperidine. Yield 50%, m.p. 240° C. (decomp.), $C_{21}H_{26}FN_3O_4$, m/z 404 (M+1).

EXAMPLE 5

1-Cyclopropyl-6-fluoro-1,4-dihydro-8-methoxy-7-(4-ethylamino-3-methyl-1-piperidinyl)-4-oxo-quinoline-3-carboxylic acid It was prepared in a similar manner as described in Example 1, where 4-ethylamino-3-methylpiperidine was used in place of 4-amino-3-methylpiperidine. Yield 52%, m.p. 160-62° C., $C_{22}H_{28}FN_3O_4$, m/z 418 (M+1).

EXAMPLE 6

1-Cyclopropyl-6-fluoro-1,4-dihydro-8-methoxy-7-(4-cyclopropylamino-3-methyl-1-piperidinyl)-4-oxo-quinoline-3-carboxylic acid It was prepared in a similar manner as described in Example 1, where 4-cyclopropyl amino-3-methylpiperidine was used in place of 4-amino-3-methylpiperidine. Yield 60%, m.p. 182-84° C., $C_{23}H_{28}FN_3O_4$, m/z 430 (M+1).

EXAMPLE 7

1-Cyclopropyl-6-fluoro-1,4-dihydro-8-methoxy-7-(4-dimethylamino-3-methyl-1-piperidinyl)-4-oxo-quinoline-3-carboxylic acid It was prepared in a similar manner as described in Example 1, where 4-dimethyl amino-3-methylpiperidine was used in place of 4-amino-3-methylpiperidine. Yield 74%, m.p. 180-82° C., $C_{22}H_{28}FN_3O_4$, m/z 418 (M+1), PMR (CD$_3$OD): 0.88-1.28 (m, 7H), 1.8-2.3 (m, 3H), 2.92 (s, 6H), 2.66-3.62 (m, 5H), 3.76 (s, 3H), 4.14 (m, 1H), 7.68(d, 1H), 8.78 (s, 11H).

EXAMPLE 8

1-Cyclopropyl-6-fluoro-1,4-dihydro-8-methoxy-7-(4-ethoxycarbonylamino-3,3-dimethyl-1-piperidinyl)-4-oxo-quinoline-3-carboxylic acid It was prepared in a similar manner as described in Example 1, where 4-1-carbethoxy amino-3,3-dimethyl piperidine was used in place of 4-amino-3-methyl-piperidine. Yield 16%, m.p. 222° C., $C_{24}H_{30}FN_3O_6$, m/z 476 (M+1), PMR (CDCl$_3$): 1.04 (m, 9H), 1.26 (m, 4H), 1.86 (m, 2H), 3.02-3.68 (m, 4H), 3.72 (s, 3H), 4.02 (m, 1H), 4.16 (q, 2H), 4.58 (m, 1H), 7.86 (d, 1H), 8.82 (s, 1H), 14.8 (s, 1H, D$_2$O exchangeable).

EXAMPLE 9

(±)-1-Cyclopropyl-6-fluoro-1,4-dihydro-8-methoxy-7-(4-benzyloxycarbonylamino-3,3-dimethyl-1-piperidinyl)-4-oxo-quinoline-3-carboxylic acid It was prepared in a similar manner as described in Example 1, where 4-(±)-benzyloxy carbonylamino-3,3-dimethylpiperidine was used in place of 4-amino-3-methylpiperidine: Yield 47%, m.p. 158-60° C., $C_{29}H_{32}FN_3O_6$, m/z 538 (M+1), PMR (CDCl$_3$): 1.0 (s, 6H), 1.26 (m, 4H), 1.84 (m, 2H), 3.04-3.7 (m, 4H), 3.76 (s, 3H), 4.06 (m, 1H), 4.72 (m, 1H), 5.18 (s, 1H), 7.4 (m, 5H), 7.86 (d, 1H), 8.84 (s, 1H), 14.8 (s, 1H, D$_2$O exchangeable).

EXAMPLE-10

(±)-1-Cyclopropyl-6-fluoro-1,4-dihydro-8-methoxy-7-(4-amino-3,3-dimethyl-1-piperidinyl)-4-oxo-quinoline-3-carboxylic acid 4-Benzyloxycarbonylamino-3,3-dimethyl piperidine (100 g, 0.381 mol) was suspended in 200 ml acetonitrile under stirring. To the solution was added (1-cyclopropyl-6,7-difluoro-8-methoxy-1,4-dihydro-4-oxo-quinoline-3-carboxylate O$^3$, O$^4$) difluoroboron chelate (65 g, 0.189 mol) and stirring was started at temperature between 25-35° C. The reaction mixture was stirred for 4-5 hrs at this temperature. After the reaction was completed, the solvent was removed under vacuum to dryness to obtain a solid. To the solid was charged 200 ml ethyl alcohol followed by triethylamine (20 g, 0.198 mol). The reaction mixture was stirred at reflux temperature for 2-3 hrs. The solution was left overnight at 25-35° C. The solid separated in the reaction mixture was filtered and washed with 50 ml ethanol. The filtered solid was stirred with reflux at 100-110° C. in concentrated hydrochloric acid (250 ml) for 2 hr. The resulting solution was taken to dryness by evaporating the acid under vacuum to obtain a residue. To the residue was added 1 L acetone and the suspension stirred for 1 hr. The resulting solid was filtered and washed with acetone. The residue was suspended in 600 ml chloroform and was refluxed for 30 minutes. The suspension was filtered and the residue washed with chloroform. The residue was suspended in methanol (600 ml) and was stirred at 30-35° C. for 30 minutes. The suspension was filtered to obtain a solid, which was dissolved in 1 L water under stirring at 60-70° C. The pH of the solution was adjusted between 8.0-9.0 by adding 30% aqueous sodium hydroxide solution. The reaction mixture was extracted with 600 ml×2 chloroform. The organic layers were combined and washed with water, dried over Na$_2$SO$_4$ and evaporated under reduced pressure to afford a solid which was further triturated with methyl alcohol and filtered to give 43 g (56%) titled compound.

m/z (M+1) 404, mp 222-224° C.

NMR(CDCl$_3$): 0.95-1.3 (m, 10H); 1.7-1.8 (m, 2H); 2.6 (t, 1H); 3.0 (dd, 1H); 3.3 (m, 2H); 3.6 (m, 1H), (3.7 s, 3H); 4.02 (m, 1H), 7.9 (d, 1H); 8.8 (s, 1H).

An alternate procedure to prepare this compound is by a method similar to that described in Example 1 where 4-amino-3,3-dimethylpiperidine was used in place of 4-amino-3-methylpiperidine.

A second alternate procedure to prepare this compound is by treating 1-cyclopropyl-6-fluoro-1,4-dihydro-8-methoxy-7-(4-1-carbethoxyamino-3,3-dimethyl-1-piperidinyl)-4-oxo-quinoline-3-carboxylic acid [obtained from condensation of 1-cyclopropyl-6,7-difluoro-1,4-dihydro-8-methoxy-4-oxo-quinoline-3-carboxylic acid difluoroborane chelate and 4-1-carbethoxyamino-3,3-dimethylpiperidine] (2.0 g, 4.0 mmol) under reflux with aqueous NaOH (0.6M, 100 ml) for 4 hr with stirring, filtered and the residue dried. The obtained crude product was adjusted to pH 3-5 by 3 N HCl, concentrated, triturated with acetone and crystallisation from methanol furnished the required product.

EXAMPLE-11

(±)-1-Cyclopropyl-6-fluoro-1,4-dihydro-8-methoxy-7-(4-amino-3,3-dimethyl-1-piperidinyl)-4-oxo-quinoline-3-carboxylic acid. hydrochloride The hydrochloride salt was obtained by modifying the procedure in Example 10 after obtaining the solid residue from filtration of the suspension in methanol before dissolving in water and adjusting the pH to 8.9 by adding 30% aqueous sodium hydroxide solution. The residue obtained from filtration of the suspension from methanol was dissolved in 2.0 ltr at reflux temperature. It was then filtered hot and concentrated to approximately one fourth of its volume and left overnight. The crystals obtained were filtered at 25-35° C. and were dried in an oven at 70-80° C. under pump vacuum to yield 38.0 g (48%) titled compound.

mp 256-260° C.,

NMR (CD$_3$OD): selected values 1.0-1.5 (m, 2H); 1.20 (d, 6H); 1.21-1.30 (m, 2H); 1.90-2.20 (m, 2H); 3.6-3.7 (m, 1H); 3.8 (s, 3H); 4.20 (m, 1H), 7.8 (d, 1H); 8.9 (s, 1H).

EXAMPLE 12

(±)-1-Cyclopropyl-6-fluoro-1,4-dihydro-8-methoxy-7-(4-amino-3,3-dimethyl-1-piperidinyl)-4-oxo-quinoline-3-carboxylic acid methanesulfonate 6.50 Grams (16.13 mol) of 1-cyclopropyl-6-fluoro-1,4-dihydro-8-methoxy-7-(4-amino-3,3-dimethyl-1-piperidinyl)-4-oxo-quinoline-3-carboxylic acid were suspended in 65 ml of isopropyl alcohol. The suspension was heated to 70-80° C. under stirring and then 1.90 g (19.79 mol) methanesulfonic acid was added. The reaction mixture was heated at reflux for 30 minutes. It was cooled to 30-35° C. and filtered. The solid was washed with 10 ml isopropyl alcohol and dried for 16 hrs in oven under vacuum at 50° C. to give 6.80 g (84%) titled compound, mp 286-290° C., NMR (CD$_3$OD): selected values 1.0-1.5 (m, 2H); 1.20 (d, 6H); 1.9-2.2 (m, 2H); 2.7 (s, 3H);3.2-3.7 (m, 4H); 3.8 (s, 3H); 4.20 (m, 1H), 7.8 (d, 1H); 8.9 (s, 1H).

EXAMPLE 13

(±)-1-Cyclopropyl-6-fluoro-1,4-dihydro-8-methoxy-7-(4-amino-3,3-dimethyl-1-piperidinyl)-4-oxo-quinoline-3-carboxylic acid. gluconate To a suspension of 2.50 g (6.20 mol) 1-cyclopropyl-6-fluoro-1,4-dihydro-8-methoxy-7-(4-amino-3,3-dimethyl-1-piperidinyl)-4-oxo-quinoline-3-carboxylic acid and 50 ml isopropyl alcohol was added 2.4 ml (1.50 g, 7.64 mol) 50% aqueous D-gluconic acid at 80° C. under stirring. The clear solution was stirred for 30 minute at this temperature, and cooled to 30-35° C. to give a solid. The solid was filtered and washed with 10 ml isopropyl alcohol. The obtained solid was crystallized from methanol to give 2.0 g (54%) of the gluconate salt. mp. 160-162° C.

EXAMPLE 14

(+)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride (+)-3,3-Dimethyl-4-$^t$-butyloxycarbonylamino piperidine (46 g, 0.201 mol) was suspended in 200 ml acetonitrile understirring. To the solution was added (1-cyclopropyl-6,7-difluoro-8-methoxy-1,4-dihydro-4-oxo-quinoline-3-carboxylate O³, O⁴) difluoroboron chelate (35 g, 0.102 mol) and the reaction mixture was stirred for 24 hrs between 25-35° C. temperature. Triethylamine (10.3 g, 0.102 mol) was added to the reaction mixture and it was stirred at 80-85° C. temperature for 4-5 hrs. After reaction was completed, solvent was removed under vacuum to dryness to obtain a residue. To the residue was charged 200 ml ethyl alcohol followed by triethylamine (12.32 g, 0.122 mol). The reaction mixture was stirred at reflux temperature for 5-6 hrs. The solution was left overnight at 25-35° C. The solid separated in the reaction mixture was filtered and washed with 50 ml ethanol. The solid was stirred with concentrated hydrochloric acid (100 ml) for 1 hr. The resulting solution was taken to dryness by evaporating the acid under vacuum to obtain a residue. To the residue was added 600 ml acetone and the suspension stirred for 1 hr. The resulting solid was filtered and washed with acetone. The solid was suspended in 300 ml chloroform and was refluxed for 30 minutes. The suspension was filtered and was washed with chloroform. The wet solid was suspended in methanol 100 ml and was stirred at 30-35° C. for 30 minutes. The reaction mixture was filtered. The residue was dissolved in 1.3 L methanol at reflux temperature. It was filtered hot and concentrated to approximately one fourth of its volume and was left overnight. Crystals obtained were filtered at 25-35° C. and were dried in an oven at 70-80° C. under vacuum to yield 15 g (33.5%) titled compound, mp 256-260° C., NMR(CD₃OD): 0.95-1.3 (m, 10H); 1.90-2.20 (m, 2H); 3.15-3.4(m, 5H); 3.8 (s, 3H); 4.20 (m, 1H); 7.8 (d, 1H); 8.9 (s, 1H).

$[\alpha]_D^{25}$ value +132.0° (c=1, methanol).

The enantiomeric purity was established by making N-'-butyloxycarbonylalanine derivative of (+)-1-cyclopropyl-6-fluoro-1,4-dihydro-8-methoxy-7-(4-amino-3,3-dimethyl-1-piperidinyl)-4-oxo-quinoline-3-carboxylic acid. This derivative was analyzed on HPLC against N-'-butyloxycarbonylalanine derivative of racemic 1-cyclopropyl-6-fluoro-1,4-dihydro-8-methoxy-7-(4-amino-3,3-dimethyl-1-piperidinyl)-4-oxo-quinoline-3-carboxylic acid.

The ratio of enantiomers was found to be 98.49:1.50.

EXAMPLE-15

(−)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride The compound was prepared in 30% yield as per procedure described for its (+) isomer.$[\alpha]_D^{25}$ value −127.27° (c=1, methanol).

Enantiomeric purity was established by making N-'-butyloxycarbonylalanine derivative of (−)-1-cyclopropyl-6-fluoro-1,4-dihydro-8-methoxy-7-(4-amino-3,3-dimethyl-1-piperidinyl)-4-oxo-quinoline-3-carboxylic acid. This derivative was analyzed on HPLC against N-'-butyloxycarbonylalanine derivative of racemic 1-cyclopropyl-6-fluoro-1,4-dihydro-8-methoxy-7-(4-amino-3,3-dimethyl-1-piperidi-nyl)-4-oxo-quinoline-3-carboxylic acid. The ratio of enantiomers was found to be 96.37:3.62.

EXAMPLE-16

(+)-1-Cyclopropyl-6-fluoro-1,4-dihydro-8-methoxy-7-(4-amino-3,3-dimethyl-1-piperidinyl)-4-oxo-quinoline-3-carboxylic acid Grams (19.34 mmol) of (+)-1-cyclopropyl-6-fluoro-1,4-dihydro-8-methoxy-7-(4-amino-3,3-dimethyl-1-piperidi-nyl)-4-oxo-quinoline-3-carboxylic acid hydrochloride were dissolved in 250 ml water under stirring. The solution pH was adjusted between 8.0-9.0 by adding 30% aqueous sodium hydroxide solution. The reaction mixture was extracted with 200 ml×2 chloroform. Combined organic layer was washed with water, dried over Na₂SO₄ and evaporated under reduced pressure to afford a solid which was further triturated with isopropyl alcohol and filtered to give 7.34 g (94%) above mentioned compound, mp 221-224° C.

NMR (CDCl₃): 0.95-1.3 (m, 10H); 1.7-1.8 (m, 2H); 2.6 (t, 1H); 3.0 (dd, 1H); 3.3 (m, 2H); 3.6 (m, 1H), (3.7 s, 3H); 4.02 (m, 1H), 7.9 (d, 1H); 8.8 (s, 1H).

$[\alpha]_D^{25}$ value +133.84° (c=1, chloroform).

EXAMPLE-17

(−)-1-Cyclopropyl-6-fluoro-1,4-dihydro-8-methoxy-7-(4-amino-3,3-dimethyl-1-piperidinyl)-4-oxo-quinoline-3-carboxylic acid Similarly, by using the procedure mentioned above, 8.40 g (19.11 mmol) of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was converted to 6.65 g (86%) titled compound. mp 222-225° C., $[a]D^{25}$ value −125.06⁰ (c=1, chloroform).

EXAMPLE-18

(+)-1-Cyclopropyl-6-fluoro-1,4-dihydro-8-methoxy-7-(4-amino-3,3-dimethyl-1-piperidinyl)-4-oxo-quinoline-3-carboxylic acid. Methanesulfonate 6.50 Grams (16.13 mmol) of (+)-1-cyclopropyl-6-fluoro-1,4-dihydro-8-methoxy-7-(4-amino-3,3-dimethyl-1-piperidinyl)-4-oxo-quinoline-3-carboxylic acid were suspended in 65 ml of isopropyl alcohol. The suspension was heated to 70-80° C. under stirring and then 1.90 g (19.79 mmol) methanesulfonic acid was added. The reaction mixture became clear for a moment and a solid was separated. The suspension was heated at reflux for 30 minutes. It was cooled to 30-35° C. and filtered. The solid was washed with 10-ml isopropyl alcohol and dried for 16 hrs in oven under vacuum at 50° C. to give 6.80 g (84%) titled compound, mp 286-290° C., NMR (CD₃OD): 0.95-1.25 (m, 10H); 1.95-2.20 (m, 2H); 2.7 (s, 3H); 3.2-3.4 (m, 4H); 3.6-3.7 (m, 1H); 3.8 (s, 3H); 4.20 (m, 1H), 7.8 (d, 1H); 8.9 (s, 1H).

$[\alpha]_D^{25}$ value +113.97° (c=1, methanol).

EXAMPLE-19

(−)-1-Cyclopropyl-6-fluoro-1,4-dihydro-8-methoxy-7-(4-amino-3 3-dimethyl-1-piperidinyl)-4-oxo-quinoline-3-carboxylic acid methanesulfonate Similarly, by using the procedure mentioned above, 6.30 g (15.63 mmol) of (−)-1-cyclopropyl-6-fluoro-1,4-dihydro-8-methoxy-7-(4-amino-3,3-dimethyl-1-piperidinyl)-4-oxo-quinoline-3-carboxylic acid was converted to 5.60 g (72%) titled compound, mp 288-290° C.

$[\alpha]_D^{25}$ value −112.410 (c=1, methanol).

EXAMPLE 20

(+)-1-Cyclopropyl-6-fluoro-1,4-dihydro-8-methoxy-7-(4-amino-3,3-dimethyl-1-piperidinyl)-4-oxo-quinoline-3-carboxylic acid gluconate To a suspension of 2.50 g (6.20 mmol) (+)-1-cyclopropyl-6-fluoro-1,4-dihydro-8-methoxy-7-(4-amino-3,3-dimethyl-1-piperidinyl)-4-oxo-quinoline-3-carboxylic acid and 50 ml isopropyl alcohol was added 2.4 ml (1.50 g, 7.64 mmol) 50% aqueous D-gluconic acid at 80° C. under stirring. The clear solution was stirred for 30 minute at this temperature, cooled to 30-35° C. to give a solid. The solid was filtered and washed with 10 ml isopropyl alcohol. he obtained solid was crystallized from methanol to give 2.0 g (54%) gluconate salt of (+)-1-cyclopropyl-6-fluoro-1,4-dihydro-8-methoxy-7-(4-amino-3,3-dimethyl-1-piperidinyl)-4-oxo-quinoline-3-carboxylic acid, mp 158-60° C.

EXAMPLE-21

(−)-1-Cyclopropyl-6-fluoro-1,4-dihydro-8-methoxy-7-(4-amino-3,3-dimethyl-1-piperidinyl)-4-oxo-quinoline-3-carboxylic acid gluconate Similarly, by using the procedure mentioned above, 2.20 g (54.60 mmol) of (−)-1-cyclopropyl-6-fluoro-1,4-dihydro-8-methoxy-7-(4-amino-3,3-dimethyl-1-piperidinyl)-4-oxo-quinoline-3-carboxylic acid was converted to 1.65 g (50%) titled compound, mp 154-156° C.

EXAMPLE 22

1-Cyclopropyl-6-fluoro-1,4-dihydro-8-methoxy-7-(4-acetylamino-3,3-dimethyl-1-piperidinyl)-4-oxo-quinoline-3-carboxylic acid It was prepared in a similar manner as described in Example 1, where 4-acylamino-3,3-dimethylpiperidine was used in place of 4-amino-3-methylpiperidine. Yield 20%, m.p. 194-96° C., $C_{23}H_{28}FN_3O_5$, m/z 446 (M+1).

EXAMPLE 23

1-Cyclopropyl-6-fluoro-1,4-dihydro-8-methoxy-7-(4-$^t$-butyloxycarbonylamino-3,3-dimethyl-1-piperidinyl)}-4-oxo-quinoline-3-carboxylic acid Di-t-butoxycarbonate (0.32 g, 1.1 mmol) was added to a stirred solution of 1-cyclopropyl-6-fluoro-1,4-dihydro-8-methoxy-7-(4-amino-3,3-dimethyl-1-piperidinyl)}-4-oxo-quinoline-3-carboxylic acid (0.3 g, 7.4 mmol) in dioxane (10 ml) and water (5 ml) at ambient temperature and stirring was continued for 14 hr and concentrated to dryness. The obtained solid was dissolved in ethyl acetate, washed with water, dried ($Na_2SO_4$) and concentrated to give titled product. Yield 72%, m.p. 218-20° C., $C_{26}H_{34}FN_3O_6$, m/z 504 (M+1).

EXAMPLE 24

1-Cyclopropyl-6-fluoro-1,4-dihydro-8-methoxy-7-(4-methylamino-3,3-dimethyl-1-piperidinyl)}-4-oxo-quinoline-3-carboxylic acid It was prepared in a similar manner as described in Example 1, where 4-methylamino-3,3-dimethylpiperidine was used in place of 4-amino-3-methylpiperidine Yield 50%, m.p. 246-48° C., $C_{22}H_{28}FN_3O_4$, m/z 418 (M+1).

EXAMPLE 25

1-Cyclopropyl-6-fluoro-1,4-dihydro-8-methoxy-7-(4-ethylamino-3,3-dimethyl-1-piperidinyl)}-4-oxo-quinoline-3-carboxylic acid It was prepared in a similar manner as described in Example 1, where 4-ethylamino-3,3-dimethylpiperidine was used in place of 4-amino-3-methylpiperidine Yield 60%, m.p. 230-32° C., $C_{23}H_{30}FN_3O_4$, m/z 432 (M+1).

EXAMPLE 26

1-Cyclopropyl-6-fluoro-1,4-dihydro-8-methoxy-7-(4-cyclopropylamino-3,3-dimethyl-1-piperidinyl)}-4-oxo-quinoline-3-carboxylic acid It was prepared in a similar manner as described in Example 1, where 4-cyclopropyl amino-3,3-dimethylpiperidine was used in place of 4-amino-3-methylpiperidine Yield 31%, m.p. 190-92° C., $C_{24}H_{30}FN_3O_4$, m/z 444 (M+1), PMR ($CDCl_3$): 1.22 (6H, s), 0.8-1.48 (8H, m), 1.88 (2H, m), 2.28-3.7 (6H, m), 3.72 (s, 3H), 4.06 (m, 1H), 7.74 (d, 1H), 8.74 (s, 1H), 14.7 (bs, 1H, $D_2O$ exchangeable).

EXAMPLE 27

1-Cyclopropyl-6-fluoro-1,4-dihydro-8-methoxy-7-(4-dimethylamino-3,3-dimethyl-1-piperidinyl)-4-oxo-quinoline-3-carboxylic acid It was prepared in a similar manner as described in Example 1, where 4-dimethyl amino-3,3-dimethylpiperidine was used in place of 4-amino-3-methylpiperidine Yield 35%, m.p. 210° C., $C_{23}H_{30}FN_3O_4$, m/z 432 (M+1), PMR ($CDCl_3$): 1.02 (d, 6H), 0.92-1.4 (m, 4H), 1.8 (m, 2H), 2.32 (s, 6H) 2.28-3.65 (m, 5H), 3.68 (s, 3H), 4.01 (m, 1H, m), 7.68 (d, 11H), 8.86 (s, 1H), 14.9 (bs, 1H, $D_2O$ exchangeable).

EXAMPLE 28

1-Cyclopropyl-6-fluoro-1,4-dihydro-8-methoxy-7-{4-amino-3-ethyl-3-methyl-1-piperidinyl}-4-oxo-quinoline-3-carboxylic acid It was prepared in a similar manner as described in Example 1, where 4-amino-3-ethyl-3-methylpiperidine was used in place of 4-amino-3-methylpiperidine. m.p. 152-54° C., $C_{22}H_{28}FN_3O_4$, m/z 418 (M+1).

EXAMPLE 29

1-Cyclopropyl-6-fluoro-1,4-dihydro-8-methoxy-7-(4-methylamino-3-ethyl-3-methyl-1-piperidinyl)}-4-oxo-quinoline-3-carboxylic acid It was prepared in a similar manner as described in Example 1, where 4-methylamino-3-ethyl-3-methylpiperidine was used in place of 4-amino-3-methylpiperidine m.p. 182-84° C., $C_{23}H_{30}FN_3O_4$, m/z 432 (M+1).

EXAMPLE 30

1-Cyclopropyl-6-fluoro-1,4-dihydro-8-methoxy-7-(4-cyclopropylamino-3-ethyl-3 methyl-1-piperidinyl)}-4-oxo-quinoline-3-carboxylic acid It was prepared in a similar manner as described in Example 1, where 4-cyclopropyl amino-3-ethyl-3-methylpiperidine was used in place of 4-amino-3-methylpiperidine m.p. 210-12° C., $C_{25}H_{32}FN_3O_4$, m/z 458 (M+1).

EXAMPLE 31

1-cyclopropyl-6-fluoro-1,4-dihydro-8-methoxy-7-(4-dimethylamino-3-ethyl-3-methyl-1-piperidinyl)}-4-oxo-quinoline-3-carboxylic acid It was prepared in a similar manner as described in Example 1, where 4-dimethyl amino-3-ethyl-3-methylpiperidine was used in place of 4-amino-3-methylpiperidine, m.p. 210-12° C., $C_{24}H_{32}FN_3O_4$, m/z 446 (M+1).

EXAMPLE 32

Mixtures A+B of 1-cyclopropyl-6-fluoro-1,4-dihydro-8-methoxy-7-(4-amino-3,5-dimethyl-1-piperidinyl)-4-oxo-quinoline-3-carboxylic acid It was prepared in a similar manner as described in Example 1, where 4-amino-3,5-dimethylpiperidine was used in place of 4-amino-3-methylpiperidine, m.p. 178-80° C., $C_{21}H_{26}FN_3O_4$, m/z 404 (M+1).

EXAMPLE 33

Mixture A of Isomers of 1-cyclopropyl-6-fluoro-1,4-dihydro-8-methoxy-7-(4-amino-3,5-dimethyl-1-piperidinyl)-4-oxo-quinoline-3-carboxylic acid It was prepared in a similar manner as described in Example 1, where Mixture A of isomers of 4-amino-3,5-dimethylpiperidine was used in place of 4-amino-3-methylpiperidine, m.p. 238-40° C., $C_{21}H_{26}FN_3O_4$, m/z 404 (M+1).

EXAMPLE 34

Mixture B of Isomers of 1-cyclopropyl-6-fluoro-1,4-dihydro-8-methoxy-7-(4-amino-3,5-dimethyl-1-piperidinyl)-4-oxo-quinoline-3-carboxylic acid It was prepared in a similar manner as described in Example 1, where Mixture B of isomers of 4-amino-3,5-dimethylpiperidine was used in place of 4-amino-3-methylpiperidine, m.p. 200-04° C., $C_{21}H_{26}FN_3O_4$, m/z 404 (M+1).

EXAMPLE 35

Mixtures A+B of 1cyclopropyl-6-fluoro-1,4-dihydro-8-methoxy-7-{4-methylamino-3,5-dimethyl-1-piperidinyl)}-4-oxo-quinoline-3-carboxylic acid It was prepared in a similar manner as described in Example 1, where 4-methylamino-3,5-dimethylpiperidine was used in place of 4-amino-3-methylpiperidine, m.p. 268-72° C., $C_{22}H_{28}FN_3O_4$, m/z 418 (M+1).

EXAMPLE 36

Mixture A of Isomers of 1-cyclopropyl-6-fluoro-1,4-dihydro-8-methoxy-7-(4-methylamino-3,5-dimethyl-1-piperidinyl)-4-oxo-quinoline-3-carboxylic acid It was prepared in a similar manner as described in Example 1, where Mixture A of isomers of 4-methylamino-3,5-dimethylpiperidine was used in place of 4-amino-3-methylpiperidine, $C_{22}H_{28}FN_3O_4$, m/z 418 (M+1).

EXAMPLE 37

Mixture B of Isomers of 1-cyclopropyl-6-fluoro-1,4-dihydro-8-methoxy-7-(4-methylamino-3,5-dimethyl-1-piperidinyl)-4-oxo-quinoline-3-carboxylic acid It was prepared in a similar manner as described in Example 1, where Mixture A of isomers of 4-methylamino-3,5-dimethylpiperidine was used in place of 4-amino-3-methylpiperidine, $C_{22}H_{28}FN_3O_4$, m/z 418 (M+1).

EXAMPLE 38

Mixture A of Isomers of 1-cyclopropyl-6-fluoro-1,4-dihydro-8-methoxy-7-(4-ethylamino-3,5-dimethyl-1-piperidinyl)-4-oxo-quinoline-3-carboxylic acid It was prepared in a similar manner as described in Example 1, where Mixture A of isomers of 4-methylamino-3,5-dimethylpiperidine was used in place of 4-amino-3-methylpiperidine, m.p. 250-52° C., $C_{23}H_{30}FN_3O_4$, m/z 432 (M+1).

EXAMPLE 39

Mixture B of isomers of 1-cyclopropyl-6-fluoro-1,4-dihydro-8-methoxy-7-(4-ethylamino-3,5-dimethyl-1-piperidinyl)-4-oxo-quinoline-3-carboxylic acid It was prepared in a similar manner as described in Example 1, where Mixture B of isomers of 4-methylamino-3,5-dimethylpiperidine was used in place of 4-amino-3-methylpiperidine, m.p. 250-55° C., $C_{23}H_{30}FN_3O_4$, m/z 432 (M+1).

EXAMPLE 40

Mixture A of Isomers of 1-cyclopropyl-6-fluoro-1,4-dihydro-8-methoxy-7-(4-cyclopropylamino-3,5-dimethyl-1-piperidinyl)-4-oxo-quinoline-3-carboxylic acid It was prepared in a similar manner as described in Example 1, where Mixture A of isomers of 4-cyclopropyl amino-3,5-dimethylpiperidine was used in place of 4-amino-3-methyl-piperidine, $C_{24}H_{30}FN_3O_4$, m/z 444 (M+1)

EXAMPLE 41

Mixture B of isomers of 1-cyclopropyl-6-fluoro-1,4-dihydro-8-methoxy-7-(4-cyclopropylamino-3,5-dimethyl-1-piperidinyl)-4-oxo-quinoline-3-carboxylic acid It was prepared in a similar manner as described in Example 1, where Mixture B of isomers of 4-cyclopropyl amino-3,5-dimethylpiperidine was used in place of 4-amino-3-methyl-piperidine, m.p. 240-42° C., $C_{24}H_{30}FN_3O_4$, m/z 444 (M+1)

EXAMPLE 42

1-Cyclopropyl-6-fluoro-1,4-dihydro-8-methoxy-7-(4-amino-3,3,5-trimethyl-1-piperidinyl)-4-oxo-quinoline-3-carboxylic acid It was prepared in a similar manner as described in Example 1, where 4-amino-3,3,5-trimethylpiperidine was used in place of 4-amino-3-methylpiperidine, m.p. 218-20° C., $C_{22}H_{28}FN_3O_4$, m/z 418 (M+1).

EXAMPLE 43

5-Amino-1-cyclopropyl-6-fluoro-1,4-dihydro-8-methoxy-7-(4-methylamino-3,3-dimethyl-1-piperidinyl)-4-oxo-quinoline-3-carboxylic acid A suspension of 5-amino-1-cyclopropyl-6,7-difluoro-1,4-dihydro-8-methoxy-4-oxo-quinoline-3-carboxylic acid (0.17 g, 0.55 mmol), 3,3-dimethyl-4-methylamino piperidine (0.15 g, 1.06 mmol) and triethylamine (1 g, 10 mmol) in a mixture of dimethylsulfoxide (10 ml) and acetonitrile (10 ml) was heated at 70° C. for 18 hr. Acetonitrile was distilled off, filtered to remove suspended impurities, diluted with water (5 ml). The precipitate thus separated was filtered, washed with water, dried and purified by silicagel column chromatography. Elute from a mixture of ethyl acetate and methanol furnished the required product. Yield 0.12 g (50%), m.p. 250° C. (decomp.), $C_{22}H_{29}FN_4O_4$, m/z 433 (M+1), PMR (DMSO-$d_6$): 0.9 (m, 2H), 1.0 (m, 2H), 1.0 (s, 3H), 1.1 (s, 3H), 1.8-2.0 (m, 2H), 2.6 (s, 3H), 2.8-3.2 (m, 4H), 3.5 (s, 3H), 3.6 (s, 3H), 3.65 (m, 1H), 4.0 (m, 1H), 7.2 (bs, 2H, $D_2O$ exchangeable), 8.6 (s, 1H).

EXAMPLE 44

5-Amino-1-cyclopropyl-6-fluoro-1,4-dihydro-8-methoxy-7-(4-amino-3-methyl-1-piperidinyl)-4-oxo-quinoline-3-carboxylic acid It was prepared in a similar manner as described in Example 43, where 4-amino-3-methylpiperidine was used in place of 3,3-dimethyl-4-methylaminopiperidine. Yield 40%, m.p. 260-62° C., $C_{20}H_{25}FN_4O_4$, m/z 405 (M+1), PMR ($CD_3OD$): 0.8-1.18 (m, 7H), 1.8-2.2 (m, 3H), 2.82-3.54 (m, 5H), 3.6 (s, 3H), 4.01 (m, 1H), 8.62 (s, 1H).

EXAMPLE 45

5-Amino-1-cyclopropyl-6-fluoro-1,4-dihydro-8-methoxy-7-(4-methylamino-3-methyl-1-piperidinyl)-4-oxo-quinoline-3-carboxylic acid It was prepared in a similar manner as described in Example 43, where 4-methylamino-3-methylpiperidine was used in place of 3,3-dimethyl-4-methylamino piperidine. Yield 30%, m.p. 228-30° C. (decomp.), $C_{21}H_{27}FN_4O_4$, m/z 419 (M+1).

EXAMPLE 46

5-Amino-1-cyclopropyl-6-fluoro-1,4-dihydro-8-methoxy-7-(4-ethylamino-3-methyl-1-piperidinyl)-4-oxo-quinoline-3-carboxylic acid It was prepared in a similar manner as described in Example 43, where 4-ethyl amino-3-methylpiperidine was used in place of 3,3-dimethyl-4-methylamino piperidine. Yield 35%, m.p. 230-32° C., $C_{22}H_{29}FN_4O_4$, m/z 433 (M+1).

EXAMPLE 47

5-Amino-1-cyclopropyl-6-fluoro-1,4-dihydro-8-methoxy-7-(4-cyclopropylamino-3-methyl-1-piperidinyl)-4-oxo-quinoline-3-carboxylic acid It was prepared in a similar manner as described in Example 43, where 4-cyclo propylamino-3-methylpiperidine was used in place of 3,3-dimethyl-4-methyl aminopiperidine. Yield 35%, m.p. 218-20° C., $C_{23}H_{29}FN_4O_4$, m/z 445 (M+1).

EXAMPLE 48

5-Amino-1-cyclopropyl-6-fluoro-1,4-dihydro-8-methoxy-7-(4-dimethylamino-3-methyl-1-piperidinyl)-4-oxo-quinoline-3-carboxylic acid It was prepared in a similar manner as described in Example 43, where 4-dimethylamino-3-methylpiperidine was used in place of 3,3-dimethyl-4-methylamino piperidine. Yield 30%, m.p. 210° C., $C_{22}H_{29}FN_4O_4$, m/z 433 (M+1), PMR ($CD_3OD$): 0.81-1.22 (m, 7H), 1.8-2.25 (m, 3H), 2.92 (s, 6H), 2.61-3.52 (m, 5H), 3.61 (s, 3H), 4.04 (m, 1H), 8.62 (s, 1H).

EXAMPLE 49

5-Amino-1-cyclopropyl-6-fluoro-1,4-dihydro-8-methoxy-7-(4-amino-3,3-dimethyl-1-piperidinyl)-4-oxo-quinoline-3-carboxylic acid It was prepared in a similar manner as described in Example 44, where 4-amino-3,3-dimethylpiperidine was used in place of 3,3-dimethyl-4-methylaminopiperidine, m.p. 205° C., $C_{21}H_{27}FN_4O_4$, m/z 419 (M+1), PMR (DMSO-$d_6$): 0.8 (m, 2H), 1.0 (m, 2H), 1.0 (s, 3H), 1.1 (s, 3H), 1.4-1.6 (m, 2H), 2.6-2.8 (m, 4H), 3.6 (s, 3H), 3.65 (m, 1H), 4.0 (m, 1H), 6.2 (bs, 2H, $D_2O$ exchangeable), 7.2 (bs, 2H, $D_2O$ exchangeable), 8.6 (s, 1H).

EXAMPLE 50

5-Amino-1-cyclopropyl-6-fluoro-1,4-dihydro-8-methoxy-7-(4-ethylamino-3,3-dimethyl-1-piperidinyl)}-4-oxo-quinoline-3-carboxylic acid It was prepared in a similar manner as described in Example 43, where 4-ethylamino-3,3-dimethylpiperidine was used in place of 3,3-dimethyl-4-methyl-aminopiperidine, m.p. 205° C. (decomp.), $C_{23}H_{31}FN_4O_4$, m/z 447 (M+1), PMR ($CDCl_3$): 0.8 (m, 2H), 1.0 (m, 2H), 1.05 (s, 3H), 1.1 (s, 3H), 1.2 (t, 3H), 1.6-2.0 (m, 2H), 2.4-2.8 (m, 6H), 3.5 (s, 3H), 3.6 (m, 1H), 3.9 (m, 1H), 6.4 (bs, 2H, $D_2O$ exchangeable), 8.4 (bs, 1H, $D_2O$ exchangeable), 8.8 (s, 1H).

EXAMPLE 51

5-Amino-1-cyclopropyl-6-fluoro-1,4-dihydro-8-methoxy-7-(4-dimethylamino-3,3-dimethyl-1-piperidinyl)-4-oxo-quinoline-3-carboxylic acid It was prepared in a similar manner as described in Example 43, where 4-dimethylamino-3,3-dimethylpiperidine was used in place of 3,3-dimethyl-4-methyl-aminopiperidine, m.p. 178° C. (decomp.), $C_{23}H_{31}FN_4O_4$, m/z 447 (M+1).

EXAMPLE 52

Mixture A of Isomers of 5-amino-1-cyclopropyl-6-fluoro-1,4-dihydro-8-methoxy-7-(4-amino-3,5-dimethyl-1-piperidinyl)-4-oxo-quinoline-3-carboxylic acid It was prepared in a similar manner as described in Example 43, where Mixture A of isomers of 4-amino-3,5-dimethylpiperidine was used in place of 3,3-dimethyl-4-methylamino piperidine, m.p. 238-40° C., $C_{21}H_{27}FN_4O_4$, m/z 419 (M+1),

EXAMPLE 53

Mixture B of isomers of 5-Amino-1-cyclopropyl-6-fluoro-1,4-dihydro-8-methoxy-7-(4-amino-3,5-dimethyl-1-piperidinyl)-4-oxo-quinoline-3-carboxylic acid It was prepared in a similar manner as described in Example 43, where Mixture B of isomers of 4-amino-3,5-dimethylpiperidine was used in place of 3,3-dimethyl-4-methylamino-piperidine, m.p. 248-50° C. (decomp.), $C_{21}H_{27}FN_4O_4$, m/z 419 (M+1).

EXAMPLE 54

5-Amino-1-cyclopropyl-6-fluoro-14-dihydro-8-methoxy-7-(4-methylamino-3,5-dimethyl-1-piperidinyl)-4-oxo-quinoline-3-carboxylic acid It was prepared in a similar manner as described in Example 43, where 4-methylamino-3,5-dimethylpiperidine was used in place of 3,3-dimethyl-4-methylaminopiperidine, m.p. 224-26° C., $C_{22}H_{29}FN_4O_4$, m/z 433 (M+1).

EXAMPLE 55

Mixture A of Isomers of 5-amino-1-cyclopropyl-6-fluoro-1,4-dihydro-8-methoxy-7-(4-methylamino-3,5-dimethyl-1-piperidinyl)-4-oxo-quinoline-3-carboxylic acid It was prepared in a similar manner as described in Example 43, where Mixture A of isomers of 4-methylamino-3,5-dimethylpiperidine was used in place of 3,3-dimethyl-4-methylaminopiperidine, $C_{22}H_{29}FN_4O_4$, m/z 433 (M+1).

EXAMPLE 56

Mixture B of Isomers of 5-amino-1-cyclopropyl-6-fluoro-1,4-dihydro-8-methoxy-7-(4-methylamino-3,5-dimethyl-1-piperidinyl)-4-oxo-quinoline-3-carboxylic acid It was prepared in a similar manner as described in Example 43, where Mixture B of isomers of 4-methylamino-3,5-dimethylpiperidine was used in place of 3,3-dimethyl-4-methyl-aminopiperidine, $C_{22}H_{29}FN_4O_4$, m/z 433 (M+1).

EXAMPLE 57

Mixture A of isomers of 5-amino-1-cyclopropyl-6-fluoro-1,4-dihydro-8-methoxy-7-(4-ethylamino-3,5-dimethyl-1-piperidinyl)-4-oxo-quinoline-3-carboxylic acid It was prepared in a similar manner as described in Example 43, where Mixture A of isomers of 4-ethylamino-3,5-dimethylpiperidine was used in place of 3,3-dimethyl-4-methyl-aminopiperidine. Yield 52% m.p. 202-4° C., $C_{23}H_{31}FN_4O_4$, m/z 447 (M+1).

EXAMPLE 58

Mixture B of Isomers of 5-amino-1-cyclopropyl-6-fluoro-1,4-dihydro-8-methoxy-7-(4-ethylamino-3,5-dimethyl-1-piperidinyl)-4-oxo-quinoline-3-carboxylic acid It was prepared in a similar manner as described in Example 43, where Mixture B of isomers of 4-ethylamino-3,5-dimethylpiperidine was used in place of 3,3-dimethyl-4-methyl-aminopiperidine. Yield 80%, m.p. 255-58° C., $C_{23}H_{31}FN_4O_4$, m/z 447 (M+1).

EXAMPLE 59

Mixture A of Isomers of 5-amino-1-cyclopropyl-6-fluoro-1,4-dihydro-8-methoxy-7-(4-cyclopropylamino-3,5-dimethyl-1-piperidinyl)-4-oxo-quinoline-3-carboxylic acid It was prepared in a similar manner as described in Example 43, where Mixture A of isomers of 4-cyclopropylamino-3,5-dimethylpiperidine was used in place of 3,3-dimethyl-4-methylaminopiperidine, $C_{24}H_{31}FN_4O_4$, m/z 459 (M+1)

EXAMPLE 60

Mixture B of Isomers of 5-Amino-1-cyclopropyl-6-fluoro-1,4-dihydro-8-methoxy-7-(4-cyclopropylamino-3,5-dimethyl-1-piperidinyl) -4-oxo-quinoline-3-carboxylic acid It was prepared in a similar manner as described in Example 43, where Mixture B of isomers of 4-cyclopropylamino-3,5-dimethylpiperidine was used in place of 3,3-dimethyl-4-methylaminopiperidine, m.p. 248° C., $C_{24}H_{31}FN_4O_4$, m/z 459 (M+1)

EXAMPLE 61

5-Amino-1-cyclopropyl-6-fluoro-1,4-dihydro-8-methoxy-7-(4-amino-3-ethyl-3-methyl-1-piperidinyl)-4-oxo-quinoline-3-carboxylic acid It was prepared in a similar manner as described in Example 43, where 4-amino-3-ethyl-3-methylpiperidine was used in place of 3,3-dimethyl-4-methylaminopiperidine, m.p. 210° C. (decompose), $C_{22}H_{29}FN_4O_4$, m/z 433 (M+1).

EXAMPLE 62

5-Amino-1-cyclopropyl-6-fluoro-1,4-dihydro-8-methoxy-7-(4-methylamino-3-ethyl-3-methyl-1-piperidinyl)}-4-oxo-quinoline-3-carboxylic acid It was prepared in a similar manner as described in Example 43, where 4-methylamino-3-ethyl-3-methylpiperidine was used in place of 3,3-dimethyl-4-methylaminopiperidine, m.p. 164-66° C., $C_{23}H_{31}FN_4O_4$, m/z 447 (M+1).

EXAMPLE 63

5-Amino-1-cyclopropyl-6-fluoro-1,4-dihydro-8-methoxy-7-(4-cyclopropylamino-3-ethyl-3-methyl-1-piperidinyl)1-4-oxo-quinoline-3-carboxylic acid It was prepared in a similar manner as described in Example 43, where 4-cyclopropyl amino-3-ethyl-3-methylpiperidine was used in place of 3,3-dimethyl-4-methylaminopiperidine, m.p. 186-88° C., $C_{25}H_{33}FN_4O_4$, m/z 473 (M+1).

EXAMPLE 64

5-Amino-1-cyclopropyl-6-fluoro-1,4-dihydro-8-methoxy-7-(4-dimethylamino-3-ethyl-3-methyl-1-piperidinyl)-4-oxo-quinoline-3-carboxylic acid It was prepared in a similar manner as described in Example 43, where 4-dimethyl amino-3-ethyl-3-methylpiperidine was used in place of 3,3-dimethyl-4-methylaminopiperidine, m.p. 194-96° C., $C_{24}H_{33}FN_4O_4$, m/z 461 (M+1).

EXAMPLE 65

5-Amino-1-cyclopropyl-6-fluoro-1,4-dihydro-8-methoxy-7-(4-amino-3,3,5-Trimethyl-1-piperidinyl)-4-oxo-quinoline-3-carboxylic acid It was prepared in a similar manner as described in Example 43, where 4-amino-3,3,5-trimethylpiperidine was used in place of 3,3-dimethyl-4-methylaminopiperidine, m.p. 248-52° C., $C_{22}H_{29}FN_4O_4$, m/z 433 (M+1).

EXAMPLE 66 trans-1-Cyclopropyl-6-fluoro-1,4-dihydro-8-methyl-7-(4-amino-3-methyl-1-piperidinyl)-4-oxo-quinoline-3-carboxylic acid A Mixture of [1-cyclopropyl-6,7-difluoro-8-methyl-1,4-dihydro-4-oxo-quinoline-3-carboxylate-$O^3$, $O^4$] difluoroboron (0.5 g, 1.52 mmol), and trans-4-amino-3-methylpiperidine (0.86 g, 7.64 mmol) in 10 ml acetonitrile was heated to reflux for 8 hr. The reaction mixture was concentrated to dryness. The obtained residue was treated with 10 ml ethanol and triethylamine (0.154 ml, 1.52 mmol) and refluxed for 3 hr. Solvent was evaporated to dryness under reduced pressure and the residue was purified on preparative HPLC to give titled product, m. p. 223-225° C. $C_{20}H_{24}FN_3O_3$, m/z 374 (M+1), PMR (CD3OD): 0.85 (m, 2H), 1.05 (d, 3H), 1.2 (m, 2H), 1.7-2.1(m, 3H), 2.8 (s, 3H), 2.9-3.1(m, 3H), 3.3-3.4(m, 2H), 4.25 (m, 1H), 7.8(d, 1H), 8.9(s, 1H).

EXAMPLE 67 cis-1-Cyclopropyl-6-fluoro-1,4-dihydro-8-methyl-7-(4-amino-3-methyl-1-piperidinyl)-4-oxo-quinoline-3-carboxylic acid The compound was prepared by a procedure as described in Example 66, by using cis-4-amino-3-methylpiperidine, m. p. 224-228° C., $C_{20}H_{24}FN_3O_3$, m/z 374 (M+1), PMR (CD3OD): 0.8-1.0 (m, 2H), 1.15 (d, 3H), 1.15-1.25(m, 2H), 1.8-2.3(m, 3H), 2.8 (s, 3H), 3.1-3.4(m, 3H), 3.4-3.6(m, 2H), 4.25 (m, 1H), 7.8(d, 1H), 8.9(s, 1H).

EXAMPLE 68

(±)-1-Cyclopropyl-6-fluoro-1,4-dihydro-8-methyl-7-(4-amino-3,3-dimethyl-1-piperidinyl)-4-oxo-quinoline-3-carboxylic acid The compound was prepared by a procedure as described in Example 66, by using (±)-4-amino-3,3-dimethylpiperidine, m. p. 198-200° C. $C_2, H_{26}FN_3O_3$, m/z 388 (M+1), PMR (CD3OD): 0.8-1.1 (m, 2H), 1.10 (d, 6H), 1.1-1.4 (m, 2H), 1.9-2.2 (m, 2H), 2.8 (s, 3H), 2.9-3.1(m, 1H), 3.2-3.4 (m, 3H), 4.3 (m, 1H), 7.8 (d, 1H), 8.9 (s, 1H).

EXAMPLE 69

(−)-1-Cyclopropyl-6-fluoro-1,4-dihydro-8-methyl-7-(4-amino-3,3-dimethyl-1-piperidinyl)-4-oxo-quinoline-3-carboxylic acid The compound was prepared by a procedure as described in Example 66, by using (−)-4-amino-3,3-dimethylpiperidine, m. p. 195-198° C., $C_{21}H_{26}FN_3O_3$, m/z 388 (M+1).

EXAMPLE-70

(+)-1-Cyclopropyl-6-fluoro-1,4-dihydro-8-methyl-7-(4-amino-3,3-dimethyl-1-piperidinyl)4-oxo-quinoline-3-carboxylic acid The compound was prepared by a procedure as described in Example 66, by using (+)-4-amino-3,3-dimethylpiperidine, m. p. 195-198° C., $C_{21}H_{26}FN_3O_3$, m/z 388 (M+1).

EXAMPLE 71

1-Cyclopropyl-6-fluoro-1,4-dihydro 8-methyl-7-(4-methylamino-3-methyl-1-piperidinyl)-4-oxo-quinoline-3-carboxylic acid The compound was prepared by a procedure as described in Example 66, by using 4-methylamino-3-methylpiperidine, m. p 233-235° C., $C_{21}H_{26}FN_3O_3$, m/z 388 (M+1), PMR (CD3OD): 0.8-1.4 (m, 7H), 1.9-2.4 (m, 3H), 2.8 (s, 3H), 2.9 (s, 3H), 3.2-3.7 (m, 5H), 4.3 (m, 1H), 7.9 (d, 1H), 8.9 (s, 1H).

EXAMPLE 72

1-Cyclopropyl-6-fluoro-1,4-dihydro-8-methyl-7-(4-dimethylamino-3-methyl-1-piperidinyl)-4-oxo-quinoline-3-carboxylic acid The compound was prepared by a procedure as described in Example 66, by using 4-dimethylamino-3-methylpiperidine, m. p. 221° C., $C_{22}H_{28}FN_3O_3$, m/z 402 (M+1), PMR (CD3OD): 0.8-1.4 (m, 7H), 2.0-2.2 (m, 2H), 2.5 (m, 2H), 2.8 (s, 3H), 3.0 (s, 6H), 3.2-3.7 (m, 4H), 4.4 (m, 1H), 7.8 (d, 1H), 8.95 (s, 1H).

EXAMPLE 73

1-Cyclopropyl-6-fluoro-1,4-dihydro-8-methyl-7-(4-ethylamino-3,3-dimethyl-1-piperidinyl)-4-oxo-quinoline-3-carboxylic acid The compound was prepared by a procedure as described in Example 66, by using 4-ethylamino-3,3-dimethylpiperidine, m. p. 201-203° C., $C_{23}H_{30}FN_3O_3$, m/z 416 (M+1), PMR (CD3OD): 0.8-1.1 (m, 2H), 1.2-1.5 (m, 11H), 2.0-2.2 (m, 2H), 2.8 (s, 3H), 2.9-3.5 (m, 7H), 4.3 (m, 1H), 7.9 (d, 1H), 9.0 (s, 1H).

EXAMPLE 74

1-Cyclopropyl-6-fluoro-1,4-dihydro-8-methyl-7-(4-dimethylamino-3,3-dimethyl-1-piperidinyl)-4-oxo-quinoline-3-carboxylic acid The compound was prepared by a procedure as described in Example 66, by using 4-dimethylamino-3,3-dimethylpiperidine, m. p. 209-210° C., $C_{23}H_{29}FN_3O_3$, m/z 416 (M+1), PMR (CD3OD): 0.8-1.0 (m, 2H), 1.05-1.40 (m, 8H), 2.0-2.2 (m, 2H), 2.8-3.1 (m, 10H), 3.2-3.6 (m, 3H), 4.3 (m, 1H), 7.9 (d, 1H), 9.0 (s, 1H).

EXAMPLE-75 trans-1-Cyclopropyl-6-fluoro-1,4-dihydro-8-ethyl-7-(4-amino-3-methyl-1-piperidinyl)-4-oxo-quinoline-3-carboxylic acid A mixture of [1-cyclopropyl-6,7-difluoro-8-ethyl-1,4-dihydro-4-oxo-quinoline-3-carboxylate-$0^3$, $0^4$] difluoroboron (0.5 g, 1.49 mmol), and trans-4-amino-3-methylpiperidine (0.86 g, 7.64 mmol) in 10 ml acetonitrile was heated to reflux for 8 hr. The reaction mixture was concentrated to dryness. The obtained residue was treated with 10 ml ethanol and triethylamine (0.154 ml, 1.52 mmol) and refluxed for 3 hr. Solvent was evaporated to dryness under reduced pressure and the residue was purified on preparative HPLC to give titled product, $C_{21}H_{26}FN_3O_3$, m/z 388 (M+1), PMR (CD3OD): 0.9-1.3 (m, 10H), 1.8-2.2 (m, 2H), 2.9-3.7 (m, 8H), 4.2 (m, 1H), 7.9 (d, 1H), 9.0 (s, 1H).

EXAMPLE-76 cis-1-Cyclopropyl-6-fluoro-1,4-dihydro-8-ethyl-7-(4-amino-3-methyl-1-piperidinyl)-4-oxo-quinoline-3-carboxylic acid The compound was prepared by a procedure as described in Example 75, by using cis-4-amino-3-methylpiperidine, $C_{21}H_{26}FN_3O_3$, m/z 388 (M+1), PMR (CD3OD): 0.8-1.4 (m, 10H), 1.8-2.4 (m, 3H), 3.0-3.8 (m, 9H), 4.2 (m, 1H), 7.9 (d, 1H), 9.0 (s, 1H).

EXAMPLE 77

(±)-1-Cyclopropyl-6-fluoro-1,4-dihydro-8-ethyl-7-(4-amino-3,3-dimethyl-1-piperidinyl)-4-oxo-quinoline-3-carboxylic acid The compound was prepared by a procedure as described in Example 75, by using (±)-4-amino-3,3-dimethylpiperidine, $C_{22}H_{25}FN_3O_3$, m/z 402 (M+1), PMR (CD3OD): 0.8-1.3 (m, 13H), 1.6-2.0 (m, 2H), 2.7-3.0 (m, 2H), 3.0-3.8 (m, 5H), 4.1 (m, 1H), 7.8 (d, 1H), 8.9 (s, 1H).

EXAMPLE 78

(−)-1-Cyclopropyl-6-fluoro-1,4-dihydro-8-ethyl-7-(4-amino-3,3-dimethyl-1-piperidinyl)-4-oxo-quinoline-3-carboxylic acid The compound was prepared by a procedure as described in Example 75, by using (−)-4-amino-3,3-dimethylpiperidine, $C_{22}H_{28}FN_3O_3$, m/z 402 (M+1).

EXAMPLE 79

(+)-1-Cyclopropyl-6-fluoro-1,4-dihydro-8-ethyl-7-(4-amino-3,3-dimethyl-1-piperidinyl)4-oxo-quinoline-3-carboxylic acid The compound was prepared by a procedure as described in Example 75, by using (+)-4-amino-3,3-dimethylpiperidine, $C_{22}H_{28}FN_3O_3$, m/z 402 (M+1).

EXAMPLE 80

1-Cyclopropyl-6-fluoro-1,4-dihydro-8-ethyl-7-(4-amino-1-piperidinyl)-4-oxo-quinoline-3-carboxylic acid The compound was prepared by a procedure as described in Example 75, by using 4-aminopiperidine, m.p. 248-249° C. $C_{20}H_{24}FN_3O_3$, m/z 374 (M+1), PMR (CD3OD): selected values 0.9 (m, 2H), 1.1 (t, 3H), 1.3 (m, 2H), 1.7-2.2 (m, 4H), 3.6 (m, 2H), 4.2 (m, 1H), 7.9 (d, 1H), 9.0 (s, 1H).

EXAMPLE 81 trans-5-Amino-1-cyclopropyl-6-fluoro-1,4-dihydro-8-methyl-7-(4-amino-3-methyl-1-piperidinyl)-4-oxo-quinoline-3-carboxylic acid A mixture of [1-cyclopropyl-6,7-difluoro-8-methyl-1,4-dihydro-4-oxo-quinoline-3-carboxylate-$0^3$, $0^4$] difluoroboron (0.5 g, 1.46 mmol), and trans-4-amino-3-methylpiperidine (0.86 g, 7.64 mmol) in 10 ml acetonitrile was heated to reflux for 8 hr. The reaction mixture was concentrated to dryness. The obtained residue was treated with 10 ml ethanol and triethylamine (0.154 ml, 1.52 mmol) and refluxed for 3 hr. Solvent was evaporated to dryness under reduced pressure and the residue was purified on preparative HPLC to give titled product, $C_{20}H_{25}FN_4O_3$, m/z 389 (M+1),

EXAMPLE 82 cis-5-Amino-1-cyclopropyl-6-fluoro-1,4-dihydro-8-methyl-7-(4-amino-3-methyl-1-piperidinyl)-4-oxo-quinoline-3-carboxylic acid The compound was prepared by a procedure as described in Example 81, by using cis-4-amino-3-methylpiperidine, $C_{20}H_{25}FN_4O_3$, m/z 389 (M+1).

EXAMPLE 83

(±)-5-Amino-1-cyclopropyl-6-fluoro-1,4-dihydro-8-methyl-7-(4-amino-3,3-dimethyl-1-piperidinyl)-4-oxo-quinoline-3-carboxylic acid The compound was prepared by a procedure as described in Example 81, by using (±)-4-amino-3,3-dimethylpiperidine, $C_{21}H_{27}FN_4O_3$, m/z 403 (M+1).

EXAMPLE 84

(−)-5-Amino-1-cyclopropyl-6-fluoro-1,4-dihydro-8-methyl-7-(4-amino-3,3-dimethyl-1-piperidinyl)-4-oxo-quinoline-3-carboxylic acid The compound was prepared by a procedure as described in Example 81, by using (−)-4-amino-3,3-dimethylpiperidine, $C_{21}H_{27}FN_7O_3$, m/z 403 (M+1).

EXAMPLE 85

(+)-5-Amino-1-cyclopropyl-6-fluoro-1,4-dihydro-8-methyl-7-(4-amino-3,3-dimethyl-1-piperidinyl)-4-oxo-quinoline-3-carboxylic acid The compound was prepared by a procedure as described in Example 81, by using -(+)-4-amino-3,3-dimethylpiperidine, $C_{21}H_{27}FN_7O_3$, m/z 403 (M+1).

EXAMPLE 86 cis-1-Cyclopropyl-6-fluoro-1,4-dihydro-8-methyl-7-(4-amino-3-methyl-1-piperidinyl)-4-oxo-quinoline-3-carboxylic acid hydrochloride A mixture of [1-cyclopropyl-6,7-difluoro-8-methyl-1,4-dihydro-4-oxo-quinoline-3-carboxylate-$O^3$, $O^4$] difluoroboron (2.4 g, 7.34 mmol), and cis-4-t-butyloxycarbonylamino-3-methylpiperidine (4.45 g, 20.8 mmol) in 10 ml acetonitrile was stirred at 50° C. for 30 hr. The reaction mixture was concentrated to dryness. The obtained residue was treated with 10 ml ethanol and 1 ml triethylamine and refluxed for 1 hr. Solvent was evaporated to dryness under vacuum and the residue was purified by silica gel column chromatoghraphy using 3% methanol chloroform solvent mixture as an eluent to give a crude product. The crude product was dissolved in 10 ml conc HCl and stirred for 30 minutes. The solvent was evaporated under vacuum. The resultant solid was dissolved in methanol and re-crystallized by adding ethyl acetate to provide titled compound 1.56 g (52%) yield as a solid. m. p. 255-260° C. $C_{20}H_{25}FN_3O_3Cl$, m/z 374 (M+1), PMR (CD$_3$OD): 0.95 (m, 2H), 1.2 (d, 3H), 1.2-1.4 (m, 2H), 1.8-2.4 (m, 3H), 2.8 (s, 3H), 3.2-3.4 (m, 3H), 3.5-3.7 (m, 2H), 4.3 (m, 1H), 7.8 (d, 1H), 9.0 (s, 1H).

EXAMPLE 87 trans-1-Cyclopropyl-6-fluoro-1,4-dihydro-8-methyl-7-(4-amino-3-methyl-1-piperidinyl)-4-oxo-quinoline-3-carboxylic acid hydrochloride The compound was prepared by a procedure described in Example 86 by using trans-4-t-butyloxycarbonylamino-3-methylpiperidine instead cis-4-t-butyloxycarbonylamino-3-methylpiperidine. Yield: 56% m. p. 262-265° C. $C_{20}H_{25}FN_3O_3Cl$, m/z 374 (M+1).

EXAMPLE 88 cis/trans-1-Cyclopropyl-6-fluoro-8-methyl-7-(4-hydroxy-3-methyl-1-piperidinyl)-1,4-dihydro-4-oxo-quinoline-3-carboxylic acid The compound was prepared by a procedure described in Example 86 by using cis/trans-4-hydroxy-3-methylpiperidine instead of trans-4-amino-3-methylpieridine and product was purified on preparative HPLC to give titled product. M. p. 202-206° C., mass (ES$^+$) 375, Molecular Formula $C_{20}H_{23}FN_2O_4$, H$^1$NMR (CD$_3$OD) 0.92 (s, 2H), 1.04 (d, 3H), 1.22-1.38 (m, 2H), 1.62-1.82 (m, 2H), 1.82-2.10 (m, 2H), 2.8 (s, 3H), 2.90-3.24 (m, 4H), 3.95 (q, 1H), 4.30 (m, 1H), 7.80-7.88 (d, 1H), 8.95 (s, 1H).

EXAMPLE 89 cis -1-Cyclopropyl-6-fluoro-8-methyl-7-(4-hydroxy-3-methyl-1-piperidinyl)-1,4-dihydro-4-oxoquinoline-3-carboxylic acid The compound was prepared by a procedure described in Example 86 by using cis-4-hydroxy-3-methylpiperidine instead of trans-4-amino-3-methylpieridine and product was purified on preparative HPLC to give titled product. M. p. 206-210° C., mass (ES$^+$) 375, Molecular Formula $C_{20}H_{23}FN_2O_4$, H$^1$NMR (CD$_3$OD) 0.92 (s, 2H), 1.04 (d, 3H), 1.22-1.38 (m, 2H), 1.62-1.82 (m, 2H), 1.82-2.10 (m, 2H), 2.8 (s, 3H), 3.0-3.15 (s, 1H), 3.22-3.40 (s, 1H), 3.50-3.62 (m, 2H), 4.0-4.10 (q, 1H), 4.10-4.20 (m, 1H), 7.80-7.88 (d, 1H), 8.95 (s, 1H).

EXAMPLE 90 trans-1-Cyclopropyl-6-fluoro-8-methyl-7-(4-hydroxy-3-methyl-1-piperidinyl)-1,4-dihydro-4-oxo-quinoline-3-carboxylic acid The compound was prepared by a procedure described in Example 86 by using trans-4-hydroxy-3-methylpiperidine instead of trans-4-amino-3-methylpieridine and product was purified on preparative HPLC to give titled product. M. p. 214-216° C., mass (ES$^+$) 375, Molecular Formula $C_{20}H_{23}FN_2O_4$, H$^1$NMR (CD$_3$OD) 0.92 (s, 2H), 1.04 (d, 3H), 1.22-1.38 (m, 2H), 1.62-1.82 (m, 2H), 1.82-2.10 (m, 2H), 2.8 (s, 3H), 3.0-3.15 (s, 1H), 3.22-3.40 (s, 1H), 3.50-3.62 (m, 2H), 4.0-4.10 (q, 1H), 4.10-4.20 (m, 1H), 7.80-7.88 (d, 1H), 8.95 (s, 1H).

EXAMPLE 91 cis/trans-1-Cyclopropyl-6-fluoro-8-methyl-7-(4-hydroxy-3-ethyl-1-piperidinyl)-1,4-dihydro-4-oxoquinoline-3-carboxylic acid The compound was prepared by a procedure described in Example 86 by using cis/trans-4-hydroxy-3-ethylpiperidine instead of trans-4-amino-3-methylpieridine and product was purified on preparative HPLC to give titled product. m. p. 185-190° C., mass (ES$^+$) 389, Molecular Formula $C_{21}H_{25}FN_2O_4$, H$^1$NMR (CD$_3$OD) 0.92-1.02 (m, 7H), 1.22-2.18 (m, 4H), 2.78 (s, 3H), 2.90-3.72 (m, 4H), 4.15 (q; 1H), 7.85-7.98 (d, 1H), 8.95 (s, 1H).

EXAMPLE 92 cis/trans-1-Cyclopropyl-6-fluoro-8-ethyl-7-(4-hydroxy-3-ethyl-1-piperidinyl)-1,4-dihydro-4-oxoguinoline-3-carboxylic acid The compound was prepared by a procedure described in Example 86 by using cis/trans-4-hydroxy-3-ethylpiperidine instead of trans-4-amino-3-methylpieridine and product was purified on preparative HPLC to give titled product. m. p. 170-172° C., mass (ES$^+$) 403, Molecular Formula $C_{22}H_{27}FN_2O_4$, H$^1$NMR (CD$_3$OD) 0.92-1.02 (m, 10H), 1.22-2.18 (m, 6H), 2.80-3.62 (m, 4H), 4.0-4.22 (m, 2H), 7.86-8.02 (d, 1H), 8.95 (s, 1H).

EXAMPLE 93 cis/trans-1-Cyclopropyl-6-fluoro-8-methoxy-(4-hydroxy-3-methyl-1-piperidinyl)-1,4-dihydro-4-oxoguinoline-3-carboxylic acid The compound was prepared by a procedure described in Example 1 by using cis/trans-4-hydroxy-3-methylpiperidine instead of 4-amino-3-methylpiperidine and product was purified on preparative HPLC to give titled product. m. p. 114-216° C., mass (ES$^+$) 391, Molecular Formula $C_{20}H_{23}FN_2O_5$, H$^1$NMR (CDCl$_3$) 1.00-1.12 (m, 4H), 1.20-1.32 (d, 3H), 1.78-2.22 (m, 3H), 2.20-2.70 (m, 4H), 3.58-3.80 (s, 3H), 4.00-4.18 (m, 1H), 7.82-8.0 (d, 1H), 8.82 (s, 1H).

EXAMPLE 94 cis/trans-1-Cyclopropyl-6-fluoro-8-methoxy-7-(4-hydroxy-3-ethyl-1-piperidinyl)-1,4-dihydro-4-oxoguinoline-3-carboxylic acid The compound was prepared by a procedure described in Example 1 by using cis/trans-4-hydroxy-3-ethylpiperidine instead of 4-amino-3-methylpiperidine and product was purified on preparative HPLC to give titled product. m. p. 188-190° C., mass (ES$^+$) 405, Molecular Formula $C_{21}H_{25}FN_2O_5$, H$^1$NMR (CHCl$_3$) 0.98-1.05 (t, 3H), 1.06-1.58 (m, 4H), 1.60-2.02 (m, 3H), 3.30 (s, 3H), 3.60-3.75 (m, 4H), 3.75-3.90 (q, 3H), 4.00-4.20 (m, 2H), 7.85-7.98 (d, 1H), 8.80 (s, 1H).'

EXAMPLE 95 cis/trans-5-Amino-1-cyclopropyl-6-fluoro-8-methoxy-7-(4-hydroxy-3-methyl-1-piperidinyl)-1,4-dihydro-4-oxoquinoline-3-carboxylic acid The above compound was prepared by a procedure described in Example 43 by using cis/trans-4-hydroxy-3-methylpiperidine instead of 3,3-dimethyl-4-methylaminopiperidine and product was purified on preparative HPLC to give titled product.

m. p. 240-244° C., mass (ES$^+$) 406, Molecular Formula $C_{20}H_{24}FN_3O_5$.

EXAMPLE 96 cis/trans-5-Amino-1-cyclopropyl-6-fluoro-8-methoxy-7-(4-hydroxy-3-ethyl-1-piperidinyl)-1,4-dihydro-4-oxoguinoline-3-carboxylic acid The above compound was prepared by a procedure described in Example 43 by using cis/trans-4-hydroxy-3-ethylpiperidine instead of 3,3-dimethyl-4-methylaminopiperidine and product was purified on preparative HPLC to give titled product.

m. p. 217-19° C., mass (ES$^+$) 420, Molecular Formula $C_{21}H_{26}FN_3O_5$, H$^1$NMR (CDCl$_3$) 0.82 (d, 2H), 1.02 (t, 3H), 1.18 (d, 2H), 3.18-3.40 (m, 4H), 3.60 (s, 3H), 3.90-4.02 (q, 2H), 4.18 (m, 1H), 8.70 (s, 1H).

EXAMPLE 97

(±)-1-Cyclopropyl-6-fluoro-1,4-dihydro-8-methyl-7-(4-amino-3,3-dimethyl-1-piperidinyl)-4-oxo-quinoline-3-carboxylic acid hydrochloride The product obtained in example 68 (1 gm; 2.58 mmol) was suspended in 10 ml ethanol and ethanolic hydrochloric acid (2.6 ml) was added at a temperature between 20-30° C. under stirring. To this solution, 20 ml ether was added after 30 minutes and the solid separated was filtered and dried under vacuum. Yield –0.89 gm (83%). m.p. 242-244° C., $C_{21}H_{26}FN_3O_3$.HCl, m/z 388 (M+1).

Similarly by using above procedure other inorganic acid salts are made.

EXAMPLE 98

(–)-1-Cyclopropyl-6-fluoro-1,4-dihydro-8-methyl-7-(4-amino-3,3-dimethyl-1-piperidinyl)-4-oxo-quinoline-3-carboxylic acid hydrochloride The product obtained in example 69 (1 gm; 2.58 mmol) was suspended in 10 ml ethanol and ethanolic hydrochloric acid (2.6 ml) was added at a temperature between 20-30° C. under stirring. To this solution, 20 ml ether was added after 30 minutes and the solid separated was filtered and dried under vacuum. Yield –0.91 gm (83%). m. p. (by DSC) 300° C., $C_{21}H_{26}FN_3O_3$.HCl, m/z 388 (M+1), $[\alpha]_D^{25}$ value =–278.14° (c=0.5, methanol).

Similarly by using above procedure other inorganic acid salts are made.

EXAMPLE 99

(+)-1-Cyclopropyl-6-fluoro-1,4-dihydro-8-methyl-7-(4-amino-3,3-dimethyl-1-piperidinyl)-4-oxo-quinoline-3-carboxylic acid hydrochloride The product obtained in example 70 (1 gm; 2.58 mmol) was suspended in 10 ml ethanol and ethanolic hydrochloric acid (2.6 ml) was added at a temperature between 20-30° C. under stirring. To this solution, 20 ml ether was added after 30 minutes and the solid separated was filtered and dried under vacuum. Yield –0.86 gm (83%). m. p. (by DSC) 300° C., $C_{21}H_{26}FN_3O_3$.HCl, m/z 388 (M+1), $[\alpha]_D^{25}$ value =+275° (c=0.5, methanol).

Similarly by using above procedure other inorganic acid salts are made.

EXAMPLE 100

(+)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate The product obtained in example 68 (1 gm; 2.58 mmol) was suspended in 10 ml isopropyl alcohol. The reaction mixture was heated to 70 to 80° C. Methane sulfonic acid (0.25 g, 2.6 mmol) was added. The reaction mixture was cooled after 30 minutes f refluxing and was filtered at 10 to 20° C., dried under vacuum. Yield −0.76 gm (60%). $C_{21}H_{26}FN_3O_3.CH_4SO_3$, m/z 388 (M+1).

Similarly by using above procedure other organic acid salts are made.

EXAMPLE 101

(−)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate The product obtained in example 69 (1 gm; 2.58 mmol) was suspended in 10 ml isopropyl alcohol. The reaction mixture was heated to 70 to 80° C. Methane sulfonic acid (0.25 g, 2.6 mmol) was added. The reaction mixture was cooled after 30 minutes f refluxing and was filtered at 10 to 20° C., dried under vacuum. Yield −0.80 gm (64%). $C_{21}H_{26}FN_3O_3.CH_4SO_3$, m/z 388 (M+1).

Similarly by using above procedure other organic acid salts are made.

EXAMPLE 102

(+)-1-Cyclopropyl-6-fluoro-1,4-dihydro-8-methyl-7-(4-amino-3,3-dimethyl-1-piperidinyl)-4-oxo-quinoline-3-carboxylic acid methane sulfonate The product obtained in example 70 (1 gm; 2.58 mmol) was suspended in 10 ml isopropyl alcohol. The reaction mixture was heated to 70 to 80° C. Methan sulfonic acid (0.25 g, 2.6 mmol) was added. The reaction mixture was cooled after 30 minutes f refluxing and was filtered at 10 to 20° C., dried under vacuum. Yield −0.83 gm (66%). $C_{21}H_{26}FN_3O_3.CH_4SO_3$, m/z 388 (M+1).

Similarly by using above procedure other organic acid salts are made.

TEST EXAMPLE-1

X-Ray Diffraction Analysis 300 mg of racemic or optically active 1-cyclopropyl-6-fluoro-1,4-dihydro-8-methoxy-7-(4-amino-3,3-dimethyl-1-piperidinyl)-4-oxo-quinoline-3-carboxylic acid hydrochloride was thinly spread on a sample holder. X-ray diffraction analyses (40 kv×40 mA Rigaku D/max 2200) were performed under the conditions listed below:

Scan speed 5°/min
Sampling time 7 min
Scan mode: continuous
2θ/θ reflection
Cu target (Ni filter)

TEST EXAMPLE 2

Differential Scanning Calorimetry Analysis

Thermal Analysis of Racemic or Optically Active 1-cyclopropyl-6-fluoro-1,4-dihydro-8-methoxy-7-(4-amino-3,3-dimethyl-1-piperidinyl)-4-oxo-quinoline-3-carboxylic acid hydrochloride For the Differential Scanning Calorimetry, PERKINELMER DSC-7 system was used. 3 to 5 mg of the sample was weighed into the aluminum pan, which was then press sealed with an aluminum lid. The sample was tested by heating from 30° C. to 350° C. at a rate of 10° C./min.

TEST EXAMPLE-3

Infra-Red Spectrum

Infra-Red Spetrum Analysis of Racemic or Optically Active 1-cyclopropyl-6-fluoro-1,4-dihydro-8-methoxy-7-(4-amino-3,3-dimethyl-1-piperidinyl)-4-oxo-quinoline-3-carboxylic acid hydrochloride A KBr pellet of the sample (2% w/w) was scanned on Bruker FT-IR spectrophotometer. The instrument was calibrated with polystyrene film. Scan range 4000 $cm^{-1}$ to 400 $cm^{-1}$. Resolution 2 $cm^{-1}$. Scan time 16 scans.

EXAMPLE 103

Crystalline Polymorphic Form of (±)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1

50 gm of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 4.0 liter methanol at reflux temperature. The clear solution was filtered through a celite bed and the resultant solution was concentrated to approximately 1 liter, cooled to a temperature between 25-35° C. and filtered under suction after 12 hours. The solid obtained was farther dried at 70° C. under vacuum to provide crystalline material (35.6 gm).

The polymorph was characterized by the following analytical data.

Differential Scanning Colorimetry (DSC):
Endotherm at 252.33° C. (onset at 246.19° C.) exotherm at 205.0 (onset at 200.68° C.) and 259.00° C. (onset at 255.83° C.).

X-ray powder diffraction:
(2θ values): 11.16±0.2, 12.06±0.2, 13.74±0.2, 15.06±0.2, 16.46±0.2, 18.60±0.2, 21.72±0.2, 22.44±0.2, 23.72±0.2, 24.66±0.2, 25.90±0.2, 30.08±0.2, 32.58±0.2.

IR values ($cm^{-1}$): 3442, 2957, 1728, 1623, 1512, 1460, 1318, 1277, 1184, 1056, 938.

EXAMPLE 104

Crystalline Polymorphic Form of (±)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A2

3 gm of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride salt was dissolved in 15 ml of water at reflux temperature, allowed to crystallize by cooling to a temperature between 25-35° C. and filtered under suction. The solid obtained was further dried at 70° C. under vacuum to provide crystalline material (2.8 gm).

The polymorph was characterized by the following analytical data.

Differential Scanning Colorimetry (DSC):
Endotherm at 144.66 (onset 115.25) and 254.83° C. (onset at 251.00° C.), exotherm at 211.33 (onset at 208.35° C.) and 259.66° C. (onset at 257.18° C.).

X-ray powder diffraction:

(2θ values): 8.58±0.2, 13.08±0.2, 14.9±0.2, 16.72±0.2, 18.34±0.2, 22.68±0.2, 25.38±0.2, 25.92±0.2, 27.6±0.2, 28.18±0.2.

IR values (cm$^{-1}$): 3476, 3332, 2880, 1712, 1619, 1528, 1448, 1329, 1273, 1234, 1180, 1066, 1035, 989.

EXAMPLE-105

Crystalline Polymorphic Form of (−)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1

30 gm of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 3.0 liter methanol at reflux temperature. The clear solution was filtered through a celite bed and the resultant solution was concentrated to approximately 500 ml, cooled to a temperature between 25-35° C. and filtered under suction. The solid obtained was further dried at 70° C. under vacuum to provide crystalline material (24.0 gm).

The polymorph was characterized by the following analytical data.

Differential Scanning Colorimetry (DSC):

Endotherm at 126.5° C. (onset 93.94° C.) and 252.50° C. (onset at 245.14° C.), exotherm at 202.83 (onset at 200.02° C.) and 257.17° C. (onset at 255.66° C.).

X-ray powder diffraction: Crystalline nature.

(2θ values): 11.30±0.2, 12.06±0.2, 13.64±0.2, 14.4±0.2, 15.16±0.2, 16.48±0.2, 18.52±0.2, 21.48±0.2, 22.72±0.2, 23.94±0.2, 24.76±0.2, 26.42±0.2, 30.24±0.2, 30.60±0.2.

IR values (cm$^{-1}$): 3363, 2957, 1727, 1625, 1512, 1461, 1377, 1323, 1289, 1183, 1056, 942.

EXAMPLE 106

Crystalline Polymorphic Form of (−)-1-Cyclopropyl-6-fluoro-14-dihydro-8-methoxy-7-(4-amino-3,3-dimethyl-1-piperidinyl)-4-oxo-quinoline-3-carboxylic acid hydrochloride-Polymorph A2

5 gm of (−)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 10 ml mixture of 50% aqueous iso-propanol at reflux temperature, cooled to a temperature between 25-35° C. and filtered under suction. The solid obtained was further dried at 70° C. under vacuum to provide crystalline material (2.78 gm).

The polymorph was characterized by the following analytical data.

EXAMPLE 107

Crystalline Polymorphic Form of (+)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride-Polvmorph A1

30 gm of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 3.0 liter methanol at reflux temperature. The clear solution was filtered through a celite bed and the resultant solution was concentrated to approximately 500 ml, cooled to a temperature between 25-35° C. and filtered under suction. The solid obtained was further dried at 70° C. under vacuum to provide crystalline material (24.0 gm).

The polymorph was characterized by the following analytical data.

Differential Scanning Colorimetry (DSC):

Endotherm at 131.5° C. (onset 92.32° C.) and 253.33° C. (onset at 248.28° C.), exotherm at 204.0° C. (onset at 200.8° C.) and 258.0° C. (onset at 256.83° C.).

X-ray powder diffraction: (2θ values): 11.34±0.2, 12.08±0.2, 13.68±0.2, 14.44±0.2, 15.18±0.2, 16.50±0.2, 18.56±0.2, 21.50±0.2, 22.76±0.2, 23.98±0.2, 24.78±0.2, 26.24±0.2, 30.28±0.2, 30.64±0.2, 32.52±0.2.

IR values (cm$^{-1}$): 3653, 3369, 2960, 1727, 1627, 1511, 1465, 1377, 1331, 1279, 1183, 1058, 940.

EXAMPLE 108

Crystalline Polymorphic Form of (+)-1-Cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A2

5 gm of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride was dissolved in 10 ml mixture of 50% aqueous iso-propanol at reflux temperature, cooled to a temperature between 25-35° C. and filtered under suction. The solid obtained was further dried at 70° C. under vacuum to provide crystalline material (3.40 gm).

The polymorph was characterized by the following analytical data.

Differential Scanning Colorimetry (DSC):

Endotherm at 136.66° C. (onset 101.0° C.) and 256.83° C. (onset at 251.92° C.) exotherm at 201.50° C. (onset at 198.60° C.) and 261.16° C. (onset at 259.83° C.).

X-ray powder diffraction:

(2θ values): 7.00±0.2, 7.66±0.2, 8.00±0.2, 12.32±0.2, 12.72±0.2, 13.58±0.2, 14.88±0.2, 15.36±0.2, 16.08±0.2, 18.38±0.2, 19.36±0.2, 20.58±0.2, 23.18±0.2, 25.40±0.2, 26.72±0.2, 72.82±0.2, 29.80±0.2, 30.60±0.2, 32.28±0.2, 36.94±0.2.

IR values (cm$^{-1}$): 3401, 2845, 2632, 1711, 1621, 1537, 1458, 1378, 1321, 1275, 1207, 1061, 989, 806.

BIOLOGICAL EXAMPLES

Microbiological and pharmacological studies can be used to determine the relative potency, and the profile of specificity of the compounds of the invention as antibacterial agent with a spectrum of activity as described in the specification above.

In the following examples, the compounds of the invention are numbered as per the list of the specific compounds of the invention described earlier in the text.

Biological Example 1

In-vitro Antimicrobial Tests

The comparative antimicrobial activity of representative compounds of the invention and reference compounds against various sensitive and resistant microorganisms is given in Tables 17 to 20. The test method was in accordance with the standard NCCLS protocol (Methods for Dilution Antimicrobial Susceptibility Tests for Bacteria that grow Aerobicially, Approved Standards, M7-A5, Fifth Edition, January 2000).

The antibacterial activities (minimum inhibitory concentration: MIC, mcg/ml) were determined by using the two-fold serial agar dilution method recommended by NCCLS. The media used for preculture and main culture were Tryptic Soya broth (Difco) and Mueller Hinton medium (Difco), respectively. The Mueller Hinton agar was supplemented with 5% sheep blood for streptococci. Overnight cultures were diluted with buffered saline (pH 7.2) to the final cell density of $5 \times 10^6$-$10^7$ CFU/ml, and each bacterial suspension was applied with a replicator (Denley's multipoint inoculator, UK) onto a series of Mueller-Hinton agar plates containing antibacterial agents at various concentrations. Final inoculum was approximately $10^4$ CFU/spot. The plates were incubated for 18 hrs at 37° C. The MIC was defined as the lowest concentration of an antibacterial agent that inhibits the development of visible microbial growth on agar. The results obtained are shown in tables 17 to 20.

TABLE 18

Activity Against Fluoroquinolone-Resistant Strains.

| Compound No. | MRSA 032 | FQ$^R$ S. pneumoniae 718 | Cipro$^R$ S. sanguis 941 | Cipro$^R$ S. mitis 938 |
|---|---|---|---|---|
| | | MICs (µg/ml) | | |
| 18 | 0.8 | 0.8 | 0.4 | 1.56 |
| 22 | 0.8 | 0.4 | 0.2 | 0.8 |
| 26 | 0.8 | 0.8 | 0.4 | 1.56 |
| 93 | 0.2 | 0.8 | 0.4 | 0.4 |
| 94 | 0.2 | 0.8 | 0.4 | 0.4 |
| 95 | 0.2 | 0.8 | 0.4 | 0.4 |
| 97 | 0.8 | 3.12 | 3.12 | 3.12 |
| 98 | 1.56 | 1.56 | 3.12 | 1.56 |
| 100 | 1.56 | 1.56 | 3.12 | 1.56 |
| 102 | 0.8 | 0.8 | 1.56 | 1.56 |
| 106 | 1.56 | 1.56 | 6.25 | 6.25 |
| 110 | 0.4 | 0.4 | 1.56 | 0.8 |
| Levofloxacin | 6.25 | 12.5 | 12.5 | 25.0 |
| Moxifloxacin | 3.12 | 3.12 | 6.25 | 6.25 |

TABLE 17

Activity Against Fluoroquinolone Sensitive Strains

| Compound No. | MSSA ATCC 25923 | S. pneumoniae ATCC 49619 | S. sanguis ATCC 10556* | E. faecalis ATCC 29212 | E. coli ATCC 25922 | P. aeruginosa ATCC 27853 |
|---|---|---|---|---|---|---|
| | | | MICs (µg/ml) | | | |
| 1 | 0.05 | 0.2 | — | — | 0.05 | — |
| 17 | 0.4 | 1.56 | — | — | 0.4 | — |
| 18 | 0.05 | 0.05 | 0.1 | 0.1 | 0.2 | 6.25 |
| 22 | 0.05 | 0.05 | 0.1 | 0.1 | 0.2 | 6.25 |
| 26 | 0.05 | 0.1 | 0.1 | 0.1 | 0.2 | 6.25 |
| 30 | 0.05 | 0.1 | — | — | 0.05 | — |
| 46 | 0.05 | 0.1 | — | — | 0.1 | — |
| 48 | 1.56 | >6.25 | — | — | 6.25 | — |
| 70 | 0.05 | 0.2 | — | — | 0.4 | — |
| 75 | 0.05 | 0.2 | — | — | 0.2 | — |
| 92 | 0.1 | — | — | — | 0.05 | — |
| 93 | 0.003 | 0.025 | 0.05 | 0.05 | 0.2 | 3.12 |
| 94 | 0.003 | 0.025 | 0.025 | 0.1 | 0.2 | 3.12 |
| 95 | 0.003 | 0.025 | 0.025 | 0.05 | 0.2 | 3.12 |
| 97 | 0.012 | 0.1 | 0.2 | 0.2 | 0.4 | 12.5 |
| 98 | 0.025 | 0.05 | 0.025 | 0.1 | 0.006 | 1.56 |
| 100 | 0.025 | 0.05 | 0.025 | 0.1 | 0.0012 | 3.12 |
| 102 | 0.025 | 0.025 | 0.025 | 0.05 | 0.025 | 3.12 |
| 106 | 0.025 | 0.1 | 0.1 | 0.2 | 0.05 | 6.25 |
| 110 | 0.025 | 0.025 | 0.05 | 0.05 | 0.025 | 1.56 |
| 114 | 0.05 | 0.05 | — | — | 0.05 | — |
| 120 | 0.1 | 0.8 | — | — | 0.8 | — |
| 131 | 0.8 | — | — | — | 1.56 | — |
| 133 | 0.025 | 0.2 | — | — | 0.4 | — |
| 145 | 0.025 | 0.4 | — | — | 1.56 | — |
| 147 | <0.006 | 0.1 | — | — | 0.4 | — |
| Levofloxacin | 0.2 | 0.8 | 1.56 | 0.8 | 0.025 | 3.12 |
| Moxifloxacin | 0.05 | 0.2 | 0.4 | 0.2 | 0.05 | 6.25 |

*S. sanguis 10556 belongs to the group of Viridans Streptococci. 3 other strains of the group S. oralis 900, S. salivaris 1062 and S. mitis 1303 provided similar MICs ranging from 0.025-0.40 µg/ml in comparison to the reference compounds which had MIC values ranging from 0.1-3.12.

TABLE 19

Activity Against Trovafloxacin-Resistant and Vancomycin-Resistant Enterococci

| Compound No. | Trova-Resist MRSE** 110 | V R E*** 336 |
|---|---|---|
| | MICs (µg/ml) | |
| 93 | 0.4 | 3.12 |
| 94 | 0.4 | 3.12 |
| 95 | 0.4 | 3.12 |
| Ref. comp. 1* | 1.56 | 6.25 |
| Ref. comp. 2* | 1.56 | 6.25 |
| Ref. comp. 3* | 1.56 | 6.25 |

*Ref. Comp. 1, 2 and 3 are reference compounds cited in our pending U.S. patent application 09/850,669 and WO 01/85728
Ref. Comp. 1 is S-(−)-9-fluoro-6,7-dihydro-8-(4-hydroxy-3-methylpiperidin-1-yl)-5-methyl-1-oxo-1H,5H-benzo[i, j]quinolizine-2-carboxylic acid (mixture of cis racemate and trans racemate)
Ref. Comp. 2 is S-(−)-9-fluoro-6,7-dihydro-8-{cis-4-(RS)-hydroxy-3-(RS)-methylpiperidin-1-yl}-5-methyl-1-oxo-1H,5H-benzo[i, j]quinolizine-2-carboxylic acid.
Ref. Comp. 3 is S-(−)-9-fluoro-6,7-dihydro-8-{trans-4-(RS)-hydroxy-3-(RS)-methylpiperidin-1-yl}-5-methyl-1-oxo-1H,5H-benzo[i, j]quinolizine-2-carboxylic acid
**MRSE stands for methicillin-resistant *S. epidermidis*
***VRE stands for vancomycin-resistant *Enterococcus faecium*

TABLE 20

Activity Against Clinical Isolate MRSA 5076 with Mutations in DNA Gyrase and Topoisomerase IV as well as bearing an Efflux Pump

| Compound No. | *S. aureus* (sensitive) ATCC 25293 | MRSA 5076 (triple resistance) | MRSA 5076 + efflux inhibitor reserpine |
|---|---|---|---|
| | MICs (µg/ml) | | |
| 18 | 0.05 | 3.12 | 1.56 |
| 22 | 0.05 | 1.56 | 1.56 |
| 26 | 0.05 | 3.12 | 1.56 |
| 95 | 0.003 | 0.2 | 0.2 |
| 110 | 0.05 | 0.8 | 0.8 |
| Ciprofloxacin | 0.8 | 100 | 25.0 |
| Moxifloxacin | 0.05 | 12.5 | 6.25 |

The data shows that the reference compounds, which although are active against sensitive staphylococci, are rendered quite unattractive due to serious loss in their potency against clinical isolate MRSA 5076 expressing triple fluoroquinolone-resistance mechanisms. The fold difference between the MIC values for each compound in the last columns indicates the effect of the efflux pump mechanism on the susceptibility of the strains to the respective compounds. The compounds of the invention are 4-fold to 500-fold more potent than the reference compounds against the resistance strain as seen in column 3.

Resistance to Resistance Development

Compound No. 18 was evaluated in comparison with Moxifloxacin and Trovafloxin in terms of resistance to resistance development on sequential transfer/passages through respective drug-containing media. Initially all the three drugs had comparable activity against MRSA 5027 (0.4 µg/ml). However, after 10 passages in drug containing medium, MIC for Moxifloxacin and Trovafloxacin was 6.25 µg/ml and 50 µg/ml respectively, while compound No. 18 showed no elevation and remained 0.4 µ/ml. The data indicates that compound No. 18 has a remarkable property of resisting the development and selection of MRSA strains resistant to it and is significantly less likely to select resistant mutants in a clinical scenario, thus obviating the risk of treatment failure in patients.

Biological Example 2

In-vivo Antimicrobial Tests

Protocol for Systemic Infection Model

The in vivo efficacy was studied through mouse septicemia model of infection in Swiss male and female mice (4 weeks old, 20+2 g weight) using 6 animals in each group. Infective organisms were inoculated intraperitonially. Compound were administered by oral route 1 hour and 5 hours post-infection. By Probit analysis protective doses were calculated from the survival rate on day 7 in terms of $ED_{50}$ (50% survival dose) values. Appropriate comparators were included in the study.

TABLE 22

In-vivo Activity Against Multidrug-Resistant (MDR) Pneumococcal Infections

| COMPOUND | $ED_{50}$ p.o. (mg/kg) MDR *S. pneumoniae* 718* |
|---|---|
| 18 | 30 |
| 22 | 20 |
| 26 | 50 |
| 100 | 30 |
| 102 | 30 |
| 110 | 20 |
| Levofloxacin | >100 |
| Moxifloxacin | >100 |
| Gatifloxacin | >100 |

*Resistant to β-lactams, macrolides and fluoroquinolones

Biological Example 3

Acute Toxicity

Each test compound or reference compound was administered orally to groups of 10 swiss mice (body weight: 22-26 gms) each, whereby its acute toxicity was investigated. The compounds were administered in solution form. As a result it was found that the median lethal dose ($LD_{50}$) values of compounds 18, 19 and 20 were 650 mg/kg, 600 mg/g and 650 mg/kg respectively. The $LD_{50}$ of reference compound moxifloxacin was 600 mg/kg. On the basis of data of $ED_{50}$ values (provided in table 22) the therapeutic index ($LD_{50}/ED_{50}$) for the test compounds is 3.0 to 7.5 times higher than that for moxifloxacin

Biological Example 4

Cytotoxicity

Protocol for Cytotoxicity Test

Compounds were evaluated for their cytotoxic potential against two celllines viz J 744 (mouse macrophage) and V79 (Chinese Hamster Lung). Cells were grown for 3-4 days a culture flask using D-MEM (Dulbecco's Modified Eagle Medium) supplemented with 10% fetal bovine serum (FBS). Freshly grown cells were distributed in microtiter plates at a cell density of $10^5$-$10^6$ cells /well and allowed to adhere and form monolayer by incubating the microtiter plate at 37° C. for 24 hrs. Medium form each well was aspirated and replaced with fresh D-MEM (supplemented with 2.5% FBS) containing various concentrations of compounds. Following 3 hrs. of drug exposure, cells were washed with D-MEM and incubated further for 96 hrs. Cytotoxic effects of drugs were monitored through daily microscopic observation and by ascertaining the metabolic status through redox indicator Alamar blue. Healthy actively metabolising cells bring about colour change of Alamar blue from blue to pink within an overnight incubation. Cytotoxic drugs inhibit this reaction resulting into blue coloured wells. Minimum drug concentration inhibiting Alamar blue color change i.e. resulting into blue coloured wells for a given drug is considered cytotoxic concentration.

TABLE 23

| Compound No. | J 744 Macrophage | V 79 CHL |
|---|---|---|
| | (Cytotoxic concentration mcg/ml) | |
| 18 | >1000 | >1000 |
| 22 | >1000 | 1000 |
| 26 | >1000 | >1000 |
| 93 | >1000 | >1000 |
| 94 | >1000 | >1000 |
| 95 | >1000 | >1000 |
| 97 | >1000 | >1000 |
| 98 | 1000 | 250 |
| 100 | 1000 | 125 |
| 102 | 1000 | 750 |
| 106 | >1000 | >1000 |
| 110 | 1000 | 250 |
| Trovafloxacin | 500 | 62.5-120 |

Biological Example 5

Phototoxicity

Six groups of healthy Swiss Albino mice consisting of 6 males per group were orally administered with a single dose of a compound of the invention or a reference compound at dose levels of 50, 100, 200, 300 and 400 mg/kg. The stock solutions for different doses were prepared freshly on the day of experimentation. Appropriate concentration of each dose was chosen to give a constant dosage volume of 0.3-0.4 ml/20 g body weight of mouse. The treated mice were exposed to UVA light source immediately after dosing for 4 hours and for 4 consecutive days. The mean light intensity in the UVA chamber was adjusted to 0.9-1.2 $mW/cm^2$. The total irradiation dose was approximately 18 $Joules/cm^2$/day. A phototoxic dose is one which causes ear erythema and oeadema. The phototoxic doses of compounds 18, 19 and 20 of the present invention were greater than 500 mg/kg, whereas the phototoxic dose for reference compound sparfloxacin was 25 mg/kg, thus indicating that the compounds of the present invention induced no phototoxicity.

The invention claimed is:

1. A compound selected from the group consisting of:
   a) crystalline polymorphic form of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1, said polymorph characterized by the following analytical data:
   Differential Scanning Colorimetry (DSC):
   Endotherm at 252.33° C. (onset at 246.19° C.) exotherm at 205.0 (onset at 200.68° C.) and 259.00° C. (onset at 255.83° C.);
   X-ray powder diffraction;
   (2θ values): 11.16±0.2, 12.06±0.2, 13.74±0.2, 15.06±0.2, 16.46±0.2, 18.60±0.2, 21.72±0.2, 22.44±0.2, 23.72±0.2, 24.66±0.2, 25.90±0.2, 30.08±0.2, 32.58±0.2; and
   IR values ($cm^{-1}$): 3442, 2957, 1728, 1623, 1512, 1460, 1318, 1277, 1184, 1056, 938;
   b) crystalline polymorphic form of (±)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A2, said polymorph characterized by the following analytical data:
   Differential Scanning Colorimetry (DSC):
   Endotherm at 144.66 (onset 115.25) and 254.83° C. (onset at 251.00° C.), exotherm at 211.33 (onset at 208.35° C.) and 259.66° C. (onset at 257.18° C.);
   X-ray powder diffraction:
   (2θ values): 8.58±0.2, 13.08±0.2, 14.9±0.2, 16.72±0.2, 1834±0.2, 22.68±0.2, 25.38±0.2, 25.92±0.2, 27.6±0.2, 28.18±0.2; and
   IR values ($cm^{-1}$): 3476, 3332, 2880, 1712, 1619, 1528, 1448, 1329, 1273, 1234, 1180, 1066, 1035, 989;
   c) crystalline polymorphic form of (−)-1-cyclopropyl-6-fluoro-1,4-dihydro-8-methoxy-7-(4-amino-3,3-dimethyl-1-piperidinyl)-4-oxo-quinoline-3-carboxylic acid hydrocloride-Polymorph A1, said polymorph characterized by the following analytical data:
   Differential Scanning Colorimetry (DSC):
   Endotherm at 126.5° C. (onset 93.94° C.) and 252.50° C. (onset at 245.14° C.), exotherm at 202.83 (onset at 200.02° C.) and 257.17° C. (onset at 255.66° C.).
   X-ray powder diffraction:
   (2θ values): 11.30±0.2, 12.06±0.2, 13.64±0.2, 14.4±0.2, 15.16±0.2, 16.48±0.2, 18.52±0.2, 21.48±0.2, 22.72±0.2, 23.94±0.2, 24.76±0.2, 26.42±0.2, 30.24±0, 2, 30.60±0.2; and
   IR values ($cm^{-1}$): 3363, 2957, 1727, 1625, 1512, 1461, 1377, 1323, 1289, 1183, 1056, 942;
   d) crystalline polymorphic form of (−)-1-cyclopropyl-6-fluoro-1,4-dihydro -8-methoxy-7-(4-amino-3,3-dimethyl-1-piperidinyl)-4-oxo-quinoline-3-carboxylic acid hydrochloride-Polymorph A2, said polymorph characterized by the following analytical data:
   Differential Scanning Colorimetry (DSC):
   Endotherm at 123.5 (onset 101.7) and 201,83° C. (onset at 189.84° C.), 244.83° C. (onset at 230.73° C.) exotherm at 210.5 (onset at 206.6° C.) and 253.17° C. (onset at 249.50° C.); and
   X-ray powder diffraction
   (2θ values): 6.70±0.2, 7.06±0.2, 7.72±0.2, 8.24±0.2, 12.40±0.2, 13.66±0.2, 14.96±0.2, 18.62±0.2, 19.40±0.2, 23.24±0.2, 24.90±0.2, 27.86±0.2;
   e) crystalline polymorphic form of (+)-1-cyclopropyl-6-fluoro-1,4-dihydro-8-methoxy-7-(4-amino-3,3-dimethyl-1-piperidinyl)-4-oxo-quinoline-3-carboxylic acid hydrochloride-Polymorph A1, said polymorph characterized by the following analytical data:

Differential Scanning Colorimetry (DSC):

Endotherm at 131.5° C. (onset 92.32° C.) and 253.33° C. (onset at 248.280° C.), exotherm at 204.0° C. (onset at 200.8° C.) and 258.0° C. (onset at 256.83° C.);

X-ray powder diffraction: (2θ values): 11.34±0.2, 12.08±0.2, 13.68±0.2, 14.44±0.2, 15.18±0.2, 16.50±0.2, 18.56±0.2, 21.50±0.2, 22.76±0.2, 23.98±0.2, 24.78±0.2, 26.24±0.2, 30.28±0.2, 30.64±0.2, 32.52±0.2; and IR values (cm$^{-1}$): 3653, 3369, 2960, 1727, 1627, 1511, 1465, 1377, 1331, 1279, 1183, 1058, 940; and f) crystalline polymorphic form of (+)-1-cyclopropyl-6-fluoro-1,4-dihydro-8-methoxy-7-(4-amino-3,3 -dimethyl-1-piperidinyl)-4-oxo-quinoline-3-carboxylic acid hydrochloride-Polymorph A2, said polymorph characterized by the following analytical data;

Differential Scanning Colorimetry (DSC):

Endotherm at 136.66° C. (onset 101.0° C.) and 256.83° C. (onset at 251.92° C.) exotherm at 201.50° C. (onset at 198.60° C.) and 261.16° C. (onset at 259.83° C.);

X-ray powder diffraction:

(2θ values): 7.00±0.2, 7.66±0.2, 8.00±0.2, 12.32±0.2, 12.72±0.2, 13.58±0.2, 14.88±0.2, 15.36±0.2, 16.08±0.2, 18.38±0.2, 19.36±0.2, 20.58±0.2, 23.18±0.2, 25.40±0.2, 26.72±0.2, 72.82±0.2, 29.80±0.2, 30.60±0.2, 32.28±0.2, 36.94±0; and IR values (cm$^{-1}$): 3401, 2845, 2632, 1711, 1621, 1537, 1458, 1378, 1321, 1275, 1207, 1061, 989, 806.

* * * * *